(12) United States Patent
Gordon-Kamm et al.

(10) Patent No.: US 9,340,796 B2
(45) Date of Patent: *May 17, 2016

(54) AP2 DOMAIN TRANSCRIPTION FACTOR ODP2 (OVULE DEVELOPMENT PROTEIN 2) AND METHODS OF USE

(71) Applicant: Pioneer Hi-Bred International, Inc., Johnston, IA (US)

(72) Inventors: William J. Gordon-Kamm, Urbandale, IA (US); Timothy G. Helentjaris, Ankeny, IA (US); Keith S. Lowe, Johnston, IA (US); Bo Shen, Johnston, IA (US); Mitchell C. Tarczynski, West Des Moines, IA (US); Peizhong Zheng, Johnston, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/790,641

(22) Filed: Mar. 8, 2013

(65) Prior Publication Data

US 2013/0254935 A1 Sep. 26, 2013

Related U.S. Application Data

(63) Continuation of application No. 12/503,482, filed on Jul. 15, 2009, now Pat. No. 8,420,893, which is a continuation of application No. 11/045,802, filed on Jan. 28, 2005, now Pat. No. 7,579,529.

(60) Provisional application No. 60/541,122, filed on Feb. 2, 2004.

(51) Int. Cl.
| | | |
|---|---|---|
| C12N 15/82 | (2006.01) | |
| A01H 1/08 | (2006.01) | |
| C07K 14/415 | (2006.01) | |

(52) U.S. Cl.
CPC ............. *C12N 15/8243* (2013.01); *A01H 1/08* (2013.01); *C07K 14/415* (2013.01); *C12N 15/8201* (2013.01); *C12N 15/8209* (2013.01); *C12N 15/8261* (2013.01); *C12N 15/8287* (2013.01)

(58) Field of Classification Search
None
See application file for complete search history.

(56) References Cited

U.S. PATENT DOCUMENTS

| | | |
|---|---|---|
| 6,093,874 A | 7/2000 | Jofuku et al. |
| 6,512,165 B1 | 1/2003 | Ross et al. |
| 7,151,170 B1 | 12/2006 | Boutilier et al. |
| 7,256,322 B2 | 8/2007 | Lowe et al. |
| 7,348,468 B1 | 3/2008 | Cahoon et al. |
| 7,414,172 B2 | 8/2008 | Pages et al. |
| 7,579,529 B2 * | 8/2009 | Gordon-Kamm et al. . 800/320.1 |
| 7,700,829 B2 | 4/2010 | Zuo et al. |
| 7,816,580 B2 | 10/2010 | Zuo et al. |
| 8,420,893 B2 * | 4/2013 | Gordon-Kamm et al. .... 800/298 |
| 2003/0049835 A1 | 3/2003 | Helliwell et al. |
| 2003/0082813 A1 | 5/2003 | Zuo et al. |
| 2003/0135889 A1 | 7/2003 | Ross et al. |
| 2004/0166563 A1 | 8/2004 | Lowe et al. |
| 2004/0247620 A1 | 12/2004 | Julien |
| 2005/0044595 A1 | 2/2005 | Arias et al. |
| 2007/0271628 A1 | 11/2007 | Lowe et al. |
| 2011/0165679 A1 | 7/2011 | Gordon-Kamm et al. |
| 2011/0167516 A1 | 7/2011 | Gordon-Kamm et al. |

FOREIGN PATENT DOCUMENTS

| | | |
|---|---|---|
| EP | 1 033 405 A2 | 9/2000 |
| EP | 1 054 891 A1 | 11/2000 |
| EP | 1 057 891 A | 12/2000 |
| EP | 1 094 112 A2 | 4/2001 |
| EP | 1 185 656 A1 | 3/2002 |
| WO | WO 98/07842 A | 2/1998 |
| WO | WO 99/15178 | 4/1999 |
| WO | WO 99/21574 | 5/1999 |
| WO | WO 99/41974 | 8/1999 |
| WO | WO 00/40694 A | 7/2000 |
| WO | WO 00/75330 | 12/2000 |
| WO | WO 01/23575 A2 | 4/2001 |
| WO | 02/059294 A1 | 8/2002 |
| WO | 02/097059 A2 | 12/2002 |
| WO | WO 03/001902 A2 | 1/2003 |
| WO | WO 03/002751 A | 1/2003 |
| WO | WO 03/037072 A2 | 5/2003 |
| WO | WO 2005/063990 A2 | 7/2005 |
| WO | 2009/132057 A1 | 10/2009 |

OTHER PUBLICATIONS

Marsch-Martinez et al (2006, Plant Mol. Biol. 62:825-843).*
Boutilier et al (2002, The Plant Cell 14:1737-1749).*
Whitelaw et al (2003, NCBI Accession No. CC603221).*
Bowie et al, Science 247:1306-1310, 1990.*
McConnell et al, Nature 411 (6838):709-713, 2001.*
Boutilier, K., et al., "Ectopic Expression of Baby Boom Triggers a Conversation from Vegetative to Embryonic Growth," *The Plant Cell*, 2002, pp. 1737-1749, vol. 14.
Bowie, J.U., et al., "Deciphering the Message in Protein Sequences: Tolerance to Amino Acid Substitutions," *Science*, 1990, pp. 1306-1310, vol. 247.
Feng, Q., et al., "Sequence and Analysis of Rice Chromosome 4," *Nature*, 2002, pp. 316-320, vol. 420.
GenBank Report for Accession No. AAD30633, Direct Submission on Oct. 30, 2002.

(Continued)

*Primary Examiner* — Stuart F Baum

(57) ABSTRACT

Methods and compositions for modulating plant development are provided. Nucleotide sequences and amino acid sequences encoding Ovule Development Protein 2 (ODP2) proteins are provided. The sequences can be used in a variety of methods including modulating development, developmental pathways, altering oil content in a plant, increasing transformation efficiencies, modulating stress tolerance, and modulating the regenerative capacity of a plant. Transformed plants, plant cells, tissues, and seed are also provided.

19 Claims, 6 Drawing Sheets

(56) References Cited

OTHER PUBLICATIONS

GenBank Report for Accession No. AAL47205, Direct Submission on May 31, 2002.
GenBank Report for Accession No. AAM33800, Direct Submission on Oct. 10, 2002.
GenBank Report for Accession No. AAM33801, Direct Submission on Oct. 10, 2002.
GenBank Report for Accession No. AAM33803, Direct Submission on Oct. 10, 2002.
GenBank Report for Accession No. AY062108, Direct Submission on Oct. 31, 2001.
GenBank Report for Accession No. AY062180, Jun. 3, 2002.
GenBank Report for Accession No. AY062180, Direct Submission on Oct. 31, 2001.
GenBank Report for Accession No. BAB02492, Direct Submission on Feb. 14, 2004.
GenBank Report for Accession No. BAB89946, Direct Submission on Aug. 31, 2004.
GenBank Report for Accession No. CAE02944, Direct Submission on Apr. 16, 2005.
GenBank Report for Accession No. CAE05555, Direct Submission on Apr. 16, 2005.
GenBank Report for Accession No. CC603221, 2003.
GenBank Report for Accession No. CC667986, Jun. 20, 2003.
GenBank Report for Accession No. CL960366, Sep. 22, 2004.
GenBank Report for Accession No. F96549, Direct Submission on Mar. 31, 2001.
GenBank Report for Accession No. NP175530, Direct Submission on Feb. 23, 2005.
GenBank Report for Accession No. NP197245, Direct Submission on Feb. 23, 2005.
Gidoni, D., et al., "Embryonal recombination and germline inheritance of recombined *FRT* loci mediated by constitutively expressed FLP in tobacco," *Euphytica*, 2001, vol. 121, pp. 145-156.
Huang, X.-Q., et al., "High-frequency plant regeneration through callus initiation from mature embryos of maize (*Zea mays* L.)," *Plant Cell Rep*, 2004, vol. 22, pp. 793-800.
Kamiya, N., et al., "Isolation and Characterization of a Rice *WUSCHEL*-type Homeobox Gene that is Specifically Expressed in the Central Cells of a Quiescent Center in the Root Apical Meristem," *The Plant Journal*, 2003, pp. 429-441, vol. 35.
Kizis, D., et al., "Role of AP2/EREBP Transcription Factors in Gene Regulation During Abiotic Stress," *FEBS Letters*, 2001, pp. 187-189, vol. 498.
Marsch-Martinez, N., et al., "Bolita, an Arabidopsis AP2/ERF-Like Transcription Factor that Affects Cell Expansion and Proliferation/Differentiation Pathway," *Plant Mol Biol.*, 2006, pp. 825-843, vol. 62.
Mayer, K., et al., "Role of *WUSCHEL* in Regulating Stem Cell Fate in the *Arabidopsis* Shoot Meristem," *Cell*, 1998, pp. 805-815, vol. 95.
McConnell, J.R., et al., "Role of PHABULOSA and PHAVOLUTA in determining Radial Patterning in Shoots," *Nature*, 2001 pp. 709-713, vol. 411.
Mizukami, Y., and Robert L. Fischer, "Plant Organ Size Control: *AINTEGUMENTA* Regulates Growth and Cell Numbers During Organogenesis," *PNAS*, 2000, pp. 942-947, vol. 97(2).
Nardmann, J., et al., "The Shoot Stem Cell Niche in Angiosperms: Expression Patters of *WUS* Orthologues in Rice and Maize Imply Major Modifications in the Course of Mono-and Dicot Evolution," *Mol. Viol. Evol.*, 2006, vol. 23(12), pp. 2492-2504.
Ouakfaoui, S., et al., "Control of Somatic Embryogenesis and Embryo Development by AP2 Transcription Factors," *Plant Mol. Biol.*, 2010, published online Aug. 27, 2010 (with supplementary materials).
Riechmann, J. L., et al., "The AP2/EREBP Family of Plant Transcription Factors," *Biological Chemistry*, 1998, pp. 633-646, vol. 379.
Sasakl, T., et al. "The Genome Sequence and Structure of Rice Chromosome 1," *Nature*, 2002, pp. 312-316, vol. 420.
Sato, S., et al., "Structural Analysis of *Arabidopsis thaliana* Chromosome 3. I. Sequence Features of the Regions of 4,504,864 by Covered by Sixty P1 and TAC Clones," *DNA Research*, 2000, pp. 131-135, vol. 7.
Theologis, A., et al. "Sequence and Analysis of Chromosome 1 of the Plant *Arabidopsis thaliana*," *Nature*, 2000, pp. 816-820, vol. 408.
Töpfer, R., et al., "Uptake and Transient Expression of Chimeric Genes in Seed-Derived Embryos," *The Plant Cell*, 1989, vol. 1, pp. 133-139.
Wang, Andrew S., "Callus induction and plant generation from maize mature embryos," *Plant Cell Reports*, 1987, vol. 6, pp. 360-362.
International Search Report—PCT/US2005/003135 Nov. 10, 2005.
Written Opinion of the International Searching Authority—PCT/US2005/003135 Nov. 10, 2005.
Invitrogen Corporation, "Gateway® pDONR™ Vectors," User Manual, Version E, 2007, retrieved from http://wolfson.huji.ac.il/expression/gateway_pdonr_vectors.pdf, XP002627486.
Srinivasan, C., et al., "Heterologous expression of the Baby Boom AP2/ERF transcription factor enhances the regeneration capacity of tobacco (Nicotiana tabacum L.)," Planta, 2007, vol. 225, pp. 341-351.
U.S. Appl. No. 12/982,180, filed Dec. 30, 2010.
U.S. Appl. No. 14/087,775, filed Nov. 22, 2013.
U.S. Appl. No. 61/291,257, filed Dec. 30, 2009.
Written Opinion of the International Searching Authority— PCT/US2010/062531 Sep. 5, 2011.
International Search Report—PCT/US2010/062531 Sep. 5, 2011.

\* cited by examiner

```
                            1                                                  50
         ZM-ODP2      (1)   MATVNNWLAFSLSPQELPPSQTTDSTLISAAT-------ADHV GDVCFN
   OsAnt(BAB89946)    (1)   MATMNNWLAFSLSPQDQLPPSQTNSTLISAAAT--TTTAGDSSTGDVCFN
   OSBNM(AAL47205)    (1)   MATMNNWLAFSLSPQDQLPPSQTNSTFISAAAT--TTTAGDSSTGDVCFN
   OSODP(CAE05555)    (1)   MASADNWLGFSLSGQGNPQHHQNGSPSAAGDA-------AIDISGSGDFYG
   AtODP(NP_197245)   (1)   MNSMNNWLGFSLSPHDQNHHRTDVDSSTTRTA-------VDVAGGYCFDL
   AtBBM(AAM33803)    (1)   MNSMNNWLGFSLSPHDQNHHRTDVDSSTTRTA-------VDVAGGYCFDL
   BnBBM1(AAM33800)   (1)   --MNNNWLGFSLSPYEQNHHRKDVYSSTTTTV-------VDVAGEYCYDP
   BnBBM2(AAM33801)   (1)   --MNNNWLGFSLSPYEQNHHRKDVCSSTTTTA-------VDVAGEYCYDP
   AtODP(NP_175530)   (1)   -MNSNNWLAFFLSPTRSSLPPHIHSSQNSHFNLGLVNDNIDNPFQNQGWN
   AtODP(BAB02492)    (1)   -----------------------------------------MDNPFQTQEWN
   AtODP(AAD30633)    (1)   --------------------------------------------------
         Consensus    (1)   M S NNWLGFSLSP DQ       S  S A      VD A     F 51                                                100
         ZM-ODP2     (44)   IPQDWSMRGSELSALVAEPKLEDFLGGISFS-EQHHKANCNMIPSTSSTV
   OsAnt(BAB89946)   (49)   IPQDWSMRGSELSALVAEPKLEDFLGGISFSEQQHHHGGKGGVIPSSAAA
   OSBNM(AAL47205)   (49)   IP-----------------------------QAHPS--------------
   OSODP(CAE05555)   (45)   LPTPDAHHIGMAGEDAPYGVMDAFNRGTHETQDWAMRGLDYGGGSSDLSM
   AtODP(NP_197245)  (44)   AAPSDESSAVQTSFLSPFGVTLEAFTRDN---NSHSRDWDINGGACNNIN
   AtBBM(AAM33803)   (44)   AAPSDESSAVQTSFLSPFGVTLEAFTRDN---NSHSRDWDINGGACNTLT
   BnBBM1(AAM33800)  (42)   TAASDESSAIQTSFPSPFGVVVDAFTRDN---NSHSRDWDINGCACNNIH
   BnBBM2(AAM33801)  (42)   TAASDESSAIQTSFPSPFGVVLDAFTRDN---NSHSRDWDINGSACNNIH
   AtODP(NP_175530)  (50)   MINPHGGGGE----GGEVPKVADFLGVS----KSGDHHTDHNLVPYNDIH
   AtODP(BAB02492)   (12)   MINPHGGGGDE---GGEVPKVADFLGVS----KPDENQS-------NHLV
   AtODP(AAD30633)    (1)   MINPHGGGGE----GGEVPKVADFLGVS----KSGDHHTDHNLVPYNDIH
         Consensus   (51)   I         G    S    V DF        NSH R   D N   A N I 101                                               150
         ZM-ODP2     (93)   CYASSGASTGYHHQLYHQPTSSALHFADSVMVASSAGVHDGGAMLSAAAA
   OsAnt(BAB89946)   (99)   CYASSGSSV---GYLYPPPSSSSLQFADSVMVATSSPVVAHDGVSGGGMV
   OSBNM(AAL47205)   (56)   --------------------------------------------------
   OSODP(CAE05555)   (95)   LVGSSGGGRRTVAGDGVGEAPKLENFLDGNSFSDVHGQAAGGYLYSGSAV
   AtODP(NP_197245)  (91)   NNEQNG------------P--KLENFLGRTTTIYNTNETVVDGNG-----
   AtBBM(AAM33803)   (91)   NNEQNG------------P--KLENFLGRTTTIYNTNETVVDGNG-----
   BnBBM1(AAM33800)  (89)   NDEQDG------------P--KLENFLGRTTTIYNTNENVGDSGS----
   BnBBM2(AAM33801)  (89)   NDEQDG------------P--KLENFLGRTTTIYNTNENVGDIDGS----
   AtODP(NP_175530)  (92)   QTNAS-----------------DYYFQTNSLLP-----------------
   AtODP(BAB02492)   (48)   AYNDS-----------------DYYFHTNSLMPS---V-----------
   AtODP(AAD30633)   (43)   QTNAS-----------------DYYFQTNSLLP-----------------
         Consensus  (101)   N   SG                P     ENF     S I 151                                               200
         ZM-ODP2    (143)   NGVA--GAASANGGGIGLSMIKNWLRSQPAPMQPRVAAAEGAQGLSLSMN
   OsAnt(BAB89946) (146)    SAAA--AAAASGNGGIGLSMIKNWLRSQPAPQP--------AQALSLSMN
   OSBNM(AAL47205)  (56)    -------TPAIGNGGIGLSMIKNWLRSQPAPQP--------AQALSLSMN
   OSODP(CAE05555) (145)    GGAGGYSNGGCGGGTIELSMIKTWLRSNQSQQQP-------SPPQHADQG
   AtODP(NP_197245)(122)    ---DCGGGDGGGGSLGLSMIKTWLSNHSVANANH----------------
   AtBBM(AAM33803) (122)    ---DCGGGDGGGGSLGLSMIKTWLSNHSVANANH----------------
   BnBBM1(AAM33800)(121)    ---GCYGGGDGGGGSLGLSMIKTWLRNQPVDNVDN--------------
   BnBBM2(AAM33801)(121)    ---GCYGGGDGGGGSLGLSMIKTWLRNQPVDNVDN--------------
   AtODP(NP_175530)(108)    ----------------TVVTCASNAPNN---------------------
   AtODP(BAB02492)  (66)    -------------QSNDVVVAACDSNTPNNSSY-----------------
   AtODP(AAD30633)  (59)    ----------------TVVTCASNAPNN---------------------
         Consensus  (151)           GG    GGG IGLSMIKTWLRNQP   N
```

FIG. 1A

```
                      201                                                  250
     ZM-ODP2   (191)  MAGTTQGAAG--MPLLAGERAR-----APESVSTSAQGGAVVVTAPKEDS
OsAnt(BAB89946)(186)  MAGTTTAQGGGAMALLAGAGERGRTTPASESLSTSAHGATTATMAGGRKE
OSBNM(AAL47205) (91)  MAGTTTAQGGGAMALLAGAGERGRTTPASESLSTSAHGATTATMAGGRKE
OSODP(CAE05555)(188)  MSTDASASSYACSDVLVGSCGGGG---AGGTASSHGQGLALSMSTGSVAA
AtODP(NP_197245)(154) -------------------------------QDNGNGARGLSLSMNSSTS-D
AtBBM(AAM33803)(154)  -------------------------------QDNGNGARGLSLSMNSSTS-D
BnBBM1(AAM33800)(153) -------------------------------QENGNAAKGLSLSMNSSTSCD
BnBBM2(AAM33801)(153) -------------------------------QENGNGAKGLSLSMNSSTSCD
AtODP(NP_175530)(120) -------------------------------YELQESAHNLQSLTLSMGSTGA-A
AtODP(BAB02492) (86)  -------------------------------HELQESAHNLQSLTLSMGTT----
AtODP(AAD30633) (71)  -------------------------------YELQESAHNLQSLTLSMGSTGA-A
      Consensus (201)                                QE S  A GLTLSM SS S D 251                                                  300
     ZM-ODP2   (234)  G---GSGVAGALVAVSTDTGGS----GGASADNTARKTVDTFGQRTSIYR
OsAnt(BAB89946)(236)  INEEGSGSAGAVVAVGSESGGSGAVVEAGAAAAAARKSVDTFGQRTSIYR
OSBNM(AAL47205)(141)  INEEGSGSAGAVVAVGSESGGSGAVVEAGAAAAAARKSVDTFGQRTSIYR
OSODP(CAE05555)(235)  AG--GGGAVVAAESSSSENKRVDSP-GGAVDGAVPRKSIDTFGQRTSIYR
AtODP(NP_197245)(174) SNNYNNNDDVVQEKTIVDVVET---------TPK--KTIESFGQRTSIYR
AtBBM(AAM33803)(174)  SNNYNNNDDVVQEKTIVDVVET---------TPK--KTIESFGQRTSIYR
BnBBM1(AAM33800)(174) NNNDSNNNVVAQGKTIDDSVEA---------TPK--KTIESFGQRTSIYR
BnBBM2(AAM33801)(174) NNNYSSNNLVAQGKTIDDSVEA---------TPK--KTIESFGQRTSIYR
AtODP(NP_175530)(193) AAEVATVKASPAETSADNSSSTTNTSGGAIVEATPRRTLETFGQRTSIYR
AtODP(BAB02492)(106)  AGNNVVDKASPSETTGDNAS--G-GALAVVETATPRRALDTFGQRTSIYR
AtODP(AAD30633) (94)  AAEVATVKASPAETSADNSSSTTNTSGGAIVEATPRRTLETFGQRTSIYR
      Consensus (251) AN  GS   A AET  DS T       GA   A RKTIETFGQRTSIYR 301                                                  350
     ZM-ODP2   (277)  GVTRHRWTGRYEAHLWDNSCRREGQTRKGRQVYLGGYDKEEKAARAYDLA
OsAnt(BAB89946)(286)  GVTRHRWTGRYEAHLWDNSCRREGQTRKGR---QGGYDKEEKAARAYDLA
OSBNM(AAL47205)(191)  GVTRHRWTGRYEAHLWDNSCRREGQTRKGR---QGGYDKEEKAARAYDLA
OSODP(CAE05555)(282)  GVTRHRWTGRYEAHLWDNSCRREGQSRKGR---QGGYDKEDKAARAYDLA
AtODP(NP_197245)(213) GVTRHRWTGRYEAHLWDNSCKREGQTRKGR---QGGYDKEEKAARAYDLA
AtBBM(AAM33803)(213)  GVTRHRWTGRYEAHLWDNSCKREGQTRKGRQVYLGGYDKEEKAARAYDLA
BnBBM1(AAM33800)(213) GVTRHRWTGRYEAHLWDNSCKREGQTRKGRQVYLGGYDKEEKAARAYDLA
BnBBM2(AAM33801)(213) GVTRHRWTGRYEAHLWDNSCKREGQTRKGRQVYLGGYDKEEKAARAYDLA
AtODP(NP_175530)(193) GVTRHRWTGRYEAHLWDNSCRREGQSRKGR---QGGYDKEEKAARAYDLA
AtODP(BAB02492)(153)  GVTRHRWTGRYEAHLWDNSCRREGQSRKGR---QGGYDKEDKAARSYDLA
AtODP(AAD30633)(144)  GVTRHRWTGRYEAHLWDNSCRREGQSRKGR---QGGYDKEEKAARAYDLA
      Consensus (301) GVTRHRWTGRYEAHLWDNSCRREGQTRKGR   QGGYDKEEKAARAYDLA 351                                                  400
     ZM-ODP2   (327)  ALKYWGATTTTNFPVSNYEKELEDMKHMTRQEFVASLRRKSSGFSRGASI
OsAnt(BAB89946)(333)  ALKYWGPTTTTNFPVNNYEKELEEMKHMTRQEFVASLRRKSSGFSRGASI
OSBNM(AAL47205)(238)  ALKYWGPTTTTNFPVNNYEKELEEMKHMTRQEFVASLRRKSSGFSRGASI
OSODP(CAE05555)(329)  ALKYWGTTTTTNFPMSNYEKELEEMKHMTRQEYIAHLRRNSGFSRGASK
AtODP(NP_197245)(260) ALKYWGTTTTTNFPLSEYEKEVEEMKHMTRQEYVASLRRKSSGFSRGASI
AtBBM(AAM33803)(263)  ALKYWGPTTTTNFPLSEYEKEVEEMKHMTRQEYVASLRRKSSGFSRGASI
BnBBM1(AAM33800)(263) ALKYWGTTTTTNFPMSEYEKEVEEMKHMTRQEYVASLRRKSSGFSRGASI
BnBBM2(AAM33801)(263) ALKYWGTTTTTNFPMSEYEKEIEEMKHMTRQEYVASLRRKSSGFSRGASI
AtODP(NP_175530)(240) ALKYWGPSTTTNFPITNYEKEVEEMKNMTRQEFVASIRRKSSGFSRGASM
AtODP(BAB02492)(200)  ALKYWGPSTTTNFPITNYEKEVEEMKHMTRQEFVAAIRRKSSGFSRGASM
AtODP(AAD30633)(191)  ALKYWGPSTTTNFPITNYEKEVEEMKNMTRQEFVASIRRKSSGFSRGASM
      Consensus (351) ALKYWGPTTTTNFPISNYEKEVEEMKHMTRQEFVASLRRKSSGFSRGASI
```

FIG. 1B

```
                              551                                          450
     ZM-ODP2    (377) YRGVTRHHQHGRWQARIGRVAGNKDLYLGTFSTQEEAAEAYDIAAIKFRG
OsAnt(BAB89946) (383) YRGVTRHHQHGRWQARIGRVAGNKDLYLGTFSTQEEAAEAYDIAAIKFRG
OSBNM(AAL47205) (288) YRGVTRHHQHGRWQARIGRVAGNKDLYLGTFSTQEEAAEAYDIAAIKFRG
OSODP(CAE05555) (379) YRGVTRHHQHGRWQARIGRVAGNKDIYLGTFSTEEEAAEAYDIAAIKFRG
AtODP(NP_197245)(310) YRGVTRHHQHGRWQARIGRVAGNKDLYLGTFGTQEEAAEAYDIAAIKFRG
 AtBBM(AAM33803)(313) YRGVTRHHQHGRWQARIGRVAGNKDLYLGTFGTQEEAAEAYDIAAIKFRG
BnBBM1(AAM33800)(313) YRGVTRHHQHGRWQARIGRVAGNKDLYLGTFGTQEEAAEAYDIAAIKFRG
BnBBM2(AAM33801)(313) YRGVTRHHQHGRWQARIGRVAGNKDLYLGTFGTQEEAAEAYDIAAIKFRG
AtODP(NP_175530)(290) YRGVTRHHQHGRWQARIGRVAGNKDLYLGTFSTEEEAAEAYDIAAIKFRG
 AtODP(BAB02492)(250) YRGVTRHHQHGRWQARIGRVAGNKDLYLGTFSTEEEAAEAYDIAAIKFRG
 AtODP(AAD30633)(241) YRGVTRHHQHGRWQARIGRVAGNKDLYLGTFSTEEEAAEAYDIAAIKFRG
      Consensus (401) YRGVTRHHQHGRWQARIGRVAGNKDLYLGTFSTQEEAAEAYDIAAIKFRG 551                                          500
     ZM-ODP2    (427) LNAVTNFDMSRYDVKSILDSSALPIG-SAAKRLKEAEAAASAQHHHAGVV
OsAnt(BAB89946) (433) LNAVTNFDMSRYDVKSILDSAALPVG-TAAKRLKDAEAAA----------
OSBNM(AAL47205) (338) LNAVTNFDMSRYDVKSILDSAALPVG-TAAKRLKDAEAAA----------
OSODP(CAE05555) (429) LNAVTNFDMSRYDVKSILDSSTLPVG-GAARRLKEAEVAA--------A--
AtODP(NP_197245)(360) LSAVTNFDMNRYNVKAILESPSLPIG-SSAKRLKDVNNPVP---------
 AtBBM(AAM33803)(363) LSAVTNFDMNRYNVKAILESPSLPIG-SSAKRLKDVNNPVP---------
BnBBM1(AAM33800)(363) LTAVTNFDMNRYNVKAILESPSLPIG-SAAKRLKEANRPVPS--------
BnBBM2(AAM33801)(363) LTAVTNFDMNRYNVKAILESPSLPIG-SAAKRLKEANRPVPS--------
AtODP(NP_175530)(340) LNAVTNFEINRYDVKAILESNTLPIGGGAAKRLKEAQALESSRKR-----
 AtODP(BAB02492)(300) LNAVTNFEINRYDVKAILESSTLPIGGGAAKRLKEAQALESSRKRE----
 AtODP(AAD30633)(291) LNAVTNFEINRYDVKAILESNTLPIGGGAAKRLKEAQALESSRKR-----
      Consensus (451) LNAVTNFDMNRYDVKAILES SLPIG SAAKRLKEANA      S 551                                          550
     ZM-ODP2    (476) SYDVGRIASQLGDGGALA--AAYGAHYHG--AAWPTIAFQPGAAS----T
OsAnt(BAB89946) (472) AYDVGRIASHLGGDGAYA--AHYGHHHHSAAAAWPTIAFQAAAAPPPHAA
OSBNM(AAL47205) (377) AYDVGRIASHLGGDGAYA--AHYGHHHHSAAAAWPTIAFQAAAAPPPHAA
OSODP(CAE05555) (469) AAGGGVIVSHLADGG--------VGGYYYG---CGPTIAFGGGGQQPAPLA
AtODP(NP_197245)(400) ---AMMISNNVSESAN------NVSGWQNTAFQHHQGMDLSLLQQQQERYV
 AtBBM(AAM33803)(403) ---AMMISNNVSESAN------NVSGWQNTAFQHHQGMDLSLLQQQQERYV
BnBBM1(AAM33800)(404) ---MMMISNNVSESEN------SASGWQNAAVQHHQGVDLSLLHQHQERYN
BnBBM2(AAM33801)(404) ---MMMISNNVSESEN------NASGWQNAAVQHHQGVDLSLLQQHQERYN
AtODP(NP_175530)(385) -EEMIALGSNFHQYGAASGSSSVASSSRLQLQPYPLSIQQPFEHLHHHQP
 AtODP(BAB02492)(346) -AEMIALGSSFQYGGGSS-TGSGSTSSRLQLQPYPLSIQQPLEPFLSLQN
 AtODP(AAD30633)(336) -EEMIALGSNFHQYGAASGSSSVASSSRLQLQPYPLSIQQPFEHLHHHQP
      Consensus (501)     DMM ISSNL E GA A      SG    A Q HP I  Q 551                                          600
     ZM-ODP2    (518) GLYHPYAQQPMRGGGWCKQEQDHAVIAAAHSLQDLHHLNLG--AAGAHDF
OsAnt(BAB89946) (520) GLYHPYAQPLR---GWCKQEQDHAVIAAAHSLQDLHHLNLG--AAAAAHD
OSBNM(AAL47205) (425) GLYHPYAQPLR---GWCKQEQDHAVIAAAHSLQDLHHLNLG--AAAAAHD
OSODP(CAE05555) (509) VHYPSYGQASG----WCKPE-QDAVIAAGHCATDLQHLHLGSGGAAATHN
AtODP(NP_197245)(442) GYYN-GGNLST-----------ESTRVCFKQEEEQQHFLRN--SPSHMTN
 AtBBM(AAM33803)(445) GYYN-GGNLST-----------ESTRVCFKQEEEQQHFLRN--SPSHMTN
BnBBM1(AAM33800)(446) GYYNGGNLSS------------ESARACFKQEDDQHRFLSN--TQSLMTN
BnBBM2(AAM33801)(446) GYYNGGNLSS------------ESARACFKQEDDQHRFLSN--TQSLMTN
AtODP(NP_175530)(434) LLTLQNNN-----------DISQYHDSFSYIQTQLHLHQQ--QTNNYLQ
 AtODP(BAB02492)(394) NDISHYNNNNA---------HDSSSFNHHSYIQTQLHLHQQ--TNNYLQQ
 AtODP(AAD30633)(385) LLTLQNNN-----------DISQYHDSFSYIQTQLHLHQQ--QTNNYLQ
      Consensus (551) G Y   GN            S    AAF IQDQ HL  N    S    N
```

FIG. 1C

```
                        601                                              650
      ZM-ODP2   (566)   FSAGQQAAAAAMHGLGSIDSASLEHSTGSNSVVYNGGVGDSNGASAVGGS
OsAnt(BAB89946)  (565)   FFS---QAMQQQHGLGSIDNASLEHSTGSNSVVYNGDNG--------GGG
OSBNM(AAL47205)  (470)   FFS---QAMQQQHGLGSIDNASLEHSTGSNSVVYNGDNG--------GGG
OSODP(CAE05555)  (554)   FFQ------QPASS------------------SAVYGNGGG---------GG
AtODP(NP_197245) (478)   VDHHS--------------------STSDDSVTVCGNVVS-------YGG
 AtBBM(AAM33803) (481)   VDHHS--------------------STSDDSVTVCGNVVS-------YGG
BnBBM1(AAM33800) (483)   IDHQS--------------------SVSDDSVTVCGNVVG-------YGG
BnBBM2(AAM33801) (483)   IDHQS--------------------SVSDDSVTVCGNVVG-------YGG
AtODP(NP_175530) (470)   SSS---------------------------HTSQLYNAYLQS-N-----PGL
 AtODP(BAB02492) (433)   QSSQ--------------------------NSQQLYNAYLHS-N-----PAL
 AtODP(AAD30633) (421)   SSS---------------------------HTSQLYNAYLQS-N-----PGL
     Consensus  (601)   S                         S    SVVYNG V          GG 651                                              700
      ZM-ODP2   (616)   GGGYMMPMSAAGATTTSAMVSHEQVHARAYDEAKQAAQMGYESYLVNAEN
OsAnt(BAB89946)  (604)   GGYIMAPMSAVSATATAVASSHDHG-----GDGGKQVQMGYDSYLVGADA
OSBNM(AAL47205)  (509)   GGYIMAPMSAVSATATAVASSHDHG-----GDGGKQVQMGYDSYLVGADA
OSODP(CAE05555)  (573)   GNAFMMPMGAVVAAADHGGQSSAYGG----GDESGRLVVGYDGVVDPYAA
AtODP(NP_197245) (501)   YQGFAIPVGTSVNYDPFTAAEIAYN------------AR-NHYYYAQHQQ
 AtBBM(AAM33803) (504)   YQGFAIPVGTSVNYDPFTAAEIAYN------------AR-NHYYYAQHQQ
BnBBM1(AAM33800) (506)   YQGFAAPV-----NCDAYAASEFDYN------------AR-NHYYFAQQQQ
BnBBM2(AAM33801) (506)   YQGFAAPV-----NCDAYAASEFDYN------------AR-NHYYFAQQQQ
AtODP(NP_175530) (489)   LHGFVS-----DNNNTSG------------FLGNNGIGIGSSSTVGSSAE
 AtODP(BAB02492) (453)   LHGLVSTS-IVDNNNNNGGSSGSYNTAA--FLGNHGIGIGSSSTVGS---T
 AtODP(AAD30633) (440)   LHGFVS-----DNNNTSG------------FLGNNGIGIGSSSTVGSSAE
     Consensus  (651)        GFMAPM   N   GAS  Y       G    IAIG    SYVA 701                                           745
      ZM-ODP2   (666)   NGGGRMSAWGTVVSAAAAAASSNDNMAADVGHGGAQLFSVWNDT
OsAnt(BAB89946)  (649)   YGGGGAGRMPSWAMTPASAPAATSSSDMTGVCHG-AQLFSVWNDT
OSBNM(AAL47205)  (554)   YGGGGAGRMPSWAMTPASAPAATSSSDMTGVCHG-AQLFSVWNDT
OSODP(CAE05555)  (619)   MRSAYELSQGSSSSSVSVAKAANGYPDNWSSPFNGMG--------
AtODP(NP_197245) (538)   QQQIQQSPGGDFPVAISNNHSSNMYFHGEGGGEG-APTFSVWNDT
 AtBBM(AAM33803) (541)   QQQIQQSPGGDFPVAISNNHSSNMYFHGEGGGEG-APTFSVWNDT
BnBBM1(AAM33800) (539)   TQ---QSPGGDFPAAMTNNVGSNMYYHGEGGGEV-APTFTVWNDN
BnBBM2(AAM33801) (539)   TQ---HSPGGDFPAAMTNNVGSNMYYHGEGGGEV-APTFTVWNDN
AtODP(NP_175530) (522)   EEFPAVKVDYDMPPSGGATGYGGWNSGESAQGSNPGGVFTMWNE-
 AtODP(BAB02492) (498)   EEFPTVKTDYDMPSSDGTGGYSGWTS-ESVQGSNPGGVFTMWNE-
 AtODP(AAD30633) (473)   EEFPAVKVDYDMPPSGGATGYGGWNSGESAQGSNPGGVFTMWNE-
     Consensus  (701)              GDFP A A   AS         G G   A LFSVWND
```

FIG. 1D

```
                                 1                                                50
ZM-ODP2_unmodifiedPEP    (1)
ZM-ODP2_modifiedPEP_id_97.3  (1)
ZM-ODP2_modifiedPEP_id_92.4  (1)
ZM-ODP2_modifiedPEP_id_87.3  (1)
ZM-ODP2_modifiedPEP_id_82.4  (1)
              Consensus   (1)   MATINNWLAFSLSPQEIPPSQTTDSTILSAATADHISGDVCFNLPQDWSM
                                 51                                               100
ZM-ODP2_unmodifiedPEP   (51)
ZM-ODP2_modifiedPEP_id_97.3 (51)
ZM-ODP2_modifiedPEP_id_92.4 (51)
ZM-ODP2_modifiedPEP_id_87.3 (51)
ZM-ODP2_modifiedPEP_id_82.4 (51)
              Consensus  (51)   RGSEISAIIAEPKIEDFIGGLSFSEQHHKANCNMLPSTSSTICYASSGAS
                                 101                                              150
ZM-ODP2_unmodifiedPEP  (101)
ZM-ODP2_modifiedPEP_id_97.3 (101)
ZM-ODP2_modifiedPEP_id_92.4 (101)
ZM-ODP2_modifiedPEP_id_87.3 (101)
ZM-ODP2_modifiedPEP_id_82.4 (101)
              Consensus (101)   TGYHHQIYHQPTSSAIHFADSIMIASSAGIHDGGAMISAAAANGIAGAAS
                                 151                                              200
ZM-ODP2_unmodifiedPEP  (151)
ZM-ODP2_modifiedPEP_id_97.3 (151)
ZM-ODP2_modifiedPEP_id_92.4 (151)
ZM-ODP2_modifiedPEP_id_87.3 (151)
ZM-ODP2_modifiedPEP_id_82.4 (151)
              Consensus (151)   ANGGGIGLSMIKNWLRSQPAPMQPRIAAAEGAQGISISMNMAGTTQGAAG
                                 201                                              250
ZM-ODP2_unmodifiedPEP  (201)
ZM-ODP2_modifiedPEP_id_97.3 (201)
ZM-ODP2_modifiedPEP_id_92.4 (201)
ZM-ODP2_modifiedPEP_id_87.3 (201)
ZM-ODP2_modifiedPEP_id_82.4 (201)
              Consensus (201)   MPIVAGERARAPESISTSAQGGAIIITAPKEDSGGSGLAGAVLALSTDTG
                                 251                                              300
ZM-ODP2_unmodifiedPEP  (251)
ZM-ODP2_modifiedPEP_id_97.3 (251)
ZM-ODP2_modifiedPEP_id_92.4 (251)
ZM-ODP2_modifiedPEP_id_87.3 (251)
ZM-ODP2_modifiedPEP_id_82.4 (251)
              Consensus (251)   GSGGASADNTARKTVDTFGQRTSIYRGVTRHRWTGRYEAHLWDNSCRREG
                                 301                                              350
ZM-ODP2_unmodifiedPEP  (301)
ZM-ODP2_modifiedPEP_id_97.3 (301)
ZM-ODP2_modifiedPEP_id_92.4 (301)
ZM-ODP2_modifiedPEP_id_87.3 (301)
ZM-ODP2_modifiedPEP_id_82.4 (301)
              Consensus (301)   QTRKGRQVYLGGYDKEEKAARAYDLAALKYWGATTTTNFPVSNYEKELED
                                 351                                              400
ZM-ODP2_unmodifiedPEP  (351)
ZM-ODP2_modifiedPEP_id_97.3 (351)
ZM-ODP2_modifiedPEP_id_92.4 (351)
ZM-ODP2_modifiedPEP_id_87.3 (351)
ZM-ODP2_modifiedPEP_id_82.4 (351)
              Consensus (351)   MKHMTRQEFVASLRRKSSGFSRGASIYRGVTRHHQHGRWQARIGRVAGNK
                                 401                                              450
ZM-ODP2_unmodifiedPEP  (401)
ZM-ODP2_modifiedPEP_id_97.3 (401)
ZM-ODP2_modifiedPEP_id_92.4 (401)
ZM-ODP2_modifiedPEP_id_87.3 (401)
ZM-ODP2_modifiedPEP_id_82.4 (401)
              Consensus (401)   DLYLGTFSTQEEAAEAYDIAAIKFRGLNAVTNFDMSRYDVKSILDSSALP
```

FIG. 2A

```
                              451                                                    500
     ZM-ODP2_unmodifiedPEP   (451)                    AA A    A   VV    A        A AAA A
     ZM-ODP2_modifiedPEP_id_97.3 (451)                AA A    A   VV  VA   L     A AAA A
     ZM-ODP2_modifiedPEP_id_92.4 (451)                AA A    A LL  L VA  V      AVAAA A
     ZM-ODP2_modifiedPEP_id_87.3 (451)                AA A    A LL  L VA  V      AVAAA A
     ZM-ODP2_modifiedPEP_id_82.4 (451)                         G LL  L V   V      V    G
                   Consensus   (451) IGSAAKRLKEAEAAASAQHHHAGLLSYDLGRVASQVGDGGAVAAAYGAHY
                              501                                                    550
     ZM-ODP2_unmodifiedPEP   (501)    AA  A    AA      A              A  AAA
     ZM-ODP2_modifiedPEP_id_97.3 (501) AA  VA   AA     A              A VAAA  L
     ZM-ODP2_modifiedPEP_id_92.4 (501) AA  VA   AA   V A              ALVAAA  V
     ZM-ODP2_modifiedPEP_id_87.3 (501) AA  VA   AA   V A              ALVAAA  V
     ZM-ODP2_modifiedPEP_id_82.4 (501)    V     GG   V              G LV     V
                   Consensus   (501) HGAAWPTVAFQPGAASTGVYHPYAQQPMRGGGWCKQEQDHALVAAAHSVQ
                              551                                                    600
     ZM-ODP2_unmodifiedPEP   (551)  L  L  AA A   A   AAAA     L   L
     ZM-ODP2_modifiedPEP_id_97.3 (551)  L  L AA A   A   AAAA   V     V
     ZM-ODP2_modifiedPEP_id_92.4 (551) V  V V AA A   A   AAAA   V  V   V
     ZM-ODP2_modifiedPEP_id_87.3 (551) V  V V AA A   A   AAAA   V  V   V
     ZM-ODP2_modifiedPEP_id_82.4 (551) V  V V GG       G           V  V   V
                   Consensus   (551) DVHHVNVGAAGAHDFFSAGQQAAAAMHGVGSVDSASVEHSTGSNSVVYN
                              601                                                    650
     ZM-ODP2_unmodifiedPEP   (601)   V            V                        V
     ZM-ODP2_modifiedPEP_id_97.3 (601)  V           V                        V
     ZM-ODP2_modifiedPEP_id_92.4 (601)  I      L              V       L   V
     ZM-ODP2_modifiedPEP_id_87.3 (601)  L      L              L       L
     ZM-ODP2_modifiedPEP_id_82.4 (601)  L      L              L       L
                   Consensus   (601) GGLGDSNGASALGGSGGGYMMPMSAAGATTTSAMLSHEQVHARAYDEAKQ
                              651                                                    700
     ZM-ODP2_unmodifiedPEP   (651)                       VV
     ZM-ODP2_modifiedPEP_id_97.3 (651)                   VV
     ZM-ODP2_modifiedPEP_id_92.4 (651)                   VV
     ZM-ODP2_modifiedPEP_id_87.3 (651)                     L
     ZM-ODP2_modifiedPEP_id_82.4 (651)                     L
                   Consensus   (651) AAQMGYESYLVNAENNGGGRMSAWGTVVSAAAAAAASSNDNMAADVGHGG
                              701
     ZM-ODP2_unmodifiedPEP   (701)
     ZM-ODP2_modifiedPEP_id_97.3 (701)
     ZM-ODP2_modifiedPEP_id_92.4 (701)
     ZM-ODP2_modifiedPEP_id_87.3 (701)
     ZM-ODP2_modifiedPEP_id_82.4 (701)
                   Consensus   (701) AQLFSVWNDT
```

AP2 DOMAIN TRANSCRIPTION FACTOR ODP2 (OVULE DEVELOPMENT PROTEIN 2) AND METHODS OF USE

CROSS-REFERENCE TO RELATED APPLICATIONS

This application is a continuation of U.S. application Ser. No. 12/503,482, filed on Jul. 15, 2009, which is a continuation of U.S. application Ser. No. 11/045,802, filed on Jan. 28, 2005, now U.S. Pat. No. 7,579,529, which claims priority to U.S. Provisional Application No. 60/541,122, filed on Feb. 2, 2004, all of which are hereby incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 429680SEQLIST.TXT, created on Mar. 6, 2013, and having a size of 243 kilobytes and is filed concurrently with the specification. The sequence listing contained in this ASCII formatted document is part of the specification and is herein incorporated by reference in its entirety.

FIELD OF THE INVENTION

The invention relates to the field of the genetic manipulation of plants, particularly the modulation of gene activity and development in plants.

BACKGROUND OF THE INVENTION

Cell division plays a crucial role during all phases of plant development. The continuation of organogenesis and growth responses to a changing environment requires precise spatial, temporal and developmental regulation of cell division activity in meristems. Such control of cell division is also important in organs themselves for example, leaf expansion, and secondary growth. A complex network controls cell proliferation in eukaryotes. Various regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions. The regulation of cell division impacts a variety of developmental pathways including transformation and plant regeneration.

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming.

For example, it is difficult to obtain a culture response from some maize genotypes. Typically, a suitable culture response has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be more efficiently introduced into and evaluated directly into inbreds.

Accordingly, methods are needed in the art to increase transformation efficiencies of plants.

Influencing cell cycle and cell division can also affect various developmental pathways in a plant. Pathways of interest include those that influence embryo development. The AP2/ERF family of proteins is a plant-specific class of putative transcription factors that have been shown to regulate a wide-variety of developmental processes and are characterized by the presence of a AP2/ERF DNA binding domain. The AP2/ERF proteins have been subdivided into two distinct subfamilies based on whether they contains one (ERF subfamily) or two (AP2 subfamily) DNA binding domains.

One member of the AP2 family that has been implicated in a variety of critical plant cellular functions is the Baby Boom protein (BBM). The BBM protein from *Arabidopsis* is preferentially expressed in seed and has been shown to play a central role in regulating embryo-specific pathways. Overexpression of BBM has been shown to induce spontaneous formation of somatic embryos and cotyledon-like structures on seedlings. See, Boutiler et al. (2002) *The Plant Cell* 14:1737-1749. Thus, members of the AP2 protein family promote cell proliferation and morphogenesis during embryogenesis. Such activity finds potential use in promoting apomixis in plants.

Apomixis refers to the production of a seed from the maternal ovule tissue in the absence of egg cell fertilization (Koltunow (1995) *Plant Physiol* 108:1345-1352). Apomixis is a valuable trait for crop improvement since apomictic seeds give rise to clonal offspring and can therefore be used to genetically fix hybrid lines. The production of hybrid lines is intensive and costly. Production of seed through apomixis avoids these problems in that once a hybrid has been produced, it can be maintained clonally, thereby eliminating the need to maintain and cross separate parent lines. The use of apomictic seeds also eliminates the use of cuttings or tissue culture techniques to propagate lines, reduces the spread of disease which are easily spread through vegetative-propagated tissues and in many species reduces the size of the propagule leading to lower shipping and planting costs. Methods are therefore needed for the efficient production of apomictic seed.

Members of the APETALA2 (AP2) family of proteins play critical roles in a variety of important biological events including development, plant regeneration, cell division, etc. Accordingly, it is valuable to the field of agronomic development to identify and characterize novel AP2 family members and develop novel methods to modulate embryogenesis, transformation efficiencies, oil content, starch content and yield in a plant.

BRIEF SUMMARY OF THE INVENTION

Methods and compositions are provided to modulate plant development using DNA, RNA or protein derived from the maize AP2 family member ZmODP2. The present invention provides an isolated polypeptide comprising an amino acid sequence selected from the group consisting of: (a) the polypeptide comprising the amino acid sequence of SEQ ID NO:2, 26, or 28; (b) the polypeptide having at least 50%, sequence identity to SEQ ID NO:2, 26, or 28, wherein the polypeptide has Ovule Development Protein 2 (ODP2) activity; (c) the polypeptide encoded by a polynucleotide that hybridizes under stringent conditions to a polynucleotide comprising the complement of SEQ ID NOS: 1, 3, 25, or 27, wherein the stringent conditions comprise hybridization in 50% formamide, 1 M NaCl, 1% SDS at 37° C., and a wash in 0.1×SSC at 60° C. to 65° C.; and, (d) the polypeptide having at least 70 consecutive amino acids of SEQ ID NO:2, 26, or 28, wherein the polypeptide retains ODP2 activity.

Further compositions of the invention include an isolated polynucleotide selected from the group consisting of: (a) the polynucleotide comprising SEQ ID NO:1, 3, 25 or 27; (b) the polynucleotide encoding the amino acid sequence of SEQ ID NO:2, 26 or 28; (c) the polynucleotide having at least 50% sequence identity to SEQ ID NO:1, 3, 25 or 27, wherein the polynucleotide encodes a polypeptide having ODP2 activity; (d) the polynucleotide having at least 200 consecutive nucleotides of SEQ ID NO:1, 3, 25 or 27 or a complement thereof; and, (e) the polynucleotide that hybridizes under stringent conditions to the complement of the polynucleotide of (a), wherein the stringent conditions comprise hybridization in 50% formamide, 1 M NaCl, 1% SDS at 37° C., and a wash in 0.1×SSC at 60° C. to 65° C. Nucleotide constructs comprising the polynucleotide of the invention are also provided.

Additional compositions of the invention include plants having a heterologous polynucleotide of the invention operably linked to a promoter that drives expression in the plant. The plant can be a plant cell, a plant part, a seed, or a grain. Methods are provided to modulate development in a plant. In one embodiment, the plant of the invention has an altered oil phenotype. In specific embodiments the oil content of the plant is decreased. In other embodiments, starch production of the plant is modified. In specific embodiments, the starch content of the plant is increased. In another embodiment, the regenerative capacity of the plant is modified. In yet another embodiment, the plant produces an asexually derived embryo. In still another embodiment, the transformation efficiency of the plant is increased. In another embodiment, the seed set is increased or maintained during periods of abiotic stress. In still another embodiment, haploid embryos are produced from male or female gametes.

Methods of the invention comprise methods for modulating the activity and/or level of a polypeptide in a plant. This method comprises providing to the plant an ODP2 sequence of the invention.

The present invention further provides a method for altering the oil phenotype in a plant. The method comprises providing to the plant an ODP2 sequence of the invention; and, thereby altering the oil phenotype of the plant.

The present invention further provides a method for modifying starch production in a plant. The method comprises providing to the plant an ODP2 sequence of the invention; and, thereby modifying starch production of the plant.

The present invention further provides a method for producing asexually derived embryos. The method comprises introducing into a plant ODP2 sequence of the present invention; and, thereby producing asexually derived embryos. The asexually derived embryos can be somatic embryos, adventitious embryos, or gametophytic embryos.

The present invention also provides a method for modifying the regenerative capacity of a plant. The method comprises introducing into the plant an ODP2 nucleotide sequence of the invention, and thereby modifying the regenerative capacity of the plant.

The present invention also provides a method of transforming a plant. The method comprises providing to target plant an ODP2 sequence of the invention, and, transforming into the target plant a nucleotide sequence of interest. The regenerative capacity can be modified to include tissues normally not amenable to culture including but not limited to leaves, stems, and mature seed.

The invention further provides a method for increasing transformation efficiency in a plant. The method comprises providing to the plant an ODP2 nucleotide sequence of the invention, and thereby increasing the transformation efficiency of the plant.

The invention further provides a method for increasing or maintaining yield in a plant under abiotic stress. The method comprises providing to the plant an ODP2 nucleotide sequence of the invention, and thereby increasing the stress tolerance of the plant.

BRIEF DESCRIPTION OF THE DRAWINGS

FIGS. 1A-1D show an alignment of the amino acid sequence of maize Ovule Development Protein 2 (Zm-ODP2) (SEQ ID NO:2) with OsAnt (Accession No. BAB89946; SEQ ID NO:26), OSBNM (Accession No. AAL47205; SEQ ID NO:28); OSODP (Accession No. CAEO5555; SEQ ID NO:29); AtODP (NP_197245; SEQ ID NO:30); ATBBM (Accession No. AAM33803; SEQ ID NO:31); BnBBM1 (AAM33800; SEQ ID NO:32); BnBBM2 (Accession No. AAM33801; SEQ ID NO:33); ATODP (Accession No. NP_175530; SEQ ID NO:34); AtODP (Accession No. BAB02492; SEQ ID NO:35); AtODP (Accession No. AAD30633; SEQ ID NO:36). All 11 proteins present in the alignment have two AP2 (APETALA2; pfam00847.8) domains. Using the amino acid numbering of the Zm-ODP2 polypeptide, the first AP2 domain is from about amino acid 273 to about 343 and the second AP2 domain is from about amino acid 375 to about 437. A consensus sequence for all 11 aligned polypeptides is also provided (SEQ ID NO:37).

FIGS. 2A-2B provide an amino acid alignment of the Zm-ODP2 amino acid sequence (ZM-ODP2_unmodifiedPEP; SEQ ID NO:2) with four polypeptide variants of the Zm-ODP2 sequence. The variant amino acid sequences include ZM-ODP2_modifiedPEP_id_97.3 (SEQ ID NO:20) which shares 97.3% amino acid sequence identity with SEQ ID NO:2; ZM-ODP2_modifiedPEP_id_92.4 (SEQ ID NO:21) which shares 92.4% amino acid sequence identity with SEQ ID NO:2; ZM-ODP2 modifiedPEP_id_87.3 (SEQ ID NO:22) which shares 87.3% amino acid sequence identity with SEQ ID NO:2; and, ZM-ODP2_modifiedPEP_id_82.4 (SEQ ID NO:23) which shares 82.4% amino acid sequence identity with SEQ ID NO:2. The consensus sequence is set forth in SEQ ID NO:24.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The article "a" and "an" are used herein to refer to one or more than one (i.e., to at least one) of the grammatical object of the article. By way of example, "an element" means one or more element.

Compositions

Compositions of the invention include polynucleotide sequence and amino acid sequence of Ovule Development Protein 2 (ODP2) proteins that are involved in regulating plant growth and development. In particular, the present invention provides for isolated nucleic acid molecules comprising nucleotide sequences encoding the amino acid sequences shown in SEQ ID NO:2, 26, or 28. Further provided are polypeptides having an amino acid sequence encoded by a nucleic acid molecule (SEQ ID NO: 1, 3, 25, or 27) described herein, and fragments and variants thereof.

The ODP2 polypeptides of the invention contain two predicted APETALA2 (AP2) domains and are members of the AP2 protein family (PFAM Accession PF00847). The AP2 domains of the maize ODP2 polypeptide are located from about amino acids S273 to N343 and from about S375 to R437 of SEQ ID NO:2). The AP2 family of putative transcription factors have been shown to regulate a wide range of developmental processes, and the family members are characterized by the presence of an AP2 DNA binding domain. This conserved core is predicted to form an amphipathic alpha helix that binds DNA. The AP2 domain was first identified in APETALA2, an *Arabidopsis* protein that regulates meristem identity, floral organ specification, seed coat development, and floral homeotic gene expression. The AP2 domain has now been found in a variety of proteins.

The ODP2 polypeptides of the invention share homology with several polypeptides within the AP2 family. FIGS. 1A-1D provide an alignment of the maize and rice ODP2 polypeptides of the present invention with 8 other proteins having two AP2 domains. A consensus sequence of all proteins appearing in the alignment is also provided in FIG. 1. The alignment of FIGS. 1A-1D was generated using Align X® which employs a modified Clustal W algorithm to generate multiple sequence alignments. FIGS. 1A-1D demonstrate that the maize ODP2 polypeptide of the present invention (SEQ ID NO:2) shares about 51.7% sequence identity and 62.3% sequence similarity across the full sequence with the rice sequences of OsBNM3 (ovule development aintegumenta-like protein) (Genbank Accession No. AAL47205; SEQ ID NO:28). In addition, the ODP2 polypeptide of SEQ ID NO:2 shares 65.4% sequence identity and 72.7% sequence similarity across the full sequence to a putative ovule development protein from rice (OS) (Genbank Accession No. BAB89946; SEQ ID NO:26).

The OsBNM3 polypeptide sequence (SEQ ID NO:28), the OS polypeptide (SEQ ID NO:26), as well as the ODP2 sequence (SEQ ID NO:2) share homology with *Arabidopsis* Baby Boom (AtBBM, AAM33803; SEQ ID NO:31). Blast alignments demonstrate that Zm-ODP2 shares about 38.1% sequence identity and about 46.3% sequence similarity across the full length of the *Arabidopsis* Baby Boom polypeptide (AtBBM). See FIGS. 1A-1D. The AtBBM polypeptide encodes an AP2 domain transcription factor and is optimally expressed in the developing embryo and seeds. AtBBM has been shown to trigger formation of somatic embryos and cotyledon-like structures on seedlings and thus activates signal transduction pathways leading to the induction of embryo development from differentiated somatic cells. See, for example, Boutiler et al. (2002) *Plant Cell* 14:1737-49), herein incorporated by reference. Accordingly, the ODP2 sequences of the present invention also find use in modifying the regenerative capabilities of plants and rendering the plant embryogenic.

In addition, other polypeptides that influence ovule and embryo development and stimulate cell growth, such as, Lec1, Kn1 family, WUSCHEL, Zwille, and Aintegumeta (ANT) allow for increased transformation efficiencies when expressed in plants. See, for example, U.S. Application No. 2003/0135889, herein incorporated by reference. In fact, a maize Lec1 homologue of the *Arabidopsis* embryogenesis controlling gene AtLEC1, has been shown to increase oil content and transformation efficiencies in plants. See, for example, WO 03001902 and U.S. Pat. No. 6,512,165. Accordingly, the Zm-ODP2 sequences of the invention find further use in increasing transformation efficiencies in plants.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Optimally, an "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence have ODP2 activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

By "ODP2 activity" or "Ovule Development Protein 2 activity" is intended the ODP2 polypeptide has at least one of the following exemplary activities: increases the regenerative capability of a plant cell, renders the plant cell embryogenic, increases the transformation efficiencies of a plant cell, alters the oil content of a plant cell, binds DNA, increases abiotic stress tolerance, increases or maintains yield under abiotic stress, increases asexual embryo formation, alters starch content, alters embryo size or activates transcription. Methods to assay for such activity are known in the art and are described more fully below.

A fragment of an ODP2 nucleotide sequence that encodes a biologically active portion of an ODP2 protein of the invention will encode at least 15, 25, 30, 50, 100, 150, 200, 250, 300, 350, 400, 450, 500, 550, 600, 650, 700, 709 contiguous amino acids, or up to the total number of amino acids present in a full-length ODP2 protein of the invention (for example, 710 amino acids for SEQ ID NO: 2, 692 amino acids for SEQ ID NO: 25 and 597 for SEQ ID NO:27). Fragments of an ODP2 nucleotide sequence that are useful as hybridization probes or PCR primers generally need not encode a biologically active portion of an ODP2 protein.

Thus, a fragment of an ODP2 nucleotide sequence may encode a biologically active portion of an ODP2 protein, or it may be a fragment that can be used as a hybridization probe or PCR primer using methods disclosed below. A biologically active portion of an ODP2 protein can be prepared by isolating a portion of one of the ODP2 nucleotide sequences of the invention, expressing the encoded portion of the ODP2 protein (e.g., by recombinant expression in vitro), and assessing the activity of the encoded portion of the ODP2 protein. Nucleic acid molecules that are fragments of an ODP2 nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1,500, 1,600, 1,700, 1,800, 1,900, 2,000, 2,100, 2,200 contiguous nucleotides, or up to the number of nucleotides present in a full-length ODP2 nucleotide sequence disclosed herein (for example, 2,260, 2133, 2079, and 1794 nucleotides for SEQ ID NOS: 1, 3, 25 and 27, respectively).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the ODP2 polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an ODP2 protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:2, 26, or 28 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, the polypeptide has ODP2 activity (i.e., modulating the regenerative capability of a plant, rendering the plant embryogenic, increasing the transformation efficiency of a plant, altering oil content of a plant, increasing cell proliferation, increasing abiotic stress tolerance, increasing or maintaining yield under abiotic stress, modifying starch content, increasing asexual embryo formation, binding DNA or regulating transcription) as described herein. Such variants may result from, for example, genetic polymorphism or from human manipulation. Biologically active variants of a native ODP2 protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the ODP2 proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ODP2 activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. Various methods for screening for ODP2 activity are discussed in detail elsewhere herein.

Variant nucleotide sequences and proteins also encompass sequences and proteins derived from a mutagenic and recombinogenic procedure such as DNA shuffling. With such a procedure, one or more different ODP2 coding sequences can be manipulated to create a new ODP2 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the ODP2 gene of the invention and other known ODP2 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants including other monocots. In this manner, methods such as PCR, hybridization, and the like can be used to identify such sequences based on their sequence homology to the sequence set forth herein. Sequences isolated based on their sequence identity to the entire ODP2 sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode for an ODP2 protein and which hybridize under stringent conditions to the ODP2 sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the ODP2 sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire ODP2 sequence disclosed herein, or one or more portions thereof, may be used as a probe capable of specifically hybridizing to corresponding ODP2 sequences and messenger RNAs. To achieve specific hybridization under a variety of conditions, such probes include sequences that are unique among ODP2 sequences and are optimally at least about 10 nucleotides in length, and at least about 20 nucleotides in length. Such probes may be used to amplify corresponding ODP2 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, optimally at least 80%, more optimally at least 90%, and most optimally at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more optimally at least 70%, 80%, 90%, and most optimally at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, optimally 80%, more optimally 85%, most optimally at least 90% or 95% sequence identity to the reference sequence over a specified comparison window. Optimally, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention further provides plants, plant cells, and plant parts having altered levels and/or activities of the ODP2 polypeptides of the invention. In some embodiments, the plants of the invention have stably incorporated the ODP2 sequences of the invention. As discussed elsewhere herein, altering the level/activity of the ODP2 sequences of the invention can produce a variety to phenotypes. As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein "grain" is intended the mature seed produced by commercial growers for purposes other than growing or reproducing the species. Progeny, variants, and mutants of the regenerated plants are also included within the scope of the invention, provided that these parts comprise the introduced nucleic acid sequences.

A "subject plant or plant cell" is one in which an alteration, such as transformation or introduction of a polypeptide, has occurred, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

Methods

I. Providing Sequences

The use of the term "nucleotide constructs" or "polynucleotide" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The nucleic acid sequences of the present invention can be introduced/expressed in a host cell such as bacteria, yeast, insect, mammalian, or optimally plant cells. It is expected that those of skill in the art are knowledgeable in the numerous systems available for the introduction of a polypeptide or a nucleotide sequence of the present invention. No attempt to describe in detail the various methods known for providing proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form and/or genomic location.

By "host cell" is meant a cell, which comprises a heterologous nucleic acid sequence of the invention. Host cells may be prokaryotic cells such as $E. coli$, or eukaryotic cells such as yeast, insect, amphibian, or mammalian cells. Optimally, host cells are monocotyledonous or dicotyledonous plant cells. A particularly optimal monocotyledonous host cell is a maize host cell.

The ODP2 sequences of the invention can be provided in expression cassettes for expression in the plant of interest. The cassette can include 5' and 3' regulatory sequences operably linked to an ODP2 sequence of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites for insertion of the ODP2 sequence to be under the transcriptional regulation of the regulatory regions. The expression cassette may additionally contain selectable marker genes.

The expression cassette can include in the 5'-3' direction of transcription, a transcriptional initiation region (i.e., a promoter) and translational initiation region, an ODP2 sequence of the invention, and a transcriptional and translational termination region (i.e., termination region) functional in plants. The promoter may be native/analogous or foreign to the plant host and/or to the ODP2 sequence of the invention. In one embodiment, the promoter employed in the methods of the invention is the native ODP2 promoter. See, for example, U.S. Provisional Application No. 60/541,171, entitled "ODP2 Promoter and Methods of Use", filed on Feb. 2, 2004. Additionally, the promoter may be a natural sequence or alternatively a synthetic sequence. Where the promoter is "foreign" to the plant host, it is intended that the promoter is not found in the native plant into which the promoter is introduced. Where the promoter is "foreign" to the ODP2 sequence of the invention, it is intended that the promoter is not the native or naturally occurring promoter for the operably linked ODP2 sequence of the invention. As used herein, a chimeric gene comprises a coding sequence operably linked to a transcription initiation region that is heterologous to the coding sequence.

While it may be optimal to express the sequences using foreign promoters, the native promoter sequences may be used. Such constructs would change expression levels of ODP2 in the plant or plant cell. Thus, the phenotype of the plant or plant cell can be altered.

The termination region may be native with the transcriptional initiation region, may be native with the operably linked ODP2 sequence of interest, may be native with the plant host, or may be derived from another source (i.e., foreign to the promoter, the ODP2 sequence of interest, the plant host, or any combination thereof). Convenient termination regions are available from the Ti-plasmid of $A. tumefaciens$, such as the octopine synthase and nopaline synthase termination regions. See also Guerineau et al. (1991) *Mol. Gen.*

*Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology, Vol.* 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention. The promoters can be selected based on the desired outcome. That is, the nucleic acid can be combined with constitutive, tissue-preferred, developmentally regulated, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced ODP2 expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.*

6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and, mi1ps (myo-inositol-1-phosphate synthase); (see WO 00/11177 and U.S. Pat. No. 6,225,529; herein incorporated by reference). Gamma-zein is another endosperm-specific promoter (Boronat et al. (1986) *Plant Science* 47:95-102). Globulin-1 (Glob-1) is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa, 22 kDa zein, 27 kDa zein, gamma-zein, waxy, shrunken 1, shrunken 2, globulin 1, etc. See also WO 00/12733, where seed-preferred promoters from end1 and end2 genes are disclosed; herein incorporated by reference. Additional seed-preferred promoters include the oleosin promoter (WO 00/0028058), the lipid transfer protein (LTP) promoter (U.S. Pat. No. 5,525,716). Additional seed-preferred promoters include the Lec1 promoter, the Jip1 promoter, and the mi1ps3 promoter (see, WO 02/42424).

The methods of the invention involve introducing a nucleotide construct or a polypeptide into a plant. By "introducing" is intended presenting to the plant the nucleotide construct (i.e., DNA or RNA) or a polypeptide in such a manner that the nucleic acid or the polypeptide gains access to the interior of a cell of the plant. The methods of the invention do not depend on a particular method for introducing the nucleotide construct or the polypeptide to a plant, only that the nucleotide construct gains access to the interior of at least one cell of the plant. Methods for introducing nucleotide constructs and/or polypeptide into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct or the polypeptide introduced into a plant does not integrate into the genome of the plant.

Thus the ODP2 sequences of the invention can be provided to a plant using a variety of transient transformation methods including, but not limited to, the introduction of ODP2 protein or variants thereof directly into the plant and the introduction of the an ODP2 transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the various viral vector systems can be used for transient expression or the ODP2 nucleotide construct can be precipitated in a manner that precludes subsequent release of the DNA (thus, transcription from the particle-bound DNA can occur, but the frequency with which its released to become integrated into the genome is greatly reduced). Such methods include the use of PEI, as outlined in more detail in Example 13.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the an ODP2 polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al.

(1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Optimally, plants of the present invention are crop plants (for example, corn, alfalfa, sunflower, Brassica, soybean, cotton, safflower, peanut, sorghum, wheat, millet, tobacco, etc.), more optimally corn and soybean plants, yet more optimally corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235); Mosbach et al. (1983) *Nature* 302: 543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/ transfected plant cells, as discussed infra, are employed as expression systems for production of the proteins of the instant invention.

Synthesis of heterologous polynucleotides in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773-781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. In other embodiments, the polypeptide of the invention is introduced. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

A method for modulating the concentration and/or activity of the polypeptide of the present invention is provided. By "modulation" is intended any alteration in the level and/or activity (i.e., increase or decrease) that is statistically significant compared to a control plant or plant part. In general, concentration, composition or activity is increased or decreased by at least 5%, 10%, 20%, 30%, 40%, 50%, 60%, 70%, 80%, or 90% relative to a control plant, plant part, or cell. The modulation may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In specific embodiments, the polypeptides of the present invention are modulated in monocots, particularly maize.

The level of the ODP2 polypeptide may be measured directly, for example, by assaying for the level of the ODP2 polypeptide in the plant, or indirectly, for example, by measuring the ODP2 activity of the ODP2 polypeptide in the plant. Methods for determining the presence of ODP2 activity are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may incorporate into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprises at least one nucleotide.

In some embodiments, the activity and/or level of the ODP2 polypeptide of the invention is increased. An increase in the level or activity of the ODP2 polypeptide of the invention can be achieved by providing to the plant an ODP2 polypeptide. As discussed elsewhere herein, many methods are known the art for providing a polypeptide to a plant including, but not limited to, direct introduction of the polypeptide into the plant and/or introducing into the plant (transiently or stably) a nucleotide construct encoding a polypeptide having ODP2 activity. In other embodiments, the level or activity of an ODP2 polypeptide may be increased by altering the gene encoding the ODP2 polypeptide or its promoter. See, e.g. U.S. Pat. No. 5,565,350 and PCT/US93/03868. The invention therefore encompasses mutagenized plants that carry mutations in ODP2 genes, where the mutations increase expression of the ODP2 gene or increase the ODP2 activity of the encoded ODP2 polypeptide.

In some embodiments, the activity and/or level of the ODP2 polypeptide of the invention of is reduced or eliminated by introducing into a plant a polynucleotide that inhibits the level or activity of the ODP2 polypeptide of the invention. The polynucleotide may inhibit the expression of ODP2 directly, by preventing translation of the ODP2 messenger RNA, or indirectly, by encoding a polypeptide that inhibits the transcription or translation of an ODP2 gene encoding an ODP2 protein. Methods for inhibiting or eliminating the expression of a gene in a plant are well known in the art, and any such method may be used in the present invention to inhibit the expression of ODP2 in a plant. In other embodiments of the invention, the activity of ODP2 polypeptide is reduced or eliminated by transforming a plant cell with an expression cassette comprising a polynucleotide encoding a polypeptide that inhibits the activity of the ODP2 polypeptide. In other embodiments, the activity of an ODP2 polypeptide may be reduced or eliminated by disrupting the gene encoding the ODP2 polypeptide. The invention encompasses mutagenized plants that carry mutations in ODP2 genes, where the mutations reduce expression of the ODP2 gene or inhibit the ODP2 activity of the encoded ODP2 polypeptide.

Reduction of the activity of specific genes (also known as gene silencing or gene suppression) is desirable for several aspects of genetic engineering in plants. Methods for inhibiting gene expression are well known in the art and include, but are not limited to, homology-dependent gene silencing, antisense technology, RNA interference (RNAi), and the like. The general term homology-dependent gene silencing encompasses the phenomenon of cis-inactivation, trans-inactivation, and cosuppression. See Finnegan et al. (1994) *Biotech.* 12:883-888; and Matzke et al. (1995) *Plant Physiol.* 107:679-685; both incorporated herein in their entirety by reference. These mechanisms represent cases of gene silencing that involve transgene/transgene or transgene/endogenous gene interactions that lead to reduced expression of protein in plants. A "transgene" is a recombinant DNA construct that has been introduced into the genome by a transformation procedure. As one alternative, incorporation of antisense RNA into plants can be used to inhibit the expression of endogenous genes and produce a functional mutation within the genome. The effect is achieved by introducing into the cell(s) DNA that encodes RNA that is complementary to the sequence of mRNA of the target gene. See e.g. Bird et al. (1991) *Biotech and Gen. Eng. Rev.* 9:207-226; incorporated herein in its entirety by reference. See also the more detailed discussion herein below addressing these and other methodologies for achieving inhibition of expression or function of a gene.

Many techniques for gene silencing are well known to one of skill in the art, including, but not limited to, antisense technology (see, e.g., Sheehy et al. (1988) *Proc. Natl. Acad. Sci. USA* 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12:883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507), virus-induced gene silencing (Burton et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; WO 98/53083; Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, U.S. Patent Publication No. 20030175965; Panstruga et al. (2003) *Mol. Biol. Rep.* 30:135-140; Wesley et al. (2001) *Plant J.* 27:581-590; Wang and Waterhouse (2001) *Curr. Opin. Plant Biol.* 5:146-150; U.S. Patent Publication No. 20030180945; and, WO 02/00904, all of which are herein incorporated by reference); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al.

(2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference; and other methods or combinations of the above methods known to those of skill in the art.

It is recognized that with the polynucleotides of the invention, antisense constructions, complementary to at least a portion of the messenger RNA (mRNA) for the ODP2 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used.

The polynucleotides of the present invention may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference. Thus, many methods may be used to reduce or eliminate the activity of an ODP2 polypeptide. More than one method may be used to reduce the activity of a single ODP2 polypeptide. In addition, combinations of methods may be employed to reduce or eliminate the activity of the ODP2 polypeptides.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

The ODP2 polynucleotides of the present invention can also be combined with genes implicated in transcriptional regulation, homeotic gene regulation, stem cell maintenance and proliferation, cell division, and/or cell differentiation such as other ODP2 homologues; Wuschel (see, e.g, Mayer et al. (1998) *Cell* 95:805-815); clavata (e.g., CLV1, CVL2, CLV3) (see, e.g., WO 03/093450; Clark et al. (1997) *Cell* 89:575-585; Jeong et al. (1999) *Plant Cell* 11:1925-1934; Fletcher et al. (1999) *Science* 283:1911-1914); Clavata and Embryo Surround region genes (e.g., CLE) (see, e.g., Sharma et al. (2003) *Plant Mol. Biol.* 51:415-425; Hobe et al. (2003) *Dev Genes Evol* 213:371-381; Cock & McCormick (2001) *Plant Physiol* 126:939-942; and Casamitjana-Martinez et al. (2003) *Curr Bio,* 13:1435-1441); baby boom (e.g., BNM3, BBM) (see, e.g., WO 00/75530; Boutiler et al. (2002) *Plant Cell* 14:1737-1749); Zwille (Lynn et al. (1999) *Dev* 126:469-481); leafy cotyledon (e.g., Lec1, Lec2) (see, e.g., Lotan et al. (1998) *Cell* 93:1195-1205; WO 00/28058; Stone et al. (2001) *PNAS* 98:11806-11811; and U.S. Pat. No. 6,492,577); Shoot Meristem-less (STM) (Long et al. (1996) *Nature* 379:66-69); ultrapetala (ULT) (see, e.g., Fletcher (2001) *Dev* 128:1323-1333); mitogen activated protein kinase (MAPK) (see, e.g., Jonak et al. (2002) *Curr Opin Plant Biol* 5:415); kinase associated protein phosphatase (KAPP) (see, e.g., Williams et al. (1997) *PNAS* 94:10467-10472; and Trotochaud et al. (1999) *Plant Cell* 11:393-406); ROP GTPase (see, e.g., Wu et al. (2001) *Plant Cell* 13:2841-2856; and Trotochaud et al. (1999) *Plant Cell* 11:393-406); fasciata (e.g., FAS1, FAS2) (see, e.g., Kaya et al. (2001) *Cell* 104:131-142); cell cycle genes (see, e.g., U.S. Pat. No. 6,518,487; WO 99/61619; and WO 02/074909), Shepherd (SHD) (see, e.g., Ishiguro et al. (2002) *EMBO J.* 21:898-908); Poltergeist (see, e.g., Yu et al. (2000) *Dev* 127:1661-1670; Yu et al. (2003) *Curr Biol* 13:179-188); Pickle (PKL) (see, e.g., Ogas et al. (1999) *PNAS* 96:13839-13844); knox genes (e.g., KN1, KNAT1) (see, e.g., Jackson et al. (1994) *Dev* 120:405-413; Lincoln et al. (1994) *Plant Cell* 6:1859-1876; Venglat et al. (2002) *PNAS* 99:4730-4735); fertilization independent endosperm (FIE) (e.g., Ohad et al. (1999) *Plant Cell* 11:407-415), and the like, the disclosures of which are herein incorporated by reference. The combinations generated can also include multiple copies of any one of the polynucleotides of interest. The combinations may have any combination of up-regulating and down-regulating expression of the combined polynucleotides. The combinations may or may not be combined on one construct for transformation of the host cell, and therefore may be provided sequentially or simultaneously. The host cell may be a wild-type or mutant cell, in a normal or aneuploid state.

II. Altering the Oil Content in Plants

The present invention provides a method for altering the oil content of a plant. By "altering the oil phenotype" of a plant is intended any modulation (increase or decrease) in the overall level of oil in the plant or plant part (i.e., seed) when compared to a control plant. The altered oil phenotype can comprise any statistically significant increase or decrease in oil when compared to a control plant. For example, altering the oil phenotype can comprise either an increase or a decrease in overall oil content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, or greater when compared to a control plant or plant part that has not be transformed with the ODP2 sequence of the invention. Alternatively, the alteration in oil phenotype can include about a 0.5 fold, 1 fold, 2 fold, 4 fold, 8 fold, 16 fold, or 32 fold increase in overall oil phenotype in the plant or plant part when compared to a control plant that has not been transformed with the ODP2 sequence.

It is further recognized that the alteration in the oil phenotype need not be an overall increase/decrease in oil content, but also includes a change in the ratio of various components of the plant oil (i.e., a change in the ratio of any of the various fatty acids that compose the plant oil). For example, the ratio of various fatty acids such as linoleic acid, oleic acid, palmitic acid, stearic acid, myristic acid, linolenic acid, lauric acid, and the like, could be altered and thereby change the oil phenotype of the plant or plant part when compared to a control plant lacking the ODP2 sequence of the invention.

The method for altering the oil phenotype of a plant comprises providing an ODP2 sequence of the invention. An ODP2 polypeptide can be provided by introducing the polypeptide into the plant, and thereby modifying the oil content of the plant or plant part. Alternatively, an OPD2 nucleotide sequence can be provided by introducing into the plant a heterologous polynucleotide comprising an ODP2 nucleotide sequence of the invention, expressing the ODP2 sequence, and thereby modifying the oil content of the plant. In yet other embodiments, the ODP2 nucleotide construct introduced into the plant is stably incorporated into the genome of the plant.

Methods for determining if the oil phenotype of the plant has been altered are known in the art. For example, the oil phenotype can be determined using NMR. Briefly, data for plant or plant part oil percentage, total plant or plant part oil, and plant or plant part weight are collected and analyzed by NMR. If changes from the control (a plant not transformed with ODP2) are observed above base-line, a PCR co-segregation analysis can be performed to determine if the changes are correlated with the presence of the ODP2 sequence. In specific embodiments, the plant part is an embryo. Alternatively, fatty acid content and composition can be determined by gas chromatography (GC). See, for example, WO 03/001902, herein incorporated by reference.

As discussed above, one of skill will recognize the appropriate promoter to use to alter the oil content of the plant in the desired manner. Exemplary promoters for this embodiment include the ubiquitin promoter (Christensen et al. (1992) *Plant Molecular Biology* 18:675-680), a lipid transfer protein (LTP) promoter (U.S. Pat. No. 5,525,716), a gamma-zein promoter (GZP) (Boronat et al. (1986) *Plant Sciences* 47:95-102), and the oleosin promoter (WO 00/28058), the lec1 promoter (WO 02/42424), and the Zm-ODP2 promoter (U.S. Provisional Application No. 60/541,171, entitled "ODP2 Promoter and Methods of Use" filed on Feb. 2, 2004, herein incorporated by reference in its entirety.

In specific embodiments, the oil content of the plant is decreased upon increasing level/activity of the ODP2 polypeptide in a plant. A decreased oil content finds use in the wet milling industry and in the ethanol dry grind industry. In the dry grind process, raw corn is ground, mixed with water, cooked, saccharified, fermented, and then distilled to make ethanol. The process also recovers distillers dried gains with solubles that can be used in feed products. Various methods of ethanol dry grind are known in the art. See, for example, U.S. Pat. No. 6,592,921, U.S. Pat. No. 6,433,146, Taylor et al. (2003) *Applied Biochemistry and Biotechnology* 104:141-148; Taylor et al. (2000) *Biotechnol Prog.* 16:541-7, and Taylor et al. (2001) *Appl Biocehm Biotechnol* 94:41-9.

In the wet milling process, the purpose is to fractionate the kernel and isolate chemical constituents of economic value into their component parts. The process allows for the fractionation of starch into a highly purified form, as well as, for the isolation in crude forms of other material including, for example, unrefined oil, or as a wide mix of materials which commonly receive little to no additional processing beyond drying. Hence, in the wet milling process grain is softened by steeping and cracked by grinding to release the germ from the kernels. The germ is separated from the heavier density mixture of starch, hulls and fiber by "floating" the germ segments free of the other substances in a centrifugation process. This allows a clean separation of the oil-bearing fraction of the grain from tissue fragments that contain the bulk of the starch. Since it is not economical to extract oil on a small scale, many wet milling plants ship their germ to large, centralized oil production facilities. Oil is expelled or extracted with solvents from dried germs and the remaining germ meal is commonly mixed into corn gluten feed (CGF), a coproduct of wet milling. Hence, starch contained within the germ is not recovered as such in the wet milling process and is channeled to CGF. See, for example, Anderson et al. (1982) *"The Corn Milling Industry"; CRC Handbook of Processing and Utilization in Agriculture*, A. Wolff, Boca Raton, Fla., CRC Press., Inc., Vol. 11, Part 1, *Plant Products:* 31-61 and Eckhoff (Jun. 24-26, 1992) *Proceedings of the 4th Corn Utilization Conference*, St. Louis, Mo., printed by the National Corn Growers Association, CIBA-GEIGY Seed Division, and the USDA, both of which are herein incorporated by reference.

In other embodiments, the oil content of the plant or plant part is increased. Plants containing an increase in oil content can be used in a variety of applications. For example, high oil plants have an improved food efficiency, which results in greater amounts of energy in the germ. In addition, high oil plants can have an increase in lysine levels, reduced dust during grinding, and improved feed product when compared with normal plants. High oil content in seeds also yields greater amounts of oil when grain is processed into oil and provides economic advantages to starch wet milling.

Accordingly, the present invention further provides plants having an altered oil phenotype when compared to the oil phenotype of a control plant. In specific embodiments, the altered oil phenotype is in a grain. In some embodiments, the plant of the invention has an increased level/activity of the ODP2 polypeptide of the invention and has a decreased oil content. In other embodiments, such plants have stably incorporated into their genome a heterologous nucleic acid molecule comprising an ODP2 nucleotide sequence of the invention operably linked to a promoter that drives expression in the plant cell.

III. Altering Starch Production in Plants

The present invention provides a method for modifying the starch production of a plant. By "starch" is intended a polymer of glucose and normally comprises amylose, amylopectin or a mixture of these two polymer types. Functionally analogous chemical compounds, also included within the definition of starch, include phytoglycogen (which occurs in select types of corn) and water soluble polysaccharides (glucose polymers lacking the crystalline structure of starch granules).

By "modify starch production" of a plant is intended any modulation (increase or decrease) in the overall level of starch in the plant or plant part (i.e., seed, grain, etc.) when compared to a control plant. The modification in starch production can comprise any statistically significant increase or decrease in starch levels when compared to a control plant. For example, modifying starch production can comprise either an increase or a decrease in overall starch content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, 110%, 125% or greater when compared to a control plant or plant part that has not be transformed with the ODP2 sequence of the invention. Alternatively, the modification of starch production can include about a 0.2 fold, 0.5 fold, 1 fold, 2 fold, 4 fold, 8 fold, 16 fold, or 32 fold increase in overall starch content in the plant or plant part when compared to a control plant that has not been transformed with the ODP2 sequence.

The method for modifying the starch production in a plant comprises providing an ODP2 sequence of the invention. An ODP2 polypeptide can be provided by introducing the polypeptide into the plant, and thereby modifying the starch production of the plant or plant part. Alternatively, an ODP2 nucleotide sequence can be provided by introducing into the plant a heterologous polynucleotide comprising an ODP2 nucleotide sequence of the invention, expressing the ODP2 sequence, and thereby modifying the starch production of the plant. In yet other embodiments, the ODP2 nucleotide construct introduced into the plant is stably incorporated into the genome of the plant.

Methods for determining if the starch production in the plant or plant part has been altered are known in the art. For example, total starch measurement can be performed as outlined in McCleary et al. (1994) *Journal of Cereal Science* 20:51-58, McCleary et al. (1997) *J. Assoc. Off. Anal. Chem.* 80:571-579, and McCleary et al. (2002) *J. AOAC International* 85:1103-1111, each of which is herein incorporated by reference.

As discussed above, one of skill will recognize the appropriate promoter to use to modify starch production in a plant in the desired manner. Exemplary promoters for this embodiment include the ubiquitin promoter (Christensen et al. (1992) *Plant Molecular Biology* 18:675-680), a lipid transfer protein (LTP) promoter (U.S. Pat. No. 5,525,716), a gamma-zein promoter (GZP) (Boronat et al. (1986) *Plant Sciences* 47:95-102), and the oleosin promoter (WO 00/28058), the lec1 promoter (WO 02/42424), and the Zm-ODP2 promoter (U.S. Provisional Application No. 60/541,171, entitled "ODP2 Promoter and Methods of Use" filed on Feb. 2, 2004.

In specific embodiments, the modification of starch production results in an increase in starch content in the plant or plant part upon increasing level/activity of the ODP2 polypeptide in a plant. An increased starch content finds use in the in the wet milling industry and in the ethanol dry grind industry. In other embodiments, the starch production results in a decrease in starch content in the plant or plant part upon decreasing the level/activity of the ODP2 polypeptide in the plant.

Accordingly, the present invention further provides plants or plant parts having modified starch production when compared to the starch production of a control plant or plant part. In specific embodiments, the plant having the altered starch production is a grain. In some embodiments, the plant of the invention has an increased level/activity of the ODP2 polypeptide of the invention and has an increase in starch accumulation. In other embodiments, such plants have stably incorporated into their genome a heterologous nucleic acid molecule comprising an ODP2 nucleotide sequence of the invention operably linked to a promoter that drives expression in the plant cell.

IV. Modifying the Regenerative Capacity of Plants

The present invention further provides methods to modify the regenerative capacity of a plant. As used herein "regeneration" refers to a morphogenic response that results in the production of new tissues, organs, embryos, whole plants or parts of whole plants that are derived from a single cell or a group of cells. Regeneration may proceed indirectly via a callus phase or directly, without an intervening callus phase. "Regenerative capacity" refers to the ability of a plant cell to undergo regeneration.

In this embodiment, the method of modifying the regenerative capacity of a plant comprises providing an ODP2 sequence of the invention. In one embodiment, the regenerative capcity of the plant is modified by increasing the level and/or activity of an ODP2 polypeptide. The ODP2 sequence can be provided by introducing an ODP2 polypeptide into the plant, and thereby modifying the regenerative capacity of said plant. Alternatively, an ODP2 nucleotide sequence can be provided by introducing into the plant a heterologous polynucleotide comprising an ODP2 polynucleotide of the invention, expressing the ODP2 sequence, and thereby modifying the regenerative capacity of the plant. In yet other embodiments, the ODP2 nucleotide construct introduced into the plant is stably incorporated into the genome of the plant.

It is further recognized that providing the ODP2 sequences may be used to enhance the regenerative capacity of plant tissues both in vitro and in vivo and thereby stimulating cell proliferation and/or differentiation. In one embodiment, a method of initiating meristem formation is provided.

As discussed in further detail below, the promoter used to express the ODP2 sequence of the invention will depend, in part, on the target tissue used for regeneration. Various promoters of interest include constitutive promoters, tissue-preferred promoters, developmentally regulated promoters, and chemically-inducible systems. Various promoters that regulate ovule and embryo expression, nucellus expression, and inner integument expression are discussed in further detail below.

The ODP2 sequences of the invention also will be useful for inducing apomixis in plants. In specific embodiments, increasing the level and/or activity of the ODP2 polypeptide induces apomixis. Apomixis and methods of conferring apomixis into plants are discussed in U.S. Pat. Nos. 5,710,367; 5,811,636; 6,028,185; 6,229,064; and 6,239,327 as well as WO 00/24914, all of which are incorporated herein by reference. Reproduction in plants is ordinarily classified as sexual or asexual. The term apomixis is generally accepted as the replacement of sexual reproduction by various forms of asexual reproduction (Rieger et al., (1976) *Glossary of Genetics and Cytogenetics*, Springer-Verlag, New York, N.Y.). In general, the initiation of cell proliferation in the embryo and endosperm are uncoupled from fertilization. Apomixis is a genetically controlled method of reproduction in plants where the embryo is formed without the union of an egg and a sperm. There are three basic types of apomictic reproduction: 1) apospory-embryo develops from a chromosomally unreduced egg in an embryo sac derived from a somatic cell in the nucellus; 2) diplospory-embryo develops from an unreduced egg in an embryo sac derived from the megaspore mother cell; and, 3) adventitious embryony-embryo develops directly from a somatic cell. In most forms of apomixis, pseudogamy or fertilization of the polar nuclei to produce endosperm is necessary for seed viability.

These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species with good male sterility. It also provides a system for the production of hybrid seed in species, or between genotypes of the same species in which crossing between separate parent plants is impractical on a large scale.

In another embodiment, methods for producing embryogenic cells are provided. By "embryogenic cell" is intended a cell that has completed the transition from either a somatic or a gametophytic cell to a state where no further applied stimuli are necessary to produce an embryo. In this embodiment, the method comprises providing an ODP2 sequence of the invention. In one embodiment, the level and/or activity of the ODP2 polypeptide is increased and thereby allows for an increased production of embryogenic cells. In one embodiment, the ODP2 sequence is an ODP2 polypeptide which is provided by introducing the polypeptide into the plant, and thereby producing an embryogenic cell. Alternatively, an OPD2 nucleotide sequence can be provided by introducing into the plant a heterologous polynucleotide comprising an ODP2 nucleotide sequence of the invention, expressing the ODP2 sequence, and thereby producing an embryogenic cell. In yet other embodiments, the ODP2 nucleotide construct introduced into the plant is stably incorporated into the genome of the plant.

Further provided is a method for producing asexually derived embryos. As used herein, the term "asexually derived embryo" refers to an embryo that is generated in the absence of fertilization. The term is inclusive of apomitic and somatic embryos. The term "somatic embryogenesis" refers to non-zygotic embryogenesis. The method comprises introducing into a plant an ODP2 sequence of the invention and thereby producing asexually derived embryos. As discussed above, the embryo can be a somatic embryo, an adventitious embryos, or a gametophytic embryo.

Methods are also provided for an increase in the production of somatic embryos in a plant. In one embodiment, the level and/or activity of the ODP2 polypeptide is increased and thereby allowing for the production of somatic embryos. In one embodiment, an ODP2 sequence of the invention is provided. The polypeptide can be provided by introducing the polypeptide into the plant, and thereby increasing the production of somatic embryos. Alternatively, an OPD2 nucleotide sequence can be provided by introducing into the plant a heterologous polynucleotide comprising an ODP2 nucleotide sequence of the invention, expressing the ODP2 sequence, and thereby increasing the production of somatic embryos. In yet other embodiments, the ODP2 nucleotide construct introduced into the plant is stably incorporated into the genome of the plant.

The somatic embryo structures may form as individual embryos or as a cluster of structures. In specific embodiments, the plants (i.e., the root, leaf, seedling) expressing the ODP2 sequences are cultured in vitro. The embryos, non-embryogenic callus or both are transferred to appropriate media for the production of embryos or plantlets. While the somatic embryo can be formed independent of additional growth regulators, it is recognized that in some embodiments, growth regulators can be added to the media and include, but are not limited to, 2,4-D (Mordhorst et al. (1998) Genetics 149:549-563).

An increase in asexually derived embryos can be assayed by determining if embryogenesis or embryonic callus is initiated at a higher frequency from transgenic lines expressing ODP2 sequences of the invention compared to a control plant or plant part. See, for example, Boutiler et al. (2002) The Plant Cell 14:1737-1749, herein incorporated by reference.

It is recognized that the plant having the somatic embryo structures may form only a limited number of somatic embryo structures and then resume additional post germination growth. In other embodiments, expression of the ODP2 sequence leads to the reiteration of the embryo forming process, with the result that new embryos or cotyledons are formed continuously.

In particular embodiments, the level and/or activity of the ODP2 polypeptide will be reduced prior to the regeneration of a plant from these various embryogenic cell types. Methods for reducing the activity of the ODP2 polypeptide are discussed in detail elsewhere herein.

Embryogenesis can be induced in haploid cells, such as pollen cells, egg cells, or cells from haploid lines, to produce haploid plants. Methods of inducing embryogenesis in haploid cells comprise providing an ODP2 sequence of the invention to a plant. In one embodiment, the level and/or activity of the ODP2 polypeptide is increased and thereby allows for the induction of embryogenesis in haploid cells. An ODP2 polypeptide can be provided by introducing the polypeptide into the plant, and thereby inducing embryogenesis. Alternatively, an OPD2 nucleotide sequence can be provided by introducing into the plant a heterologous polynucleotide comprising an ODP2 nucleotide sequence of the invention, expressing the ODP2 sequence, and thereby inducing embryogenesis. In yet other embodiments, the ODP2 nucleotide construct introduced into the plant is stably incorporated into the genome of the plant.

In one embodiment, the ODP2 nucleotide sequence introduced into the plant is under the control of a tissue specific promoter that is active in a haploid cell or tissue or a promoter that is active during microspore development (such as, the maize PG47 promoter (Allen et al. (1993) Plant J. 3:261-71), the zm-G13 promoter (Hamilton et al. (1992) Plant Mol. Biol. 18:211-218). In other embodiments, the ODP2 nucleotide sequence is under the control of an inducible promoter and the application of the inducer allows expression of the ODP2 sequence therein. Alternatively, the promoter used can be both inducible and tissue-preferred, giving greater control over the process. For example, the promoter can be both haploid-tissue specific and inducible. In one embodiment, the promoter is an inducible pollen-specific promoter used to induce somatic embryogenesis in pollen cells. In still other embodiments, site-specific recombination systems can be used in combination with promoters (i.e., constitutive promoters or inducible promoters) to regulate the appropriate time and level of ODP2 expression. Thus, the methods of the invention find use in promoting embryogenesis in microspore and anther cultures.

Providing the ODP2 sequence to a haploid tissue or cell results in the formation of haploid somatic embryos, which can be grown into haploid plants using standard techniques. When an inducible promoter is used (whether tissue specific or not), an optimal method comprises exposing excised transgenic tissue containing the haploid cells (e.g., pollen or ovules) to the inducer specific for the inducible promoter for a time sufficient to induce the formation of a somatic embryo, withdrawing the inducer, and growing the somatic embryo into a transgenic haploid plant in the absence of the inducer.

Diploidization of the haploid plants to form dihaploids, either spontaneously or by treatment with the appropriate chemical (e.g. colchicine) will significantly expedite the process of obtaining homozygous plants as compared to a method of conventional genetic segregation. This technology will not only be beneficial for breeding purposes but also for basic research such as studies of mutagenesis and other genetic studies, because dihaploids are truly homozygous down to the DNA level, containing two identical copies of each gene.

In yet another embodiment, adventitious embryony can be achieved by providing an ODP2 sequence of the invention to sporophytic ovule tissues such as the nucellus, the inner integuments, or other tissues lying adjacent to or in proximity to the developing embryo sac.

The ODP2 sequences of the invention may also be used as a selectable marker to recover transgenic plants. In one embodiment, the level and/or activity of the ODP2 sequence is increased. In this embodiment, a plant is transformed with the ODP2 sequences along with a nucleotide sequence of interest. Upon expression of the ODP2 sequences, the plants can be selected based on their ability to regenerate under conditions in which wild type explants are unable to. For example, the transgenic plants may be able to regenerate in the absence of growth regulators. If the ODP2 sequence and the polynucleotide of interest are carried on separate plasmids, the ODP2 sequence can be subsequently removed from transgenic plants by routine breeding methods.

One of skill in the art will recognize that a variety of promoters can be used in the various methods of the invention. Somatic or gametophytic embryos can be obtained expressing the ODP2 polypeptide under the control of constitutive promoters, tissue-preferred, developmentally regulated, or various inducible promoters including chemical induction systems (i.e., tetracycline-inducible systems, steroid inducible promoters, and ethanol-inducible promoters). Temporal and/or spatial restriction of ODP2 is optimal when recurrent embryogenesis is not a desirable trait. Promoters of interest when microspore-derived embryo production is desired include, but are not limited to, microspore/pollen expressed genes such as NTM19 (EP 790,311), BCP1 (Xu et al. (1995) *Plant Mol. Biol.* 22:573-588, PG47 (Allen et al. (1993) *Plant J.* 3:261-71), ZmG13 (Hamilton et al. (1992) *Plant Mol. Biol.* 18:211-218), and BNM1 (Treacy et al. (1997) *Plant Mol. Biol.* 34:603-611), each reference is herein incorporated by reference. Promoters of interest when the production of somatic embryos are desired include, but are not limited to, cytokinin inducible IB6 and CK11 promoters (Brandstatter et al. (1998) *Plant Cell* 10:1009-1019). Exemplary promoters of interest when adventitious embryony, diplospory or haploid parthenogenesis of embryo sac components, include, the AtDMC1 gene (WO 98/28431), promoters that direct expression in the ovule, such as the AGL11 promoter (Rounsley et al. (1995) *Plant Cell* 10:1009-1019) and the SERK promoter (Schmidt et al. (1997) *Development* 124:2049-2062), promoters that direct expression in the nucellus such as the NUC1 promoter (WO 98/08961), promoters that regulate expression of inner integument genes such as the FBP7 promoter (Angenent et al. (1995) *Plant Cell* 7:1569-1582), microspore/pollen-preferred promoters (discussed above) and chemical induction systems. Each of these references is herein incorporated by reference.

Accordingly, the present invention further provides plants having a modified regenerative capacity, including plants that are capable of producing asexually derived embryos. In some embodiments, the plants having a modified regenerative capacity have an increased level/activity of the ODP2 polypeptide of the invention. In other embodiments, the plant comprises a heterologous ODP2 nucleotide sequence of the invention operably linked to a promoter that drives expression in the plant cell. In other embodiments, such plants have stably incorporated into their genome a heterologous nucleic acid molecule comprising an ODP2 nucleotide sequence of the invention operably linked to a promoter that drives expression in the plant cell.

In other embodiments, the OPD2 sequences of the invention can be used to modify the tolerance of a plant to abiotic stress. In one embodiment, a method is provided to increase or maintain seed set during abiotic stress episodes. During periods of stress (i.e., drought, salt, heavy metals, temperature, etc.) embryo development is often aborted. In maize, halted embryo development results in aborted kernels on the ear. Preventing this kernel loss will maintain yield. Accordingly, methods are provided to increase the stress resistance in a plant (i.e., an early developing embryo).

The method comprises providing an ODP2 sequence of the invention. The polypeptide can be provided by introducing the polypeptide into the plant, and thereby modifying the plants tolerance to abiotic stress. Alternatively, an OPD2 nucleotide sequence can be provided by introducing into the plant a heterologous polynucleotide comprising an ODP2 nucleotide sequence of the invention, expressing the ODP2 sequence, and thereby modifying the plants tolerance to abiotic stress. In yet other embodiments, the ODP2 nucleotide construct introduced into the plant is stably incorporated into the genome of the plant.

A variety of promoters can be employed in this method. In one embodiment, the ODP2 sequence is under the control of an early promoter. An early embryo is defined as the stages of embryo development including the zygote and the developing embryo up to the point where embryo maturation begins. An "early embryo promoter" is a promoter that drives expression predominately during the early stages of embryo development (i.e., before 15-18 DAP). Alternatively, the early embryo promoter can drive expression during both early and late stages. Early embryo promoters include, but are not limited to, to Lec 1 (WO 02/42424); cim1, a pollen and whole kernel specific promoter (WO 00/11177); the seed-preferred promoter end1 (WO 00/12733); and, the seed-preferred promoter end2 (WO 00/12733) and lpt2 (U.S. Pat. No. 5,525, 716). Additional promoter include, smi1ps, an embryo specific promoter and cz19B1 a whole kernel specific promoter. See, for example, WO 00/11177, which is herein incorporated by reference. All of these references is herein incorporated by reference.

Methods to assay for an increase in seed set during abiotic stress are known in the art. For example, plants having the ODP2 sequences of the invention can be monitored under various stress conditions and compared to controls plants (not having had the ODP2 introduced). For instance, the plant having the OPD2 sequence can be subjected to various degrees of stress during flowering and seed set. Under identical conditions, the genetically modified plant having the ODP2 sequences will have a higher number of developing kernels than a wild type (non-transformed) plant.

Accordingly, the present invention further provides plants having increased yield or maintaining their yield during periods of abiotic stress (i.e. drought, salt, heavy metals, temperature, etc). In some embodiments, the plants having an increased or maintained yield during abiotic stress have an increased level/activity of the ODP2 polypeptide of the invention. In other embodiments, the plant comprises a heterologous ODP2 nucleotide sequence of the invention operably linked to a promoter that drives expression in the plant cell. In other embodiments, such plants have stably incorporated into their genome a heterologous nucleic acid molecule comprising an ODP2 nucleotide sequence of the invention operably linked to a promoter that drives expression in the plant cell.

V. Modifying the Transformation Efficiency in Plants

The present invention provides novel methods for transformation and for increasing transformation frequencies. As used herein "responsive target plant cell" is a plant cell that exhibits increased transformation efficiency after the introduction of the ODP2 sequences of the invention when compared to a control plant or plant part. The increase in transformation efficiency can comprise any statistically significant increase when compared to a control plant. For example, an increase in transformation efficiency can comprises about 0.2%, 0.5%, 5%, 10%, 15%, 20%, 25%, 30%, 35%, 40%, 45%, 50%, 55%, 60%, 65%, 70%, 75%, 80%, 85%, 90%, 95%, 120%, 125% or greater increase when compared to a control plant or plant part. Alternatively, the increase in transformation efficiency can include about a 0.2 fold, 0.5 fold, 1 fold, 2 fold, 4 fold, 8 fold, 16 fold, or 32 fold or greater increase in transformation efficiency in the plant when compared to a control plant or plant part.

Many maize genotypes, and in particular elite germplasm developed in commercial breeding programs, are recalcitrant to in vitro culture and transformation. Such genotypes do not produce an appropriate embryogenic or organogenic culture response on culture media developed to elicit such responses from typically suitable explants such as immature embryos. Furthermore, when exogenous DNA is introduced into these immature embryos (for example, using particle bombardment or *Agrobacterium*), no transgenic events are recovered after selection (or so few events are recovered as to make transformation of such a genotype impractical). When the ODP2 gene is expressed (either transiently or stably) in immature embryos of such genotypes, vigorously growing transgenic events can be readily recovered.

Thus, the present invention finds use in increasing the transformation of a recalcitrant plant or explants. As used herein "recalcitrant plant or explant" means a plant or explant that is more difficult to transform than model systems. In maize such a model system is High type-II maize. Elite maize inbreds are typically recalcitrant. In soybeans such model systems are Peking or Jack.

In one embodiment of the invention, a method for increasing the transformation efficiency in a plant is provided. The method comprises providing an ODP2 sequence of the invention. An ODP2 polypeptide can be provided by introducing the polypeptide to the plant, and thereby increasing the transformation efficiency of the plant. Alternatively, an OPD2 nucleotide sequence can be provided by introducing into the plant a heterologous polynucleotide comprising an ODP2 nucleotide sequence of the invention, expressing the ODP2 sequence, and thereby increasing the transformation efficiency of the plant. In yet other embodiments, the ODP2 nucleotide construct introduced into the plant is stably incorporated into the genome of the plant. Through the introduction of an ODP2 into a recalcitrant plant and producing a positive influence on transformation, the methods of the invention provide the potential to increase the overall genetic transformation throughput of various recalcitrant germplasm.

Accordingly, the present invention further provides plants having increased transformation efficiencies when compared to the transformation efficiency of a control plant. In some embodiments, the plants having increased transformation efficiencies have an increased level/activity of the ODP2 polypeptide of the invention. In other embodiments, the plant comprises a heterologous ODP2 nucleotide sequence of the invention operably linked to a promoter that drives expression in the plant cell. In other embodiments, such plants have stably incorporated into their genome a heterologous nucleic acid molecule comprising an ODP2 nucleotide sequence of the invention operably linked to a promoter that drives expression in the plant cell.

In another embodiment, a method of transforming in a plant is provided. The method comprises providing a target plant, where the target plant had been provided an ODP2 sequence of the invention. In some embodiments, the OPD2 nucleotide sequence is provided by introducing into the plant a heterologous polynucleotide comprising an ODP2 nucleotide sequence of the invention, expressing the ODP2 sequence. In yet other embodiments, the ODP2 nucleotide construct introduced into the target plant is stably incorporated into the genome of the plant. The target plant is transformed with a polynucleotide of interest. It is recognized that the target plant having had the ODP2 sequence introduced (referred to herein as a "modified target plant"), can be grown under conditions to produce at least one cell division to produce a progeny cell expressing the ODP2 sequence prior to transformation with one or more polynucleotides of interest. As used herein "re-transformation" refers to the transformation of a modified cell.

The modified target cells having been provided the ODP2 sequence can be obtained from T0 transgenic cultures, regenerated plants or progeny whether grown in vivo or in vitro so long as they exhibit stimulated growth compared to a corresponding cell that does not contain the modification. This includes but is not limited to transformed callus, tissue culture, regenerated T0 plants or plant parts such as immature embryos or any subsequent progeny of T0 regenerated plants or plant parts.

Once the target cell is provided with the ODP2 nucleotide sequence it is re-transformed with at least one gene of interest. The transformed cell can be from transformed callus, transformed embryo, T0 regenerated plants or its parts, progeny of T0 plants or parts thereof as long as the ODP2 sequence of the invention is stably incorporated into the genome.

Methods to determine transformation efficiencies or the successful transformation of the polynucleotide of interest are known in the art. For example, transgenic plants expressing a selectable marker can be screened for transmission of the gene(s) of interest using, for example, chemical selection, phenotype screening standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes.

The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Seeds derived from plants regenerated from re-transformed plant cells, plant parts or plant tissues, or progeny derived from the regenerated plants, may be used directly as feed or food, or further processing may occur.

Any polynucleotide of interest can be used in the methods of the invention. Various changes in phenotype are of interest including modifying the fatty acid composition in a plant, altering the amino acid content, starch content, or carbohydrate content of a plant, altering a plant's pathogen defense mechanism, affecting kernel size, sucrose loading, and the like. The gene of interest may also be involved in regulating the influx of nutrients, and in regulating expression of phytate genes particularly to lower phytate levels in the seed. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703, 049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, methionine-rich plant proteins such as from sunflower seed (Lilley et al. (1989) *Proceedings of the World Congress on Vegetable Protein Utilization in Human Foods and Animal Feedstuffs,* ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference) could be used. Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and, the like.

Genes encoding disease resistance traits include detoxification genes, such as against fumonosin (U.S. Pat. No. 5,792, 931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The following examples are offered by way of illustration and not by way of limitation.

EXPERIMENTAL

Example 1

Cloning of ZM-ODP2

The protein encoded by maize EST clone cpf1c.pk009.f4 was initially identified as the homologue of a rice putative ovule development protein (BAB89946). The EST clone was subjected to full-insert sequencing. Comparison of rice BAB89946 and the protein sequence encoded by the longest open reading frame (ORF) from cpf1c.pk009.f4 suggests that this clone may have an internal deletion which causes premature termination of the protein by at least 120 amino acids. A genomic fragment encompassing the potential deletion was amplified by PCR using DNA isolated from Hi II callus. Sequencing results confirm the presence of an extra 146 base pairs in the genomic fragment. When added to cDNA clone cpf1c.pk009.f4, this 146-bp can be read through in the same reading frame and the ORF is extended to encode a protein very similar to BAB89946 in length.

The full-length Zm-ODP2 (SEQ ID NO:1) used in the transformation was created by combining the 5' end of cDNA clone cpf1c.pk009.f4 and part of the genomic clone from Hi II callus that contains the missing 146-bp. More specifically, a 1790-bp EcoRI-SbfI fragment from cpf1c.pk009.f4 and a 582-bp SbfI-SalI genomic fragment were ligated into pBluescript II KS+ digested with EcoRI and SalI to form PHP20430.

The full-length Zm-ODP2 sequence is 2260 nucleotides in length. The open reading frame is 2133 nucleotides in length and starts at nucleotide 128 and ends at nucleotide 2260 of SEQ ID NO:1. The nucleotide sequence of the Zm-ODP2 open reading frame is set forth in SEQ ID NO:3. The 710 amino acid sequence encoded by the Zm-ODP2 sequence is set forth in SEQ ID NO:2.

Example 2

Sequence Analysis of Zm-ODP2

The ZM-ODP2 sequence of the invention was analyzed for conserved domains. FIGS. 1A-1D show an alignment of the amino acid sequence of Zm-ODP2 (SEQ ID NO:2) with various polypeptides sharing sequence similarity to the Zm-ODP2 sequence. Specifically, Zm-ODP2 shares over its full-length about 65.4% sequence identity and 72.7% sequence similarity with OsAnt (Accession No. BAB89946; SEQ ID NO:25). Zm-ODP2 shares over its full-length about 57.1% sequence identity and about 62.3% sequence similarity to OSBNM (Accession No. AAL47205; SEQ ID NO:27). Zm-ODP2 shares over its full-length about 42% sequence identity and about 53.2% sequence similarity to OSODP (Accession No. CAE05555; SEQ ID NO:29). Zm-ODP2 shares over its full-length about 37% sequence identity and about 45% sequence similarity to BnBBM2 (Accession No. AAM33801; SEQ ID NO:33). Zm-ODP2 shares over its full-length about 38% sequence identity and about 47% sequence similarity to BnBBM1 (AAM33800; SEQ ID NO:32). Zm-ODP2 shares over its full-length about 38.1% sequence identity and about 46.3% sequence similarity to ATBBM (Accession No. AAM33803; SEQ ID NO:31). Zm-ODP2 shares over its full-length about 40% sequence identity and about 43% sequence similarity to AtODP (Accession No. AAD30633; SEQ ID NO:36). Zm-ODP2 shares over its full-length about 35.6% sequence identity and about 50% sequence similarity to ATODP (Accession No. NP_175530; SEQ ID NO:34). Zm-ODP2 shares over its full-length about 34.9% sequence identity and about 44.6% sequence similarity to AtODP (Accession No. BAB02492; SEQ ID NO:35). Zm-ODP2 shares over its full-length about 38.4% sequence identity and about 46% sequence similarity to AtODP (NP_197245; SEQ ID NO:30). A consensus sequence for all 11 aligned polypeptides is also provided (SEQ ID NO:37).

All 11 proteins present in the alignment have two AP2 (APETALA2; pfam00847.8) domains. Using the amino acid numbering of the Zm-ODP2, the first AP2 domain is from about amino acid 273 to about 343 and the second AP2 domain is from about amino acid 375 to about 437. The consensus sequence for the APETALA2 PFAM family is

```
                                          (SEQ ID NO: 38)
SKYRGVRQRPWGKWVAEIRDPRKGTRVWLGTFDTAEEAARAYDVAALK

LRGPSAVLNFPNEL.
```

Example 3

Variants of Zm-ODP2

A. Variant Nucleotide Sequences of Zm-ODP2 (SEQ ID NO:1) that do not Alter the Encoded Amino Acid Sequence The Zm-ODP2 nucleotide sequence set forth in SEQ ID NO:1 was used to generate 6 variant nucleotide sequences having the nucleotide sequence of the open reading frame with about 70.6%, 76.1%, 81.2%, 86.3%, 92.1%, and 97.1% nucleotide sequence identity when compared to the starting unaltered ORF nucleotide sequence of SEQ ID NO:1. These functional variants were generated using a standard codon table. While the nucleotide sequence of the variant was altered, the amino acid sequence encoded by the open reading frame did not change.

The variants of Zm-ODP2 using this method are set forth in SEQ ID NOS: 6-11. Specifically, SEQ ID NO: 6 shares about 97.1% nucleic acid sequence identity to the Zm-ODP2 sequence of SEQ ID NO: 1; SEQ ID NO: 7 shares about 92.1% nucleic acid sequence identity to SEQ ID NO:1, SEQ ID NO:8 shares about 86.3% nucleic acid sequence identity to SEQ ID NO:1; SEQ ID NO:9 shares about 81.2% nucleic acid sequence identity to SEQ ID NO:1; SEQ ID NO:10 shares about 76.1% nucleic acid sequence identity to SEQ ID NO:1; and SEQ ID NO:11 shares about 70.6% nucleic acid sequence identity to SEQ ID NO:1.

B. Variant Amino Acid Sequences of Zm-ODP2

Variant amino acid sequences of Zm-ODP2 were generated. In this example, one amino acid was altered. Specifically, the open reading frame set forth in SEQ ID NO:3 was reviewed to determined the appropriate amino acid alteration. The selection of the amino acid to change was made by consulting the protein alignment (with the other orthologs and other gene family members from various species). See FIGS. 1A-1D. An amino acid was selected that was deemed not to be under high selection pressure (not highly conserved) and which could be rather easily substituted by an amino acid with similar chemical characteristics (i.e., similar functional side-chain). Using the protein alignment set forth in FIGS. 1A-1D and focusing at the N-terminus (amino acids 1-50), the serine at amino acid position 37 (shaded) was changed to a threonine, which is chemically similar. Thus, the "TCC" serine codon in the nucleic acid sequence is changed to an "ACC" codon for threonine. The Zm-ODP2 sequence having the single change from "TCC" to "ACC" is set forth in SEQ ID NO:12.

Once the targeted amino acid was identified, the procedure outlined in Example 3A was followed. Variants having about 70.4% (SEQ ID NO:18), 75.9% (SEQ ID NO:17), 81.5% (SEQ ID NO:16), 86.6% (SEQ ID NO:15), 91.9% (SEQ ID NO:14), and 97.3% (SEQ ID NO:13) nucleic acid sequence identity to SEQ ID NO:3 were generated using this method. SEQ ID NOS: 13-18 all encode the same polypeptide, which is set forth in SEQ ID NO: 19.

C. Additional Variant Amino Acid Sequences of Zm-ODP2

In this example, artificial protein sequences were created at a narrower interval range (82.5%, 87.5%, 92.5%, and 97.5% identity relative to the reference protein sequence). This latter effort requires identifying conserved and variable regions from the alignment set forth in FIGS. 1A-1D and then the judicious application of an amino acid substitutions table. These parts will be discussed in more detail below.

Largely, the determination of which amino acid sequences were altered was made based on the conserved regions among AP2 protein or among the other ODP-like genes. See FIGS. 1A-1D. Based on the sequence alignment, the various regions of the Zm-ODP2 that can likely be altered are represented in lower case letters, while the conserved regions are represented by capital letters. It is recognized that conservative substitutions can be made in the conserved regions below without altering function. In addition, one of skill will understand that functional variants of the ODP2 sequence of the invention can have minor non-conserved amino acid alterations in the conserved domain. This sequence is set forth in SEQ ID NO:2.

```
MAtvNNWLAFSLSPqelppsqttdstlisaatADhvsGDVCFNipqdwsmrgselsalvaepkle dflggisfseqhhkancnmipstsstvcyassgastgyhhqlyhqptssalhfadsvmvassagv hdggamlsaaaangvagaasanGGGIGLSMIKNWLRSQPapmqprvaaaegaqglslsmnmagtt qgaagmpllagerarapesvstsaqggavvvtapkedsggsgvagalvavstdtggsggasadnt aRKTVDTFGQRTSIYRGVTRHRWTGRYEAHLWDNSCRREGQTRKGRQVYLGGYDKEEKAARAYDL

AALKYWGATTTTNFPVSNYEKELEDMKHMTRQEFVASLRRKSSGFSRGASIYRGVTRHHQHGRWQ

ARIGRVAGNKDLYLGTFSTQEEAAEAYDIAAIKFRGLNAVTNFDMSRYDVKSILDSSALPIGSAA

KRLKEAEAaasaqhhhagvvsydvgriasqlgdggalaaaygahyhgaawptiafqpgaastgly hpyaqqpmrgggwckqeqdhaviaaahslqdlhhlnlgaagahdffsagqqaaaaamhglgsids aslehSTGSNSVVYNGGvgdsngasavgGSGGGYmmpmsaagatttsamvsheqvharaydeakq aaqmGYESYLVnaenngggrmsawgtvvsaaaaaaassndnmaaDVGHGGAQLFSVWNDT
```

The conserved regions are found between about amino acid 1-2; 5-14; 33-34; 38-43; 153-169; 262-463; 591-602; 614-619; 655-661; and 695-710 of SEQ ID NO: 2. The non-conserved regions are from about amino acids 3-4; 15-32; 35-37; 44-152; 170-261; 464-590; 603-613; 620-654; and 662-694 of SEQ ID NO: 2.

The goal was to create four artificial protein sequences that are different from the original in the intervals of 80-85%, 85-90%, 90-95%, and 95-100% identity. Midpoints of these intervals were targeted, with liberal latitude of plus or minus 1%, for example. The amino acids substitutions will be effected by a custom Perl script. The substitution table is provided below in Table 1.

TABLE 1

| Substitution Table | | | |
|---|---|---|---|
| Amino Acid | Strongly Similar and Optimal Substitution | Rank of Order to Change | Comment |
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |

TABLE 1-continued

| Substitution Table | | | |
|---|---|---|---|
| Amino Acid | Strongly Similar and Optimal Substitution | Rank of Order to Change | Comment |
| M | L | 17 | First methionine cannot change |
| H | | Na | No good substitutes |
| C | | Na | No good substitutes |
| P | | Na | No good substitutes |

First, any conserved amino acids in the protein that should not be changed was identified and "marked off" for insulation from the substitution. The start methionine will of course be added to this list automatically. Next, the changes were made.

H, C, and P will not be changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involved a 50:50 substitution of the two alternate optimal substitutions.

Four amino acid sequences were written as output. Perl script was used to calculate the percent identities. Using this procedure, variants of Zm-ODP2 were generating having about 82.4% (SEQ ID NO:23), 87.3% (SEQ ID NO:22), 92.4% (SEQ ID NO:21), and 97.3% (SEQ ID NO:20) amino acid identity to the starting unaltered ORF nucleotide sequence of SEQ ID NO:2. FIGS. 2A-2B provide an amino acid alignment of SEQ ID NO:2 and the modified proteins set forth in SEQ ID NOS: 20-23.

TABLE 2

| Summary of the ODP2 sequences and exemplary variants thereof (SEQ ID NOS 1-25) | | |
|---|---|---|
| SEQ ID NO | Nucleotide or Amino Acid | Description of Sequence |
| 1 | nucleic acid | ZM-ODP2 full length |
| 2 | amino acid | ZM-ODP2 full length |
| 3 | nucleic acid | ZM-ODP2—open reading frame |

TABLE 2-continued Summary of the ODP2 sequences and exemplary variants thereof (SEQ ID NOS 1-25)

| SEQ ID NO | Nucleotide or Amino Acid | Description of Sequence |
|---|---|---|
| 4 | nucleic acid | ZM-ODP2 cDNA insert from EST clone cpf1c.pk009.f4 |
| 5 | nucleic acid | cDNA insert from EST clone cpc1c.pk005.c19 |
| 6 | nucleic acid | Nucleic acid variant of Zm-ODP2 having 97.2% nucleic acid sequence identity to SEQ ID NO: 2 |
| 7 | nucleic acid | Nucleic acid variant of Zm-ODP2 having 92.1% nucleic acid sequence identity to SEQ ID NO: 2 |
| 8 | nucleic acid | Nucleic acid variant of Zm-ODP2 having 86.3% nucleic acid sequence identity to SEQ ID NO: 2 |
| 9 | nucleic acid | Nucleic acid variant of Zm-ODP2 having 81.2% nucleic acid sequence identity to SEQ ID NO: 2 |
| 10 | nucleic acid | Nucleic acid variant of Zm-ODP2 having 76.1% nucleic acid sequence identity to SEQ ID NO: 2 |
| 11 | nucleic acid | Nucleic acid variant of Zm-ODP2 having 70.6% nucleic acid sequence identity to SEQ ID NO: 2 |
| 12 | nucleic acid | Variant of Zm-ODP2 having the seine 37 codon altered from "tcc" to the threonine codon of "acc". The ORF encodes the amino acid sequence set forth in SEQ ID NO: 19. |
| 13 | nucleic acid | Variant of Zm-ODP2 having 97.3% nucleic acid sequence identity to SEQ ID NO: 3 (Zm-ODP2). The ORF encodes the amino acid sequence set forth in SEQ ID NO: 2 with a single amino acid alteration (i.e., S37 to T37). The ORF encodes the amino acid sequence set forth in SEQ ID NO: 19. |
| 14 | nucleic acid | Variant of Zm-ODP2 having 91.9% nucleic acid sequence identity to SEQ ID NO: 3 (Zm-ODP2). The ORF encodes the amino acid sequence set forth in SEQ ID NO: 2 with a single amino acid alteration (i.e., S37 to T37). |
| 15 | nucleic acid | Variant of Zm-ODP2 having 86.6% nucleic acid sequence identity to SEQ ID NO: 3 (Zm-ODP2). The ORF encodes the amino acid sequence set forth in SEQ ID NO: 2 with a single amino acid alteration (i.e., S37 to T37). |
| 16 | nucleic acid | Variant of Zm-ODP2 having 81.5% nucleic acid sequence identity to SEQ ID NO: 3 (Zm-ODP2). The ORF encodes the amino acid sequence set forth in SEQ ID NO: 2 with a single amino acid alteration (i.e., S37 to T37). |
| 17 | nucleic acid | Variant of Zm-ODP2 having 75.9% nucleic acid sequence identity to SEQ ID NO: 3 (Zm-ODP2). The ORF encodes the amino acid sequence set forth in SEQ ID NO: 2 with a single amino acid alteration (i.e., S37 to T37). |
| 18 | nucleic acid | Variant of Zm-ODP2 having 70.4% nucleic acid sequence identity to SEQ ID NO: 3 (Zm-ODP2). The ORF encodes the amino acid sequence set forth in SEQ ID NO: 2 with a single amino acid alteration (i.e., S37 to T37). |
| 19 | Amino acid | Variant of Zm-ODP2 having a single amino acid alteration at S37 to T37. |
| 20 | Amino acid | Variant of Zm-ODP2 having 97.3% amino acid sequence identity to SEQ ID NO: 2 (Zm-ODP2). |
| 21 | Amino acid | Variant of Zm-ODP2 having 92.4% amino acid sequence identity to SEQ ID NO: 2 (Zm-ODP2). |
| 22 | Amino acid | Variant of Zm-ODP2 having 87.3% amino acid sequence identity to SEQ ID NO: 2 (Zm-ODP2). |
| 23 | Amino acid | Variant of Zm-ODP2 having 82.4% amino acid sequence identity to SEQ ID NO: 2 (Zm-ODP2). |
| 24 | Amino acid | Consensus sequence of FIGS. 2A-2B. |

Example 4

*Agrobacterium*-Mediated Transformation

For *Agrobacterium*-mediated transformation of maize with a plasmid containing the Zm-ODP2 operably linked to an oleosin promoter and the selectable marker gene PAT, optimally the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the ODP2 sequence to at least one cell of at least one of the immature embryos (step 1: the infection step). In this step the immature embryos are optimally immersed in an *Agrobacterium* suspension for the initiation of inoculation. The embryos are co-cultured for a time with the *Agrobacterium* (step 2: the co-cultivation step). Optimally the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Optimally the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Optimally, the immature embryos are cultured on solid medium with a selective agent resulting in the selective growth of transformed cells. The callus is then regenerated into plants (step 5: the regeneration step), and optimally calli grown on selective medium are cultured on solid medium to regenerate the plants.

Example 5

Altering Oil Content and Starch Content of Maize

The full length ODP2 sequence described in Example 1, was used for construction of the oleosin driven expression cassette: OLE PRO::ZM-ODP2::NOS TERM. This cassette was inserted into a final transformation plasmid using standard protocols. The final transformation vector contains OLE PRO::ZM-ODP2::NOS TERM and MO-PAT selection marker is transformed into High type-II maize/PHR03 via *Agrobacterium* transformation. Methods of *Agrobacterium* transformation are outlined in Example 4.

Transgenic events are recovered and advanced to the greenhouse. The plants are self-pollinated. At maturity, ears are collected and a portion of seeds (typically 20 kernels from each ear) dissected to separate the embryo from the endosperm. Dissected seeds are dried down in a lyophilizer overnight. The amount of oil in each embryo is determined using NMR. Data for embryo oil %, total embryo oil and embryo weight are collected and analyzed. If changes from High type-II maize/PHR03 baseline are observed, a PCR co-segregation analysis is performed to determine if the changes are correlated with the presence of transgene (ZM-ODP2).

In addition, germs are also isolated from mature kernels for determination of starch and oil concentrations of the seed part. Individual dry seed are soaked overnight at 4° C. in 1 mL of solution containing 20 mM acetate (pH 6.5) and 10 mM mercuric chloride. (Adkins et al. (1966) *Starch* 7: 213-218). Intact germ is dissected from the seed, dried by lyophilization and recorded for dry weight. Individual germ is ground for 10 sec in a Silamet amalgam mixer and transferred with hexane washing into a microcentrifuge tube. The tissue is extracted by stirring with 1 mL of hexane 3×60 min and centrifuged after each extraction period. The supernatant of extractions is collected and placed into a preweighed aluminum pan. After evaporation of hexane from the weigh pans in a fumehood, final traces of solvent are removed in a forced draft oven at 105° C. for 15 minutes. Cooled weigh pans are reweighed to determine the total weight of oil extracted from the germ. The meal remaining after oil extraction is twice washed with water and centrifugation (10 min; 1,000×g) and analyzed for starch by a modified procedure for total starch measurement (McCleary et al. (1994) *Journal of Cereal Science* 20: 51-58). Free sugars are removed by extraction with 80% ethanol and the starch dissolved in 90% dimethylsulfoxide. Heat stable α-amylase and high purity amyloglucosidase (very low in β-glucanse activities) are used to degrade the starch to monomeric carbohydrate. The resulting glucose will be quantitated according to (Jones et al. (1977) *Plant Physiol.* 60: 379-383) with modification to a microplate format.

Example 6

Placing ODP2 Sequence Under the Control of a Tissue-Preferred Promoter

The ODP2 gene can be placed under control of an inducible expression system, as described in Zuo et al. (2000) *Plant J* 24:265-273 and in U.S. Patent Application Publication No. US 2003/0082813 A1, the entire contents of which are herein incorporated by reference. The G10-90 promoter in the XVE vector can be replaced with a tissue-preferred promoter (e.g. a pollen-, root-stem- or leaf-specific promoter). A variety of tissue-preferred promoters are well known to those of skill in the art. Because expression of a transgene is activated by the chimeric XVE gene which is controlled by a tissue-preferred promoter in this Example, the $O^{lexA}$-46 promoter controlling the ODP2 transgene is therefore tissue-preferred in an inducer-dependent manner. This means that ODP2 will be induced only in the presence of an inducer and only in the specific tissue corresponding to the tissue specific promoter. Appropriate tissues or cell types, can then be collected from the transgenic plants and used for induction of somatic embryos and regeneration of plants.

Particularly when pollen derived from transgenic plants carrying a pollen-specific promoter-XVE/$O^{lexA}$-46-ODP2 vector is used, progeny plants generated from pollen-derived somatic embryos should be haploid instead of diploid (see, e.g., Twell et al. (1989) *Mol. Gen. Genetics* 217:240-245 and Twell et al. (1990) *Development* 109:705-714 for pollen-specific promoters). In this embodiment of the invention, a transgenic plant having in its genome a ODP2 gene under the control of an inducible, pollen-specific promoter would not normally express the gene. Pollen from such a plant can be cultured in the presence of the inducer until somatic embryogenesis occurs, after which the inducer is removed and the haploid embryos are permitted to develop into haploid clones according to standard techniques.

Example 7

Generating an Apomictic Plant

Apomixis can be induced by introducing ODP2 into a plant cell in such a manner that the ODP2 gene is expressed in the appropriate tissues (e.g., nucellus tissue). This can be by means of, but is not limited to, placing the ODP2 gene under the control of a tissue-preferred promoter (e.g., a nucellus-specific promoter), an inducible promoter, or a promoter that is both inducible and tissue-preferred. Inducing expression of the ODP2 gene, e.g. in the nucellus, produces fertilization-independent embryo formation leading to an apomictic plant. This plant may then be used to establish a true-breeding plant line. Additionally, the vector utilized to transfer ODP2 into the plant cell can include any other desired heterologous gene in addition to ODP2, including but not limited to, a marker gene or a gene to confer a desirable trait upon the plant, e.g., a gene resulting in larger plants, faster growth, resistance to stress, etc. This would lead to the development of an apomictic line with the desired trait.

In a variation of the scheme, plant expression cassettes, including but not limited to monocot or dicot expression cassettes, directing ODP2 expression to the inner integument or nucellus can easily be constructed. An expression cassette directing expression of the ODP2 DNA sequences to the nucellus can be made using the barley Nuc1 promoter (Doan et al. (1996) *Plant Mol. Biol.* 2:276-284). Such an expression can be used for plant transformation. Other genes which confer desirable traits can also be included in the cassette.

It is anticipated that transgenic plants carrying the expression cassette will then be capable of producing de novo embryos from ODP2 expressing nucellar cells. In the case of maize, this is complemented by pollinating the ears to promote normal central cell fertilization and endosperm development. In another variation of this scheme, Nuc1:ODP2 transformations could be done using a fie (fertility-independent endosperm)-null genetic background which would promote both de novo embryo development and endosperm development without fertilization (Ohad et al. (1999) *The Plant Cell* 11:407-416). Upon microscopic examination of the developing embryos it will be apparent that apomixis has occurred by the presence of embryos budding off the nucellus. In yet another variation of this scheme the ODP2 DNA sequences could be delivered as described above into a homozygous zygotic-embryo-lethal genotype. Only the adventive embryos produced from somatic nucellus tissue would develop in the seed.

Example 8

Transformation and Regeneration of Maize Embryos

Immature maize embryos from greenhouse donor plants are bombarded with a plasmid containing the ODP2 sequence of the invention operably linked to a promoter. This could be a weak promoter such as nos, a tissue-specific promoter, such as globulin-1, an inducible promoter such as In2, or a strong promoter such as ubiquitin plus a plasmid containing the selectable marker gene PAT (Wohlleben et al. (1988) *Gene* 70:25-37) that confers resistance to the herbicide Bialaphos. Transformation is performed as follows.

Maize ears are harvested 8-14 days after pollination and surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560 L medium 4 days prior to bombardment in the dark. Medium 560 L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560 L with high sucrose concentration).

A plasmid vector comprising the ODP2 sequence operably linked to the selected promoter is constructed. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water, 10 μl (1 μg) DNA in TrisEDTA buffer (1 μg total), 100 μl 2.5M $CaCl_2$, 10 μl 0.1M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 μl 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are positioned 2 levels below the stooping plate for bombardment in a DuPont Helium Particle Gun. All samples receive a single shot at 650 PSI, with a total of ten aliquots taken from each tube of prepared particles/DNA. As a control, embryos are bombarded with DNA containing the PAT selectable marker as described above without the gene of invention.

Following bombardment, the embryos are kept on 560Y medium, an N6 based medium, for 2 days, then transferred to 560R selection medium, an N6 based medium containing 3 mg/liter Bialaphos, and subcultured every 2 weeks. After approximately 10 weeks of selection, bialaphos-resistant callus clones are sampled for PCR and activity of the gene of interest. In treatments containing the ODP2 gene, it is expected that growth will be stimulated and transformation frequencies increased, relative to the control. Positive lines are transferred to 288J medium, an MS based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the gene of interest.

Example 9

Ectopic Expression of Maize ODP2 to Induce Embryogenesis

Using the genotype High type II as an example, immature embryos are isolated 15 days after pollination and cultured on 560P medium for 3-5 days. At this developmental stage the embryos are too large for callus initiation under standard culture conditions (see above). Twelve hours before bombardment these embryos are transferred to high osmotic 560Y medium. Expression cassettes containing the ODP2 cDNA are then co-introduced into the scutella of these embryos along with an expression cassette containing genes encoding a screenable markers, such as green fluorescent protein (GFP) or cyan fluorescent protein (CFP) using methods well described in the art for particle gun transformations. Twelve to 24 hours following bombardment, embryos are then transferred back to 560P culture medium and incubated in the dark at 26° C. Cultures are then transferred every two weeks until transformed colonies appear. It is expected that expression of ODP2 will stimulate adventive embryo formation. This will be apparent when the cultures are compared to controls (transformed without the ODP2 cDNA). Using either inducible expression cassettes, tissue specific promoters, or promoters of varying strengths it will be possible to control the levels of expression to maximize the formation of adventive embryos. Using either non-responsive genotypes or sub-optimal culture conditions with responsive genotypes, only the transformed cells expressing the ODP2 cDNA will form embryos and regenerate plants. In this manner, ODP2-induced embryo proliferation can be used as a positive selective marker (only the cells expressing the gene will form embryos) and transformants can be recovered without a negative selective agent (i.e. bialaphos, basta, kanamycin, etc.).

Example 10

Ectopic Expression of Maize ODP2 is Sufficient to Stimulate Organogenesis/Embryogenesis and Increases Transformation Frequencies in Recalicitrant Tissues There exists only a small developmental window in which maize embryos are amenable to tissue culture growth, a prerequisite for transformation. Normally this occurs between 9-12 days after pollination when the immature embryos are between 1.0-1.5 mm in length. Older, larger embryos fail to produce embryogenic callus and thus cannot be transformed. To demonstrate that ODP2 can be used to induce embryogenesis, embryos from the maize inbred PH581, ATCC deposit PTA-4432, were isolated 17 days after pollination and used for transformation experiments. Isolated embryos were cultured on 605J medium (a medium containing both full strength MS salts (macro and micronutient) and 0.6×N6 macronutrient salts plus additional B5 micronutrients, with a mixture of SH and Eriksson's vitamin, L-proline and casamino acids, silver nitrate, 0.3 mg/l 2,4-D and 1.2 mg/l Dicamba, 2% sucrose and 0.06% glucose, solidified with agar). The embryos were incubated in the dark at 28° C.

overnight. Embryos were shot in a method similar to that in Example 8 substituting 0.6 µm gold particles for tungsten. DNA was delivered using co-transformation, as noted above. As a control, embryos were shot with a 1:1 mixture of plasmid DNA's containing a Ubiquitin driven yellow fluorescence protein (YFP) and a plasmid containing a Ubiquitin driven uidA gene (GUS). In the ODP2 treatment the embryos were bombarded with a 1:1 mixture of plasmid DNA's containing the Ubiquitin promoter driving expression of YFP (Ubi:YFP) and a plasmid containing ODP2 (SEQ ID NO: 3) driven by the maize Ubiquitin promoter (Ubi:ODP2). Each treatment contained 20 embryos. After one month of culture the embryos were observed under the dissecting microscope using epifluorescence.

As mentioned above, it is well known in the art that there is a narrow window in embryo ontogeny where embryos are culture/transformation responsive and this window occurs when embryos are in 1-2 mm in length which is typically 9-12 days after pollination. Since these embryos were taken at 17 days after pollination no multicellular colonies were expected in the control treatment. As expected, hundreds of cells transiently expressing the YFP protein were visible under a fluorescent microscope in the control treatment, and in this population of fluorescing cells, cell division was very rare. Cells transiently expressing YFP were also apparent in the ODP2 treatment. However, in the ODP2 treatment, cell division was apparent in all of the bombarded embryos with up to 50 multicellular colonies observed per embryo (data not shown). No events were observed in the control treatment while 100% of the ODP2 embryos were transformed with 5-50 events/embryo. Embryo morphology was clearly visible in many of these growing transgenic colonies.

As mentioned above ODP2 expression was sufficient to induce embryogenesis in larger and normally non-responsive embryos. In a similar manner, controlled ODP2 expression should allow transformation of other vegetative tissues such as leaves, stems, and even seed. ODP2 driven by the ubiquitin promoter was used to transform stem tissues. Transformed embryos were recovered from stem tissues (data not shown).

Example 11

Transient Expression of the ODP2 Gene Product to Induce Embryogenesis

It may be desirable to "kick start" meristem formation by transiently expressing the ODP2 gene product. This can be done by delivering ODP2 5' capped polyadenylated RNA, expression cassettes containing ODP2 DNA, or ODP2 protein. All of these molecules can be delivered using a biolistics particle gun. For example, 5' capped polyadenylated ODP2 RNA can easily be made in vitro using Ambion's mMessage mMachine kit. Following a delivery procedure outlined above, RNA is co-delivered along with DNA containing an agronomically useful expression cassette. It is expected that cells receiving ODP2 will form embryos and a large portion of these will have integrated the agronomic gene. Plants regenerated from these embryos can then be screened for the presence of the agronomic gene.

Example 12

Modifying the Regenerative Capacity of a Plant

To demonstrate that ODP2 improves the regenerative capacity of maize tissues transformants were produced in the genotype High Type II with constructs containing the ODP2 gene driven by the maize Oleosin promoter. The Oleosin promoter is highly specific and is expressed only in scutella of developing embryos. Transformants were produced using both particle gun (as described in example 4 above) and Agrobacterium (U.S. Pat. No. 5,981,840). Putative transformants were grown in the greenhouse and were completely normal in phenotype. Ears were pollinated and segregating embryos were isolated from a particle gun event at 17 DAP (days after pollination) and from Agrobacterium derived events at 24 DAP. Embryos cultured at such late stages would be expected to germinate on regeneration medium. This was observed in the wild-type segregates but germination was delayed in the transformed embryos. In addition to delayed germination, somatic embryos proliferated from the scutella of the transformed embryos (data not shown) when cultured on regeneration medium. The maize Oleosin promoter is highly expressed at these late stages of development and this result demonstrates that the maize ODP2 gene is sufficient to induce embryogenesis in a normally non-responsive tissue.

Example 13

Transient Expression of ODP2 Enhances Transformation

Parameters of the transformation protocol can be modified to insure that the increased ODP2 activity is transient. One such method involves precipitating the ODP2-containing plasmid in a manner that precludes subsequent release of the DNA (thus, transcription from the particle-bound DNA can occur, but the frequency with which its released to become integrated into the genome is greatly reduced. Such a precipitation relies on the chemical PEI, and it could be used as discussed below.

The ODP2 plasmid is precipitated onto gold particles with PEI, while the transgenic expression cassette (UBI::moPAT~GFPm::pinII) to be integrated is precipitated onto gold particles using the standard $Ca^{++}$ method. Briefly, coating gold particles with PEI is done as follows. First, the gold particles are washed. Thirty-five mg of gold particles, for example 1.0 µM in average diameter (A.S.I. #162-0010), are weighed out in a microcentrifuge tube, and 1.2 ml absolute EtOH is added and vortexed for one minute. The tube is set aside for 15 minutes at room temperature and then centrifuged at high speed using a microfuge for 15 minutes at 4° C. The supernatant is discarded and a fresh 1.2 ml aliquot of EtOH is added, vortexed for one minute, centrifuged for one minute and the supernatant again discarded (this is repeated twice). A fresh 1.2 ml aliquot of EtOH is added, and this suspension (gold particles in EtOH) can be stored at −20° C. for weeks. To coat particles with polyethylimine (PEI; Sigma #P3143), start with 250 µl of washed gold particle/EtOH, centrifuge and discard EtOH. Wash once in 100 µl ddH2O to remove residual ethanol. Add 250 µl of 0.25 mM PEI, pulse-sonicate to suspend particles and then plunge tube into dry ice/EtOH bath to flash-freeze suspension into place. Lyophilize overnight. At this point, dry, coated particles can be stored at −80° C. for at least 3 weeks. Before use, rinse particles 3 times with 250 µl aliquots of 2.5 mM HEPES buffer, ph 7.1, with 1× pulse-sonication and then quick vortex before each centrifugation. Suspend in final volume of 250 µl HEPES buffer. Aliquot 25 µl to fresh tubes before attaching DNA. To attach uncoated DNA, pulse-sonicate the particles, then add DNA's and mix by pipetting up and down a few times with a Pipetteman™. Let sit for at least 2 minutes, spin briefly (i.e. 10 seconds), remove supernatant and add 60 µl EtOH. Spot onto macrocarriers and bombard following standard protocol. The Ca$^{++}$ precipitation and bombardment follows standard protocol for the PDS-1000.

The two particle preparations are mixed together; and the mixture is bombarded into scutellar cells on the surface of immature embryos (some cells receiving only an ODP2 particle, some cells receiving only a PAT~GFP particle and some cells receiving both). PEI-mediated precipitation results in a high frequency of transiently expressing cells on the surface of the immature embryo and extremely low frequencies of recovery of stable transformants (relative to the Ca$^{++}$ method). Thus, the PEI-precipitated ODP2 cassette expresses transiently and stimulates a burst of embryogenic growth on the bombarded surface of the tissue (i.e. the scutellar surface), but this plasmid does not integrate. The PAT~GFP plasmid released from the Ca$^{++}$/gold particles integrates and expresses the selectable marker at a frequency that result in substantially improved recovery of transgenic events.

As a control treatment, PEI-precipitated particles containing a UBI::GUS::pinII (instead of ODP2) are mixed with the PAT~GFP/Ca$^{++}$ particles. Immature embryos from both treatments are moved onto culture medium containing 3 mg/l bialaphos. After 6-8 weeks, GFP+, bialaphos-resistant calli are observed in the PEI/ODP2 treatment at a much higher frequency relative to the control treatment (PEI/GUS).

The ODP2 plasmid is precipitated onto gold particles with PEI, and then introduced into scutellar cells on the surface of immature embryos, and subsequent transient expression of the ODP2 gene elicits a rapid proliferation of embryogenic growth. During this period of induced growth, the explants are treated with *Agrobacterium* using standard methods for maize (Zhao et al., U.S. Pat. No. 5,981,840), with T-DNA delivery into the cell introducing a transgenic expression cassette such as UBI::moPAT~GFPm::pinII. After co-cultivation, explants are allowed to recover on normal culture medium, and then are moved onto culture medium containing 3 mg/l bialaphos. After 6-8 weeks, GFP$^+$, bialaphos-resistant calli are observed in the PEI/ODP2 treatment at a much higher frequency relative to the control treatment (PEI/GUS).

Example 14

Transient Expression of the ODP2 Polynucleotide Product to Induce Somatic Embryogenesis It may be desirable to "kick start" somatic embryogenesis by transiently expressing the ODP2 polynucleotide product. This can be done by delivering ODP2 5' capped polyadenylated RNA, expression cassettes containing ODP2 DNA, or ODP2 protein. All of these molecules can be delivered using a biolistics particle gun. For example 5' capped polyadenylated ODP2 RNA can easily be made in vitro using Ambion's mMessage mMachine kit. Following the procedure outline above RNA is co-delivered along with DNA containing an agronomically useful expression cassette, and a marker used for selection/screening such as Ubi::moPAT~GFPm::pinII. The cells receiving the RNA will immediately form somatic embryos and a large portion of these will have integrated the agronomic gene, and these can further be validated as being transgenic clonal colonies because they will also express the PAT~GFP fusion protein (and thus will display green fluorescence under appropriate illumination). Plants regenerated from these embryos can then be screened for the presence of the agronomic gene.

Example 15

Ectopic Expression of ODP2 in Early Zygotic Embryos Increases Seed Set During Abiotic Stress Episodes During periods of abiotic stress such as during a drought episode, embryo development often is halted resulting in aborted kernels on the ear. Preventing this kernel loss will increase or maintain yield. To increase seed set during periods of abiotic stress, the ODP2 gene is cloned into an expression cassette behind an early-embryo promoter such as LEC1, and this expression cassette is cloned along with a selectable/screenable marker into an *Agrobacterium* T-DNA region. For example, the following T-DNA is constructed: RB-LEC1::ODP2::pinII/Ubi::moPAT~GFPm::pinII-LB. This T-DNA is introduced into a maize inbred using standard *Agrobacterium* transformation methods. Transgenic plants are screened for single-copy integrations, and then planted in individual pots in the greenhouse. Transgenic plants are selfed and outcrossed to wild-type plants. Plants transgenic for the ODP2 expression cassette are easily tracked (using the cosegregating marker) through either BASTA resistance or green fluorescence conferred by the PAT~GFP fusion protein. Transgenic plants are planted in the field, and subjected to various degrees of drought stress during flowering and seed-set. Under identical stress regimes, the transgenic plants have much higher numbers of developed kernels relative to wild-type (non-transgenic) plants.

Example 16

Expression of ODP2 in Double-Haploid Production

There are two necessary steps in the production of double-haploid germplasm from maize inbreds. The first is induction of embryogenesis from a haploid cell, and the second is chromosome doubling to convert the haploid to a doubled-haploid.

The ODP2 gene can be used to generate haploid plants at high frequencies (i.e. improving the efficiency of step one of the process). Various strategies for accomplishing this are described below.

A. The following expression cassettes are placed in between a single set of T-DNA borders. T-DNA cassette #1 comprises RB-loxP/gal::FLP::pinII/PG47::C1-GAL-EcR::pinII/Ubi::PAT::pinII/Ubi:frt:YFP::pinII:frt:ODP2::pinII/LEC1::Cre::pinII/loxP-LB. To use this construct, it is first transformed into a maize genotype using *Agrobacterium* methods for 2-T-DNA transformation into immature embryos (Miller et al. (2002) *Transgene Research* 11:381-96).

In addition to the T-DNA diagramed above, this method also introduces T-DNA cassette #2 containing RB-Ole::WUS2::pinII/Ubi::CFP::pinII-LB, but which integrates at an unlinked location in the genome. T-DNA cassette #2 provides a means of recovering transformed events without chemical selection and then later segregating the T-DNA cassette #2 away from #1. Standard tissue culture and regeneration methods are used.

Transgenic plants are grown until the microspores in the developing tassel are at the uninucleate stage. At this point, the tassel is excised and pretreated by wrapping in moist paper towel and incubated for 14-17 days at 8-10° C. Following pre-treatment, tassels are surface sterilized by soaking for 10 minutes in sodium hypochlorite solution (i.e. 50% Chlorox), and then rinsed twice in sterile water. The anthers are then excised from the tassel and placed on solid anther culture medium using standard media formulations developed for maize anther culture (see Petolino and Genovesi (1994) in *The Maize Handbook*, (Walbot and Freeling, eds), pages 701-704). Once the anthers are on solid medium, the inducing agent methoxifenozide is pipetted directly onto the solid medium (for example, a 10 mM stock of methoxyfenozide is diluted to 10 uM by pipetting 30 ul of the stock onto the surface of 30 ml of solid medium and allowed to equilibrate before adding plant tissue). This will induce expression of FLP recombinase in the uninucleate microspores in the anther. FLP activity would excise the YFP gene, functionally linking the strong Ubiquitin promoter with the ODP2 gene. This burst of ODP2 expression will induce embryogenesis at high frequencies in the haploid uninucleate microspores. After the embryos begin developing, the embryogenic-specific promoter LEC1 will turn on Cre expression and this recombinase will excise the entire transgene cassette. Excision of the expression cassette and the concomitant loss of ODP2 expression will permit embryo maturation and subsequent plant regeneration to occur. During embryo development stimulated by the process described above, colchicine can be added (i.e. a 0.01 to 1.0% solution) to induce chromosome doubling. Doubled haploid plants are recovered that no longer contain T-DNA cassette #2 (because it was segregated away) and only contain the RB-loxP-LB sequence left behind after excision of almost all of cassette #1.

An alternative way to accomplish the above scenario would be to place the ODP2 gene behind a promoter that is active during microspore development. For example the maize promoters PG47, Zm-POL67 and Zm-POL95 are all promoters active during microspore development. In transgenic plants containing the PG47::ODP2 expression cassette, embryo formation is initiated in the microspores of the developing tassel. An embryo-specific promoter such as LEC1 or Glb1 is then used to drive expression of the Cre gene, which excises the loxP-flanked ODP2 and Cre expression cassettes. These embryos are then capable of maturing and germinating into haploid plants, or if exposed to a doubling agent such as colchicines, double-haploid plats are generated.

Example 17

ODP2 Expression for Positive Selection

It is expected that transformants can be recovered using ODP2 expression to provide a positive selection means under reduced auxin levels or in the absence of auxins in the medium, and in the absence of herbicide or antibiotic selection.

To determine if ODP2 can be used in a positive selection scheme, transformation experiments, using any standard method including particle gun or *Agrobacterium*, can be performed. Transformants are selected on medium with normal auxin levels, or on medium with reduced or no auxin, or visually (using GFP) on medium without bialaphos. Transformation frequencies are based on numbers of embryos with one or more multicellular GFP positive cell clusters. For example, one can test this concept using two treatment variables. The first is that immature embryos are bombarded with a control plasmid (UBI:PAT~GFP) or with UBI:PAT~GFP+In2:ODP2. The second variable is that the bombarded embryos are divided onto either normal bialaphos-containing selection medium (with normal auxin levels of 2 mg/L 2,4-D), or medium with no bialaphos and reduced 2,4-D levels (0.5 mg/L). It is expected from previous studies of positive selection that on bialaphos selection the ODP2 treatment will result in higher transformation frequency than the control. It is also anticipated that the low auxin medium (0.5 mg/L 2,4-D) will result in reduced growth rates. Consistent with this, it is expected that for the control plasmid treatment (UBI:PAT~GFP), recovery of GFP-expressing (fluorescent) colonies will be reduced relative to highly effective bialaphos selection treatment. In contrast, it is expected that ODP2 expression, through its stimulation of embryogenesis, may compensate for the low auxin environment, providing a growth advantage to the transgenic colonies, and maintaining the efficiency of transformant recovery at approximately the same range as the ODP2/bialaphos-selected treatment.

On medium completely devoid of auxin, it is expected that colonies will only be observed in the ODP2 treatment. In this experiment, immature embryos are transformed with either the control plasmid (UBI:PAT~GFP) or with UBI:PAT~GFP+In2:ODP2, and then plated either onto 3.0 mg/L bialaphos, 2.0 mg/L 2,4-D medium or onto no-bialaphos, no 2,4-D medium (in this latter treatment, wild-type maize callus will not exhibit embryonic growth). Again, it is expected that expression of the ODP2 polynucleotide will increase transformation significantly over the control plasmid value on normal auxin-containing, bialaphos selection medium. Also, it is expected that no transformants will be recovered with the control plasmid on medium devoid of exogenous auxin.

Even on auxin-containing medium, the ODP2 polynucleotide in combination with GFP+ expression can be used to recover transformants without chemical selection. For example, under these conditions it is expected that the recovery of transformants will be relatively efficient, but may require more diligence than the low- or no-auxin treatments above to separate the GFP-expressing colonies from the growing callus population.

Example 18

Soybean Embryo Transformation

Soybean embryos are bombarded with a plasmid containing the ODP2 sequence operably linked to a promoter. This could be a weak promoter such as nos, a tissue-specific promoter, such as globulin-1, an inducible promoter such as In2, or a strong promoter such as ubiquitin plus a plasmid containing the selectable marker gene PAT (Wohlleben et al. (1988) Gene 70:25-37) that confers resistance to the herbicide Bialaphos. Transformation is performed as follows.

To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A Du Pont Biolistic PDS 1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the ODP2 operably linked to the promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 19

Sunflower Meristem Tissue Transformation
Prophetic Example

Sunflower meristem tissues are transformed with an expression cassette containing the ODP2 sequence operably linked to a promoter. This could be a weak promoter such as nos, a tissue-specific promoter, such as globulin-1, an inducible promoter such as In2, or a strong promoter such as ubiquitin plus a plasmid containing the selectable marker gene PAT (Wohlleben et al. (1988) *Gene* 70:25-37) that confers resistance to the herbicide Bialaphos. Transformation is performed as follows. See also European Patent Number EP 0 486233, herein incorporated by reference, and Malone-Schoneberg et al. (1994) *Plant Science* 103:199-207).

Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/16-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ODP2 gene operably linked to the promoter is introduced into *Agrobacterium* strain EHA105 via freeze-thawing as described by Holsters et al. (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for ODP2 activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of TO plants (parental generation) maturing in the greenhouse are identified by NPTII ELISA and/or by ODP2 activity analysis of leaf extracts while transgenic seeds harvested from NPTII-positive TO plants are identified by ODP2 activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374 C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374 C medium are screened for ODP2 activity using assays known in the art. After positive (i.e., for ODP2 expression) explants are identified, those shoots that fail to exhibit ODP2 activity are discarded, and every positive explant is subdivided into nodal explants. One nodal explant contains at least one potential node. The nodal segments are cultured on GBA medium for three to four days to promote the formation of auxiliary buds from each node. Then they are transferred to 374 C medium and allowed to develop for an additional four weeks. Developing buds are separated and cultured for an additional four weeks on 374 C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for ODP2 expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A polynucleotide designed for expression in a plant selected from the group consisting of:
   (a) the polynucleotide comprising SEQ ID NO:1 or 3;
   (b) the polynucleotide encoding the amino acid sequence of SEQ ID NO:2;
   (c) the polynucleotide encoding an amino acid sequence having at least 85% sequence identity to SEQ ID NO:2, wherein said polynucleotide encodes a polypeptide comprising two AP2 domains and that renders a plant cell embryogenic when expressed in the plant cell; and,
   (d) the polynucleotide comprising a full length complement of the polynucleotide of (a)-(c);
   wherein the polynucleotide is operably linked to a heterologous regulatory sequence.

2. An expression cassette comprising the polynucleotide of claim 1, wherein said heterologous regulatory sequence is a promoter that drives expression in a plant.

3. A plant comprising a heterologous polynucleotide operably linked to a promoter that drives expression in the plant, wherein said polynucleotide is selected from the group consisting of:
   (a) the polynucleotide comprising SEQ ID NO:1 or 3;
   (b) the polynucleotide encoding the amino acid sequence of SEQ ID NO:2;
   (c) the polynucleotide encoding an amino acid sequence having at least 85% sequence identity to SEQ ID NO:2, wherein said polynucleotide encodes a polypeptide comprising two AP2 domains and that renders a plant cell embryogenic when expressed in the plant cell; and,
   (d) the polynucleotide comprising a full length complement of the polynucleotide of (a)-(c).

4. The plant of claim 3, wherein said plant comprises a plant part selected from the group consisting of a cell, a seed, and a grain.

5. The plant of claim 3, wherein said promoter is a constitutive promoter, a tissue-preferred promoter, an inducible promoter, or a developmentally regulated promoter.

6. The plant of claim 3, wherein said plant is a monocot.

7. The plant of claim 6, wherein said monocot is maize, wheat, rice, barley, *sorghum*, or rye.

8. The plant of claim 3, wherein said plant is a dicot.

9. The plant of claim 3, wherein said heterologous polynucleotide is stably incorporated into the genome of the plant.

10. The plant of claim 3, wherein said plant has an increased level of a polypeptide selected from the group consisting of
    (a) the polypeptide comprising the amino acid sequence of SEQ ID NO:2; and,
    (b) the polypeptide having at least 85% sequence identity to SEQ ID NO:2, wherein the polypeptide comprises two AP2 domains and renders a plant cell embryogenic when expressed in the plant cell.

11. A method of increasing the activity of a polypeptide in a plant comprising introducing into said plant a polynucleotide selected from the group consisting of:
    (a) the polynucleotide comprising SEQ ID NO:1 or 3;
    (b) the polynucleotide encoding the amino acid sequence of SEQ ID NO:2; and,
    (c) the polynucleotide encoding an amino acid sequence having at least 85% sequence identity to SEQ ID NO:2, wherein said polynucleotide encodes a polypeptide comprising two AP2 domains and that renders a plant cell embryogenic when expressed in the plant cell, wherein the polynucleotide is operably linked to a heterologous regulatory sequence.

12. The method of claim 11, wherein said polynucleotide is transiently expressed.

13. The method of claim 11, wherein said polynucleotide is stably integrated into the genome of the plant.

14. The method of claim 11, wherein said heterologous regulatory sequence is a constitutive promoter, a tissue-preferred promoter, an inducible promoter, or a developmentally regulated promoter.

15. The method of claim 11, wherein said plant comprises a plant part selected from the group consisting of a plant cell and a seed.

16. The method of claim 11, wherein said plant is a dicot.

17. The method of claim 11, wherein said plant is a monocot.

18. The method of claim 17, wherein said monocot is maize, wheat, rice, barley, *sorghum*, or rye.

19. The expression cassette of claim 2, wherein said heterologous regulatory sequence is a constitutive promoter, a tissue-preferred promoter, an inducible promoter, or a developmentally regulated promoter.

* * * * *

SEQUENCE LISTING

```
<160> NUMBER OF SEQ ID NOS: 38

<210> SEQ ID NO 1
<211> LENGTH: 2260
<212> TYPE: DNA
<213> ORGANISM: Zea mays
<220> FEATURE:
<221> NAME/KEY: CDS
<222> LOCATION: (128)...(2260)
<220> FEATURE:
<221> NAME/KEY: misc_feature
<222> LOCATION: (0)...(0)
<223> OTHER INFORMATION: Full length nucleotide sequence of Zm-ODP2,
      including the 5' untranslated region
```

-continued

```
<400> SEQUENCE: 1
cttccctaac ctttgcactg tccaaaatgg cttcctgatc ccctcacttc ctcgaatcaa         60
tctaagaaga aactcaagcc gcaaccatta ggggcagatt aattgctgca ctttcagata        120 atcaacc atg gcc act gtg aac aac tgg ctc gct ttc tcc ctc tcc ccg         169
        Met Ala Thr Val Asn Asn Trp Leu Ala Phe Ser Leu Ser Pro
         1               5                  10 cag gag ctg ccg ccc tcc cag acg acg gac tcc aca ctc atc tcg gcc         217
Gln Glu Leu Pro Pro Ser Gln Thr Thr Asp Ser Thr Leu Ile Ser Ala
 15              20                  25                  30 gcc acc gcc gac cat gtc tcc ggc gat gtc tgc ttc aac atc ccc caa         265
Ala Thr Ala Asp His Val Ser Gly Asp Val Cys Phe Asn Ile Pro Gln
                 35                  40                  45 gat tgg agc atg agg gga tca gag ctt tcg gcg ctc gtc gcg gag ccg         313
Asp Trp Ser Met Arg Gly Ser Glu Leu Ser Ala Leu Val Ala Glu Pro
             50                  55                  60 aag ctg gag gac ttc ctc ggc ggc atc tcc ttc tcc gag cag cat cac         361
Lys Leu Glu Asp Phe Leu Gly Gly Ile Ser Phe Ser Glu Gln His His
 65                  70                  75 aag gcc aac tgc aac atg ata ccc agc act agc agc aca gtt tgc tac         409
Lys Ala Asn Cys Asn Met Ile Pro Ser Thr Ser Ser Thr Val Cys Tyr
 80                  85                  90 gcg agc tca ggt gct agc acc ggc tac cat cac cag ctg tac cac cag         457
Ala Ser Ser Gly Ala Ser Thr Gly Tyr His His Gln Leu Tyr His Gln
 95                 100                 105                 110 ccc acc agc tca gcg ctc cac ttc gcg gac tcc gta atg gtg gcc tcc         505
Pro Thr Ser Ser Ala Leu His Phe Ala Asp Ser Val Met Val Ala Ser
                115                 120                 125 tcg gcc ggt gtc cac gac ggc ggt gcc atg ctc agc gcg gcc gcc gct         553
Ser Ala Gly Val His Asp Gly Gly Ala Met Leu Ser Ala Ala Ala Ala
                130                 135                 140 aac ggt gtc gct ggc gct gcc agt gcc aac ggc ggc ggc atc ggg ctg         601
Asn Gly Val Ala Gly Ala Ala Ser Ala Asn Gly Gly Gly Ile Gly Leu
                145                 150                 155 tcc atg att aag aac tgg ctg cgg agc caa ccg gcg ccc atg cag ccg         649
Ser Met Ile Lys Asn Trp Leu Arg Ser Gln Pro Ala Pro Met Gln Pro
 160                 165                 170 agg gtg gcg gcg gct gag ggc gcg cag ggg ctc tct ttg tcc atg aac         697
Arg Val Ala Ala Ala Glu Gly Ala Gln Gly Leu Ser Leu Ser Met Asn
175                 180                 185                 190 atg gcg ggg acg acc caa ggc gct gct ggc atg cca ctt ctc gct gga         745
Met Ala Gly Thr Thr Gln Gly Ala Ala Gly Met Pro Leu Leu Ala Gly
                195                 200                 205 gag cgc gca cgg gcg ccc gag agt gta tcg acg tca gca cag ggt gga         793
Glu Arg Ala Arg Ala Pro Glu Ser Val Ser Thr Ser Ala Gln Gly Gly
                210                 215                 220 gcc gtc gtc gtc acg gcg ccg aag gag gat agc ggt ggc agc ggt gtt         841
Ala Val Val Val Thr Ala Pro Lys Glu Asp Ser Gly Gly Ser Gly Val
                225                 230                 235 gcc ggc gct cta gta gcc gtg agc acg gac acg ggt ggc agc ggc ggc         889
Ala Gly Ala Leu Val Ala Val Ser Thr Asp Thr Gly Gly Ser Gly Gly
 240                 245                 250 gcg tcg gct gac aac acg gca agg aag acg gtg gac acg ttc ggg cag         937
Ala Ser Ala Asp Asn Thr Ala Arg Lys Thr Val Asp Thr Phe Gly Gln
255                 260                 265                 270 cgc acg tcg att tac cgt ggc gtg aca agg cat aga tgg act ggg aga         985
Arg Thr Ser Ile Tyr Arg Gly Val Thr Arg His Arg Trp Thr Gly Arg
                275                 280                 285 tat gag gca cat ctt tgg gat aac agt tgc aga agg gaa ggg caa act        1033
Tyr Glu Ala His Leu Trp Asp Asn Ser Cys Arg Arg Glu Gly Gln Thr
```

```
Tyr Glu Ala His Leu Trp Asp Asn Ser Cys Arg Arg Glu Gly Gln Thr
            290                 295                 300 cgt aag ggt cgt caa gtc tat tta ggc ggc tat gat aaa gag gag aaa    1081
Arg Lys Gly Arg Gln Val Tyr Leu Gly Gly Tyr Asp Lys Glu Glu Lys
        305                 310                 315 gct gct agg gct tat gat ctt gct gct ctg aag tac tgg ggt gcc aca    1129
Ala Ala Arg Ala Tyr Asp Leu Ala Ala Leu Lys Tyr Trp Gly Ala Thr
    320                 325                 330 aca aca aca aat ttt cca gtg agt aac tac gaa aag gag ctc gag gac    1177
Thr Thr Thr Asn Phe Pro Val Ser Asn Tyr Glu Lys Glu Leu Glu Asp
335                 340                 345                 350 atg aag cac atg aca agg cag gag ttt gta gcg tct ctg aga agg aag    1225
Met Lys His Met Thr Arg Gln Glu Phe Val Ala Ser Leu Arg Arg Lys
                355                 360                 365 agc agt ggt ttc tcc aga ggt gca tcc att tac agg gga gtg act agg    1273
Ser Ser Gly Phe Ser Arg Gly Ala Ser Ile Tyr Arg Gly Val Thr Arg
            370                 375                 380 cat cac caa cat gga aga tgg caa gca cgg att gga cga gtt gca ggg    1321
His His Gln His Gly Arg Trp Gln Ala Arg Ile Gly Arg Val Ala Gly
        385                 390                 395 aac aag gat ctt tac ttg ggc acc ttc agc acc cag gag gag gca gcg    1369
Asn Lys Asp Leu Tyr Leu Gly Thr Phe Ser Thr Gln Glu Glu Ala Ala
    400                 405                 410 gag gcg tac gac atc gcg gcg atc aag ttc cgc ggc ctc aac gcc gtc    1417
Glu Ala Tyr Asp Ile Ala Ala Ile Lys Phe Arg Gly Leu Asn Ala Val
415                 420                 425                 430 acc aac ttc gac atg agc cgc tac gac gtg aag agc atc ctg gac agc    1465
Thr Asn Phe Asp Met Ser Arg Tyr Asp Val Lys Ser Ile Leu Asp Ser
                435                 440                 445 agc gcc ctc ccc atc ggc agc gcc gcc aag cgc ctc aag gag gcc gag    1513
Ser Ala Leu Pro Ile Gly Ser Ala Ala Lys Arg Leu Lys Glu Ala Glu
            450                 455                 460 gcc gca gcg tcc gcg cag cac cac cac gcc ggc gtg gtg agc tac gac    1561
Ala Ala Ala Ser Ala Gln His His His Ala Gly Val Val Ser Tyr Asp
        465                 470                 475 gtc ggc cgc atc gcc tcg cag ctc ggc gac ggc gga gcc ctg gcg gcg    1609
Val Gly Arg Ile Ala Ser Gln Leu Gly Asp Gly Gly Ala Leu Ala Ala
    480                 485                 490 gcg tac ggc gcg cac tac cac ggc gcc gcc tgg ccc acc atc gcg ttc    1657
Ala Tyr Gly Ala His Tyr His Gly Ala Ala Trp Pro Thr Ile Ala Phe
495                 500                 505                 510 cag ccg ggc gcc gcc agc aca ggc ctg tac cac ccg tac gcg cag cag    1705
Gln Pro Gly Ala Ala Ser Thr Gly Leu Tyr His Pro Tyr Ala Gln Gln
                515                 520                 525 cca atg cgc ggc ggc ggg tgg tgc aag cag gag cag gac cac gcg gtg    1753
Pro Met Arg Gly Gly Gly Trp Cys Lys Gln Glu Gln Asp His Ala Val
            530                 535                 540 atc gcg gcc gcg cac agc ctg cag gac ctc cac cac ctg aac ctg ggc    1801
Ile Ala Ala Ala His Ser Leu Gln Asp Leu His His Leu Asn Leu Gly
        545                 550                 555 gcg gcc ggc gcg cac gac ttt ttc tcg gca ggg cag cag gcc gcc gcc    1849
Ala Ala Gly Ala His Asp Phe Phe Ser Ala Gly Gln Gln Ala Ala Ala
    560                 565                 570 gct gcg atg cac ggc ctg ggt agc atc gac agt gcg tcg ctc gag cac    1897
Ala Ala Met His Gly Leu Gly Ser Ile Asp Ser Ala Ser Leu Glu His
575                 580                 585                 590 agc acc ggc tcc aac tcc gtc gtc tac aac ggc ggg gtc ggc gac agc    1945
Ser Thr Gly Ser Asn Ser Val Val Tyr Asn Gly Gly Val Gly Asp Ser
                595                 600                 605
```

```
aac  ggc  gcc  agc  gcc  gtc  ggc  ggc  agt  ggc  ggt  ggc  tac  atg  atg  ccg    1993
Asn  Gly  Ala  Ser  Ala  Val  Gly  Gly  Ser  Gly  Gly  Gly  Tyr  Met  Met  Pro
              610                      615                      620 atg  agc  gct  gcc  gga  gca  acc  act  aca  tcg  gca  atg  gtg  agc  cac  gag    2041
Met  Ser  Ala  Ala  Gly  Ala  Thr  Thr  Thr  Ser  Ala  Met  Val  Ser  His  Glu
         625                      630                      635 cag  gtg  cat  gca  cgg  gcc  tac  gac  gaa  gcc  aag  cag  gct  gct  cag  atg    2089
Gln  Val  His  Ala  Arg  Ala  Tyr  Asp  Glu  Ala  Lys  Gln  Ala  Ala  Gln  Met
              640                      645                      650 ggg  tac  gag  agc  tac  ctg  gtg  aac  gcg  gag  aac  aat  ggt  ggc  gga  agg    2137
Gly  Tyr  Glu  Ser  Tyr  Leu  Val  Asn  Ala  Glu  Asn  Asn  Gly  Gly  Gly  Arg
655                      660                      665                      670 atg  tct  gca  tgg  ggg  act  gtc  gtg  tct  gca  gcc  gcg  gca  gca  gca        2185
Met  Ser  Ala  Trp  Gly  Thr  Val  Val  Ser  Ala  Ala  Ala  Ala  Ala  Ala
                   675                      680                      685 agc  agc  aac  gac  aac  atg  gcc  gcc  gac  gtc  ggc  cat  ggc  ggc  gcg  cag    2233
Ser  Ser  Asn  Asp  Asn  Met  Ala  Ala  Asp  Val  Gly  His  Gly  Gly  Ala  Gln
              690                      695                      700 ctc  ttc  agt  gtc  tgg  aac  gac  act  taa                                      2260
Leu  Phe  Ser  Val  Trp  Asn  Asp  Thr
              705                      710

<210> SEQ ID NO 2
<211> LENGTH: 710
<212> TYPE: PRT
<213> ORGANISM: Zea mays

<400> SEQUENCE: 2

Met Ala Thr Val Asn Asn Trp Leu Ala Phe Ser Leu Ser Pro Gln Glu
 1               5                  10                  15

Leu Pro Pro Ser Gln Thr Thr Asp Ser Thr Leu Ile Ser Ala Ala Thr
             20                  25                  30

Ala Asp His Val Ser Gly Asp Val Cys Phe Asn Ile Pro Gln Asp Trp
         35                  40                  45

Ser Met Arg Gly Ser Glu Leu Ser Ala Leu Val Ala Glu Pro Lys Leu
     50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                 85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Asn Gly
    130                 135                 140

Val Ala Gly Ala Ala Ser Ala Asn Gly Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Gly Ser Gly Val Ala Gly
```

```
            225                 230                 235                 240
Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
                260                 265                 270

Ser Ile Tyr Arg Gly Val Thr Arg His Arg Trp Thr Gly Arg Tyr Glu
                275                 280                 285

Ala His Leu Trp Asp Asn Ser Cys Arg Arg Glu Gly Gln Thr Arg Lys
                290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
                340                 345                 350

His Met Thr Arg Gln Glu Phe Val Ala Ser Leu Arg Arg Lys Ser Ser
                355                 360                 365

Gly Phe Ser Arg Gly Ala Ser Ile Tyr Arg Gly Val Thr Arg His His
                370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
                420                 425                 430

Phe Asp Met Ser Arg Tyr Asp Val Lys Ser Ile Leu Asp Ser Ser Ala
                435                 440                 445

Leu Pro Ile Gly Ser Ala Ala Lys Arg Leu Lys Glu Ala Glu Ala Ala
                450                 455                 460

Ala Ser Ala Gln His His His Ala Gly Val Val Ser Tyr Asp Val Gly
465                 470                 475                 480

Arg Ile Ala Ser Gln Leu Gly Asp Gly Ala Leu Ala Ala Ala Tyr
                485                 490                 495

Gly Ala His Tyr His Gly Ala Ala Trp Pro Thr Ile Ala Phe Gln Pro
                500                 505                 510

Gly Ala Ala Ser Thr Gly Leu Tyr His Pro Tyr Ala Gln Gln Pro Met
                515                 520                 525

Arg Gly Gly Gly Trp Cys Lys Gln Glu Gln Asp His Ala Val Ile Ala
                530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Ala Ala Ala Ala Ala
                565                 570                 575

Met His Gly Leu Gly Ser Ile Asp Ser Ala Ser Leu Glu His Ser Thr
                580                 585                 590

Gly Ser Asn Ser Val Val Tyr Asn Gly Gly Val Gly Asp Ser Asn Gly
                595                 600                 605

Ala Ser Ala Val Gly Gly Ser Gly Gly Gly Tyr Met Met Pro Met Ser
                610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
                645                 650                 655
```

```
Glu Ser Tyr Leu Val Asn Ala Glu Asn Asn Gly Gly Gly Arg Met Ser
            660                 665                 670

Ala Trp Gly Thr Val Val Ser Ala Ala Ala Ala Ala Ala Ser Ser
        675                 680                 685

Asn Asp Asn Met Ala Ala Asp Val Gly His Gly Gly Ala Gln Leu Phe
    690                 695                 700

Ser Val Trp Asn Asp Thr
705                 710

<210> SEQ ID NO 3
<211> LENGTH: 2133
<212> TYPE: DNA
<213> ORGANISM: Zea mays
<220> FEATURE:
<221> NAME/KEY: CDS
<222> LOCATION: (1)...(2133)
<220> FEATURE:
<221> NAME/KEY: misc_feature
<222> LOCATION: (0)...(0)
<223> OTHER INFORMATION: Open reading frame of Zm-ODP2

<400> SEQUENCE: 3 atg gcc act gtg aac aac tgg ctc gct ttc tcc ctc tcc ccg cag gag      48
Met Ala Thr Val Asn Asn Trp Leu Ala Phe Ser Leu Ser Pro Gln Glu
1               5                   10                  15 ctg ccg ccc tcc cag acg acg gac tcc aca ctc atc tcg gcc gcc acc      96
Leu Pro Pro Ser Gln Thr Thr Asp Ser Thr Leu Ile Ser Ala Ala Thr
                20                  25                  30 gcc gac cat gtc tcc ggc gat gtc tgc ttc aac atc ccc caa gat tgg     144
Ala Asp His Val Ser Gly Asp Val Cys Phe Asn Ile Pro Gln Asp Trp
            35                  40                  45 agc atg agg gga tca gag ctt tcg gcg ctc gtc gcg gag ccg aag ctg     192
Ser Met Arg Gly Ser Glu Leu Ser Ala Leu Val Ala Glu Pro Lys Leu
        50                  55                  60 gag gac ttc ctc ggc ggc atc tcc ttc tcc gag cag cat cac aag gcc     240
Glu Asp Phe Leu Gly Gly Ile Ser Phe Ser Glu Gln His His Lys Ala
65                  70                  75                  80 aac tgc aac atg ata ccc agc act agc agc aca gtt tgc tac gcg agc     288
Asn Cys Asn Met Ile Pro Ser Thr Ser Ser Thr Val Cys Tyr Ala Ser
                85                  90                  95 tca ggt gct agc acc ggc tac cat cac cag ctg tac cac cag ccc acc     336
Ser Gly Ala Ser Thr Gly Tyr His His Gln Leu Tyr His Gln Pro Thr
            100                 105                 110 agc tca gcg ctc cac ttc gcg gac tcc gta atg gtg gcc tcc tcg gcc     384
Ser Ser Ala Leu His Phe Ala Asp Ser Val Met Val Ala Ser Ser Ala
        115                 120                 125 ggt gtc cac gac ggc ggt gcc atg ctc agc gcg gcc gcc gct aac ggt     432
Gly Val His Asp Gly Gly Ala Met Leu Ser Ala Ala Ala Ala Asn Gly
130                 135                 140 gtc gct ggc gct gcc agt gcc aac ggc ggc ggc atc ggg ctg tcc atg     480
Val Ala Gly Ala Ala Ser Ala Asn Gly Gly Gly Ile Gly Leu Ser Met
145                 150                 155                 160 att aag aac tgg ctg cgg agc caa ccg gcg ccc atg cag ccg agg gtg     528
Ile Lys Asn Trp Leu Arg Ser Gln Pro Ala Pro Met Gln Pro Arg Val
                165                 170                 175 gcg gcg gct gag ggc gcg cag ggg ctc tct ttg tcc atg aac atg gcg     576
Ala Ala Ala Glu Gly Ala Gln Gly Leu Ser Leu Ser Met Asn Met Ala
            180                 185                 190 ggg acg acc caa ggc gct gct ggc atg cca ctt ctc gct gga gag cgc     624
Gly Thr Thr Gln Gly Ala Ala Gly Met Pro Leu Leu Ala Gly Glu Arg
        195                 200                 205
```

-continued

| | |
|---|---|
| gca cgg gcg ccc gag agt gta tcg acg tca gca cag ggt gga gcc gtc<br>Ala Arg Ala Pro Glu Ser Val Ser Thr Ser Ala Gln Gly Gly Ala Val<br>210                         215                   220 | 672 |
| gtc gtc acg gcg ccg aag gag gat agc ggt ggc agc ggt gtt gcc ggc<br>Val Val Thr Ala Pro Lys Glu Asp Ser Gly Gly Ser Gly Val Ala Gly<br>225                      230                   235                 240 | 720 |
| gct cta gta gcc gtg agc acg gac acg ggt ggc agc ggc ggc gcg tcg<br>Ala Leu Val Ala Val Ser Thr Asp Thr Gly Gly Ser Gly Gly Ala Ser<br>                   245                   250                 255 | 768 |
| gct gac aac acg gca agg aag acg gtg gac acg ttc ggg cag cgc acg<br>Ala Asp Asn Thr Ala Arg Lys Thr Val Asp Thr Phe Gly Gln Arg Thr<br>            260                   265                 270 | 816 |
| tcg att tac cgt ggc gtg aca agg cat aga tgg act ggg aga tat gag<br>Ser Ile Tyr Arg Gly Val Thr Arg His Arg Trp Thr Gly Arg Tyr Glu<br>         275                   280                 285 | 864 |
| gca cat ctt tgg gat aac agt tgc aga agg gaa ggg caa act cgt aag<br>Ala His Leu Trp Asp Asn Ser Cys Arg Arg Glu Gly Gln Thr Arg Lys<br>290                        295                   300 | 912 |
| ggt cgt caa gtc tat tta ggt ggc tat gat aaa gag gag aaa gct gct<br>Gly Arg Gln Val Tyr Leu Gly Gly Tyr Asp Lys Glu Glu Lys Ala Ala<br>305                        310                   315                 320 | 960 |
| agg gct tat gat ctt gct gct ctg aag tac tgg ggt gcc aca aca aca<br>Arg Ala Tyr Asp Leu Ala Ala Leu Lys Tyr Trp Gly Ala Thr Thr Thr<br>                   325                   330                 335 | 1008 |
| aca aat ttt cca gtg agt aac tac gaa aag gag ctc gag gac atg aag<br>Thr Asn Phe Pro Val Ser Asn Tyr Glu Lys Glu Leu Glu Asp Met Lys<br>            340                   345                 350 | 1056 |
| cac atg aca agg cag gag ttt gta gcg tct ctg aga agg aag agc agt<br>His Met Thr Arg Gln Glu Phe Val Ala Ser Leu Arg Arg Lys Ser Ser<br>         355                   360                 365 | 1104 |
| ggt ttc tcc aga ggt gca tcc att tac agg gga gtg act agg cat cac<br>Gly Phe Ser Arg Gly Ala Ser Ile Tyr Arg Gly Val Thr Arg His His<br>370                        375                   380 | 1152 |
| caa cat gga aga tgg caa gca cgg att gga cga gtt gca ggg aac aag<br>Gln His Gly Arg Trp Gln Ala Arg Ile Gly Arg Val Ala Gly Asn Lys<br>385                        390                   395                 400 | 1200 |
| gat ctt tac ttg ggc acc ttc agc acc cag gag gag gca gcg gag gcg<br>Asp Leu Tyr Leu Gly Thr Phe Ser Thr Gln Glu Glu Ala Ala Glu Ala<br>                   405                   410                 415 | 1248 |
| tac gac atc gcg gcg atc aag ttc cgc ggc ctc aac gcc gtc acc aac<br>Tyr Asp Ile Ala Ala Ile Lys Phe Arg Gly Leu Asn Ala Val Thr Asn<br>            420                   425                 430 | 1296 |
| ttc gac atg agc cgc tac gac gtg aag agc atc ctg gac agc agc gcc<br>Phe Asp Met Ser Arg Tyr Asp Val Lys Ser Ile Leu Asp Ser Ser Ala<br>         435                   440                 445 | 1344 |
| ctc ccc atc ggc agc gcc gcc aag cgc ctc aag gag gcc gag gcc gca<br>Leu Pro Ile Gly Ser Ala Ala Lys Arg Leu Lys Glu Ala Glu Ala Ala<br>450                        455                   460 | 1392 |
| gcg tcc gcg cag cac cac cac gcc ggc gtg gtg agc tac gac gtc ggc<br>Ala Ser Ala Gln His His His Ala Gly Val Val Ser Tyr Asp Val Gly<br>465                        470                   475                 480 | 1440 |
| cgc atc gcc tcg cag ctc ggc gac ggc gga gcc ctg gcg gcg gcg tac<br>Arg Ile Ala Ser Gln Leu Gly Asp Gly Gly Ala Leu Ala Ala Ala Tyr<br>                   485                   490                 495 | 1488 |
| ggc gcg cac tac cac ggc gcc gcc tgg ccg acc atc gcg ttc cag ccg<br>Gly Ala His Tyr His Gly Ala Ala Trp Pro Thr Ile Ala Phe Gln Pro<br>            500                   505                 510 | 1536 |
| ggc gcc gcc agc aca ggc ctg tac cac ccg tac gcg cag cag cca atg<br>Gly Ala Ala Ser Thr Gly Leu Tyr His Pro Tyr Ala Gln Gln Pro Met | 1584 |

```
                515                 520                 525
cgc ggc ggc ggg tgg tgc aag cag gag cag gac cac gcg gtg atc gcg      1632
Arg Gly Gly Gly Trp Cys Lys Gln Glu Gln Asp His Ala Val Ile Ala
            530                 535                 540 gcg gcg cac agc ctg cag gac ctc cac cac ctg aac ctg ggc gcg gcc      1680
Ala Ala His Ser Leu Gln Asp Leu His His Leu Asn Leu Gly Ala Ala
545                 550                 555                 560 ggc gcg cac gac ttt ttc tcg gca ggg cag cag gcc gcc gcc gct gcg      1728
Gly Ala His Asp Phe Phe Ser Ala Gly Gln Gln Ala Ala Ala Ala Ala
                565                 570                 575 atg cac ggc ctg ggt agc atc gac agt gcg tcg ctc gag cac agc acc      1776
Met His Gly Leu Gly Ser Ile Asp Ser Ala Ser Leu Glu His Ser Thr
            580                 585                 590 ggc tcc aac tcc gtc gtc tac aac ggc ggg gtc ggc gac agc aac ggc      1824
Gly Ser Asn Ser Val Val Tyr Asn Gly Gly Val Gly Asp Ser Asn Gly
            595                 600                 605 gcc agc gcc gtc ggc ggc agt ggc ggt ggc tac atg atg ccg atg agc      1872
Ala Ser Ala Val Gly Gly Ser Gly Gly Gly Tyr Met Met Pro Met Ser
610                 615                 620 gct gcc gga gca acc act aca tcg gca atg gtg agc cac gag cag gtg      1920
Ala Ala Gly Ala Thr Thr Thr Ser Ala Met Val Ser His Glu Gln Val
625                 630                 635                 640 cat gca cgg gcc tac gac gaa gcc aag cag gct gct cag atg ggg tac      1968
His Ala Arg Ala Tyr Asp Glu Ala Lys Gln Ala Ala Gln Met Gly Tyr
                645                 650                 655 gag agc tac ctg gtg aac gcg gag aac aat ggt ggc gga agg atg tct      2016
Glu Ser Tyr Leu Val Asn Ala Glu Asn Asn Gly Gly Gly Arg Met Ser
            660                 665                 670 gca tgg ggg act gtc gtg tct gca gcc gcg gca gca gca agc agc           2064
Ala Trp Gly Thr Val Val Ser Ala Ala Ala Ala Ala Ala Ser Ser
            675                 680                 685 aac gac aac atg gcc gcc gac gtc ggc cat ggc ggc gcg cag ctc ttc      2112
Asn Asp Asn Met Ala Ala Asp Val Gly His Gly Gly Ala Gln Leu Phe
690                 695                 700 agt gtc tgg aac gac act taa                                           2133
Ser Val Trp Asn Asp Thr
705                 710

<210> SEQ ID NO 4
<211> LENGTH: 2392
<212> TYPE: DNA
<213> ORGANISM: Zea mays
<220> FEATURE:
<221> NAME/KEY: misc_feature
<222> LOCATION: (0)...(0)
<223> OTHER INFORMATION: ZM-ODP2 cDNA insert from EST clone cpflc.pk009.
      f4

<400> SEQUENCE: 4
cttccctaac ctttgcactg tccaaaatgg cttcctgatc ccctcacttc ctcgaatcaa       60
tctaagaaga aactcaagcc gcaaccatta ggggcagatt aattgctgca ctttcagata      120
atcaaccatg ccactgtgta caactggct cgctttctcc ctctcccgc aggagctgcc       180 gccctcccag acgacggact ccacactcat ctcggccgcc accgcgacc atgtctccgg      240 cgatgtctgc ttcaacatcc cccaagattg gagcatgagg ggatcagagc tttcggcgct      300
cgtcgcggag ccgaagctgg aggacttcct cggcggcatc tccttctccg agcagcatca      360
caaggccaac tgcaacatga tacccagcac tagcagcaca gtttgctacg cgagctcagg      420
tgctagcacc ggctaccatc accagctgta ccaccagccc accagctcag cgctccactt      480
```

```
cgcggactcc gtaatggtgg cctcctcggc cggtgtccac gacggcggtg ccatgctcag      540
cgcggccgcc gctaacggtg tcgctggcgc tgccagtgcc aacggcggcg catcgggct      600
gtccatgatt aagaactggc tgcggagcca accggcgccc atgcagccga gggtggcggc      660
ggctgagggc gcgcaggggc tctctttgtc catgaacatg gcggggacga cccaaggcgc      720
tgctggcatg ccacttctcg ctggagagcg cgcacgggcg cccgagagtg tatcgacgtc      780
agcacagggt ggagccgtcg tcgtcacggc gccgaaggag gatagcggtg gcagcggtgt      840
tgccggcgct ctagtagccg tgagcacgga cacgggtggc agcggcggcg cgtcggctga      900
caacacggca aggaagacgg tggacacgtt cgggcagcgc acgtcgattt accgtggcgt      960
gacaaggcat agatggactg ggagatatga ggcacatctt tgggataaca gttgcagaag     1020
ggaagggcaa actcgtaagg gtcgtcaagt ctatttaggt ggctatgata agaggagaa     1080
agctgctagg gcttatgatc ttgctgctct gaagtactgg ggtgccacaa caacaacaaa     1140
tttccagtg agtaactacg aaaaggagct cgaggacatg aagcacatga caaggcagga     1200
gtttgtagcg tctctgagaa ggaagagcag tggtttctcc agaggtgcat ccatttacag     1260
gggagtgact aggcatcacc aacatggaag atggcaagca cggattggac gagttgcagg     1320
gaacaaggat ctttacttgg gcaccttcag cacccaggag gaggcagcgg aggcgtacga     1380
catcgcggcg atcaagttcc gcggcctcaa cgccgtcacc aacttcgaca tgagccgcta     1440
cgacgtgaag agcatcctgg acagcagcgc cctccccatc ggcagcgccg ccaagcgcct     1500
caaggaggcc gaggccgcag cgtccgcgca gcaccaccac gccggcgtgg tgagctacga     1560
cgtcggccgc atcgcctcgc agctcggcga cggcggagcc ctggcggcgg cgtacgcgc     1620
gcactaccac ggcgccgcct ggccgaccat cgcgttccag ccgggcgccg ccagcacagg     1680
cctgtaccac ccgtacgcgc agcagccaat gcgcggcggc gggtggtgca agcaggagca     1740
ggaccacgcg gtgatcgcgg ccgcgcacag cctgcaggac ctccaccacc tgaacctggg     1800
cacggccggc gcgcacgact ttttctcggc ggtggctaca tgatgccgat gagcgctgcc     1860
ggagcgacca ctacatcggc aatggtgagc cacgagcaga tgcatgcacg ggcctacgac     1920
gaagccaagc aggctgctca gatggggtac gagagctacc tggtgaacgc ggagaacaat     1980
ggtggcggaa ggatgtctgc atgggggact gtcgtgtctg cagccgcggc ggcagcagca     2040
agcagcaacg acaacatggc cgccgacgtc ggccatggcg gcgcgcagct cttcagtgtc     2100
tggaacgaca cttaagctac gcgtacgtgc cggcctggct ctccgaattc gaaccgatcg     2160
atgcgtcgta aaaccgtaca ctgacataag taacaacact tagggttctt catggagagg     2220
tggccagtaa gttgttactt gtcatatgtt ttaagttctc aatttgtagc tggaaggaaa     2280
gctagggttt cttctgaaaa aaaaaaaaaa aaaaaaaaaa aaaaaaaaaa aaaaaaaaaa     2340
aaaaaaaaaa aaaaaaaaaa aaaaaaaaaa aaaaaaaaaa aaaaaaaaaa aa            2392
```

<210> SEQ ID NO 5
<211> LENGTH: 224
<212> TYPE: DNA
<213> ORGANISM: Zea mays
<220> FEATURE:
<221> NAME/KEY: misc_feature
<222> LOCATION: (0)...(0)
<223> OTHER INFORMATION: EST clone cpclc.pk005.c19

<400> SEQUENCE: 5

```
ccgccagcac aggcctgtac cacccgtacg cgcagcagcc aatgcgcggc ggcgggtggt       60
gcaagcagga gcaggaccac gcggtgatcg cggccgcgca cagcctgcag gacctccacc      120
```

```
acctgaacct gggcacggcc ggcgcgcacg acttttttctc ggcagggcag caggccgccg    180
ccgccgccgc gatgcacggc ctgggtagca ttgacagtgc gtcg                      224
```

<210> SEQ ID NO 6
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 97.1% seq id to
      SEQ ID NO:1 (Zm-ODP2). The ORF encodes
      the aa seq set forth in SEQ ID NO:2.
<220> FEATURE:
<221> NAME/KEY: CDS
<222> LOCATION: (1)...(2133)

<400> SEQUENCE: 6

```
atg gcc act gtg aac aac tgg ctc gct ttc tcc ctc tcc ccg cag gag     48
Met Ala Thr Val Asn Asn Trp Leu Ala Phe Ser Leu Ser Pro Gln Glu
1               5                   10                  15 ctg ccg ccc tcc cag acg acg gac tcc aca ctc atc tcg gcc gcg acg     96
Leu Pro Pro Ser Gln Thr Thr Asp Ser Thr Leu Ile Ser Ala Ala Thr
            20                  25                  30 gcc gac cat gtc agc ggc gat gtc tgc ttc aac atc ccc caa gat tgg    144
Ala Asp His Val Ser Gly Asp Val Cys Phe Asn Ile Pro Gln Asp Trp
        35                  40                  45 agc atg agg gga tca gag ctt tcg gcg ctg gtc gcg gag ccg aag ctg    192
Ser Met Arg Gly Ser Glu Leu Ser Ala Leu Val Ala Glu Pro Lys Leu
    50                  55                  60 gag gac ttc ctc ggc ggc atc agc ttt tcc gag cag cat cat aag gcc    240
Glu Asp Phe Leu Gly Gly Ile Ser Phe Ser Glu Gln His His Lys Ala
65                  70                  75                  80 aac tgc aac atg ata ccc agc act agc agc aca gtt tgc tac gcg agc    288
Asn Cys Asn Met Ile Pro Ser Thr Ser Ser Thr Val Cys Tyr Ala Ser
                85                  90                  95 tca ggt gct agc acc ggc tac cat cac cag ctg tac cat cag ccc acc    336
Ser Gly Ala Ser Thr Gly Tyr His His Gln Leu Tyr His Gln Pro Thr
            100                 105                 110 agc tca gcg ctc cac ttc gcg gac tcc gtt atg gtg gcg tcc tcg gcc    384
Ser Ser Ala Leu His Phe Ala Asp Ser Val Met Val Ala Ser Ser Ala
        115                 120                 125 ggt gtc cac gac ggc ggt gcc atg ctc agc gcg gcc gcc gct aac ggt    432
Gly Val His Asp Gly Gly Ala Met Leu Ser Ala Ala Ala Ala Asn Gly
    130                 135                 140 gtc gct ggc gca gcg agt gcc aac ggc ggc ggc atc ggg ctc tcc atg    480
Val Ala Gly Ala Ala Ser Ala Asn Gly Gly Gly Ile Gly Leu Ser Met
145                 150                 155                 160 att aag aac tgg ctg cgg agc caa ccg gcg ccc atg cag ccg agg gtg    528
Ile Lys Asn Trp Leu Arg Ser Gln Pro Ala Pro Met Gln Pro Arg Val
                165                 170                 175 gcg gcg gct gag ggc gcg cag ggg ctc tct ctc tcc atg aac atg gcg    576
Ala Ala Ala Glu Gly Ala Gln Gly Leu Ser Leu Ser Met Asn Met Ala
            180                 185                 190 ggg acg acc caa ggc gct gct ggc atg cca ctt ctc gct gga gag cgc    624
Gly Thr Thr Gln Gly Ala Ala Gly Met Pro Leu Leu Ala Gly Glu Arg
        195                 200                 205 gca cgg gcg ccc gag agt gta tcg acg tca gca cag ggt gga gcc gtc    672
Ala Arg Ala Pro Glu Ser Val Ser Thr Ser Ala Gln Gly Gly Ala Val
    210                 215                 220 gtc gtc acg gcc ccg aag gag gat agc ggt ggc agc ggt gtt gcc ggc    720
```

```
                Val Val Thr Ala Pro Lys Glu Asp Ser Gly Ser Gly Val Ala Gly
                225                 230                 235                 240 gct cta gta gcc gtg agc acg gac acg ggt ggc agc ggc ggc gcg tcg                768
Ala Leu Val Ala Val Ser Thr Asp Thr Gly Gly Ser Gly Gly Ala Ser
                        245                 250                 255 gct gac aac acg gca agg aag acg gtg gac acg ttc ggg cag cgc acg                816
Ala Asp Asn Thr Ala Arg Lys Thr Val Asp Thr Phe Gly Gln Arg Thr
                260                 265                 270 tcg att tac cgt ggg gtc aca agg cat aga tgg aca ggg aga tac gag                864
Ser Ile Tyr Arg Gly Val Thr Arg His Arg Trp Thr Gly Arg Tyr Glu
            275                 280                 285 gca cat ctt tgg gat aac agt tgc aga agg gaa ggg caa act cgt aag                912
Ala His Leu Trp Asp Asn Ser Cys Arg Arg Glu Gly Gln Thr Arg Lys
        290                 295                 300 ggt cgt caa gtc tat tta ggt ggc tat gat aaa gag gag aaa gct gct                960
Gly Arg Gln Val Tyr Leu Gly Gly Tyr Asp Lys Glu Glu Lys Ala Ala
305                 310                 315                 320 agg gct tat gat ctt gct gct ctg aag tac tgg gga gcc aca aca aca                1008
Arg Ala Tyr Asp Leu Ala Ala Leu Lys Tyr Trp Gly Ala Thr Thr Thr
                        325                 330                 335 aca aat ttt cca gtg tcc aac tac gaa aag gag ctc gag gac atg aag                1056
Thr Asn Phe Pro Val Ser Asn Tyr Glu Lys Glu Leu Glu Asp Met Lys
                340                 345                 350 cat atg aca agg cag gag ttt gta gcg tct ctg aga agg aaa agc agt                1104
His Met Thr Arg Gln Glu Phe Val Ala Ser Leu Arg Arg Lys Ser Ser
            355                 360                 365 gga ttc tcc agg ggt gca agc att tac agg gga gtg act agg cat cac                1152
Gly Phe Ser Arg Gly Ala Ser Ile Tyr Arg Gly Val Thr Arg His His
        370                 375                 380 cag cat gga aga tgg caa gca cgg att gga cga gtt gca ggg aac aag                1200
Gln His Gly Arg Trp Gln Ala Arg Ile Gly Arg Val Ala Gly Asn Lys
385                 390                 395                 400 gat ctt tat ttg ggc acc ttt agc acc cag gaa gag gca gcg gag gcg                1248
Asp Leu Tyr Leu Gly Thr Phe Ser Thr Gln Glu Glu Ala Ala Glu Ala
                        405                 410                 415 tac gac atc gcg gcg atc aag ttc cgc ggc ctc aac gcc gtc acc aac                1296
Tyr Asp Ile Ala Ala Ile Lys Phe Arg Gly Leu Asn Ala Val Thr Asn
                420                 425                 430 ttc gac atg agc cgc tac gac gtg aag agc att ctg gac agc agc gcc                1344
Phe Asp Met Ser Arg Tyr Asp Val Lys Ser Ile Leu Asp Ser Ser Ala
            435                 440                 445 ctc ccc att ggc agc gcg gcc aaa cgc ctc aag gag gcc gag gcc gca                1392
Leu Pro Ile Gly Ser Ala Ala Lys Arg Leu Lys Glu Ala Glu Ala Ala
        450                 455                 460 gcg tcc gcg cag cac cac cac gcc ggc gtg gtg agc tac gac gtc ggc                1440
Ala Ser Ala Gln His His His Ala Gly Val Val Ser Tyr Asp Val Gly
465                 470                 475                 480 cgc atc gcc tcg cag ctc ggc gac ggg gga gcc ctg gcg gcg gcg tac                1488
Arg Ile Ala Ser Gln Leu Gly Asp Gly Gly Ala Leu Ala Ala Ala Tyr
                        485                 490                 495 ggc gcg cac tac cac ggc gcc gcc tgg ccg acc atc gcc ttc cag ccc                1536
Gly Ala His Tyr His Gly Ala Ala Trp Pro Thr Ile Ala Phe Gln Pro
                500                 505                 510 ggc gcc gcc agc aca ggc ctg tac cac ccg tat gcg cag cag cca atg                1584
Gly Ala Ala Ser Thr Gly Leu Tyr His Pro Tyr Ala Gln Gln Pro Met
            515                 520                 525 cgc ggc ggc ggg tgg tgc aag cag gag cag gac cac gcg gtc atc gcg                1632
Arg Gly Gly Gly Trp Cys Lys Gln Glu Gln Asp His Ala Val Ile Ala
        530                 535                 540
```

```
gcc gcg cac agc ctg cag gac ctc cac cat ctg aac ctg ggc gcg gcc      1680
Ala Ala His Ser Leu Gln Asp Leu His His Leu Asn Leu Gly Ala Ala
545                 550                 555                 560 ggc gcg cac gac ttt ttc agc gca ggg cag cag gcc gcc gcc gct gcg      1728
Gly Ala His Asp Phe Phe Ser Ala Gly Gln Gln Ala Ala Ala Ala Ala
                565                 570                 575 atg cac ggc ctg gga agc atc gac agt gcg tcg ctc gag cac agc acc      1776
Met His Gly Leu Gly Ser Ile Asp Ser Ala Ser Leu Glu His Ser Thr
                    580                 585                 590 ggc tcc aac agc gtc gtc tac aac ggc ggg gtc ggc gac agc aac ggc      1824
Gly Ser Asn Ser Val Val Tyr Asn Gly Gly Val Gly Asp Ser Asn Gly
                595                 600                 605 gcc agc gcc gtc ggc ggc agt ggc ggt ggc tac atg atg ccg atg agc      1872
Ala Ser Ala Val Gly Gly Ser Gly Gly Gly Tyr Met Met Pro Met Ser
610                 615                 620 gct gcc gga gca acc act act tcg gca atg gtg agc cac gag cag gtg      1920
Ala Ala Gly Ala Thr Thr Thr Ser Ala Met Val Ser His Glu Gln Val
625                 630                 635                 640 cat gca cgg gcc tac gat gaa gcc aag cag gct gct cag atg ggc tac      1968
His Ala Arg Ala Tyr Asp Glu Ala Lys Gln Ala Ala Gln Met Gly Tyr
                645                 650                 655 gag agc tac ctc gtg aac gcg gag aac aat ggt ggg ggt agg atg tct      2016
Glu Ser Tyr Leu Val Asn Ala Glu Asn Asn Gly Gly Gly Arg Met Ser
                660                 665                 670 gca tgg ggg aca gtc gtg tct gca gcc gcg gcg gca gca gca agc agc      2064
Ala Trp Gly Thr Val Val Ser Ala Ala Ala Ala Ala Ala Ala Ser Ser
                675                 680                 685 aac gac aac atg gcg gcc gat gtc ggc cat ggc ggc gcg cag ctc ttc      2112
Asn Asp Asn Met Ala Ala Asp Val Gly His Gly Gly Ala Gln Leu Phe
                690                 695                 700 agt gtc tgg aac gac act taa                                          2133
Ser Val Trp Asn Asp Thr
705                 710

<210> SEQ ID NO 7
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 92% seq id to
      SEQ ID NO:1.  The ORF encodes the
      aa seq set forth in SEQ ID NO:2.
<220> FEATURE:
<221> NAME/KEY: CDS
<222> LOCATION: (1)...(2133)

<400> SEQUENCE: 7 atg gcc act gtc aac aat tgg ctg gct ttt agc ctc tcc ccg cag gag       48
Met Ala Thr Val Asn Asn Trp Leu Ala Phe Ser Leu Ser Pro Gln Glu
1               5                   10                  15 ctg ccc ccc tcc cag acc acg gac tcc aca ctc atc tcg gcg gcc acc       96
Leu Pro Pro Ser Gln Thr Thr Asp Ser Thr Leu Ile Ser Ala Ala Thr
                20                  25                  30 gcc gac cac gtg tcc ggc gac gtg tgc ttt aat att ccc cag gat tgg      144
Ala Asp His Val Ser Gly Asp Val Cys Phe Asn Ile Pro Gln Asp Trp
            35                  40                  45 agc atg agg gga tca gag ctt tcg gcg ctc gtc gcg gag ccg aag ctg      192
Ser Met Arg Gly Ser Glu Leu Ser Ala Leu Val Ala Glu Pro Lys Leu
        50                  55                  60 gag gac ttc ctc ggc ggg atc tcc ttc tcc gaa caa cat cac aag gcc      240
Glu Asp Phe Leu Gly Gly Ile Ser Phe Ser Glu Gln His His Lys Ala
```

```
                65                  70                  75                  80
aac tgt aac atg ata ccc tcc act agc agc aca gtt tgc tac gcg agc          288
Asn Cys Asn Met Ile Pro Ser Thr Ser Ser Thr Val Cys Tyr Ala Ser
                    85                  90                  95 tca ggt gca agc acc ggg tat cat cac cag ctg tac cac cag ccc acc          336
Ser Gly Ala Ser Thr Gly Tyr His His Gln Leu Tyr His Gln Pro Thr
100                 105                 110 agc tca gcg ctc cac ttc gcg gac tcc gtt atg gtg gcc tcc tcg gcc          384
Ser Ser Ala Leu His Phe Ala Asp Ser Val Met Val Ala Ser Ser Ala
            115                 120                 125 gga gtc cac gac ggc ggt gcc atg ctg tcc gcc gcc gcc gct aac gga          432
Gly Val His Asp Gly Gly Ala Met Leu Ser Ala Ala Ala Ala Asn Gly
        130                 135                 140 gtg gct ggc gct gcc tcc gcc aac ggc ggc ggg atc ggg ctg agc atg          480
Val Ala Gly Ala Ala Ser Ala Asn Gly Gly Gly Ile Gly Leu Ser Met
145                 150                 155                 160 atc aag aac tgg ctc cgg agc caa ccg gcg ccc atg cag ccg agg gtg          528
Ile Lys Asn Trp Leu Arg Ser Gln Pro Ala Pro Met Gln Pro Arg Val
                    165                 170                 175 gcg gcg gct gag ggg gcc cag ggc ctc tct ttg tcc atg aac atg gcg          576
Ala Ala Ala Glu Gly Ala Gln Gly Leu Ser Leu Ser Met Asn Met Ala
                180                 185                 190 ggg acg acc caa ggc gca gct ggc atg cct ctt ctg gct gga gag cgc          624
Gly Thr Thr Gln Gly Ala Ala Gly Met Pro Leu Leu Ala Gly Glu Arg
            195                 200                 205 gca cgc gcg ccc gag agt gta tcg acg tca gct caa ggt gga gcg gtc          672
Ala Arg Ala Pro Glu Ser Val Ser Thr Ser Ala Gln Gly Gly Ala Val
        210                 215                 220 gtc gtc acc gcg ccg aag gaa gat tcc ggt ggc agc ggt gtt gcc ggc          720
Val Val Thr Ala Pro Lys Glu Asp Ser Gly Gly Ser Gly Val Ala Gly
225                 230                 235                 240 gct ctc gta gcg gtc agc acg gac acc ggt ggc agc ggg ggc gcg tcg          768
Ala Leu Val Ala Val Ser Thr Asp Thr Gly Gly Ser Gly Gly Ala Ser
                    245                 250                 255 gca gac aat acg gct agg aag acg gtg gac acg ttc ggg cag cgg acg          816
Ala Asp Asn Thr Ala Arg Lys Thr Val Asp Thr Phe Gly Gln Arg Thr
                260                 265                 270 tcg atc tac cgt ggg gtg aca agg cac aga tgg aca ggg aga tat gag          864
Ser Ile Tyr Arg Gly Val Thr Arg His Arg Trp Thr Gly Arg Tyr Glu
            275                 280                 285 gca cac ctt tgg gat aac agt tgc agg agg gaa ggg caa act cgt aaa          912
Ala His Leu Trp Asp Asn Ser Cys Arg Arg Glu Gly Gln Thr Arg Lys
        290                 295                 300 ggt aga caa gtc tat tta ggt ggc tat gac aaa gag gag aag gct gct          960
Gly Arg Gln Val Tyr Leu Gly Gly Tyr Asp Lys Glu Glu Lys Ala Ala
305                 310                 315                 320 agg gct tac gat ctt gca gct ctg aag tac tgg ggt gcc act act act          1008
Arg Ala Tyr Asp Leu Ala Ala Leu Lys Tyr Trp Gly Ala Thr Thr Thr
                    325                 330                 335 aca aat ttc cca gtg agt aac tac gaa aag gag ctg gag gac atg aag          1056
Thr Asn Phe Pro Val Ser Asn Tyr Glu Lys Glu Leu Glu Asp Met Lys
                340                 345                 350 cac atg act agg caa gag ttc gtt gcg tcc ctg aga aga aag agc agt          1104
His Met Thr Arg Gln Glu Phe Val Ala Ser Leu Arg Arg Lys Ser Ser
            355                 360                 365 ggt ttc tcc aga ggt gca tcc att tac agg gga gtg act agg cat cac          1152
Gly Phe Ser Arg Gly Ala Ser Ile Tyr Arg Gly Val Thr Arg His His
        370                 375                 380 caa cat gga aga tgg cag gct cgg att gga cgc gtg gca ggc aac aaa          1200
```

```
Gln His Gly Arg Trp Gln Ala Arg Ile Gly Arg Val Ala Gly Asn Lys
385                 390                 395                 400 gat ctg tac ttg ggc acc ttt agc acc cag gag gaa gca gcg gag gcg      1248
Asp Leu Tyr Leu Gly Thr Phe Ser Thr Gln Glu Glu Ala Ala Glu Ala
                    405                 410                 415 tac gac atc gcg gcc atc aaa ttc cgc ggg ctc aac gcg gtg acg aat      1296
Tyr Asp Ile Ala Ala Ile Lys Phe Arg Gly Leu Asn Ala Val Thr Asn
                420                 425                 430 ttt gac atg agc cgc tac gac gtc aag agc att ctg gat agc agc gcc      1344
Phe Asp Met Ser Arg Tyr Asp Val Lys Ser Ile Leu Asp Ser Ser Ala
            435                 440                 445 ctc ccc atc ggg agc gcc gcc aag cgc ctg aag gag gcc gaa gcc gct      1392
Leu Pro Ile Gly Ser Ala Ala Lys Arg Leu Lys Glu Ala Glu Ala Ala
        450                 455                 460 gcg tcc gcg cag cat cac cac gcc ggc gtg gtg agc tac gac gtg ggc      1440
Ala Ser Ala Gln His His His Ala Gly Val Val Ser Tyr Asp Val Gly
465                 470                 475                 480 cgc atc gcc tcg caa ctc ggc gac ggc gga gcc ctg gcg gcg gcg tac      1488
Arg Ile Ala Ser Gln Leu Gly Asp Gly Gly Ala Leu Ala Ala Ala Tyr
                    485                 490                 495 ggg gcg cac tac cac ggc gcg gcc tgg ccc acg atc gcg ttc cag ccg      1536
Gly Ala His Tyr His Gly Ala Ala Trp Pro Thr Ile Ala Phe Gln Pro
                500                 505                 510 ggc gcc gcc agc aca ggc ctc tac cac ccg tac gcc cag caa cca atg      1584
Gly Ala Ala Ser Thr Gly Leu Tyr His Pro Tyr Ala Gln Gln Pro Met
            515                 520                 525 cgc ggg ggc ggg tgg tgc aag cag gag caa gac cac gcc gtg atc gcg      1632
Arg Gly Gly Gly Trp Cys Lys Gln Glu Gln Asp His Ala Val Ile Ala
530                 535                 540 gcc gcg cac agc ctg cag gac ctg cat cac ctg aac ctc ggg gcg gcc      1680
Ala Ala His Ser Leu Gln Asp Leu His His Leu Asn Leu Gly Ala Ala
545                 550                 555                 560 ggc gcc cac gac ttt ttc tcg gca ggg caa cag gcc gcg gcc gct gcc      1728
Gly Ala His Asp Phe Phe Ser Ala Gly Gln Gln Ala Ala Ala Ala Ala
                    565                 570                 575 atg cac ggc ctg ggt agc atc gat agt gcg tcg ctc gaa cac agc acc      1776
Met His Gly Leu Gly Ser Ile Asp Ser Ala Ser Leu Glu His Ser Thr
                580                 585                 590 ggc agc aac tcc gtc gtc tat aac ggc ggc gtc ggc gac agc aat ggg      1824
Gly Ser Asn Ser Val Val Tyr Asn Gly Gly Val Gly Asp Ser Asn Gly
            595                 600                 605 gcc agc gcg gtc ggc ggc tcc ggg ggt ggc tat atg atg ccc atg agc      1872
Ala Ser Ala Val Gly Gly Ser Gly Gly Gly Tyr Met Met Pro Met Ser
610                 615                 620 gct gcc ggt gca acg aca aca agc gca atg gtg agc cac gag caa gtc      1920
Ala Ala Gly Ala Thr Thr Thr Ser Ala Met Val Ser His Glu Gln Val
625                 630                 635                 640 cat gca cgg gcc tac gac gaa gcc aag cag gct gct cag atg ggg tac      1968
His Ala Arg Ala Tyr Asp Glu Ala Lys Gln Ala Ala Gln Met Gly Tyr
                    645                 650                 655 gag agc tac ctg gtc aac gcg gag aac aat ggt ggc gga aga atg tct      2016
Glu Ser Tyr Leu Val Asn Ala Glu Asn Asn Gly Gly Gly Arg Met Ser
                660                 665                 670 gca tgg ggg act gtc gtg tct gca gcc gcg gcg gca gct gct tcc agc      2064
Ala Trp Gly Thr Val Val Ser Ala Ala Ala Ala Ala Ala Ala Ser Ser
            675                 680                 685 aac gac aac atg gcc gcc gac gtg ggc cat ggg ggg gcg cag ctc ttt      2112
Asn Asp Asn Met Ala Ala Asp Val Gly His Gly Gly Ala Gln Leu Phe
690                 695                 700
```

-continued

```
agt gtc tgg aac gat act taa                                              2133
Ser Val Trp Asn Asp Thr
705             710

<210> SEQ ID NO 8
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 86.3% seq id
      to SEQ ID NO:1.  The ORF encodes the
      aa seq set forth in SEQ ID NO:2.
<220> FEATURE:
<221> NAME/KEY: CDS
<222> LOCATION: (1)...(2133)

<400> SEQUENCE: 8 atg gcc aca gtg aac aat tgg ctg gct ttt agc ctc tcc ccc caa gag           48
Met Ala Thr Val Asn Asn Trp Leu Ala Phe Ser Leu Ser Pro Gln Glu
1               5                   10                  15 ctg ccc ccg tcc cag acg acg gat agc aca ctg att agc gcg gcc acc           96
Leu Pro Pro Ser Gln Thr Thr Asp Ser Thr Leu Ile Ser Ala Ala Thr
            20                  25                  30 gcc gac cat gtc tcc ggg gac gtc tgc ttc aac atc ccc cag gat tgg          144
Ala Asp His Val Ser Gly Asp Val Cys Phe Asn Ile Pro Gln Asp Trp
        35                  40                  45 agc atg aga gga agc gag ctt tcg gcc ctg gtc gcg gag ccc aag ctg          192
Ser Met Arg Gly Ser Glu Leu Ser Ala Leu Val Ala Glu Pro Lys Leu
    50                  55                  60 gaa gat ttt ctg ggc ggc att agc ttc tcc gag cag cat cat aag gcg          240
Glu Asp Phe Leu Gly Gly Ile Ser Phe Ser Glu Gln His His Lys Ala
65                  70                  75                  80 aat tgc aac atg ata ccg agc act tcc tcc act gtt tgt tac gcg agc          288
Asn Cys Asn Met Ile Pro Ser Thr Ser Ser Thr Val Cys Tyr Ala Ser
                85                  90                  95 agc ggt gct agc acg ggc tat cac cat caa ctg tac cac cag ccg acc          336
Ser Gly Ala Ser Thr Gly Tyr His His Gln Leu Tyr His Gln Pro Thr
            100                 105                 110 agc tca gcg ctc cac ttc gcg gat agc gta atg gtg gcc tcg tcg gcc          384
Ser Ser Ala Leu His Phe Ala Asp Ser Val Met Val Ala Ser Ser Ala
        115                 120                 125 ggt gtc cac gat ggg ggt gcc atg ctc tcc gcg gcc gcc gct aat ggt          432
Gly Val His Asp Gly Gly Ala Met Leu Ser Ala Ala Ala Ala Asn Gly
    130                 135                 140 gtc gct ggc gct gcc agt gcg aac ggc ggg ggg atc ggg ctc tcc atg          480
Val Ala Gly Ala Ala Ser Ala Asn Gly Gly Gly Ile Gly Leu Ser Met
145                 150                 155                 160 att aag aac tgg ctg cgg agc cag ccg gcc ccc atg caa ccg agg gtg          528
Ile Lys Asn Trp Leu Arg Ser Gln Pro Ala Pro Met Gln Pro Arg Val
                165                 170                 175 gcg gcc gca gaa ggc gcg cag ggg ctc tcc ttg tcc atg aac atg gcc          576
Ala Ala Ala Glu Gly Ala Gln Gly Leu Ser Leu Ser Met Asn Met Ala
            180                 185                 190 ggc acc acg caa ggc gct gca ggg atg cct ctt ctc gct ggt gag cgg          624
Gly Thr Thr Gln Gly Ala Ala Gly Met Pro Leu Leu Ala Gly Glu Arg
        195                 200                 205 gca cgg gcc ccg gag tcc gta tcg acc agc gca cag gga gga gcg gtc          672
Ala Arg Ala Pro Glu Ser Val Ser Thr Ser Ala Gln Gly Gly Ala Val
    210                 215                 220 gtg gtg acc gcg ccg aaa gag gac tcc ggt ggc agc ggt gtg gcg ggc          720
Val Val Thr Ala Pro Lys Glu Asp Ser Gly Gly Ser Gly Val Ala Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |     |

```
gct cta gtt gcc gtg tcc acg gac acc gga ggg tcc ggc ggc gcg tcg          768
Ala Leu Val Ala Val Ser Thr Asp Thr Gly Gly Ser Gly Gly Ala Ser
                    245                 250                 255 gct gac aac acc gca agg aag acc gtg gac acg ttc ggg cag cgc acg          816
Ala Asp Asn Thr Ala Arg Lys Thr Val Asp Thr Phe Gly Gln Arg Thr
                260                 265                 270 agc atc tat cgt ggc gtc aca aga cat aga tgg act ggc agg tat gaa          864
Ser Ile Tyr Arg Gly Val Thr Arg His Arg Trp Thr Gly Arg Tyr Glu
            275                 280                 285 gca cac ctt tgg gat aac agt tgc agg aga gaa ggg cag act aga aag          912
Ala His Leu Trp Asp Asn Ser Cys Arg Arg Glu Gly Gln Thr Arg Lys
        290                 295                 300 gga cgt caa gtc tac ctg ggt ggg tac gat aaa gag gaa aaa gct gct          960
Gly Arg Gln Val Tyr Leu Gly Gly Tyr Asp Lys Glu Glu Lys Ala Ala
305                 310                 315                 320 aga gct tac gac ctt gct gct ctc aaa tac tgg gga gcg aca aca aca         1008
Arg Ala Tyr Asp Leu Ala Ala Leu Lys Tyr Trp Gly Ala Thr Thr Thr
                    325                 330                 335 act aat ttt cct gtg agt aat tac gag aaa gag ctc gaa gat atg aag         1056
Thr Asn Phe Pro Val Ser Asn Tyr Glu Lys Glu Leu Glu Asp Met Lys
                340                 345                 350 cac atg act agg cag gag ttc gtt gcg tcc ctg aga agg aaa agc tcc         1104
His Met Thr Arg Gln Glu Phe Val Ala Ser Leu Arg Arg Lys Ser Ser
            355                 360                 365 ggt ttc tcc aga ggt gct tcc atc tat aga gga gtc aca agg cat cat         1152
Gly Phe Ser Arg Gly Ala Ser Ile Tyr Arg Gly Val Thr Arg His His
        370                 375                 380 caa cat gga aga tgg cag gct cgg atc gga cgc gtg gca ggg aac aag         1200
Gln His Gly Arg Trp Gln Ala Arg Ile Gly Arg Val Ala Gly Asn Lys
385                 390                 395                 400 gat ctt tat ctc ggc acg ttc agc acg caa gaa gaa gca gcc gaa gcg         1248
Asp Leu Tyr Leu Gly Thr Phe Ser Thr Gln Glu Glu Ala Ala Glu Ala
                    405                 410                 415 tac gac atc gcc gcc atc aaa ttc cgc ggc ctg aac gcc gtc acc aat         1296
Tyr Asp Ile Ala Ala Ile Lys Phe Arg Gly Leu Asn Ala Val Thr Asn
                420                 425                 430 ttc gat atg agc cgg tac gac gtc aaa agc att ctg gac agc agc gcc         1344
Phe Asp Met Ser Arg Tyr Asp Val Lys Ser Ile Leu Asp Ser Ser Ala
            435                 440                 445 ctc ccc atc ggg agc gcc gcc aag cgg ctg aaa gag gcc gag gcc gct         1392
Leu Pro Ile Gly Ser Ala Ala Lys Arg Leu Lys Glu Ala Glu Ala Ala
        450                 455                 460 gcg agc gcg cag cac cat cat gcg ggc gtc gtc agc tat gac gtg ggg         1440
Ala Ser Ala Gln His His His Ala Gly Val Val Ser Tyr Asp Val Gly
465                 470                 475                 480 cgg att gcg agc caa ctg ggg gac ggc ggt gcc ctg gcg gcg gcc tac         1488
Arg Ile Ala Ser Gln Leu Gly Asp Gly Gly Ala Leu Ala Ala Ala Tyr
                    485                 490                 495 ggc gcg cac tac cat ggc gcc gcg tgg ccc acc atc gcg ttc caa ccg         1536
Gly Ala His Tyr His Gly Ala Ala Trp Pro Thr Ile Ala Phe Gln Pro
                500                 505                 510 ggc gcc gcc agc aca ggc ctc tat cac ccc tac gcg caa caa cca atg         1584
Gly Ala Ala Ser Thr Gly Leu Tyr His Pro Tyr Ala Gln Gln Pro Met
            515                 520                 525 cgc ggg ggc ggg tgg tgt aag cag gag caa gat cat gcg gtc atc gcg         1632
Arg Gly Gly Gly Trp Cys Lys Gln Glu Gln Asp His Ala Val Ile Ala
        530                 535                 540 gcc gcc cac agc ctc cag gat ctg cac cac ctc aac ctg ggc gcc gcc         1680
```

```
Ala Ala His Ser Leu Gln Asp Leu His His Leu Asn Leu Gly Ala Ala
545                 550                 555                 560 ggc gcg cac gac ttt ttc agc gca ggc cag caa gcg gcc gcc gca gcg      1728
Gly Ala His Asp Phe Phe Ser Ala Gly Gln Gln Ala Ala Ala Ala Ala
                565                 570                 575 atg cac ggg ctc gga agc atc gat agt gcg tcg ctc gag cac agc acg      1776
Met His Gly Leu Gly Ser Ile Asp Ser Ala Ser Leu Glu His Ser Thr
                580                 585                 590 ggc tcc aat tcc gtg gtc tac aac ggc ggc gtg ggg gat agc aac ggc      1824
Gly Ser Asn Ser Val Val Tyr Asn Gly Gly Val Gly Asp Ser Asn Gly
            595                 600                 605 gcc tcc gcc gtc ggc ggg tcc ggc ggt ggc tac atg atg ccg atg agc      1872
Ala Ser Ala Val Gly Gly Ser Gly Gly Gly Tyr Met Met Pro Met Ser
        610                 615                 620 gct gcc gga gca acc act aca tcg gca atg gtc agc cat gaa caa gtg      1920
Ala Ala Gly Ala Thr Thr Thr Ser Ala Met Val Ser His Glu Gln Val
625                 630                 635                 640 cat gca cgg gcc tat gac gaa gcg aag caa gct gct caa atg ggg tac      1968
His Ala Arg Ala Tyr Asp Glu Ala Lys Gln Ala Ala Gln Met Gly Tyr
                645                 650                 655 gaa tcc tac ctg gtg aac gcg gag aat aat gga ggc gga aga atg tct      2016
Glu Ser Tyr Leu Val Asn Ala Glu Asn Asn Gly Gly Gly Arg Met Ser
                660                 665                 670 gct tgg ggg aca gtc gtg tcc gct gcc gcg gct gca gct agc agc          2064
Ala Trp Gly Thr Val Val Ser Ala Ala Ala Ala Ala Ala Ser Ser
            675                 680                 685 aat gac aat atg gcg gcg gac gtc ggc cac ggc ggc gcg cag ctg ttc      2112
Asn Asp Asn Met Ala Ala Asp Val Gly His Gly Gly Ala Gln Leu Phe
690                 695                 700 tcc gtg tgg aat gac act taa                                          2133
Ser Val Trp Asn Asp Thr
705                 710

<210> SEQ ID NO 9
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 81.2% seq id
      to SEQ ID NO:1.  The ORF encodes the
      aa seq set forth in SEQ ID NO:2.
<220> FEATURE:
<221> NAME/KEY: CDS
<222> LOCATION: (1)...(2133)

<400> SEQUENCE: 9 atg gcg act gtc aat aat tgg ctg gca ttt agc ctc agc ccc cag gag        48
Met Ala Thr Val Asn Asn Trp Leu Ala Phe Ser Leu Ser Pro Gln Glu
1               5                   10                  15 ctg ccg ccg tcc caa acg acc gac agc aca ctg att agc gcg gcg acg       96
Leu Pro Pro Ser Gln Thr Thr Asp Ser Thr Leu Ile Ser Ala Ala Thr
                20                  25                  30 gcg gat cac gtg agc ggc gat gtg tgt ttc aac att ccc cag gac tgg      144
Ala Asp His Val Ser Gly Asp Val Cys Phe Asn Ile Pro Gln Asp Trp
            35                  40                  45 tcc atg agg ggt agc gaa ctt agc gcg ctc gtg gcg gaa ccg aaa ctg      192
Ser Met Arg Gly Ser Glu Leu Ser Ala Leu Val Ala Glu Pro Lys Leu
        50                  55                  60 gag gac ttc ctg ggg ggc atc tcc ttt tcc gag cag cat cac aaa gcg      240
Glu Asp Phe Leu Gly Gly Ile Ser Phe Ser Glu Gln His His Lys Ala
65                  70                  75                  80
```

| | | | | | | | | | | | | | | | | |
|---|---|---|---|---|---|---|---|---|---|---|---|---|---|---|---|---|
| aac | tgt | aac | atg | atc | ccc | agc | act | agc | agc | aca | gtt | tgt | tat | gcc | tcc | 288 |
| Asn | Cys | Asn | Met | Ile | Pro | Ser | Thr | Ser | Ser | Thr | Val | Cys | Tyr | Ala | Ser | |
| | | | | 85 | | | | | 90 | | | | | 95 | | |
| tca | ggt | gct | tcc | acg | ggc | tac | cac | cat | cag | ctg | tat | cac | caa | ccg | acc | 336 |
| Ser | Gly | Ala | Ser | Thr | Gly | Tyr | His | His | Gln | Leu | Tyr | His | Gln | Pro | Thr | |
| | | | 100 | | | | | 105 | | | | | 110 | | | |
| agc | tca | gcg | ctc | cac | ttt | gcg | gat | tcc | gta | atg | gtg | gcc | tcc | agc | gcc | 384 |
| Ser | Ser | Ala | Leu | His | Phe | Ala | Asp | Ser | Val | Met | Val | Ala | Ser | Ser | Ala | |
| | | 115 | | | | | 120 | | | | | 125 | | | | |
| gga | gtc | cac | gac | ggg | ggt | gcg | atg | ctc | agc | gcg | gcc | gcc | gct | aat | gga | 432 |
| Gly | Val | His | Asp | Gly | Gly | Ala | Met | Leu | Ser | Ala | Ala | Ala | Ala | Asn | Gly | |
| | 130 | | | | | 135 | | | | | 140 | | | | | |
| gtg | gca | ggg | gct | gcg | agt | gcg | aac | ggc | ggc | ggc | att | ggg | ctc | tcc | atg | 480 |
| Val | Ala | Gly | Ala | Ala | Ser | Ala | Asn | Gly | Gly | Gly | Ile | Gly | Leu | Ser | Met | |
| 145 | | | | | 150 | | | | | 155 | | | | | 160 | |
| atc | aaa | aat | tgg | ctg | cgg | tcc | cag | ccg | gcg | ccg | atg | cag | ccc | aga | gtg | 528 |
| Ile | Lys | Asn | Trp | Leu | Arg | Ser | Gln | Pro | Ala | Pro | Met | Gln | Pro | Arg | Val | |
| | | | | 165 | | | | | 170 | | | | | 175 | | |
| gcc | gcc | gct | gaa | ggc | gcc | caa | ggc | ctg | tcc | ctc | agc | atg | aac | atg | gcg | 576 |
| Ala | Ala | Ala | Glu | Gly | Ala | Gln | Gly | Leu | Ser | Leu | Ser | Met | Asn | Met | Ala | |
| | | | | 180 | | | | | 185 | | | | | 190 | | |
| ggg | acg | acc | cag | ggc | gca | gca | ggg | atg | cca | ctt | ctc | gca | ggt | gaa | cgc | 624 |
| Gly | Thr | Thr | Gln | Gly | Ala | Ala | Gly | Met | Pro | Leu | Leu | Ala | Gly | Glu | Arg | |
| | | 195 | | | | | 200 | | | | | 205 | | | | |
| gct | cgc | gcg | ccc | gag | tcc | gta | agc | acc | agc | gca | cag | gga | ggt | gcg | gtg | 672 |
| Ala | Arg | Ala | Pro | Glu | Ser | Val | Ser | Thr | Ser | Ala | Gln | Gly | Gly | Ala | Val | |
| | 210 | | | | | 215 | | | | | 220 | | | | | |
| gtg | gtc | acg | gcc | ccg | aag | gaa | gat | tcc | gga | ggg | agc | gga | gtg | gcc | ggg | 720 |
| Val | Val | Thr | Ala | Pro | Lys | Glu | Asp | Ser | Gly | Gly | Ser | Gly | Val | Ala | Gly | |
| 225 | | | | | 230 | | | | | 235 | | | | | 240 | |
| gca | ctc | gta | gcc | gtg | agc | acg | gac | acc | gga | ggg | tcc | ggg | ggg | gcc | tcg | 768 |
| Ala | Leu | Val | Ala | Val | Ser | Thr | Asp | Thr | Gly | Gly | Ser | Gly | Gly | Ala | Ser | |
| | | | | 245 | | | | | 250 | | | | | 255 | | |
| gca | gat | aat | acc | gct | aga | aaa | acg | gtc | gac | acg | ttt | ggc | cag | cgc | acg | 816 |
| Ala | Asp | Asn | Thr | Ala | Arg | Lys | Thr | Val | Asp | Thr | Phe | Gly | Gln | Arg | Thr | |
| | | | 260 | | | | | 265 | | | | | 270 | | | |
| tcg | atc | tat | aga | ggc | gtg | aca | agg | cac | aga | tgg | aca | ggc | aga | tac | gaa | 864 |
| Ser | Ile | Tyr | Arg | Gly | Val | Thr | Arg | His | Arg | Trp | Thr | Gly | Arg | Tyr | Glu | |
| | | 275 | | | | | 280 | | | | | 285 | | | | |
| gct | cac | ctt | tgg | gat | aac | agt | tgc | aga | agg | gaa | ggg | caa | act | aga | aag | 912 |
| Ala | His | Leu | Trp | Asp | Asn | Ser | Cys | Arg | Arg | Glu | Gly | Gln | Thr | Arg | Lys | |
| | 290 | | | | | 295 | | | | | 300 | | | | | |
| gga | cgt | cag | gtc | tat | ctg | gga | ggc | tac | gac | aaa | gag | gag | aag | gca | gca | 960 |
| Gly | Arg | Gln | Val | Tyr | Leu | Gly | Gly | Tyr | Asp | Lys | Glu | Glu | Lys | Ala | Ala | |
| 305 | | | | | 310 | | | | | 315 | | | | | 320 | |
| aga | gca | tac | gat | ctg | gct | gca | ctg | aaa | tac | tgg | gga | gcc | aca | act | act | 1008 |
| Arg | Ala | Tyr | Asp | Leu | Ala | Ala | Leu | Lys | Tyr | Trp | Gly | Ala | Thr | Thr | Thr | |
| | | | | 325 | | | | | 330 | | | | | 335 | | |
| act | aat | ttt | cca | gtg | agt | aac | tac | gag | aaa | gaa | ctg | gag | gac | atg | aag | 1056 |
| Thr | Asn | Phe | Pro | Val | Ser | Asn | Tyr | Glu | Lys | Glu | Leu | Glu | Asp | Met | Lys | |
| | | | 340 | | | | | 345 | | | | | 350 | | | |
| cac | atg | act | aga | caa | gaa | ttc | gta | gcg | tct | ctg | agg | aga | aag | agc | tcc | 1104 |
| His | Met | Thr | Arg | Gln | Glu | Phe | Val | Ala | Ser | Leu | Arg | Arg | Lys | Ser | Ser | |
| | | 355 | | | | | 360 | | | | | 365 | | | | |
| gga | ttc | agc | agg | ggt | gca | tcc | atc | tat | agg | ggt | gtc | aca | agg | cac | cac | 1152 |
| Gly | Phe | Ser | Arg | Gly | Ala | Ser | Ile | Tyr | Arg | Gly | Val | Thr | Arg | His | His | |
| | 370 | | | | | 375 | | | | | 380 | | | | | |
| cag | cac | gga | aga | tgg | cag | gct | cgc | atc | gga | cga | gtt | gca | ggg | aac | aaa | 1200 |
| Gln | His | Gly | Arg | Trp | Gln | Ala | Arg | Ile | Gly | Arg | Val | Ala | Gly | Asn | Lys | |

```
                385                 390                 395                 400
gat ctg tat ctc ggc acg ttt tcc acc cag gaa gaa gca gcc gag gcg       1248
Asp Leu Tyr Leu Gly Thr Phe Ser Thr Gln Glu Glu Ala Ala Glu Ala
                    405                 410                 415 tac gac atc gcg gcc atc aaa ttt cgc ggc ctc aat gcc gtc acg aat       1296
Tyr Asp Ile Ala Ala Ile Lys Phe Arg Gly Leu Asn Ala Val Thr Asn
                420                 425                 430 ttc gat atg agc cgc tat gac gtg aag tcc att ctc gat agc tcc gcg       1344
Phe Asp Met Ser Arg Tyr Asp Val Lys Ser Ile Leu Asp Ser Ser Ala
            435                 440                 445 ctc ccc atc ggg tcc gcg gcg aag cgc ctg aag gag gcc gag gcg gct       1392
Leu Pro Ile Gly Ser Ala Ala Lys Arg Leu Lys Glu Ala Glu Ala Ala
        450                 455                 460 gcc tcc gcc caa cat cat cat gcc ggc gtc gtg tcc tac gat gtc ggg       1440
Ala Ser Ala Gln His His His Ala Gly Val Val Ser Tyr Asp Val Gly
465                 470                 475                 480 cgg atc gcg agc cag ctg ggc gat ggg gga gcg ctg gcc gcg gcg tat       1488
Arg Ile Ala Ser Gln Leu Gly Asp Gly Gly Ala Leu Ala Ala Ala Tyr
                485                 490                 495 ggg gcc cac tac cac ggc gcg gcg tgg ccg acg atc gcg ttt cag ccc       1536
Gly Ala His Tyr His Gly Ala Ala Trp Pro Thr Ile Ala Phe Gln Pro
                    500                 505                 510 ggc gcg gcc agc act ggc ctg tac cac ccc tat gcc caa caa cct atg       1584
Gly Ala Ala Ser Thr Gly Leu Tyr His Pro Tyr Ala Gln Gln Pro Met
                515                 520                 525 cgg ggg ggg ggc tgg tgc aaa caa gag caa gac cat gcc gtg att gcc       1632
Arg Gly Gly Gly Trp Cys Lys Gln Glu Gln Asp His Ala Val Ile Ala
            530                 535                 540 gcg gcc cac tcc ctc cag gac ctg cat cac ctc aat ctg ggg gcc gcg       1680
Ala Ala His Ser Leu Gln Asp Leu His His Leu Asn Leu Gly Ala Ala
545                 550                 555                 560 ggg gcc cat gat ttt ttt tcg gct ggc caa caa gcg gcg gcg gct gcg       1728
Gly Ala His Asp Phe Phe Ser Ala Gly Gln Gln Ala Ala Ala Ala Ala
                565                 570                 575 atg cat ggg ctg gga agc atc gat tcc gcg agc ctc gag cat tcc acg       1776
Met His Gly Leu Gly Ser Ile Asp Ser Ala Ser Leu Glu His Ser Thr
                    580                 585                 590 ggc tcc aat agc gtc gtg tat aat ggg ggc gtg ggc gac agc aat ggc       1824
Gly Ser Asn Ser Val Val Tyr Asn Gly Gly Val Gly Asp Ser Asn Gly
                595                 600                 605 gcg agc gcg gtc ggg ggg agt ggc gga ggg tac atg atg ccg atg agc       1872
Ala Ser Ala Val Gly Gly Ser Gly Gly Gly Tyr Met Met Pro Met Ser
            610                 615                 620 gct gcg ggt gct acc aca act tcg gca atg gtg agc cac gag cag gtg       1920
Ala Ala Gly Ala Thr Thr Thr Ser Ala Met Val Ser His Glu Gln Val
625                 630                 635                 640 cat gca cgc gcc tat gac gaa gcg aaa caa gca gca caa atg ggc tac       1968
His Ala Arg Ala Tyr Asp Glu Ala Lys Gln Ala Ala Gln Met Gly Tyr
                645                 650                 655 gag agc tac ctc gtg aac gcc gaa aat aac ggt ggg ggt agg atg tct       2016
Glu Ser Tyr Leu Val Asn Ala Glu Asn Asn Gly Gly Gly Arg Met Ser
                    660                 665                 670 gct tgg ggg aca gtg gtc tcc gca gcg gcg gcc gct gca gca agc agc       2064
Ala Trp Gly Thr Val Val Ser Ala Ala Ala Ala Ala Ala Ser Ser
                675                 680                 685 aac gac aac atg gcg gcg gac gtc ggc cac ggg ggg gcc cag ctg ttc       2112
Asn Asp Asn Met Ala Ala Asp Val Gly His Gly Gly Ala Gln Leu Phe
            690                 695                 700 tcc gtc tgg aac gat aca taa                                           2133
```

Ser Val Trp Asn Asp Thr
705             710

<210> SEQ ID NO 10
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 76.1% seq id
      to SEQ ID NO:1. The ORF encodes the
      aa seq set forth in SEQ ID NO:2.
<220> FEATURE:
<221> NAME/KEY: CDS
<222> LOCATION: (1)...(2133)

<400> SEQUENCE: 10

```
atg gcg act gtg aat aat tgg ctg gct ttt agc ctg agc ccc cag gaa      48
Met Ala Thr Val Asn Asn Trp Leu Ala Phe Ser Leu Ser Pro Gln Glu
1               5                   10                  15 ctg ccc ccg tcc caa acc acc gat tcc act ctg att agc gcg gcc acg      96
Leu Pro Pro Ser Gln Thr Thr Asp Ser Thr Leu Ile Ser Ala Ala Thr
            20                  25                  30 gcc gat cat gtg tcc ggc gat gtc tgc ttt aat att ccg cag gac tgg     144
Ala Asp His Val Ser Gly Asp Val Cys Phe Asn Ile Pro Gln Asp Trp
        35                  40                  45 agc atg aga gga tca gaa ctg agc gcc ctc gtg gcg gaa ccc aaa ctc     192
Ser Met Arg Gly Ser Glu Leu Ser Ala Leu Val Ala Glu Pro Lys Leu
    50                  55                  60 gaa gat ttc ctg ggg ggg att agc ttc agc gaa cag cac cac aaa gcg     240
Glu Asp Phe Leu Gly Gly Ile Ser Phe Ser Glu Gln His His Lys Ala
65                  70                  75                  80 aat tgt aat atg ata ccg tcc act agc tcc aca gtt tgt tat gcc agc     288
Asn Cys Asn Met Ile Pro Ser Thr Ser Ser Thr Val Cys Tyr Ala Ser
                85                  90                  95 agc gga gca agc acg ggg tac cac cat cag ctc tat cat caa ccc acg     336
Ser Gly Ala Ser Thr Gly Tyr His His Gln Leu Tyr His Gln Pro Thr
            100                 105                 110 tcc agc gcc ctg cac ttt gcc gat agc gtt atg gtg gcg tcc agc gcg     384
Ser Ser Ala Leu His Phe Ala Asp Ser Val Met Val Ala Ser Ser Ala
        115                 120                 125 ggt gtc cat gac ggc ggt gcg atg ctg agc gcg gcc gct aac gga         432
Gly Val His Asp Gly Gly Ala Met Leu Ser Ala Ala Ala Asn Gly
        130                 135                 140 gtg gca ggg gct gcc tcc gcg aat ggc ggg ggg atc ggg ctc agc atg     480
Val Ala Gly Ala Ala Ser Ala Asn Gly Gly Gly Ile Gly Leu Ser Met
145                 150                 155                 160 att aaa aac tgg ctc cgc tcc caa ccc gcc ccg atg caa ccc aga gtc     528
Ile Lys Asn Trp Leu Arg Ser Gln Pro Ala Pro Met Gln Pro Arg Val
                165                 170                 175 gcc gcg gct gaa ggg gcg caa ggc ctg tcc ctc tcc atg aac atg gcc     576
Ala Ala Ala Glu Gly Ala Gln Gly Leu Ser Leu Ser Met Asn Met Ala
            180                 185                 190 ggg acc acg caa ggg gca gca ggg atg cct ctg ctg gct gga gaa cgg     624
Gly Thr Thr Gln Gly Ala Ala Gly Met Pro Leu Leu Ala Gly Glu Arg
        195                 200                 205 gct cgc gcg ccc gaa tcc gta tcg acc agc gct caa gga ggt gcg         672
Ala Arg Ala Pro Glu Ser Val Ser Thr Ser Ala Gln Gly Gly Ala Val
    210                 215                 220 gtg gtg acg gcc ccg aag gaa gac agc ggt ggg agc ggt gtg gcg ggg     720
Val Val Thr Ala Pro Lys Glu Asp Ser Gly Gly Ser Gly Val Ala Gly
225                 230                 235                 240
```

```
                                              -continued gct cta gta gcg gtc tcc acc gac acc gga ggc agc ggc ggc gcg tcg      768
Ala Leu Val Ala Val Ser Thr Asp Thr Gly Gly Ser Gly Gly Ala Ser
                245                 250                 255 gct gat aat acc gct aga aag acg gtg gat acc ttc ggc cag cgg acc      816
Ala Asp Asn Thr Ala Arg Lys Thr Val Asp Thr Phe Gly Gln Arg Thr
            260                 265                 270 agc atc tat cgt ggg gtc act aga cac agg tgg aca ggc agg tac gaa      864
Ser Ile Tyr Arg Gly Val Thr Arg His Arg Trp Thr Gly Arg Tyr Glu
        275                 280                 285 gct cat ctt tgg gat aat tcc tgt aga agg gag ggc cag act aga aag      912
Ala His Leu Trp Asp Asn Ser Cys Arg Arg Glu Gly Gln Thr Arg Lys
    290                 295                 300 ggt aga cag gtg tac tta ggt ggc tac gac aag gaa gaa aag gca gca      960
Gly Arg Gln Val Tyr Leu Gly Gly Tyr Asp Lys Glu Glu Lys Ala Ala
305                 310                 315                 320 agg gca tac gac ctg gca gct ctc aag tat tgg gga gcg act act aca     1008
Arg Ala Tyr Asp Leu Ala Ala Leu Lys Tyr Trp Gly Ala Thr Thr Thr
                325                 330                 335 aca aat ttc cca gtc agt aac tat gag aaa gaa ctg gag gat atg aaa     1056
Thr Asn Phe Pro Val Ser Asn Tyr Glu Lys Glu Leu Glu Asp Met Lys
            340                 345                 350 cat atg aca aga caa gaa ttc gtt gcc tcc ctc agg aga aaa agc agt     1104
His Met Thr Arg Gln Glu Phe Val Ala Ser Leu Arg Arg Lys Ser Ser
        355                 360                 365 gga ttc tcc agg ggt gct tcc atc tac agg ggt gtc aca agg cac cat     1152
Gly Phe Ser Arg Gly Ala Ser Ile Tyr Arg Gly Val Thr Arg His His
    370                 375                 380 cag cat gga agg tgg cag gca cgc atc gga cgc gtt gca ggc aat aaa     1200
Gln His Gly Arg Trp Gln Ala Arg Ile Gly Arg Val Ala Gly Asn Lys
385                 390                 395                 400 gat ctg tac ctc ggg acg ttc tcc acg cag gaa gaa gca gcg gag gcg     1248
Asp Leu Tyr Leu Gly Thr Phe Ser Thr Gln Glu Glu Ala Ala Glu Ala
                405                 410                 415 tat gac att gcg gcc att aag ttt cgg ggc ctc aat gcg gtc acg aat     1296
Tyr Asp Ile Ala Ala Ile Lys Phe Arg Gly Leu Asn Ala Val Thr Asn
            420                 425                 430 ttt gac atg tcc cgc tat gat gtc aaa tcc att ctc gat agc tcc gcg     1344
Phe Asp Met Ser Arg Tyr Asp Val Lys Ser Ile Leu Asp Ser Ser Ala
        435                 440                 445 ctc ccc att ggc tcc gcg gcg aag cgc ctc aaa gaa gcc gaa gcg gct     1392
Leu Pro Ile Gly Ser Ala Ala Lys Arg Leu Lys Glu Ala Glu Ala Ala
    450                 455                 460 gcc agc gcg caa cac cat cat gcc ggg gtg gtc tcc tat gac gtc ggg     1440
Ala Ser Ala Gln His His His Ala Gly Val Val Ser Tyr Asp Val Gly
465                 470                 475                 480 cgg att gcc tcg cag ctg ggg gat ggg ggt gcc ctg gcc gcc gcg tat     1488
Arg Ile Ala Ser Gln Leu Gly Asp Gly Gly Ala Leu Ala Ala Ala Tyr
                485                 490                 495 ggg gcc cat tac cat ggc gcg gcc tgg ccg acg atc gcc ttt cag ccc     1536
Gly Ala His Tyr His Gly Ala Ala Trp Pro Thr Ile Ala Phe Gln Pro
            500                 505                 510 ggg gcg gcg agc act ggg ctg tac cat ccc tac gcg caa caa cct atg     1584
Gly Ala Ala Ser Thr Gly Leu Tyr His Pro Tyr Ala Gln Gln Pro Met
        515                 520                 525 cgc ggg ggg ggc tgg tgt aaa caa gaa cag gac cat gcc gtc att gcc     1632
Arg Gly Gly Gly Trp Cys Lys Gln Glu Gln Asp His Ala Val Ile Ala
    530                 535                 540 gcg gcc cac tcc ctc cag gac ctg cat cac ctg aat ctc ggg gcg gcg     1680
Ala Ala His Ser Leu Gln Asp Leu His His Leu Asn Leu Gly Ala Ala
```

-continued

```
                 545                 550                 555                 560
ggg gcc cat gat ttc ttc tcg gct ggc caa cag gcg gcg gcg gca gcc    1728
Gly Ala His Asp Phe Phe Ser Ala Gly Gln Gln Ala Ala Ala Ala Ala
                565                 570                 575 atg cat ggg ctg gga tcc att gac tcc gcc tcg ctg gag cat tcc acg    1776
Met His Gly Leu Gly Ser Ile Asp Ser Ala Ser Leu Glu His Ser Thr
            580                 585                 590 ggc agc aac tcc gtc gtg tac aat ggc ggc gtg ggg gat tcc aat ggg    1824
Gly Ser Asn Ser Val Val Tyr Asn Gly Gly Val Gly Asp Ser Asn Gly
        595                 600                 605 gcc tcc gcg gtg ggg ggg tcc ggc gga ggg tat atg atg ccc atg agc    1872
Ala Ser Ala Val Gly Gly Ser Gly Gly Gly Tyr Met Met Pro Met Ser
    610                 615                 620 gca gcg ggt gca acc aca act tcg gct atg gtc tcc cat gaa caa gtg    1920
Ala Ala Gly Ala Thr Thr Thr Ser Ala Met Val Ser His Glu Gln Val
625                 630                 635                 640 cac gct cgg gcg tat gat gag gcg aaa caa gca gca caa atg ggg tat    1968
His Ala Arg Ala Tyr Asp Glu Ala Lys Gln Ala Ala Gln Met Gly Tyr
                645                 650                 655 gag tcc tat ctg gtg aat gcc gaa aat aac gga ggg ggt aga atg tcc    2016
Glu Ser Tyr Leu Val Asn Ala Glu Asn Asn Gly Gly Gly Arg Met Ser
            660                 665                 670 gct tgg ggg aca gtg gtc tcc gca gcg gcg gcg gct gct gca agc tcc    2064
Ala Trp Gly Thr Val Val Ser Ala Ala Ala Ala Ala Ala Ala Ser Ser
        675                 680                 685 aac gat aat atg gcc gcg gat gtg ggg cac ggg ggg gcc caa ctg ttc    2112
Asn Asp Asn Met Ala Ala Asp Val Gly His Gly Gly Ala Gln Leu Phe
    690                 695                 700 agt gtg tgg aat gac aca taa                                        2133
Ser Val Trp Asn Asp Thr
705                 710

<210> SEQ ID NO 11
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 70.6% seq id
      to SEQ ID NO:1. The ORF encodes the
      aa seq set forth in SEQ ID NO:2.
<220> FEATURE:
<221> NAME/KEY: CDS
<222> LOCATION: (1)...(2133)

<400> SEQUENCE: 11 atg gcg aca gtc aac aat tgg ctg gca ttt agc ctg agc ccc caa gaa      48
Met Ala Thr Val Asn Asn Trp Leu Ala Phe Ser Leu Ser Pro Gln Glu
1               5                   10                  15 ctc ccc ccc tcc caa acg acc gat agc act ctg att agc gcg gcc acg      96
Leu Pro Pro Ser Gln Thr Thr Asp Ser Thr Leu Ile Ser Ala Ala Thr
            20                  25                  30 gcc gat cac gtg agc ggg gac gtg tgt ttt aat att ccg cag gac tgg     144
Ala Asp His Val Ser Gly Asp Val Cys Phe Asn Ile Pro Gln Asp Trp
        35                  40                  45 agc atg aga gga tca gaa ctt tcg gcc ctg gtg gcc gag ccc aaa ctc     192
Ser Met Arg Gly Ser Glu Leu Ser Ala Leu Val Ala Glu Pro Lys Leu
    50                  55                  60 gaa gac ttt ctg ggg ggg att agc ttt agc gaa caa cac cac aaa gcc     240
Glu Asp Phe Leu Gly Gly Ile Ser Phe Ser Glu Gln His His Lys Ala
65                  70                  75                  80
```

| | | |
|---|---|---|
| aat tgt aac atg atc ccg tcc act agc tcc aca gtg tgc tat gcc tcc<br>Asn Cys Asn Met Ile Pro Ser Thr Ser Ser Thr Val Cys Tyr Ala Ser<br>                85                        90                      95 | | 288 |
| agc gga gct tcc acg ggg tac cac cat caa ctc tat cat caa ccg acg<br>Ser Gly Ala Ser Thr Gly Tyr His His Gln Leu Tyr His Gln Pro Thr<br>           100                        105                    110 | | 336 |
| agc agc gcc ctg cat ttt gcc gat agc gtt atg gtc gcc agc agc gcg<br>Ser Ser Ala Leu His Phe Ala Asp Ser Val Met Val Ala Ser Ser Ala<br>           115                        120                    125 | | 384 |
| gga gtg cat gat ggg gga gcg atg ctg tcc gcc gcg gcg gca aat gga<br>Gly Val His Asp Gly Gly Ala Met Leu Ser Ala Ala Ala Asn Gly<br>130                        135                    140 | | 432 |
| gtg gca ggc gca gcc tcc gcg aat ggg ggg ggg att ggc ctc agc atg<br>Val Ala Gly Ala Ala Ser Ala Asn Gly Gly Gly Ile Gly Leu Ser Met<br>145                        150                    155                    160 | | 480 |
| atc aaa aat tgg ctc cgc tcc cag ccc gcc ccg atg caa ccc aga gtc<br>Ile Lys Asn Trp Leu Arg Ser Gln Pro Ala Pro Met Gln Pro Arg Val<br>                      165                    170                    175 | | 528 |
| gcc gcc gca gag ggg gcc caa ggg ctg tct ctc agc atg aat atg gcg<br>Ala Ala Ala Glu Gly Ala Gln Gly Leu Ser Leu Ser Met Asn Met Ala<br>           180                        185                    190 | | 576 |
| ggc acc acg cag ggg gca gca ggg atg cct ctc ctc gca ggt gaa cgg<br>Gly Thr Thr Gln Gly Ala Ala Gly Met Pro Leu Leu Ala Gly Glu Arg<br>           195                        200                    205 | | 624 |
| gca cgc gcc ccg gaa agt gtt agc acc tca gct caa gga ggt gcc gtg<br>Ala Arg Ala Pro Glu Ser Val Ser Thr Ser Ala Gln Gly Gly Ala Val<br>210                        215                    220 | | 672 |
| gtg gtg acc gcg ccc aaa gaa gac tcc gga ggg tcc gga gtg gcc ggg<br>Val Val Thr Ala Pro Lys Glu Asp Ser Gly Gly Ser Gly Val Ala Gly<br>225                        230                    235                    240 | | 720 |
| gct ctc gtt gcc gtg tcc acc gat acc ggt ggg tcc ggg ggc gcc agc<br>Ala Leu Val Ala Val Ser Thr Asp Thr Gly Gly Ser Gly Gly Ala Ser<br>                      245                    250                    255 | | 768 |
| gca gat aat acc gct aga aaa acg gtc gat acc ttt ggc caa cgg acg<br>Ala Asp Asn Thr Ala Arg Lys Thr Val Asp Thr Phe Gly Gln Arg Thr<br>           260                        265                    270 | | 816 |
| tcg atc tat aga ggg gtc act agg cac agg tgg aca ggc agg tac gag<br>Ser Ile Tyr Arg Gly Val Thr Arg His Arg Trp Thr Gly Arg Tyr Glu<br>                      275                    280                    285 | | 864 |
| gca cac ctg tgg gac aat agt tgt agg aga gaa ggc cag aca aga aaa<br>Ala His Leu Trp Asp Asn Ser Cys Arg Arg Glu Gly Gln Thr Arg Lys<br>290                        295                    300 | | 912 |
| gga cgt cag gtc tat ctg gga ggg tac gac aag gaa gaa aag gca gca<br>Gly Arg Gln Val Tyr Leu Gly Gly Tyr Asp Lys Glu Glu Lys Ala Ala<br>305                        310                    315                    320 | | 960 |
| aga gca tat gac ctg gca gct ctg aaa tat tgg ggt gcg act act act<br>Arg Ala Tyr Asp Leu Ala Ala Leu Lys Tyr Trp Gly Ala Thr Thr Thr<br>                      325                    330                    335 | | 1008 |
| act aat ttc cct gtc tcc aat tat gag aaa gaa ctg gaa gac atg aaa<br>Thr Asn Phe Pro Val Ser Asn Tyr Glu Lys Glu Leu Glu Asp Met Lys<br>                        340                    345                    350 | | 1056 |
| cat atg act aga caa gaa ttt gtt gcc tcc ctc agg aga aaa tcc tcc<br>His Met Thr Arg Gln Glu Phe Val Ala Ser Leu Arg Arg Lys Ser Ser<br>           355                        360                    365 | | 1104 |
| gga ttt agc agg ggt gct agc atc tat aga ggt gtc aca agg cac cat<br>Gly Phe Ser Arg Gly Ala Ser Ile Tyr Arg Gly Val Thr Arg His His<br>           370                        375                    380 | | 1152 |
| caa cac gga aga tgg cag gct cgc atc ggt cgc gtg gct ggc aat aaa<br>Gln His Gly Arg Trp Gln Ala Arg Ile Gly Arg Val Ala Gly Asn Lys<br>385                        390                    395                    400 | | 1200 |

```
gac ctg tat ctc ggg acg ttt tcc acg caa gaa gag gca gcc gaa gcc    1248
Asp Leu Tyr Leu Gly Thr Phe Ser Thr Gln Glu Glu Ala Ala Glu Ala
            405                 410                 415 tat gac att gcc gcg att aag ttt cgg ggg ctg aat gcg gtg acc aat    1296
Tyr Asp Ile Ala Ala Ile Lys Phe Arg Gly Leu Asn Ala Val Thr Asn
            420                 425                 430 ttt gat atg agc cgg tat gac gtc aaa agc atc ctc gat tcc tcc gcg    1344
Phe Asp Met Ser Arg Tyr Asp Val Lys Ser Ile Leu Asp Ser Ser Ala
            435                 440                 445 ctg ccc att ggg tcc gcg gcg aaa cgg ctg aaa gaa gcg gaa gcg gct    1392
Leu Pro Ile Gly Ser Ala Ala Lys Arg Leu Lys Glu Ala Glu Ala Ala
            450                 455                 460 gcc tcc gcc caa cat cat cat gcg ggg gtc gtc agc tat gat gtg ggg    1440
Ala Ser Ala Gln His His His Ala Gly Val Val Ser Tyr Asp Val Gly
465                 470                 475                 480 cgg att gcg agc caa ctg ggg gat ggg ggt gcc ctc gcc gcc gcc tat    1488
Arg Ile Ala Ser Gln Leu Gly Asp Gly Gly Ala Leu Ala Ala Ala Tyr
                    485                 490                 495 ggg gcc cat tat cac ggg gcg gcg tgg ccc acg att gcc ttt caa ccg    1536
Gly Ala His Tyr His Gly Ala Ala Trp Pro Thr Ile Ala Phe Gln Pro
                500                 505                 510 ggc gcg gcg tcc act ggg ctc tat cat ccc tat gcc caa caa cct atg    1584
Gly Ala Ala Ser Thr Gly Leu Tyr His Pro Tyr Ala Gln Gln Pro Met
            515                 520                 525 cgg ggg ggc ggc tgg tgc aag cag gaa caa gat cat gcg gtc att gcc    1632
Arg Gly Gly Gly Trp Cys Lys Gln Glu Gln Asp His Ala Val Ile Ala
            530                 535                 540 gcc gcc cat tcc ctg caa gat ctg cat cat ctc aat ctg ggc gcg gcg    1680
Ala Ala His Ser Leu Gln Asp Leu His His Leu Asn Leu Gly Ala Ala
545                 550                 555                 560 ggg gcc cat gac ttc ttc tcg gct ggc caa caa gcg gcg gcg gca gcc    1728
Gly Ala His Asp Phe Phe Ser Ala Gly Gln Gln Ala Ala Ala Ala Ala
                565                 570                 575 atg cac ggg ctc gga tcc atc gac tcc gcc agc ctc gag cat tcc acc    1776
Met His Gly Leu Gly Ser Ile Asp Ser Ala Ser Leu Glu His Ser Thr
                580                 585                 590 ggg agc aat agc gtg gtg tat aat ggg ggc gtg ggc gat tcc aat ggg    1824
Gly Ser Asn Ser Val Val Tyr Asn Gly Gly Val Gly Asp Ser Asn Gly
            595                 600                 605 gcg tcc gcg gtc ggg ggg agt ggg gga ggg tat atg atg ccc atg tcc    1872
Ala Ser Ala Val Gly Gly Ser Gly Gly Gly Tyr Met Met Pro Met Ser
            610                 615                 620 gca gcg ggt gct acg aca act tcg gca atg gtg tcc cat gaa caa gtc    1920
Ala Ala Gly Ala Thr Thr Thr Ser Ala Met Val Ser His Glu Gln Val
625                 630                 635                 640 cac gct cgg gcg tat gat gag gcg aaa caa gca gca caa atg ggc tat    1968
His Ala Arg Ala Tyr Asp Glu Ala Lys Gln Ala Ala Gln Met Gly Tyr
                645                 650                 655 gaa agc tat ctc gtc aac gcc gaa aac aac gga ggg ggt aga atg tcc    2016
Glu Ser Tyr Leu Val Asn Ala Glu Asn Asn Gly Gly Gly Arg Met Ser
            660                 665                 670 gct tgg ggc act gtc gtc tcc gct gcg gcc gct gct gca tcc agc       2064
Ala Trp Gly Thr Val Val Ser Ala Ala Ala Ala Ala Ala Ser Ser
            675                 680                 685 aat gat aac atg gcg gcg gat gtg ggg cac ggg ggg gcc caa ctc ttt    2112
Asn Asp Asn Met Ala Ala Asp Val Gly His Gly Gly Ala Gln Leu Phe
            690                 695                 700 tcc gtg tgg aat gac aca taa                                        2133
Ser Val Trp Asn Asp Thr
```

-continued

<210> SEQ ID NO 12
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having the ser37
      altered from tcc to the thr of acc.The ORF
      encodes the aa seq set forth in SEQ ID NO: 19.
<220> FEATURE:
<221> NAME/KEY: CDS
<222> LOCATION: (1)...(2133)

<400> SEQUENCE: 12

```
atg gcc act gtg aac aac tgg ctc gct ttc tcc ctc tcc ccg cag gag        48
Met Ala Thr Val Asn Asn Trp Leu Ala Phe Ser Leu Ser Pro Gln Glu
 1               5                  10                  15 ctg ccg ccc tcc cag acg acg gac tcc aca ctc atc tcg gcc gcc acc        96
Leu Pro Pro Ser Gln Thr Thr Asp Ser Thr Leu Ile Ser Ala Ala Thr
             20                  25                  30 gcc gac cat gtc acc ggc gat gtc tgc ttc aac atc ccc caa gat tgg       144
Ala Asp His Val Thr Gly Asp Val Cys Phe Asn Ile Pro Gln Asp Trp
         35                  40                  45 agc atg agg gga tca gag ctt tcg gcg ctc gtc gcg gag ccg aag ctg       192
Ser Met Arg Gly Ser Glu Leu Ser Ala Leu Val Ala Glu Pro Lys Leu
     50                  55                  60 gag gac ttc ctc ggc ggc atc tcc ttc tcc gag cag cat cac aag gcc       240
Glu Asp Phe Leu Gly Gly Ile Ser Phe Ser Glu Gln His His Lys Ala
 65                  70                  75                  80 aac tgc aac atg ata ccc agc act agc agc aca gtt tgc tac gcg agc       288
Asn Cys Asn Met Ile Pro Ser Thr Ser Ser Thr Val Cys Tyr Ala Ser
                 85                  90                  95 tca ggt gct agc acc ggc tac cat cac cag ctg tac cac cag ccc acc       336
Ser Gly Ala Ser Thr Gly Tyr His His Gln Leu Tyr His Gln Pro Thr
            100                 105                 110 agc tca gcg ctc cac ttc gcg gac tcc gta atg gtg gcc tcc tcg gcc       384
Ser Ser Ala Leu His Phe Ala Asp Ser Val Met Val Ala Ser Ser Ala
        115                 120                 125 ggt gtc cac gac ggc ggt gcc atg ctc agc gcg gcc gcc gct aac ggt       432
Gly Val His Asp Gly Gly Ala Met Leu Ser Ala Ala Ala Ala Asn Gly
    130                 135                 140 gtc gct ggc gct gcc agt gcc aac ggc ggc ggc atc ggg ctg tcc atg       480
Val Ala Gly Ala Ala Ser Ala Asn Gly Gly Gly Ile Gly Leu Ser Met
145                 150                 155                 160 att aag aac tgg ctg cgg agc caa ccg gcg ccc atg cag ccg agg gtg       528
Ile Lys Asn Trp Leu Arg Ser Gln Pro Ala Pro Met Gln Pro Arg Val
                165                 170                 175 gcg gcg gct gag ggc gcg cag ggg ctc tct ttg tcc atg aac atg gcg       576
Ala Ala Ala Glu Gly Ala Gln Gly Leu Ser Leu Ser Met Asn Met Ala
            180                 185                 190 ggg acg acc caa ggc gct gct ggc atg cca ctt ctc gct gga gag cgc       624
Gly Thr Thr Gln Gly Ala Ala Gly Met Pro Leu Leu Ala Gly Glu Arg
        195                 200                 205 gca cgg gcg ccc gag agt gta tcg acg tca gca cag ggt gga gcc gtc       672
Ala Arg Ala Pro Glu Ser Val Ser Thr Ser Ala Gln Gly Gly Ala Val
    210                 215                 220 gtc gtc acg gcg ccg aag gag gat agc ggt ggc agc ggt gtt gcc ggc       720
Val Val Thr Ala Pro Lys Glu Asp Ser Gly Gly Ser Gly Val Ala Gly
225                 230                 235                 240
```

| | | |
|---|---|---|
| gct cta gta gcc gtg agc acg gac acg ggt ggc agc ggc ggc gcg tcg<br>Ala Leu Val Ala Val Ser Thr Asp Thr Gly Gly Ser Gly Gly Ala Ser<br>245  250  255 | | 768 |
| gct gac aac acg gca agg aag acg gtg gac acg ttc ggg cag cgc acg<br>Ala Asp Asn Thr Ala Arg Lys Thr Val Asp Thr Phe Gly Gln Arg Thr<br>260  265  270 | | 816 |
| tcg att tac cgt ggc gtg aca agg cat aga tgg act ggg aga tat gag<br>Ser Ile Tyr Arg Gly Val Thr Arg His Arg Trp Thr Gly Arg Tyr Glu<br>275  280  285 | | 864 |
| gca cat ctt tgg gat aac agt tgc aga agg gaa ggg caa act cgt aag<br>Ala His Leu Trp Asp Asn Ser Cys Arg Arg Glu Gly Gln Thr Arg Lys<br>290  295  300 | | 912 |
| ggt cgt caa gtc tat tta ggt ggc tat gat aaa gag gag aaa gct gct<br>Gly Arg Gln Val Tyr Leu Gly Gly Tyr Asp Lys Glu Glu Lys Ala Ala<br>305  310  315  320 | | 960 |
| agg gct tat gat ctt gct gct ctg aag tac tgg ggt gcc aca aca aca<br>Arg Ala Tyr Asp Leu Ala Ala Leu Lys Tyr Trp Gly Ala Thr Thr Thr<br>325  330  335 | | 1008 |
| aca aat ttt cca gtg agt aac tac gaa aag gag ctc gag gac atg aag<br>Thr Asn Phe Pro Val Ser Asn Tyr Glu Lys Glu Leu Glu Asp Met Lys<br>340  345  350 | | 1056 |
| cac atg aca agg cag gag ttt gta gcg tct ctg aga agg aag agc agt<br>His Met Thr Arg Gln Glu Phe Val Ala Ser Leu Arg Arg Lys Ser Ser<br>355  360  365 | | 1104 |
| ggt ttc tcc aga ggt gca tcc att tac agg gga gtg act agg cat cac<br>Gly Phe Ser Arg Gly Ala Ser Ile Tyr Arg Gly Val Thr Arg His His<br>370  375  380 | | 1152 |
| caa cat gga aga tgg caa gca cgg att gga cga gtt gca ggg aac aag<br>Gln His Gly Arg Trp Gln Ala Arg Ile Gly Arg Val Ala Gly Asn Lys<br>385  390  395  400 | | 1200 |
| gat ctt tac ttg ggc acc ttc agc acc cag gag gag gca gcg gag gcg<br>Asp Leu Tyr Leu Gly Thr Phe Ser Thr Gln Glu Glu Ala Ala Glu Ala<br>405  410  415 | | 1248 |
| tac gac atc gcg gcg atc aag ttc cgc ggc ctc aac gcc gtc acc aac<br>Tyr Asp Ile Ala Ala Ile Lys Phe Arg Gly Leu Asn Ala Val Thr Asn<br>420  425  430 | | 1296 |
| ttc gac atg agc cgc tac gac gtg aag agc atc ctg gac agc agc gcc<br>Phe Asp Met Ser Arg Tyr Asp Val Lys Ser Ile Leu Asp Ser Ser Ala<br>435  440  445 | | 1344 |
| ctc ccc atc ggc agc gcc gcc aag cgc ctc aag gag gcc gag gcc gca<br>Leu Pro Ile Gly Ser Ala Ala Lys Arg Leu Lys Glu Ala Glu Ala Ala<br>450  455  460 | | 1392 |
| gcg tcc gcg cag cac cac cac gcc ggc gtg gtg agc tac gac gtc ggc<br>Ala Ser Ala Gln His His His Ala Gly Val Val Ser Tyr Asp Val Gly<br>465  470  475  480 | | 1440 |
| cgc atc gcc tcg cag ctc ggc gac ggc gga gcc ctg gcg gcg gcg tac<br>Arg Ile Ala Ser Gln Leu Gly Asp Gly Gly Ala Leu Ala Ala Ala Tyr<br>485  490  495 | | 1488 |
| ggc gcg cac tac cac ggc gcc gcc tgg ccg acc atc gcg ttc cag ccg<br>Gly Ala His Tyr His Gly Ala Ala Trp Pro Thr Ile Ala Phe Gln Pro<br>500  505  510 | | 1536 |
| ggc gcc gcc agc aca ggc ctg tac cac ccg tac gcg cag cag cca atg<br>Gly Ala Ala Ser Thr Gly Leu Tyr His Pro Tyr Ala Gln Gln Pro Met<br>515  520  525 | | 1584 |
| cgc ggc ggc ggg tgg tgc aag cag gag cag gac cac gcg gtg atc gcg<br>Arg Gly Gly Gly Trp Cys Lys Gln Glu Gln Asp His Ala Val Ile Ala<br>530  535  540 | | 1632 |
| gcc gcg cac agc ctg cag gac ctc cac cac ctg aac ctg ggc gcg gcc<br>Ala Ala His Ser Leu Gln Asp Leu His His Leu Asn Leu Gly Ala Ala<br>545  550  555  560 | | 1680 |

-continued

| | |
|---|---|
| ggc gcg cac gac ttt ttc tcg gca ggg cag cag gcc gcc gcc gct gcg<br>Gly Ala His Asp Phe Phe Ser Ala Gly Gln Gln Ala Ala Ala Ala Ala<br>565                            570                           575 | 1728 |
| atg cac ggc ctg ggt agc atc gac agt gcg tcg ctc gag cac agc acc<br>Met His Gly Leu Gly Ser Ile Asp Ser Ala Ser Leu Glu His Ser Thr<br>        580                            585                          590 | 1776 |
| ggc tcc aac tcc gtc gtc tac aac ggc ggg gtc ggc gac agc aac ggc<br>Gly Ser Asn Ser Val Val Tyr Asn Gly Gly Val Gly Asp Ser Asn Gly<br>595                            600                           605 | 1824 |
| gcc agc gcc gtc ggc ggc agt ggc ggt ggc tac atg atg ccg atg agc<br>Ala Ser Ala Val Gly Gly Ser Gly Gly Gly Tyr Met Met Pro Met Ser<br>        610                            615                          620 | 1872 |
| gct gcc gga gca acc act aca tcg gca atg gtg agc cac gag cag gtg<br>Ala Ala Gly Ala Thr Thr Thr Ser Ala Met Val Ser His Glu Gln Val<br>625                            630                           635                          640 | 1920 |
| cat gca cgg gcc tac gac gaa gcc aag cag gct gct cag atg ggg tac<br>His Ala Arg Ala Tyr Asp Glu Ala Lys Gln Ala Ala Gln Met Gly Tyr<br>                        645                            650                          655 | 1968 |
| gag agc tac ctg gtg aac gcg gag aac aat ggt ggc gga agg atg tct<br>Glu Ser Tyr Leu Val Asn Ala Glu Asn Asn Gly Gly Gly Arg Met Ser<br>        660                            665                          670 | 2016 |
| gca tgg ggg act gtc gtg tct gca gcc gcg gcg gca gca agc agc<br>Ala Trp Gly Thr Val Val Ser Ala Ala Ala Ala Ala Ala Ser Ser<br>675                            680                           685 | 2064 |
| aac gac aac atg gcc gcc gac gtc ggc cat ggc ggc gcg cag ctc ttc<br>Asn Asp Asn Met Ala Ala Asp Val Gly His Gly Gly Ala Gln Leu Phe<br>        690                            695                          700 | 2112 |
| agt gtc tgg aac gac act taa<br>Ser Val Trp Asn Asp Thr<br>705                            710 | 2133 |

<210> SEQ ID NO 13
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 97.3% seq id
    to SEQ ID NO:3.  The ORF encodes the
    aa seq set forth in SEQ ID NO:2 with a
    single aa alteration (i.e., S37 to T37).
<220> FEATURE:
<221> NAME/KEY: CDS
<222> LOCATION: (1)...(2133)

<400> SEQUENCE: 13

| | |
|---|---|
| atg gcc act gtg aac aac tgg ctc gct ttc tcc ctc tcc ccg cag gag<br>Met Ala Thr Val Asn Asn Trp Leu Ala Phe Ser Leu Ser Pro Gln Glu<br>1                     5                            10                          15 | 48 |
| ctg ccg ccc tcc caa acc acg gac tcc aca ctc atc tcg gcc gcc acc<br>Leu Pro Pro Ser Gln Thr Thr Asp Ser Thr Leu Ile Ser Ala Ala Thr<br>               20                          25                           30 | 96 |
| gcc gac cat gtc acc ggc gat gtc tgc ttc aac atc ccc caa gat tgg<br>Ala Asp His Val Thr Gly Asp Val Cys Phe Asn Ile Pro Gln Asp Trp<br>                     35                        40                           45 | 144 |
| agc atg agg gga tca gag ctt tcg gcg ctc gtc gcg gag ccg aaa ctg<br>Ser Met Arg Gly Ser Glu Leu Ser Ala Leu Val Ala Glu Pro Lys Leu<br>        50                            55                          60 | 192 |
| gag gac ttc ctc ggg ggc att tcc ttc tcc gag cag cat cac aag gcc<br>Glu Asp Phe Leu Gly Gly Ile Ser Phe Ser Glu Gln His His Lys Ala<br>65                            70                            75                          80 | 240 |

-continued

| | | |
|---|---|---|
| aac tgc aac atg ata ccc tcc act agc tcc aca gtt tgc tac gcg agc<br>Asn Cys Asn Met Ile Pro Ser Thr Ser Ser Thr Val Cys Tyr Ala Ser<br>              85                       90                  95 | 288 |
| tca ggt gct agc acc ggc tac cat cac cag ctg tac cac cag ccc acc<br>Ser Gly Ala Ser Thr Gly Tyr His His Gln Leu Tyr His Gln Pro Thr<br>100                    105                110 | 336 |
| tcc tca gcg ctc cac ttc gcg gac tcc gta atg gtg gcc tcg tcg gcc<br>Ser Ser Ala Leu His Phe Ala Asp Ser Val Met Val Ala Ser Ser Ala<br>        115                120              125 | 384 |
| ggt gtc cac gac ggt ggt gcc atg ctc agc gcg gcc gcc gct aac ggt<br>Gly Val His Asp Gly Gly Ala Met Leu Ser Ala Ala Ala Ala Asn Gly<br>130                    135                140 | 432 |
| gtc gct ggc gca gcc agt gcc aac ggg ggc ggc atc ggg ctg tcc atg<br>Val Ala Gly Ala Ala Ser Ala Asn Gly Gly Gly Ile Gly Leu Ser Met<br>145                  150                  155              160 | 480 |
| att aag aac tgg ctg cgg agc caa ccg gcg ccc atg cag ccg agg gtg<br>Ile Lys Asn Trp Leu Arg Ser Gln Pro Ala Pro Met Gln Pro Arg Val<br>              165                170              175 | 528 |
| gcg gcg gct gag ggc gcg cag ggg ctc tct ttg tcc atg aat atg gcg<br>Ala Ala Ala Glu Gly Ala Gln Gly Leu Ser Leu Ser Met Asn Met Ala<br>        180                185              190 | 576 |
| ggg acg acc caa ggc gct gca ggc atg cca ctt ctc gct gga gag cgc<br>Gly Thr Thr Gln Gly Ala Ala Gly Met Pro Leu Leu Ala Gly Glu Arg<br>195                  200                205 | 624 |
| gca cgg gcg ccc gag agt gta tcg acg tca gca cag ggt gga gcc gtc<br>Ala Arg Ala Pro Glu Ser Val Ser Thr Ser Ala Gln Gly Gly Ala Val<br>          210                215              220 | 672 |
| gtc gtc acc gcg ccg aag gag gat agc ggt ggc agc ggt gtt gcc ggc<br>Val Val Thr Ala Pro Lys Glu Asp Ser Gly Gly Ser Gly Val Ala Gly<br>225                  230                  235              240 | 720 |
| gct cta gta gcc gtg agc acg gac acg ggt ggc agc ggg ggc gcg tcg<br>Ala Leu Val Ala Val Ser Thr Asp Thr Gly Gly Ser Gly Gly Ala Ser<br>                  245                250              255 | 768 |
| gct gac aac acg gca agg aag acg gtg gac acg ttt ggg cag cgg acg<br>Ala Asp Asn Thr Ala Arg Lys Thr Val Asp Thr Phe Gly Gln Arg Thr<br>        260                265              270 | 816 |
| tcg atc tac cgt ggc gtg aca aga cat aga tgg act ggg aga tat gag<br>Ser Ile Tyr Arg Gly Val Thr Arg His Arg Trp Thr Gly Arg Tyr Glu<br>275                  280                285 | 864 |
| gca cat ctt tgg gat aac agt tgc aga agg gaa ggg caa act cgt aag<br>Ala His Leu Trp Asp Asn Ser Cys Arg Arg Glu Gly Gln Thr Arg Lys<br>        290                295              300 | 912 |
| ggt cgt caa gtc tat tta ggt ggc tat gat aaa gag gag aaa gct gct<br>Gly Arg Gln Val Tyr Leu Gly Gly Tyr Asp Lys Glu Glu Lys Ala Ala<br>305                  310                  315              320 | 960 |
| agg gct tat gac ctt gct gct ctc aag tac tgg ggt gcc aca aca aca<br>Arg Ala Tyr Asp Leu Ala Ala Leu Lys Tyr Trp Gly Ala Thr Thr Thr<br>                  325                330              335 | 1008 |
| aca aat ttc cca gtg agt aac tac gaa aag gag ctc gag gac atg aag<br>Thr Asn Phe Pro Val Ser Asn Tyr Glu Lys Glu Leu Glu Asp Met Lys<br>              340                345              350 | 1056 |
| cac atg aca agg cag gag ttt gta gcg tct ctg aga agg aag agc tcc<br>His Met Thr Arg Gln Glu Phe Val Ala Ser Leu Arg Arg Lys Ser Ser<br>             355                360              365 | 1104 |
| ggt ttc tcc aga ggt gca tcc att tac agg gga gtg act agg cat cac<br>Gly Phe Ser Arg Gly Ala Ser Ile Tyr Arg Gly Val Thr Arg His His<br>370                      375                380 | 1152 |
| caa cat gga aga tgg caa gct cgg att gga cga gtt gca ggg aac aag<br>Gln His Gly Arg Trp Gln Ala Arg Ile Gly Arg Val Ala Gly Asn Lys<br>385                  390                395              400 | 1200 |

```
                                                     -continued gat ctt tac ctc ggc acc ttc agc acc cag gag gaa gct gcg gag gcg    1248
Asp Leu Tyr Leu Gly Thr Phe Ser Thr Gln Glu Glu Ala Ala Glu Ala
            405                 410                 415 tac gac atc gcg gcg atc aaa ttc cgc ggc ctc aac gcc gtc acc aac    1296
Tyr Asp Ile Ala Ala Ile Lys Phe Arg Gly Leu Asn Ala Val Thr Asn
        420                 425                 430 ttc gac atg agc cgc tac gac gtg aag agc atc ctg gac agc agc gcc    1344
Phe Asp Met Ser Arg Tyr Asp Val Lys Ser Ile Leu Asp Ser Ser Ala
        435                 440                 445 ctg ccc atc ggc agc gcc gcc aag cgc ctg aag gag gcc gag gcc gca    1392
Leu Pro Ile Gly Ser Ala Ala Lys Arg Leu Lys Glu Ala Glu Ala Ala
    450                 455                 460 gcg tcc gcg cag cac cac cac gcc ggc gtg gtg agc tac gac gtc ggg    1440
Ala Ser Ala Gln His His His Ala Gly Val Val Ser Tyr Asp Val Gly
465                 470                 475                 480 cgc atc gcc tcg cag ctc ggc gac ggc gga gcc ctg gcg gcg gcg tat    1488
Arg Ile Ala Ser Gln Leu Gly Asp Gly Gly Ala Leu Ala Ala Ala Tyr
                485                 490                 495 ggc gcg cac tac cac ggg gcc gcc tgg ccg acc atc gcg ttc cag ccg    1536
Gly Ala His Tyr His Gly Ala Ala Trp Pro Thr Ile Ala Phe Gln Pro
            500                 505                 510 ggc gcc gcc agc aca ggc ctg tac cac ccc tac gcg cag cag cca atg    1584
Gly Ala Ala Ser Thr Gly Leu Tyr His Pro Tyr Ala Gln Gln Pro Met
        515                 520                 525 cgc ggc ggc ggg tgg tgc aag cag gag cag gac cac gcg gtg atc gcg    1632
Arg Gly Gly Gly Trp Cys Lys Gln Glu Gln Asp His Ala Val Ile Ala
    530                 535                 540 gcg gcg cac agc ctg cag gac ctc cac cac ctg aac ctg ggc gcc gcc    1680
Ala Ala His Ser Leu Gln Asp Leu His His Leu Asn Leu Gly Ala Ala
545                 550                 555                 560 ggc gcg cac gac ttt ttt tcg gca ggg cag cag gcc gcc gcc gca gcc    1728
Gly Ala His Asp Phe Phe Ser Ala Gly Gln Gln Ala Ala Ala Ala Ala
                565                 570                 575 atg cac ggc ctg ggt agc atc gac agt gcg tcg ctc gaa cac tcc acc    1776
Met His Gly Leu Gly Ser Ile Asp Ser Ala Ser Leu Glu His Ser Thr
            580                 585                 590 ggc agc aac tcc gtc gtc tac aat ggc ggg gtc ggc gac agc aac ggc    1824
Gly Ser Asn Ser Val Val Tyr Asn Gly Gly Val Gly Asp Ser Asn Gly
        595                 600                 605 gcc agc gcc gtc ggc ggc tcc ggc gga ggc tat atg atg ccg atg agc    1872
Ala Ser Ala Val Gly Gly Ser Gly Gly Gly Tyr Met Met Pro Met Ser
    610                 615                 620 gct gcc gga gca acc aca aca tcg gca atg gtg agc cac gag cag gtg    1920
Ala Ala Gly Ala Thr Thr Thr Ser Ala Met Val Ser His Glu Gln Val
625                 630                 635                 640 cat gca cgg gcc tac gac gaa gcc aag cag gct gca cag atg ggg tac    1968
His Ala Arg Ala Tyr Asp Glu Ala Lys Gln Ala Ala Gln Met Gly Tyr
                645                 650                 655 gag agc tac ctg gtg aac gcg gag aac aat ggt ggc gga agg atg tct    2016
Glu Ser Tyr Leu Val Asn Ala Glu Asn Asn Gly Gly Gly Arg Met Ser
            660                 665                 670 gca tgg ggg act gtc gtg tct gca gcg gcg gca gca gca agc agc       2064
Ala Trp Gly Thr Val Val Ser Ala Ala Ala Ala Ala Ala Ser Ser
        675                 680                 685 aac gac aac atg gcc gcc gac gtc ggc cat ggc ggc gcg cag ctc ttc    2112
Asn Asp Asn Met Ala Ala Asp Val Gly His Gly Gly Ala Gln Leu Phe
    690                 695                 700 agt gtc tgg aac gac act taa                                        2133
Ser Val Trp Asn Asp Thr
```

<210> SEQ ID NO 14
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 91.9% seq id
to SEQ ID NO:3. The ORF encodes the aa
seq set forth in SEQ ID NO:2 with a
single aa alteration (i.e., S37 to T37).
<220> FEATURE:
<221> NAME/KEY: CDS
<222> LOCATION: (1)...(2133)

<400> SEQUENCE: 14

```
atg gcc aca gtg aac aac tgg ctc gct ttt agc ctg agc ccg cag gaa      48
Met Ala Thr Val Asn Asn Trp Leu Ala Phe Ser Leu Ser Pro Gln Glu
 1               5                  10                  15 ctg ccg ccc tcc cag acc acg gac tcc act ctc atc tcg gcc gcc acc      96
Leu Pro Pro Ser Gln Thr Thr Asp Ser Thr Leu Ile Ser Ala Ala Thr
             20                  25                  30 gcc gat cat gtc acc ggc gac gtc tgt ttc aat att ccc caa gat tgg     144
Ala Asp His Val Thr Gly Asp Val Cys Phe Asn Ile Pro Gln Asp Trp
         35                  40                  45 tcc atg agg gga tca gag ctt tcg gcg ctg gtc gcg gaa ccg aaa ctg     192
Ser Met Arg Gly Ser Glu Leu Ser Ala Leu Val Ala Glu Pro Lys Leu
     50                  55                  60 gaa gac ttc ctc ggc ggc atc tcc ttt tcc gaa cag cat cat aag gcc     240
Glu Asp Phe Leu Gly Gly Ile Ser Phe Ser Glu Gln His His Lys Ala
 65                  70                  75                  80 aac tgc aac atg ata ccc agc act agc agc aca gtg tgc tac gcg agc     288
Asn Cys Asn Met Ile Pro Ser Thr Ser Ser Thr Val Cys Tyr Ala Ser
                 85                  90                  95 tca ggt gct tcc acc ggc tac cac cat caa ctc tac cac caa ccg acg     336
Ser Gly Ala Ser Thr Gly Tyr His His Gln Leu Tyr His Gln Pro Thr
            100                 105                 110 agc tca gcg ctc cat ttc gcc gat tcc gta atg gtc gcc tcc tcg gcc     384
Ser Ser Ala Leu His Phe Ala Asp Ser Val Met Val Ala Ser Ser Ala
        115                 120                 125 ggt gtc cac gac ggg ggt gcc atg ctc tcc gcg gcc gcc gct aac ggt     432
Gly Val His Asp Gly Gly Ala Met Leu Ser Ala Ala Ala Ala Asn Gly
    130                 135                 140 gtc gct ggc gct gcc agt gcg aac ggc ggc ggc atc ggg ctg agc atg     480
Val Ala Gly Ala Ala Ser Ala Asn Gly Gly Gly Ile Gly Leu Ser Met
145                 150                 155                 160 atc aag aat tgg ctg cgg agc caa ccg gcg ccc atg caa ccg agg gtg     528
Ile Lys Asn Trp Leu Arg Ser Gln Pro Ala Pro Met Gln Pro Arg Val
                165                 170                 175 gcc gcg gct gag ggg gcg cag ggg ctg tct ttg agc atg aat atg gcc     576
Ala Ala Ala Glu Gly Ala Gln Gly Leu Ser Leu Ser Met Asn Met Ala
            180                 185                 190 ggg acc acg caa ggg gct gct ggc atg cca ctt ctc gct ggt gag cgg     624
Gly Thr Thr Gln Gly Ala Ala Gly Met Pro Leu Leu Ala Gly Glu Arg
        195                 200                 205 gca cgc gcc ccc gag agt gtt tcg acg tca gca cag gga ggt gcg gtg     672
Ala Arg Ala Pro Glu Ser Val Ser Thr Ser Ala Gln Gly Gly Ala Val
    210                 215                 220 gtc gtc acg gcg ccg aag gag gat agc ggt ggc agc ggt gtt gcg ggc     720
Val Val Thr Ala Pro Lys Glu Asp Ser Gly Gly Ser Gly Val Ala Gly
225                 230                 235                 240
```

```
gct ctc gta gcc gtg agc acg gac acg ggt ggc agc ggc ggc gcg tcg     768
Ala Leu Val Ala Val Ser Thr Asp Thr Gly Gly Ser Gly Gly Ala Ser
            245                 250                 255 gct gac aac acg gca agg aag acg gtg gac acg ttc ggg cag cgg acg     816
Ala Asp Asn Thr Ala Arg Lys Thr Val Asp Thr Phe Gly Gln Arg Thr
                260                 265                 270 tcg att tac cgt ggc gtg aca agg cat aga tgg act ggg agg tat gag     864
Ser Ile Tyr Arg Gly Val Thr Arg His Arg Trp Thr Gly Arg Tyr Glu
            275                 280                 285 gca cat ctt tgg gat aac agt tgc aga agg gag ggg caa act cgt aag     912
Ala His Leu Trp Asp Asn Ser Cys Arg Arg Glu Gly Gln Thr Arg Lys
        290                 295                 300 ggt aga cag gtc tac ctg ggt ggc tat gat aaa gag gag aag gct gct     960
Gly Arg Gln Val Tyr Leu Gly Gly Tyr Asp Lys Glu Glu Lys Ala Ala
305                 310                 315                 320 agg gct tat gat ctt gct gca ctg aag tac tgg ggt gcc act act aca    1008
Arg Ala Tyr Asp Leu Ala Ala Leu Lys Tyr Trp Gly Ala Thr Thr Thr
                325                 330                 335 aca aac ttt cct gtc agt aac tat gaa aag gag ctc gag gac atg aag    1056
Thr Asn Phe Pro Val Ser Asn Tyr Glu Lys Glu Leu Glu Asp Met Lys
                340                 345                 350 cac atg aca agg caa gaa ttt gtt gcg tct ctg aga agg aag agc agt    1104
His Met Thr Arg Gln Glu Phe Val Ala Ser Leu Arg Arg Lys Ser Ser
            355                 360                 365 ggt ttc tcc aga ggt gca tcc att tac agg gga gtg act agg cat cac    1152
Gly Phe Ser Arg Gly Ala Ser Ile Tyr Arg Gly Val Thr Arg His His
370                 375                 380 caa cat ggt aga tgg cag gca cgc att ggt cga gtt gca ggg aac aaa    1200
Gln His Gly Arg Trp Gln Ala Arg Ile Gly Arg Val Ala Gly Asn Lys
385                 390                 395                 400 gat ctg tat ttg ggc acc ttt agc acc caa gag gag gca gcc gag gcg    1248
Asp Leu Tyr Leu Gly Thr Phe Ser Thr Gln Glu Glu Ala Ala Glu Ala
                405                 410                 415 tac gac atc gcg gcg atc aaa ttc cgc ggc ctc aac gcc gtc acg aac    1296
Tyr Asp Ile Ala Ala Ile Lys Phe Arg Gly Leu Asn Ala Val Thr Asn
            420                 425                 430 ttc gat atg agc cgc tac gac gtc aag agc atc ctg gac agc agc gcc    1344
Phe Asp Met Ser Arg Tyr Asp Val Lys Ser Ile Leu Asp Ser Ser Ala
            435                 440                 445 ctc ccg atc ggc agc gcc gcg aaa cgc ctc aag gag gcc gag gcc gca    1392
Leu Pro Ile Gly Ser Ala Ala Lys Arg Leu Lys Glu Ala Glu Ala Ala
450                 455                 460 gcg tcc gcg cag cac cac cac gcc ggc gtg gtc agc tac gac gtc ggc    1440
Ala Ser Ala Gln His His His Ala Gly Val Val Ser Tyr Asp Val Gly
465                 470                 475                 480 cgc att gcc tcg cag ctc ggc gac ggc gga gcc ctg gcc gcg gcg tac    1488
Arg Ile Ala Ser Gln Leu Gly Asp Gly Gly Ala Leu Ala Ala Ala Tyr
                485                 490                 495 ggg gcg cac tac cac ggg gcc gcc tgg ccg acc atc gcc ttt cag ccg    1536
Gly Ala His Tyr His Gly Ala Ala Trp Pro Thr Ile Ala Phe Gln Pro
            500                 505                 510 ggc gcc gcc agc aca ggc ctg tac cat ccg tac gcg caa caa cca atg    1584
Gly Ala Ala Ser Thr Gly Leu Tyr His Pro Tyr Ala Gln Gln Pro Met
            515                 520                 525 cgc ggc ggc ggg tgg tgc aaa cag gag cag gac cac gcg gtc att gcg    1632
Arg Gly Gly Gly Trp Cys Lys Gln Glu Gln Asp His Ala Val Ile Ala
530                 535                 540 gcg gcc cat agc ctg cag gac ctc cac cac ctc aac ctg ggc gcg gcg    1680
Ala Ala His Ser Leu Gln Asp Leu His His Leu Asn Leu Gly Ala Ala
```

```
                                                  545                 550                 555                 560
ggc gcg cac gac ttt ttc tcg gca ggg caa cag gcc gcg gcc gct gcg                                                        1728
Gly Ala His Asp Phe Phe Ser Ala Gly Gln Gln Ala Ala Ala Ala Ala
                565                 570                 575 atg cac ggc ctg ggt agc att gac tcc gcg tcg ctg gag cac agc acg                                                        1776
Met His Gly Leu Gly Ser Ile Asp Ser Ala Ser Leu Glu His Ser Thr
            580                 585                 590 ggc agc aac tcc gtc gtg tac aac ggc ggc gtg ggc gac agc aac ggc                                                        1824
Gly Ser Asn Ser Val Val Tyr Asn Gly Gly Val Gly Asp Ser Asn Gly
            595                 600                 605 gcc agc gcc gtc ggg ggg agt ggg ggt ggg tac atg atg ccc atg agc                                                        1872
Ala Ser Ala Val Gly Gly Ser Gly Gly Gly Tyr Met Met Pro Met Ser
            610                 615                 620 gca gcc gga gca acc act act agc gca atg gtg agc cat gag cag gtg                                                        1920
Ala Ala Gly Ala Thr Thr Thr Ser Ala Met Val Ser His Glu Gln Val
625                 630                 635                 640 cat gca cgg gcc tac gac gag gcc aaa cag gca gca caa atg ggg tat                                                        1968
His Ala Arg Ala Tyr Asp Glu Ala Lys Gln Ala Ala Gln Met Gly Tyr
                645                 650                 655 gag agc tac ctg gtc aat gcc gag aac aat ggt ggg ggt aga atg tct                                                        2016
Glu Ser Tyr Leu Val Asn Ala Glu Asn Asn Gly Gly Gly Arg Met Ser
                660                 665                 670 gca tgg ggc act gtc gtg tct gca gcc gcg gcg gca gca gct agc tcc                                                        2064
Ala Trp Gly Thr Val Val Ser Ala Ala Ala Ala Ala Ala Ser Ser
            675                 680                 685 aac gat aac atg gcc gcc gac gtc ggc cat ggc ggg gcg caa ctc ttt                                                        2112
Asn Asp Asn Met Ala Ala Asp Val Gly His Gly Gly Ala Gln Leu Phe
690                 695                 700 tcc gtg tgg aac gat act taa                                                                                            2133
Ser Val Trp Asn Asp Thr
705                 710

<210> SEQ ID NO 15
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 86.6% seq id
      to SEQ ID NO:3.  The ORF encodes the aa
      seq set forth in SEQ ID NO:2 with a
      single aa alteration (i.e., S37 to T37).
<220> FEATURE:
<221> NAME/KEY: CDS
<222> LOCATION: (1)...(2133)

<400> SEQUENCE: 15 atg gcg act gtg aat aat tgg ctc gct ttc tcc ctc tcc ccc cag gag                                                         48
Met Ala Thr Val Asn Asn Trp Leu Ala Phe Ser Leu Ser Pro Gln Glu
1               5                   10                  15 ctc ccc ccc tcc cag acc acg gat agc aca ctc atc tcg gcc gcc acc                                                         96
Leu Pro Pro Ser Gln Thr Thr Asp Ser Thr Leu Ile Ser Ala Ala Thr
                20                  25                  30 gcg gat cat gtc acc ggc gac gtc tgt ttc aac att ccg cag gac tgg                                                        144
Ala Asp His Val Thr Gly Asp Val Cys Phe Asn Ile Pro Gln Asp Trp
            35                  40                  45 agc atg aga ggt tca gag ctt agc gcg ctc gtc gcg gaa ccg aaa ctc                                                        192
Ser Met Arg Gly Ser Glu Leu Ser Ala Leu Val Ala Glu Pro Lys Leu
        50                  55                  60 gag gac ttt ctc ggc ggc atc tcc ttc tcc gag cag cat cac aaa gcg                                                        240
Glu Asp Phe Leu Gly Gly Ile Ser Phe Ser Glu Gln His His Lys Ala
65                  70                  75                  80
```

```
aac tgt aac atg atc ccc agc act agc tcc act gtt tgc tac gcc agc       288
Asn Cys Asn Met Ile Pro Ser Thr Ser Ser Thr Val Cys Tyr Ala Ser
                85                  90                  95 tca ggt gct agc acg ggc tat cat cac cag ctg tat cat cag ccc acc       336
Ser Gly Ala Ser Thr Gly Tyr His His Gln Leu Tyr His Gln Pro Thr
            100                 105                 110 agc tca gcg ctg cat ttt gcc gat agc gta atg gtg gcg tcc tcg gcg       384
Ser Ser Ala Leu His Phe Ala Asp Ser Val Met Val Ala Ser Ser Ala
        115                 120                 125 ggt gtg cac gac ggg gga gcc atg ctc agc gcg gcc gcg gct aat ggt       432
Gly Val His Asp Gly Gly Ala Met Leu Ser Ala Ala Ala Ala Asn Gly
    130                 135                 140 gtc gca ggc gca gcg tcc gcg aac ggc ggg ggc att ggg ctg tcc atg       480
Val Ala Gly Ala Ala Ser Ala Asn Gly Gly Gly Ile Gly Leu Ser Met
145                 150                 155                 160 att aaa aac tgg ctg cgc agc cag ccg gcg ccc atg caa ccg aga gtg       528
Ile Lys Asn Trp Leu Arg Ser Gln Pro Ala Pro Met Gln Pro Arg Val
                165                 170                 175 gcc gcg gca gaa ggc gcg caa ggc ctc tcc ctc agc atg aac atg gcc       576
Ala Ala Ala Glu Gly Ala Gln Gly Leu Ser Leu Ser Met Asn Met Ala
            180                 185                 190 ggg acc acg cag ggc gct gca ggg atg cca ctg ctg gca ggt gaa cgg       624
Gly Thr Thr Gln Gly Ala Ala Gly Met Pro Leu Leu Ala Gly Glu Arg
        195                 200                 205 gca cgg gcg ccc gaa agt gta agc acg tca gca cag ggt gga gcc gtc       672
Ala Arg Ala Pro Glu Ser Val Ser Thr Ser Ala Gln Gly Gly Ala Val
    210                 215                 220 gtc gtc acg gcg ccg aag gag gac tcc ggt ggc agc ggt gtg gcg ggc       720
Val Val Thr Ala Pro Lys Glu Asp Ser Gly Gly Ser Gly Val Ala Gly
225                 230                 235                 240 gca ctc gtt gcc gtg agc acc gat acg ggt ggc agc ggg ggc gcc agc       768
Ala Leu Val Ala Val Ser Thr Asp Thr Gly Gly Ser Gly Gly Ala Ser
                245                 250                 255 gca gac aac acc gca agg aag acg gtc gac acc ttc ggg caa cgg acg       816
Ala Asp Asn Thr Ala Arg Lys Thr Val Asp Thr Phe Gly Gln Arg Thr
            260                 265                 270 agc att tac cgt ggg gtg aca aga cac agg tgg aca ggg aga tat gag       864
Ser Ile Tyr Arg Gly Val Thr Arg His Arg Trp Thr Gly Arg Tyr Glu
        275                 280                 285 gct cac ctg tgg gat aat tcc tgc aga agg gag ggc caa act cgt aag       912
Ala His Leu Trp Asp Asn Ser Cys Arg Arg Glu Gly Gln Thr Arg Lys
    290                 295                 300 ggt cgt caa gtg tat tta gga ggg tat gat aaa gag gag aaa gct gct       960
Gly Arg Gln Val Tyr Leu Gly Gly Tyr Asp Lys Glu Glu Lys Ala Ala
305                 310                 315                 320 aga gct tat gat ctt gct gct ctg aag tac tgg ggt gcc aca act aca      1008
Arg Ala Tyr Asp Leu Ala Ala Leu Lys Tyr Trp Gly Ala Thr Thr Thr
                325                 330                 335 aca aac ttt cca gtg tcc aac tat gag aag gag ctc gaa gac atg aag      1056
Thr Asn Phe Pro Val Ser Asn Tyr Glu Lys Glu Leu Glu Asp Met Lys
            340                 345                 350 cat atg aca agg caa gaa ttt gtt gcg tcc ctg agg aga aag tcc agt      1104
His Met Thr Arg Gln Glu Phe Val Ala Ser Leu Arg Arg Lys Ser Ser
        355                 360                 365 gga ttc tcc agg gga gct agc atc tat agg gga gtc aca agg cat cac      1152
Gly Phe Ser Arg Gly Ala Ser Ile Tyr Arg Gly Val Thr Arg His His
    370                 375                 380 caa cac gga aga tgg caa gct cgc att ggt cga gtt gct ggc aac aag      1200
Gln His Gly Arg Trp Gln Ala Arg Ile Gly Arg Val Ala Gly Asn Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 385 |     |     |     |     | 390 |     |     |     |     | 395 |     |     |     |     | 400 |      |
| gat | ctt | tac | ttg | ggc | acg | ttt | agc | acc | caa | gag | gag | gca | gcg | gaa | gcg | 1248 |
| Asp | Leu | Tyr | Leu | Gly | Thr | Phe | Ser | Thr | Gln | Glu | Glu | Ala | Ala | Glu | Ala |      |
|     |     |     |     | 405 |     |     |     |     | 410 |     |     |     |     | 415 |     |      |
| tat | gat | atc | gcc | gcg | atc | aaa | ttc | cgc | ggg | ctg | aat | gcc | gtc | acg | aac | 1296 |
| Tyr | Asp | Ile | Ala | Ala | Ile | Lys | Phe | Arg | Gly | Leu | Asn | Ala | Val | Thr | Asn |      |
|     |     |     | 420 |     |     |     |     | 425 |     |     |     |     | 430 |     |     |      |
| ttc | gac | atg | tcc | cgc | tac | gat | gtg | aag | agc | att | ctc | gac | agc | agc | gcg | 1344 |
| Phe | Asp | Met | Ser | Arg | Tyr | Asp | Val | Lys | Ser | Ile | Leu | Asp | Ser | Ser | Ala |      |
|     |     | 435 |     |     |     |     | 440 |     |     |     |     | 445 |     |     |     |      |
| ctg | ccg | atc | ggg | agc | gcc | gcg | aag | cgc | ctg | aag | gaa | gcg | gag | gcc | gct | 1392 |
| Leu | Pro | Ile | Gly | Ser | Ala | Ala | Lys | Arg | Leu | Lys | Glu | Ala | Glu | Ala | Ala |      |
|     | 450 |     |     |     |     | 455 |     |     |     |     | 460 |     |     |     |     |      |
| gcc | tcc | gcc | cag | cat | cat | cac | gcc | ggg | gtg | gtg | tcc | tac | gat | gtc | ggc | 1440 |
| Ala | Ser | Ala | Gln | His | His | His | Ala | Gly | Val | Val | Ser | Tyr | Asp | Val | Gly |      |
| 465 |     |     |     | 470 |     |     |     |     | 475 |     |     |     |     | 480 |     |      |
| cgc | att | gcc | tcg | cag | ctc | ggg | gac | ggg | gga | gcc | ctc | gcg | gcc | gcg | tac | 1488 |
| Arg | Ile | Ala | Ser | Gln | Leu | Gly | Asp | Gly | Gly | Ala | Leu | Ala | Ala | Ala | Tyr |      |
|     |     |     |     | 485 |     |     |     |     | 490 |     |     |     |     | 495 |     |      |
| ggc | gcc | cac | tat | cac | ggc | gcc | gcc | tgg | ccg | acc | atc | gcg | ttc | caa | ccg | 1536 |
| Gly | Ala | His | Tyr | His | Gly | Ala | Ala | Trp | Pro | Thr | Ile | Ala | Phe | Gln | Pro |      |
|     |     |     | 500 |     |     |     |     | 505 |     |     |     |     | 510 |     |     |      |
| ggc | gcg | gcc | agc | act | ggg | ctc | tat | cat | ccg | tat | gcc | cag | caa | cct | atg | 1584 |
| Gly | Ala | Ala | Ser | Thr | Gly | Leu | Tyr | His | Pro | Tyr | Ala | Gln | Gln | Pro | Met |      |
|     |     | 515 |     |     |     |     | 520 |     |     |     |     | 525 |     |     |     |      |
| cgc | ggc | ggc | ggg | tgg | tgc | aaa | cag | gag | caa | gat | cac | gcc | gtc | att | gcg | 1632 |
| Arg | Gly | Gly | Gly | Trp | Cys | Lys | Gln | Glu | Gln | Asp | His | Ala | Val | Ile | Ala |      |
|     | 530 |     |     |     |     | 535 |     |     |     |     | 540 |     |     |     |     |      |
| gcg | gcg | cac | agc | ctc | cag | gac | ctg | cat | cac | ctg | aac | ctg | ggc | gcg | gcg | 1680 |
| Ala | Ala | His | Ser | Leu | Gln | Asp | Leu | His | His | Leu | Asn | Leu | Gly | Ala | Ala |      |
| 545 |     |     |     | 550 |     |     |     |     | 555 |     |     |     |     | 560 |     |      |
| ggc | gcg | cat | gac | ttt | ttc | tcg | gct | ggg | cag | caa | gcc | gcg | gcc | gca | gcg | 1728 |
| Gly | Ala | His | Asp | Phe | Phe | Ser | Ala | Gly | Gln | Gln | Ala | Ala | Ala | Ala | Ala |      |
|     |     |     |     | 565 |     |     |     |     | 570 |     |     |     |     | 575 |     |      |
| atg | cat | ggc | ctg | ggt | tcc | atc | gat | tcc | gcg | tcg | ctg | gag | cac | agc | acc | 1776 |
| Met | His | Gly | Leu | Gly | Ser | Ile | Asp | Ser | Ala | Ser | Leu | Glu | His | Ser | Thr |      |
|     |     |     | 580 |     |     |     |     | 585 |     |     |     |     | 590 |     |     |      |
| ggc | tcc | aac | tcc | gtc | gtg | tat | aac | ggc | ggc | gtg | ggg | gac | agc | aat | ggc | 1824 |
| Gly | Ser | Asn | Ser | Val | Val | Tyr | Asn | Gly | Gly | Val | Gly | Asp | Ser | Asn | Gly |      |
|     |     | 595 |     |     |     |     | 600 |     |     |     |     | 605 |     |     |     |      |
| gcg | agc | gcg | gtg | ggg | ggc | agt | ggc | ggt | ggc | tat | atg | atg | ccc | atg | tcc | 1872 |
| Ala | Ser | Ala | Val | Gly | Gly | Ser | Gly | Gly | Gly | Tyr | Met | Met | Pro | Met | Ser |      |
|     | 610 |     |     |     |     | 615 |     |     |     |     | 620 |     |     |     |     |      |
| gct | gcc | gga | gct | acc | act | act | tcg | gca | atg | gtg | tcc | cac | gag | cag | gtg | 1920 |
| Ala | Ala | Gly | Ala | Thr | Thr | Thr | Ser | Ala | Met | Val | Ser | His | Glu | Gln | Val |      |
| 625 |     |     |     | 630 |     |     |     |     | 635 |     |     |     |     | 640 |     |      |
| cat | gct | cgc | gcc | tac | gac | gaa | gcg | aag | cag | gca | gct | caa | atg | ggc | tat | 1968 |
| His | Ala | Arg | Ala | Tyr | Asp | Glu | Ala | Lys | Gln | Ala | Ala | Gln | Met | Gly | Tyr |      |
|     |     |     |     | 645 |     |     |     |     | 650 |     |     |     |     | 655 |     |      |
| gaa | agc | tac | ctc | gtg | aat | gcg | gaa | aac | aac | gga | ggc | gga | agg | atg | tct | 2016 |
| Glu | Ser | Tyr | Leu | Val | Asn | Ala | Glu | Asn | Asn | Gly | Gly | Gly | Arg | Met | Ser |      |
|     |     |     | 660 |     |     |     |     | 665 |     |     |     |     | 670 |     |     |      |
| gca | tgg | ggc | act | gtc | gtg | tcc | gca | gcc | gcg | gct | gct | gct | agc | agc | | 2064 |
| Ala | Trp | Gly | Thr | Val | Val | Ser | Ala | Ala | Ala | Ala | Ala | Ala | Ser | Ser | |      |
|     |     | 675 |     |     |     |     | 680 |     |     |     |     | 685 |     |     | |      |
| aac | gac | aat | atg | gcc | gcc | gac | gtc | ggc | cat | ggc | ggc | gcg | cag | ctc | ttc | 2112 |
| Asn | Asp | Asn | Met | Ala | Ala | Asp | Val | Gly | His | Gly | Gly | Ala | Gln | Leu | Phe |      |
|     | 690 |     |     |     |     | 695 |     |     |     |     | 700 |     |     |     |     |      |
| agt | gtg | tgg | aat | gat | act | taa |     |     |     |     |     |     |     |     |     | 2133 |

Ser Val Trp Asn Asp Thr
705              710

<210> SEQ ID NO 16
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 81.5% seq id
      to SEQ ID NO:3. The ORF encodes the aa
      seq set forth in SEQ ID NO:2 with a
      single aa alteration (i.e., S37 to T37).
<220> FEATURE:
<221> NAME/KEY: CDS
<222> LOCATION: (1)...(2133)

<400> SEQUENCE: 16

```
atg gcg act gtc aac aat tgg ctg gca ttc agc ctg tcc ccc caa gag      48
Met Ala Thr Val Asn Asn Trp Leu Ala Phe Ser Leu Ser Pro Gln Glu
1               5                   10                  15 ctg ccc ccg agc caa acg acc gac agc aca ctc atc tcg gcc gcg acc      96
Leu Pro Pro Ser Gln Thr Thr Asp Ser Thr Leu Ile Ser Ala Ala Thr
            20                  25                  30 gcg gac cac gtc acg ggc gac gtc tgc ttc aat att ccg cag gac tgg     144
Ala Asp His Val Thr Gly Asp Val Cys Phe Asn Ile Pro Gln Asp Trp
        35                  40                  45 agc atg agg ggt tca gag ctg tcg gcg ctg gtg gcg gaa ccc aag ctc     192
Ser Met Arg Gly Ser Glu Leu Ser Ala Leu Val Ala Glu Pro Lys Leu
    50                  55                  60 gaa gat ttc ctc ggg ggg atc agc ttt agc gag cag cat cat aaa gcg     240
Glu Asp Phe Leu Gly Gly Ile Ser Phe Ser Glu Gln His His Lys Ala
65                  70                  75                  80 aac tgc aat atg atc ccc tcc act agc tcc act gtt tgt tat gcg tcc     288
Asn Cys Asn Met Ile Pro Ser Thr Ser Ser Thr Val Cys Tyr Ala Ser
                85                  90                  95 tca gga gca agc acg ggg tac cac cat caa ctg tat cac caa ccg acg     336
Ser Gly Ala Ser Thr Gly Tyr His His Gln Leu Tyr His Gln Pro Thr
            100                 105                 110 tcc tca gcc ctc cat ttc gcc gac tcc gtt atg gtc gcc agc tcg gcg     384
Ser Ser Ala Leu His Phe Ala Asp Ser Val Met Val Ala Ser Ser Ala
        115                 120                 125 ggt gtg cat gac ggg ggt gcg atg ctc agc gcc gcc gcc gct aat ggt     432
Gly Val His Asp Gly Gly Ala Met Leu Ser Ala Ala Ala Ala Asn Gly
    130                 135                 140 gtc gca ggc gct gcg tcc gcc aac ggg ggg ggg atc ggc ctg tcc atg     480
Val Ala Gly Ala Ala Ser Ala Asn Gly Gly Gly Ile Gly Leu Ser Met
145                 150                 155                 160 att aag aat tgg ctg cgc tcc caa ccg gcc ccc atg cag ccc aga gtg     528
Ile Lys Asn Trp Leu Arg Ser Gln Pro Ala Pro Met Gln Pro Arg Val
                165                 170                 175 gcc gcc gca gaa ggg gcc cag ggc ctc tct ctc tcc atg aat atg gcg     576
Ala Ala Ala Glu Gly Ala Gln Gly Leu Ser Leu Ser Met Asn Met Ala
            180                 185                 190 ggg acc acg cag ggg gca gca ggc atg cct ctg ctg gct gga gaa cgc     624
Gly Thr Thr Gln Gly Ala Ala Gly Met Pro Leu Leu Ala Gly Glu Arg
        195                 200                 205 gca cgg gcc ccc gag agt gtt agc acg agc gct cag ggt ggt gcc gtg     672
Ala Arg Ala Pro Glu Ser Val Ser Thr Ser Ala Gln Gly Gly Ala Val
    210                 215                 220 gtg gtg acc gcc ccg aaa gag gac tcc gga ggc tcc gga gtt gcc ggc     720
Val Val Thr Ala Pro Lys Glu Asp Ser Gly Gly Ser Gly Val Ala Gly
```

```
                225                 230                 235                 240
gct cta gtt gcc gtg agc acg gat acg ggt ggc tcc ggc ggg gcg agc           768
Ala Leu Val Ala Val Ser Thr Asp Thr Gly Gly Ser Gly Gly Ala Ser
                    245                 250                 255 gct gat aat acc gca aga aag acc gtc gac acc ttt ggg cag cgc acg           816
Ala Asp Asn Thr Ala Arg Lys Thr Val Asp Thr Phe Gly Gln Arg Thr
                260                 265                 270 tcg atc tac aga ggc gtc act aga cat agg tgg aca ggc aga tac gaa           864
Ser Ile Tyr Arg Gly Val Thr Arg His Arg Trp Thr Gly Arg Tyr Glu
            275                 280                 285 gca cac ctt tgg gat aac agt tgt agg agg gaa ggc caa aca cgt aaa           912
Ala His Leu Trp Asp Asn Ser Cys Arg Arg Glu Gly Gln Thr Arg Lys
        290                 295                 300 ggt aga caa gtc tat tta gga ggc tac gat aag gaa gag aag gct gca           960
Gly Arg Gln Val Tyr Leu Gly Gly Tyr Asp Lys Glu Glu Lys Ala Ala
305                 310                 315                 320 agg gca tac gac ctt gct gca ctc aag tat tgg ggt gcc aca act act          1008
Arg Ala Tyr Asp Leu Ala Ala Leu Lys Tyr Trp Gly Ala Thr Thr Thr
                325                 330                 335 aca aac ttt cca gtg agt aac tac gaa aaa gaa ctc gag gat atg aaa          1056
Thr Asn Phe Pro Val Ser Asn Tyr Glu Lys Glu Leu Glu Asp Met Lys
                340                 345                 350 cac atg act agg cag gag ttt gta gcc tcc ctc aga aga aaa tcc tcc          1104
His Met Thr Arg Gln Glu Phe Val Ala Ser Leu Arg Arg Lys Ser Ser
            355                 360                 365 gga ttt agc agg ggt gct tcc att tac aga gga gtg aca aga cac cac          1152
Gly Phe Ser Arg Gly Ala Ser Ile Tyr Arg Gly Val Thr Arg His His
        370                 375                 380 cag cat ggt agg tgg cag gca cgg att gga cga gtg gca ggc aac aaa          1200
Gln His Gly Arg Trp Gln Ala Arg Ile Gly Arg Val Ala Gly Asn Lys
385                 390                 395                 400 gac ctt tat ctc ggc acc ttt agc acg cag gaa gag gca gcg gag gcg          1248
Asp Leu Tyr Leu Gly Thr Phe Ser Thr Gln Glu Glu Ala Ala Glu Ala
                405                 410                 415 tac gac att gcc gcg att aaa ttc cgg ggc ctc aat gcg gtc acg aac          1296
Tyr Asp Ile Ala Ala Ile Lys Phe Arg Gly Leu Asn Ala Val Thr Asn
                420                 425                 430 ttt gat atg tcc cgc tat gat gtg aaa agc atc ctc gac agc agc gcc          1344
Phe Asp Met Ser Arg Tyr Asp Val Lys Ser Ile Leu Asp Ser Ser Ala
            435                 440                 445 ctc ccc att ggc agc gcg gcg aaa cgg ctc aaa gaa gcg gaa gcg gct          1392
Leu Pro Ile Gly Ser Ala Ala Lys Arg Leu Lys Glu Ala Glu Ala Ala
        450                 455                 460 gcc agc gcc cag cac cat cat gcc ggg gtg gtc agc tac gat gtg ggg          1440
Ala Ser Ala Gln His His His Ala Gly Val Val Ser Tyr Asp Val Gly
465                 470                 475                 480 cgc atc gcg agc caa ctg ggc gat ggg ggt gcc ctc gcc gcg gcc tat          1488
Arg Ile Ala Ser Gln Leu Gly Asp Gly Gly Ala Leu Ala Ala Ala Tyr
                485                 490                 495 ggc gcc cat tac cat ggc gcc gcg tgg ccg acc atc gcc ttc caa ccc          1536
Gly Ala His Tyr His Gly Ala Ala Trp Pro Thr Ile Ala Phe Gln Pro
                500                 505                 510 ggc gcc gcc agc act ggc ctc tac cac ccc tat gcc caa caa cca atg          1584
Gly Ala Ala Ser Thr Gly Leu Tyr His Pro Tyr Ala Gln Gln Pro Met
            515                 520                 525 cgc ggc ggc ggc tgg tgt aag cag gag caa gat cat gcc gtg att gcg          1632
Arg Gly Gly Gly Trp Cys Lys Gln Glu Gln Asp His Ala Val Ile Ala
        530                 535                 540 gcg gcg cac tcc ctc cag gac ctg cat cac ctg aat ctg ggc gcc gcg          1680
Ala Ala His Ser Leu Gln Asp Leu His His Leu Asn Leu Gly Ala Ala
```

```
               Ala Ala His Ser Leu Gln Asp Leu His His Leu Asn Leu Gly Ala Ala
                   545                 550                 555                 560 ggg gcc cat gat ttc ttt agc gct ggg cag caa gcg gcc gcc gca gcc                1728
Gly Ala His Asp Phe Phe Ser Ala Gly Gln Gln Ala Ala Ala Ala Ala
                565                 570                 575 atg cac ggg ctc ggt agc att gac agt gcc tcg ctg gaa cat agc acg                1776
Met His Gly Leu Gly Ser Ile Asp Ser Ala Ser Leu Glu His Ser Thr
                    580                 585                 590 ggg agc aac tcc gtg gtc tac aac ggg ggc gtg ggc gat agc aac ggc                1824
Gly Ser Asn Ser Val Val Tyr Asn Gly Gly Val Gly Asp Ser Asn Gly
                595                 600                 605 gcc agc gcg gtg ggc ggc agt ggc ggt ggc tat atg atg ccg atg agc                1872
Ala Ser Ala Val Gly Gly Ser Gly Gly Gly Tyr Met Met Pro Met Ser
                    610                 615                 620 gct gcg gga gct acg aca act agc gca atg gtc tcc cac gag caa gtc                1920
Ala Ala Gly Ala Thr Thr Thr Ser Ala Met Val Ser His Glu Gln Val
625                 630                 635                 640 cac gct cgc gcg tat gat gaa gcc aaa cag gca gct cag atg ggc tac                1968
His Ala Arg Ala Tyr Asp Glu Ala Lys Gln Ala Ala Gln Met Gly Tyr
                    645                 650                 655 gaa tcc tac ctg gtg aat gcc gaa aat aac ggt ggc gga aga atg tcc                2016
Glu Ser Tyr Leu Val Asn Ala Glu Asn Asn Gly Gly Gly Arg Met Ser
                660                 665                 670 gct tgg ggc aca gtg gtg tct gca gcc gcc gcg gct gct gca tcc agc                2064
Ala Trp Gly Thr Val Val Ser Ala Ala Ala Ala Ala Ala Ser Ser
                    675                 680                 685 aat gac aac atg gcg gcc gac gtg ggc cat ggc ggg gcg caa ctc ttt                2112
Asn Asp Asn Met Ala Ala Asp Val Gly His Gly Gly Ala Gln Leu Phe
690                 695                 700 agt gtc tgg aat gac act taa                                                    2133
Ser Val Trp Asn Asp Thr
705                 710

<210> SEQ ID NO 17
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 75.9% seq id to
      SEQ ID NO:3.  The ORF encodes the aa seq
      set forth in SEQ ID NO:2 with a single aa
      alteration (i.e., S37 to T37).
<220> FEATURE:
<221> NAME/KEY: CDS
<222> LOCATION: (1)...(2133)

<400> SEQUENCE: 17 atg gcg act gtc aat aat tgg ctg gca ttc agc ctg agc ccg caa gag                48
Met Ala Thr Val Asn Asn Trp Leu Ala Phe Ser Leu Ser Pro Gln Glu
1               5                   10                  15 ctg ccc ccg tcc caa acg acg gat tcc act ctg att agc gcg gcc acg                96
Leu Pro Pro Ser Gln Thr Thr Asp Ser Thr Leu Ile Ser Ala Ala Thr
                20                  25                  30 gcc gat cac gtg acg ggg gac gtg tgt ttt aac att ccc cag gat tgg                144
Ala Asp His Val Thr Gly Asp Val Cys Phe Asn Ile Pro Gln Asp Trp
            35                  40                  45 tcc atg aga gga tca gag ctg tcg gcc ctg gtg gcc gag ccg aaa ctc                192
Ser Met Arg Gly Ser Glu Leu Ser Ala Leu Val Ala Glu Pro Lys Leu
        50                  55                  60 gaa gat ttt ctc ggc ggg att agc ttt agc gaa caa cac cat aaa gcg                240
Glu Asp Phe Leu Gly Gly Ile Ser Phe Ser Glu Gln His His Lys Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 65  |     |     |     |     | 70  |     |     |     |     | 75  |     |     | 80  |      |
| aac | tgc | aac | atg | atc | ccc | agc | aca | tcc | tcc | act | gtt | tgc | tat | gcc | agc | 288  |
| Asn | Cys | Asn | Met | Ile | Pro | Ser | Thr | Ser | Ser | Thr | Val | Cys | Tyr | Ala | Ser |      |
|     |     |     |     | 85  |     |     |     |     | 90  |     |     |     |     | 95  |     |      |
| agc | gga | gca | tcc | acc | ggg | tat | cac | cat | caa | ctc | tat | cat | cag | ccc | acg | 336  |
| Ser | Gly | Ala | Ser | Thr | Gly | Tyr | His | His | Gln | Leu | Tyr | His | Gln | Pro | Thr |      |
|     |     |     |     | 100 |     |     |     |     | 105 |     |     |     |     | 110 |     |      |
| agc | agc | gcc | ctg | cac | ttt | gcc | gat | agc | gta | atg | gtc | gcg | agc | agc | gcg | 384  |
| Ser | Ser | Ala | Leu | His | Phe | Ala | Asp | Ser | Val | Met | Val | Ala | Ser | Ser | Ala |      |
|     |     |     |     | 115 |     |     |     |     | 120 |     |     |     |     | 125 |     |      |
| ggt | gtg | cat | gac | ggg | gga | gcg | atg | ctg | tcc | gcc | gcg | gcg | gct | aat | ggt | 432  |
| Gly | Val | His | Asp | Gly | Gly | Ala | Met | Leu | Ser | Ala | Ala | Ala | Ala | Asn | Gly |      |
|     |     | 130 |     |     |     |     | 135 |     |     |     |     | 140 |     |     |     |      |
| gtg | gca | ggg | gca | gcg | agt | gcc | aat | ggg | ggg | ggc | att | ggc | ctc | agc | atg | 480  |
| Val | Ala | Gly | Ala | Ala | Ser | Ala | Asn | Gly | Gly | Gly | Ile | Gly | Leu | Ser | Met |      |
| 145 |     |     |     |     | 150 |     |     |     |     | 155 |     |     |     |     | 160 |      |
| atc | aaa | aac | tgg | ctc | cgc | tcc | caa | ccg | gcg | ccc | atg | cag | ccc | aga | gtc | 528  |
| Ile | Lys | Asn | Trp | Leu | Arg | Ser | Gln | Pro | Ala | Pro | Met | Gln | Pro | Arg | Val |      |
|     |     |     |     | 165 |     |     |     |     | 170 |     |     |     |     | 175 |     |      |
| gcg | gcc | gca | gaa | ggc | gcc | caa | ggc | ctg | tcc | ctc | agc | atg | aat | atg | gcg | 576  |
| Ala | Ala | Ala | Glu | Gly | Ala | Gln | Gly | Leu | Ser | Leu | Ser | Met | Asn | Met | Ala |      |
|     |     |     |     | 180 |     |     |     |     | 185 |     |     |     |     | 190 |     |      |
| ggc | acc | acg | cag | ggg | gct | gca | ggg | atg | cct | ctg | ctg | gct | ggt | gag | cgg | 624  |
| Gly | Thr | Thr | Gln | Gly | Ala | Ala | Gly | Met | Pro | Leu | Leu | Ala | Gly | Glu | Arg |      |
|     |     |     |     | 195 |     |     |     |     | 200 |     |     |     |     | 205 |     |      |
| gct | cgc | gcc | ccg | gaa | agt | gta | tcg | acc | agc | gct | caa | ggt | ggt | gcc | gtc | 672  |
| Ala | Arg | Ala | Pro | Glu | Ser | Val | Ser | Thr | Ser | Ala | Gln | Gly | Gly | Ala | Val |      |
|     |     | 210 |     |     |     |     | 215 |     |     |     |     | 220 |     |     |     |      |
| gtg | gtg | acc | gcc | ccc | aaa | gag | gac | agc | ggt | ggg | tcc | gga | gtg | gcg | ggg | 720  |
| Val | Val | Thr | Ala | Pro | Lys | Glu | Asp | Ser | Gly | Gly | Ser | Gly | Val | Ala | Gly |      |
| 225 |     |     |     |     | 230 |     |     |     |     | 235 |     |     |     |     | 240 |      |
| gca | ctc | gtt | gcg | gtg | tcc | acc | gat | acc | gga | ggg | agc | ggg | ggg | gcc | tcg | 768  |
| Ala | Leu | Val | Ala | Val | Ser | Thr | Asp | Thr | Gly | Gly | Ser | Gly | Gly | Ala | Ser |      |
|     |     |     |     | 245 |     |     |     |     | 250 |     |     |     |     | 255 |     |      |
| gca | gat | aac | acc | gct | aga | aag | acc | gtc | gac | acc | ttt | ggc | cag | cgg | acg | 816  |
| Ala | Asp | Asn | Thr | Ala | Arg | Lys | Thr | Val | Asp | Thr | Phe | Gly | Gln | Arg | Thr |      |
|     |     |     |     | 260 |     |     |     |     | 265 |     |     |     |     | 270 |     |      |
| agc | atc | tac | aga | ggc | gtc | aca | aga | cac | aga | tgg | act | ggc | agg | tac | gaa | 864  |
| Ser | Ile | Tyr | Arg | Gly | Val | Thr | Arg | His | Arg | Trp | Thr | Gly | Arg | Tyr | Glu |      |
|     |     |     |     | 275 |     |     |     |     | 280 |     |     |     |     | 285 |     |      |
| gca | cac | ctt | tgg | gac | aac | agt | tgt | agg | aga | gag | ggc | caa | aca | aga | aaa | 912  |
| Ala | His | Leu | Trp | Asp | Asn | Ser | Cys | Arg | Arg | Glu | Gly | Gln | Thr | Arg | Lys |      |
|     |     | 290 |     |     |     |     | 295 |     |     |     |     | 300 |     |     |     |      |
| gga | aga | cag | gtg | tat | tta | gga | ggc | tac | gac | aag | gaa | gaa | aag | gca | gca | 960  |
| Gly | Arg | Gln | Val | Tyr | Leu | Gly | Gly | Tyr | Asp | Lys | Glu | Glu | Lys | Ala | Ala |      |
| 305 |     |     |     |     | 310 |     |     |     |     | 315 |     |     |     |     | 320 |      |
| agg | gca | tat | gac | ctg | gca | gca | ctc | aaa | tat | tgg | gga | gcc | act | aca | act | 1008 |
| Arg | Ala | Tyr | Asp | Leu | Ala | Ala | Leu | Lys | Tyr | Trp | Gly | Ala | Thr | Thr | Thr |      |
|     |     |     |     | 325 |     |     |     |     | 330 |     |     |     |     | 335 |     |      |
| aca | aac | ttt | cct | gtc | agt | aac | tac | gaa | aaa | gaa | ctc | gag | gat | atg | aaa | 1056 |
| Thr | Asn | Phe | Pro | Val | Ser | Asn | Tyr | Glu | Lys | Glu | Leu | Glu | Asp | Met | Lys |      |
|     |     |     |     | 340 |     |     |     |     | 345 |     |     |     |     | 350 |     |      |
| cac | atg | act | aga | cag | gaa | ttc | gta | gcc | tcc | ctc | agg | aga | aag | tcc | agt | 1104 |
| His | Met | Thr | Arg | Gln | Glu | Phe | Val | Ala | Ser | Leu | Arg | Arg | Lys | Ser | Ser |      |
|     |     |     |     | 355 |     |     |     |     | 360 |     |     |     |     | 365 |     |      |
| gga | ttc | agc | aga | gga | gca | tcc | atc | tat | aga | ggt | gtg | act | aga | cac | cac | 1152 |
| Gly | Phe | Ser | Arg | Gly | Ala | Ser | Ile | Tyr | Arg | Gly | Val | Thr | Arg | His | His |      |
|     |     | 370 |     |     |     |     | 375 |     |     |     |     | 380 |     |     |     |      |
| caa | cac | ggt | agg | tgg | caa | gct | cgc | atc | ggt | cgc | gtg | gct | ggc | aat | aaa | 1200 |

```
                Gln His Gly Arg Trp Gln Ala Arg Ile Gly Arg Val Ala Gly Asn Lys
                385                 390                 395                 400 gat ctg tat ctc ggg acc ttt agc acg caa gaa gag gct gcc gaa gcc          1248
Asp Leu Tyr Leu Gly Thr Phe Ser Thr Gln Glu Glu Ala Ala Glu Ala
                        405                 410                 415 tac gac att gcg gcc att aaa ttt cgc ggg ctc aat gcg gtc acc aac          1296
Tyr Asp Ile Ala Ala Ile Lys Phe Arg Gly Leu Asn Ala Val Thr Asn
                420                 425                 430 ttt gat atg tcc cgc tac gat gtg aag tcc atc ctc gac agc tcc gcc          1344
Phe Asp Met Ser Arg Tyr Asp Val Lys Ser Ile Leu Asp Ser Ser Ala
            435                 440                 445 ctc ccg atc ggg tcc gcc gcg aaa cgc ctg aaa gag gcg gaa gcg gct          1392
Leu Pro Ile Gly Ser Ala Ala Lys Arg Leu Lys Glu Ala Glu Ala Ala
        450                 455                 460 gcc tcc gcc caa cat cat cat gcg ggg gtc gtc tcc tac gac gtg ggc          1440
Ala Ser Ala Gln His His His Ala Gly Val Val Ser Tyr Asp Val Gly
465                 470                 475                 480 cgg atc gcg agc cag ctg ggg gat ggc ggt gcg ctg gcc gcc gcc tat          1488
Arg Ile Ala Ser Gln Leu Gly Asp Gly Gly Ala Leu Ala Ala Ala Tyr
                    485                 490                 495 ggc gcc cac tat cac ggg gcg gcg tgg ccc acg att gcg ttt caa ccg          1536
Gly Ala His Tyr His Gly Ala Ala Trp Pro Thr Ile Ala Phe Gln Pro
                500                 505                 510 ggg gcg gcg agc act ggg ctg tac cat ccc tat gcg caa caa cca atg          1584
Gly Ala Ala Ser Thr Gly Leu Tyr His Pro Tyr Ala Gln Gln Pro Met
            515                 520                 525 cgc ggg ggg ggc tgg tgc aaa caa gaa cag gat cat gcc gtc att gcc          1632
Arg Gly Gly Gly Trp Cys Lys Gln Glu Gln Asp His Ala Val Ile Ala
        530                 535                 540 gcg gcg cac agc ctg caa gac ctc cat cat ctc aac ctc ggc gcc gcg          1680
Ala Ala His Ser Leu Gln Asp Leu His His Leu Asn Leu Gly Ala Ala
545                 550                 555                 560 ggc gcg cac gat ttc ttc tcg gct ggg cag caa gcg gcc gcg gct gcc          1728
Gly Ala His Asp Phe Phe Ser Ala Gly Gln Gln Ala Ala Ala Ala Ala
                    565                 570                 575 atg cat ggc ctc gga tcc atc gac tcc gcc agc ctg gaa cac agc acc          1776
Met His Gly Leu Gly Ser Ile Asp Ser Ala Ser Leu Glu His Ser Thr
                580                 585                 590 ggg tcc aac agc gtc gtg tat aac ggg ggt gtc ggg gac tcc aat ggc          1824
Gly Ser Asn Ser Val Val Tyr Asn Gly Gly Val Gly Asp Ser Asn Gly
            595                 600                 605 gcg agc gcg gtg ggg ggg agt ggc gga ggg tat atg atg ccc atg agc          1872
Ala Ser Ala Val Gly Gly Ser Gly Gly Gly Tyr Met Met Pro Met Ser
        610                 615                 620 gct gcg gga gct acg aca aca tcg gct atg gtc agc cat gaa caa gtc          1920
Ala Ala Gly Ala Thr Thr Thr Ser Ala Met Val Ser His Glu Gln Val
625                 630                 635                 640 cat gct cgg gcc tat gat gag gcg aaa caa gca gca caa atg ggg tac          1968
His Ala Arg Ala Tyr Asp Glu Ala Lys Gln Ala Ala Gln Met Gly Tyr
                    645                 650                 655 gag tcc tat ctc gtc aat gcc gaa aat aat ggt ggc gga agg atg tcc          2016
Glu Ser Tyr Leu Val Asn Ala Glu Asn Asn Gly Gly Gly Arg Met Ser
                660                 665                 670 gca tgg ggg aca gtg gtc tcc gct gcc gcg gcg gct gca gct tcc tcc          2064
Ala Trp Gly Thr Val Val Ser Ala Ala Ala Ala Ala Ala Ala Ser Ser
            675                 680                 685 aat gat aat atg gcg gcg gat gtc ggg cac ggg ggg gcc cag ctg ttt          2112
Asn Asp Asn Met Ala Ala Asp Val Gly His Gly Gly Ala Gln Leu Phe
        690                 695                 700
```

```
tcc gtg tgg aac gat act taa                                                    2133
Ser Val Trp Asn Asp Thr
705                 710

<210> SEQ ID NO 18
<211> LENGTH: 2133
<212> TYPE: DNA
<213> ORGANISM: Artificial Sequence
<220> FEATURE:
<223> OTHER INFORMATION: Synthesized
<220> FEATURE:
<223> OTHER INFORMATION: Variant of Zm-ODP2 having 70.4% seq id
      to SEQ ID NO:3.  The ORF encodes the aa
      seq set forth in SEQ ID NO:2 with a
      single aa alteration (i.e., S37 to T37).
<220> FEATURE:
<221> NAME/KEY: CDS
<222> LOCATION: (1)...(2133)

<400> SEQUENCE: 18 atg gcg aca gtg aat aat tgg ctg gca ttt agc ctg agc ccg caa gaa     48
Met Ala Thr Val Asn Asn Trp Leu Ala Phe Ser Leu Ser Pro Gln Glu
1               5                  10                  15 ctc ccg ccg agc caa acc acc gat tcc act ctg att tcg gcg gcc acc     96
Leu Pro Pro Ser Gln Thr Thr Asp Ser Thr Leu Ile Ser Ala Ala Thr
            20                  25                  30 gcg gac cac gtg acg ggg gac gtg tgt ttc aat att ccg caa gac tgg    144
Ala Asp His Val Thr Gly Asp Val Cys Phe Asn Ile Pro Gln Asp Trp
        35                  40                  45 tcc atg aga gga agc gaa ctg agc gcc ctg gtg gcc gaa ccc aaa ctc    192
Ser Met Arg Gly Ser Glu Leu Ser Ala Leu Val Ala Glu Pro Lys Leu
    50                  55                  60 gaa gac ttt ctg ggg ggg att agc ttc agc gaa caa cac cat aag gcc    240
Glu Asp Phe Leu Gly Gly Ile Ser Phe Ser Glu Gln His His Lys Ala
65                  70                  75                  80 aat tgt aat atg atc ccg tcc act tcc tcc act gtg tgt tat gcc tcc    288
Asn Cys Asn Met Ile Pro Ser Thr Ser Ser Thr Val Cys Tyr Ala Ser
                85                  90                  95 agc gga gca agc acg ggc tat cac cat cag ctc tac cat caa ccg acg    336
Ser Gly Ala Ser Thr Gly Tyr His His Gln Leu Tyr His Gln Pro Thr
            100                 105                 110 tcc tca gcc ctc cac ttt gcc gat agc gtt atg gtc gcg agc agc gcg    384
Ser Ser Ala Leu His Phe Ala Asp Ser Val Met Val Ala Ser Ser Ala
        115                 120                 125 ggt gtg cat gat ggg gga gcg atg ctg tcc gcc gcg gcg gca aat gga    432
Gly Val His Asp Gly Gly Ala Met Leu Ser Ala Ala Ala Ala Asn Gly
    130                 135                 140 gtg gca ggg gca gcc agt gcg aat ggg ggg ggg att ggc ctc agc atg    480
Val Ala Gly Ala Ala Ser Ala Asn Gly Gly Gly Ile Gly Leu Ser Met
145                 150                 155                 160 atc aag aat tgg ctc cgc tcc caa ccg gcc ccc atg caa ccg aga gtc    528
Ile Lys Asn Trp Leu Arg Ser Gln Pro Ala Pro Met Gln Pro Arg Val
                165                 170                 175 gcc gcc gca gaa ggg gcc caa ggc ctg tcc ctc agc atg aac atg gcc    576
Ala Ala Ala Glu Gly Ala Gln Gly Leu Ser Leu Ser Met Asn Met Ala
            180                 185                 190 ggg acg acg cag ggg gca gca ggg atg cct ctg ctg gca gga gaa cgg    624
Gly Thr Thr Gln Gly Ala Ala Gly Met Pro Leu Leu Ala Gly Glu Arg
        195                 200                 205 gca cgc gcc ccg gaa agt gtt agc acc agc gct caa gga ggt gcg gtg    672
Ala Arg Ala Pro Glu Ser Val Ser Thr Ser Ala Gln Gly Gly Ala Val
    210                 215                 220 gtg gtg acc gcc ccc aag gaa gat tcc gga ggg tcc gga gtg gcg ggg    720
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     | Val | Val | Thr | Ala | Pro | Lys | Glu | Asp | Ser | Gly | Ser | Gly | Val | Ala | Gly |     |
|     | 225 |     |     |     | 230 |     |     |     |     | 235 |     |     |     |     | 240 |     |

```
gca ctc gtt gcg gtc tcc acc gat acc ggt ggg tcc ggg ggg gcc agc         768
Ala Leu Val Ala Val Ser Thr Asp Thr Gly Gly Ser Gly Gly Ala Ser
                        245                 250                 255 gca gat aat acc gct aga aaa acc gtc gat acc ttt ggc caa cgc acc         816
Ala Asp Asn Thr Ala Arg Lys Thr Val Asp Thr Phe Gly Gln Arg Thr
                260                 265                 270 agc atc tac aga ggg gtc act aga cac agg tgg aca ggc aga tac gaa         864
Ser Ile Tyr Arg Gly Val Thr Arg His Arg Trp Thr Gly Arg Tyr Glu
            275                 280                 285 gct cac ctg tgg gac aat agt tgt agg aga gag ggc cag aca aga aaa         912
Ala His Leu Trp Asp Asn Ser Cys Arg Arg Glu Gly Gln Thr Arg Lys
        290                 295                 300 ggt aga cag gtg tac ctg gga ggc tac gac aaa gaa gaa aag gct gca         960
Gly Arg Gln Val Tyr Leu Gly Gly Tyr Asp Lys Glu Glu Lys Ala Ala
305                 310                 315                 320 aga gca tac gac ctg gca gct ctc aaa tac tgg gga gcg aca act aca        1008
Arg Ala Tyr Asp Leu Ala Ala Leu Lys Tyr Trp Gly Ala Thr Thr Thr
                        325                 330                 335 act aac ttc cct gtc tcc aat tat gag aaa gag ctc gaa gat atg aag        1056
Thr Asn Phe Pro Val Ser Asn Tyr Glu Lys Glu Leu Glu Asp Met Lys
                340                 345                 350 cat atg act aga caa gaa ttt gtt gcg tcc ctc agg aga aaa tcc agt        1104
His Met Thr Arg Gln Glu Phe Val Ala Ser Leu Arg Arg Lys Ser Ser
            355                 360                 365 gga ttt agc agg gga gct agc atc tat aga ggt gtg aca aga cac cac        1152
Gly Phe Ser Arg Gly Ala Ser Ile Tyr Arg Gly Val Thr Arg His His
        370                 375                 380 cag cac ggt agg tgg caa gct cgc atc gga cgc gtg gct ggc aat aaa        1200
Gln His Gly Arg Trp Gln Ala Arg Ile Gly Arg Val Ala Gly Asn Lys
385                 390                 395                 400 gac ctt tat ctc ggg acg ttt tcc acg caa gaa gaa gct gcc gaa gcc        1248
Asp Leu Tyr Leu Gly Thr Phe Ser Thr Gln Glu Glu Ala Ala Glu Ala
                        405                 410                 415 tac gat att gcc gcc att aaa ttt cgg ggg ctg aat gcc gtg acg aac        1296
Tyr Asp Ile Ala Ala Ile Lys Phe Arg Gly Leu Asn Ala Val Thr Asn
                420                 425                 430 ttt gat atg tcc cgg tat gat gtc aaa tcc att ctc gat tcc tcc gcg        1344
Phe Asp Met Ser Arg Tyr Asp Val Lys Ser Ile Leu Asp Ser Ser Ala
            435                 440                 445 ctg ccg atc ggg agc gcc gcg aaa cgg ctc aag gag gcg gaa gcg gca        1392
Leu Pro Ile Gly Ser Ala Ala Lys Arg Leu Lys Glu Ala Glu Ala Ala
        450                 455                 460 gcc agc gcc cag cat cat cac gcg ggc gtc gtg tcc tat gac gtg ggg        1440
Ala Ser Ala Gln His His His Ala Gly Val Val Ser Tyr Asp Val Gly
465                 470                 475                 480 cgc atc gcc agc caa ctg ggg gat ggg ggt gcg ctc gcc gcc gcc tat        1488
Arg Ile Ala Ser Gln Leu Gly Asp Gly Gly Ala Leu Ala Ala Ala Tyr
                        485                 490                 495 ggc gcc cat tat cat ggg gcg gcg tgg ccc acc att gcg ttt cag ccc        1536
Gly Ala His Tyr His Gly Ala Ala Trp Pro Thr Ile Ala Phe Gln Pro
                500                 505                 510 ggg gcg gcg tcc act ggc ctc tat cat ccc tat gcg caa caa cct atg        1584
Gly Ala Ala Ser Thr Gly Leu Tyr His Pro Tyr Ala Gln Gln Pro Met
            515                 520                 525 cgg ggg ggg ggg tgg tgt aaa caa gaa caa gac cat gcg gtc att gcc        1632
Arg Gly Gly Gly Trp Cys Lys Gln Glu Gln Asp His Ala Val Ile Ala
        530                 535                 540
```

```
gcg gcc cat tcc ctc caa gat ctg cat cat ctg aac ctc ggg gcc gcc    1680
Ala Ala His Ser Leu Gln Asp Leu His His Leu Asn Leu Gly Ala Ala
545             550                 555                 560 ggg gcc cat gat ttt ttt agc gct ggc caa cag gcg gcg gcg gct gcc    1728
Gly Ala His Asp Phe Phe Ser Ala Gly Gln Gln Ala Ala Ala Ala Ala
                565                 570                 575 atg cat ggg ctc gga tcc att gat agt gcg agc ctg gaa cat tcc acg    1776
Met His Gly Leu Gly Ser Ile Asp Ser Ala Ser Leu Glu His Ser Thr
                580                 585                 590 ggg tcc aac agc gtg gtg tat aat ggg ggt gtg ggc gat agc aat ggc    1824
Gly Ser Asn Ser Val Val Tyr Asn Gly Gly Val Gly Asp Ser Asn Gly
            595                 600                 605 gcg tcc gcg gtc ggg ggc tcc ggg ggt ggg tat atg atg ccc atg tcc    1872
Ala Ser Ala Val Gly Gly Ser Gly Gly Gly Tyr Met Met Pro Met Ser
        610                 615                 620 gct gcc ggt gct acg aca act tcg gct atg gtc tcc cat gaa caa gtc    1920
Ala Ala Gly Ala Thr Thr Thr Ser Ala Met Val Ser His Glu Gln Val
625                 630                 635                 640 cac gct cgc gcc tat gat gag gcg aaa caa gca gca cag atg ggc tat    1968
His Ala Arg Ala Tyr Asp Glu Ala Lys Gln Ala Ala Gln Met Gly Tyr
                645                 650                 655 gaa tcc tat ctc gtc aat gcc gaa aat aat gga ggg ggt aga atg tcc    2016
Glu Ser Tyr Leu Val Asn Ala Glu Asn Asn Gly Gly Gly Arg Met Ser
                660                 665                 670 gct tgg ggc act gtg gtc tcc gct gcg gcc gcc gct gca gct tcc tcc    2064
Ala Trp Gly Thr Val Val Ser Ala Ala Ala Ala Ala Ala Ser Ser
            675                 680                 685 aat gat aac atg gcg gcg gac gtg ggg cac ggg ggg gcc caa ctc ttt    2112
Asn Asp Asn Met Ala Ala Asp Val Gly His Gly Gly Ala Gln Leu Phe
        690                 695                 700 agt gtg tgg aat gat aca taa                                        2133
Ser Val Trp Asn Asp Thr
705                 710

<210> SEQ ID NO 19
<211> LENGTH: 710
<212> TYPE: PRT
<213> ORGANISM: Artificial Sequence
<220> FEATURE:
<223> OTHER INFORMATION: Synthesized
<220> FEATURE:
<223> OTHER INFORMATION: Variant of Zm-ODP2 polypeptide having the amino
      acid sequence set forth in SEQ ID NO:2 with a
      single amino acid alteration (i.e., S37 to T37).

<400> SEQUENCE: 19

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
                20                  25                  30

Ala Asp His Val Thr Gly Asp Val Cys Phe Asn Ile Pro Gln Asp Trp
            35                  40                  45

Ser Met Arg Gly Ser Glu Leu Ser Ala Leu Val Ala Glu Pro Lys Leu
        50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Thr Val Cys Tyr Ala Ser
                85                  90                  95

Ser Gly Ala Ser Thr Gly Tyr His His Gln Leu Tyr His Gln Pro Thr
            100                 105                 110
```

```
Ser Ser Ala Leu His Phe Ala Asp Ser Val Met Val Ala Ser Ser Ala
            115                 120                 125

Gly Val His Asp Gly Gly Ala Met Leu Ser Ala Ala Ala Asn Gly
130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Gly Ser Gly Val Ala Gly
225                 230                 235                 240

Ala Leu Val Ala Val Ser Thr Asp Thr Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Ala Ala Glu Ala
                405                 410                 415

Tyr Asp Ile Ala Ala Ile Lys Phe Arg Gly Leu Asn Ala Val Thr Asn
                420                 425                 430

Phe Asp Met Ser Arg Tyr Asp Val Lys Ser Ile Leu Asp Ser Ser Ala
            435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Ala Leu Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
```

```
                530             535             540
Ala Ala His Ser Leu Gln Asp Leu His His Leu Asn Leu Gly Ala Ala
545                 550             555                 560

Gly Ala His Asp Phe Phe Ser Ala Gly Gln Gln Ala Ala Ala Ala Ala
                565             570             575

Met His Gly Leu Gly Ser Ile Asp Ser Ala Ser Leu Glu His Ser Thr
            580             585             590

Gly Ser Asn Ser Val Val Tyr Asn Gly Val Gly Asp Ser Asn Gly
            595             600             605

Ala Ser Ala Val Gly Gly Ser Gly Gly Gly Tyr Met Met Pro Met Ser
610             615             620

Ala Ala Gly Ala Thr Thr Thr Ser Ala Met Val Ser His Glu Gln Val
625             630             635             640

His Ala Arg Ala Tyr Asp Glu Ala Lys Gln Ala Ala Gln Met Gly Tyr
                645             650             655

Glu Ser Tyr Leu Val Asn Ala Glu Asn Asn Gly Gly Gly Arg Met Ser
            660             665             670

Ala Trp Gly Thr Val Val Ser Ala Ala Ala Ala Ala Ala Ser Ser
            675             680             685

Asn Asp Asn Met Ala Ala Asp Val Gly His Gly Gly Ala Gln Leu Phe
690             695             700

Ser Val Trp Asn Asp Thr
705             710

<210> SEQ ID NO 20
<211> LENGTH: 710
<212> TYPE: PRT
<213> ORGANISM: Artificial Sequence
<220> FEATURE:
<223> OTHER INFORMATION: Synthesized
<220> FEATURE:
<223> OTHER INFORMATION: Variant of Zm-ODP2 having 97.3% amino acid
      sequence identity to SEQ ID NO:2 (Zm-ODP2).

<400> SEQUENCE: 20

Met Ala Thr Val Asn Asn Trp Leu Ala Phe Ser Leu Ser Pro Gln Glu
 1               5                  10                  15

Ile Pro Pro Ser Gln Thr Thr Asp Ser Thr Ile Leu Ser Ala Ala Thr
            20                  25                  30

Ala Asp His Val Ser Gly Asp Val Cys Phe Asn Leu Pro Gln Asp Trp
        35                  40                  45

Ser Met Arg Gly Ser Glu Ile Ser Ala Ile Val Ala Glu Pro Lys Ile
    50                  55                  60

Glu Asp Phe Ile Gly Gly Leu Ser Phe Ser Glu Gln His His Lys Ala
65                  70                  75                  80

Asn Cys Asn Met Leu Pro Ser Thr Ser Thr Val Cys Tyr Ala Ser
                85                  90                  95

Ser Gly Ala Ser Thr Gly Tyr His His Gln Ile Tyr His Gln Pro Thr
            100                 105                 110

Ser Ser Ala Ile His Phe Ala Asp Ser Val Met Val Ala Ser Ser Ala
        115                 120                 125

Gly Val His Asp Gly Gly Ala Met Ile Ser Ala Ala Ala Asn Gly
    130                 135                 140

Val Ala Gly Ala Ala Ser Ala Asn Gly Gly Gly Ile Gly Leu Ser Met
145                 150                 155                 160

Ile Lys Asn Trp Leu Arg Ser Gln Pro Ala Pro Met Gln Pro Arg Val
```

```
              165                 170                 175
Ala Ala Ala Glu Gly Ala Gln Gly Ile Ser Ile Ser Met Asn Met Ala
            180                 185                 190
Gly Thr Thr Gln Gly Ala Ala Gly Met Pro Leu Leu Ala Gly Glu Arg
            195                 200                 205
Ala Arg Ala Pro Glu Ser Val Ser Thr Ser Ala Gln Gly Gly Ala Val
            210                 215                 220
Val Val Thr Ala Pro Lys Glu Asp Ser Gly Ser Gly Val Ala Gly
225                 230                 235                 240
Ala Leu Val Ala Val Ser Thr Asp Thr Gly Ser Gly Gly Ala Ser
                245                 250                 255
Ala Asp Asn Thr Ala Arg Lys Thr Val Asp Thr Phe Gly Gln Arg Thr
                260                 265                 270
Ser Ile Tyr Arg Gly Val Thr Arg His Arg Trp Thr Gly Arg Tyr Glu
                275                 280                 285
Ala His Leu Trp Asp Asn Ser Cys Arg Arg Glu Gly Gln Thr Arg Lys
                290                 295                 300
Gly Arg Gln Val Tyr Leu Gly Gly Tyr Asp Lys Glu Glu Lys Ala Ala
305                 310                 315                 320
Arg Ala Tyr Asp Leu Ala Ala Leu Lys Tyr Trp Gly Ala Thr Thr Thr
                325                 330                 335
Thr Asn Phe Pro Val Ser Asn Tyr Glu Lys Glu Leu Glu Asp Met Lys
                340                 345                 350
His Met Thr Arg Gln Glu Phe Val Ala Ser Leu Arg Arg Lys Ser Ser
                355                 360                 365
Gly Phe Ser Arg Gly Ala Ser Ile Tyr Arg Gly Val Thr Arg His His
                370                 375                 380
Gln His Gly Arg Trp Gln Ala Arg Ile Gly Arg Val Ala Gly Asn Lys
385                 390                 395                 400
Asp Leu Tyr Leu Gly Thr Phe Ser Thr Gln Glu Glu Ala Ala Glu Ala
                405                 410                 415
Tyr Asp Ile Ala Ala Ile Lys Phe Arg Gly Leu Asn Ala Val Thr Asn
                420                 425                 430
Phe Asp Met Ser Arg Tyr Asp Val Lys Ser Ile Leu Asp Ser Ser Ala
                435                 440                 445
Leu Pro Ile Gly Ser Ala Ala Lys Arg Leu Lys Glu Ala Glu Ala Ala
                450                 455                 460
Ala Ser Ala Gln His His His Ala Gly Val Val Ser Tyr Asp Val Gly
465                 470                 475                 480
Arg Val Ala Ser Gln Leu Gly Asp Gly Ala Leu Ala Ala Ala Tyr
                485                 490                 495
Gly Ala His Tyr His Gly Ala Ala Trp Pro Thr Val Ala Phe Gln Pro
                500                 505                 510
Gly Ala Ala Ser Thr Gly Leu Tyr His Pro Tyr Ala Gln Gln Pro Met
                515                 520                 525
Arg Gly Gly Gly Trp Cys Lys Gln Glu Gln Asp His Ala Val Val Ala
                530                 535                 540
Ala Ala His Ser Leu Gln Asp Leu His His Leu Asn Leu Gly Ala Ala
545                 550                 555                 560
Gly Ala His Asp Phe Phe Ser Ala Gly Gln Gln Ala Ala Ala Ala
                565                 570                 575
Met His Gly Leu Gly Ser Val Asp Ser Ala Ser Leu Glu His Ser Thr
                580                 585                 590
```

```
Gly Ser Asn Ser Val Val Tyr Asn Gly Gly Val Gly Asp Ser Asn Gly
            595                 600                 605

Ala Ser Ala Val Gly Gly Ser Gly Gly Gly Tyr Met Met Pro Met Ser
        610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
            645                 650                 655

Glu Ser Tyr Leu Val Asn Ala Glu Asn Asn Gly Gly Arg Met Ser
            660                 665                 670

Ala Trp Gly Thr Val Val Ser Ala Ala Ala Ala Ala Ala Ser Ser
            675                 680                 685

Asn Asp Asn Met Ala Ala Asp Val Gly His Gly Gly Ala Gln Leu Phe
            690                 695                 700

Ser Val Trp Asn Asp Thr
705             710

<210> SEQ ID NO 21
<211> LENGTH: 710
<212> TYPE: PRT
<213> ORGANISM: Artificial Sequence
<220> FEATURE:
<223> OTHER INFORMATION: Synthesized
<220> FEATURE:
<223> OTHER INFORMATION: Variant of Zm-ODP2 having 92.4% amino acid
      sequence identity to SEQ ID NO:2 (Zm-ODP2).

<400> SEQUENCE: 21

Met Ala Thr Ile Asn Asn Trp Leu Ala Phe Ser Leu Ser Pro Gln Glu
1               5                   10                  15

Ile Pro Pro Ser Gln Thr Thr Asp Ser Thr Ile Leu Ser Ala Ala Thr
            20                  25                  30

Ala Asp His Ile Ser Gly Asp Val Cys Phe Asn Leu Pro Gln Asp Trp
        35                  40                  45

Ser Met Arg Gly Ser Glu Ile Ser Ala Ile Ala Glu Pro Lys Ile
    50                  55                  60

Glu Asp Phe Ile Gly Gly Leu Ser Phe Ser Glu Gln His His Lys Ala
65                  70                  75                  80

Asn Cys Asn Met Leu Pro Ser Thr Ser Ser Thr Ile Cys Tyr Ala Ser
            85                  90                  95

Ser Gly Ala Ser Thr Gly Tyr His His Gln Ile Tyr His Gln Pro Thr
            100                 105                 110

Ser Ser Ala Ile His Phe Ala Asp Ser Ile Met Ile Ala Ser Ser Ala
        115                 120                 125

Gly Ile His Asp Gly Gly Ala Met Ile Ser Ala Ala Ala Asn Gly
        130                 135                 140

Ile Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Ile
            165                 170                 175

Ala Ala Ala Glu Gly Ala Gln Gly Ile Ser Ile Ser Met Asn Met Ala
        180                 185                 190

Gly Thr Thr Gln Gly Ala Ala Gly Met Pro Ile Val Ala Gly Glu Arg
        195                 200                 205

Ala Arg Ala Pro Glu Ser Ile Ser Thr Ser Ala Gln Gly Gly Ala Ile
        210                 215                 220
```

```
Ile Ile Thr Ala Pro Lys Glu Asp Ser Gly Gly Ser Gly Leu Ala Gly
225                 230                 235                 240

Ala Val Leu Ala Leu Ser Thr Asp Thr Gly Ser Gly Gly Ala Ser
            245                 250                 255

Ala Asp Asn Thr Ala Arg Lys Thr Val Asp Thr Phe Gly Gln Arg Thr
                260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
            290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
                340                 345                 350

His Met Thr Arg Gln Glu Phe Val Ala Ser Leu Arg Arg Lys Ser Ser
            355                 360                 365

Gly Phe Ser Arg Gly Ala Ser Ile Tyr Arg Gly Val Thr Arg His His
370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
            435                 440                 445

Leu Pro Ile Gly Ser Ala Ala Lys Arg Leu Lys Glu Ala Glu Ala Ala
450                 455                 460

Ala Ser Ala Gln His His His Ala Gly Leu Leu Ser Tyr Asp Leu Gly
465                 470                 475                 480

Arg Val Ala Ser Gln Val Gly Asp Gly Gly Ala Val Ala Ala Ala Tyr
                485                 490                 495

Gly Ala His Tyr His Gly Ala Ala Trp Pro Thr Val Ala Phe Gln Pro
            500                 505                 510

Gly Ala Ala Ser Thr Gly Val Tyr His Pro Tyr Ala Gln Gln Pro Met
            515                 520                 525

Arg Gly Gly Gly Trp Cys Lys Gln Glu Gln Asp His Ala Leu Val Ala
530                 535                 540

Ala Ala His Ser Val Gln Asp Val His His Val Asn Val Gly Ala Ala
545                 550                 555                 560

Gly Ala His Asp Phe Phe Ser Ala Gly Gln Gln Ala Ala Ala Ala
            565                 570                 575

Met His Gly Val Gly Ser Val Asp Ala Ser Val Glu His Ser Thr
            580                 585                 590

Gly Ser Asn Ser Val Val Tyr Asn Gly Gly Leu Gly Asp Ser Asn Gly
            595                 600                 605

Ala Ser Ala Leu Gly Gly Ser Gly Gly Gly Tyr Met Met Pro Met Ser
            610                 615                 620

Ala Ala Gly Ala Thr Thr Thr Ser Ala Met Leu Ser His Glu Gln Val
625                 630                 635                 640
```

-continued

```
His Ala Arg Ala Tyr Asp Glu Ala Lys Gln Ala Gln Met Gly Tyr
                645                 650                 655

Glu Ser Tyr Leu Val Asn Ala Glu Asn Gly Gly Gly Arg Met Ser
            660                 665                 670

Ala Trp Gly Thr Val Val Ser Ala Ala Ala Ala Ala Ala Ser Ser
        675                 680                 685

Asn Asp Asn Met Ala Ala Asp Val Gly His Gly Gly Ala Gln Leu Phe
690                 695                 700

Ser Val Trp Asn Asp Thr
705                 710

<210> SEQ ID NO 22
<211> LENGTH: 710
<212> TYPE: PRT
<213> ORGANISM: Artificial Sequence
<220> FEATURE:
<223> OTHER INFORMATION: Synthesized
<220> FEATURE:
<223> OTHER INFORMATION: Variant of Zm-ODP2 having 87.3% amino acid
      sequence identity to SEQ ID NO:2 (Zm-ODP2).

<400> SEQUENCE: 22

Met Ala Thr Ile Asn Asn Trp Leu Ala Phe Ser Leu Ser Pro Gln Glu
 1               5                  10                  15

Ile Pro Pro Ser Gln Thr Thr Asp Ser Thr Ile Leu Ser Gly Gly Thr
            20                  25                  30

Ala Asp His Ile Ser Gly Asp Val Cys Phe Asn Leu Pro Gln Asp Trp
        35                  40                  45

Ser Met Arg Gly Ser Glu Ile Ser Gly Ile Ile Gly Glu Pro Lys Ile
    50                  55                  60

Glu Asp Phe Ile Gly Gly Leu Ser Phe Ser Glu Gln His His Lys Gly
65                  70                  75                  80

Asn Cys Asn Met Leu Pro Ser Thr Ser Ser Thr Ile Cys Tyr Gly Ser
                85                  90                  95

Ser Gly Gly Ser Thr Gly Tyr His His Gln Ile Tyr His Gln Pro Thr
            100                 105                 110

Ser Ser Gly Ile His Phe Gly Asp Ser Ile Met Ile Gly Ser Ser Gly
        115                 120                 125

Gly Ile His Asp Gly Gly Gly Met Ile Ser Gly Gly Gly Asn Gly
    130                 135                 140

Ile Gly Gly Gly Gly Ser Gly Asn Gly Gly Ile Gly Leu Ser Met
145                 150                 155                 160

Ile Lys Asn Trp Leu Arg Ser Gln Pro Gly Pro Met Gln Pro Arg Ile
                165                 170                 175

Gly Gly Gly Glu Gly Gly Gln Gly Ile Ser Ile Ser Met Asn Met Gly
            180                 185                 190

Gly Thr Thr Gln Gly Gly Gly Gly Met Pro Ile Val Gly Gly Glu Arg
        195                 200                 205

Gly Arg Gly Pro Glu Ser Ile Ser Thr Ser Gly Gln Gly Gly Gly Ile
    210                 215                 220

Ile Ile Thr Ala Pro Lys Glu Asp Ser Gly Gly Ser Gly Leu Ala Gly
225                 230                 235                 240

Ala Val Leu Ala Leu Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270
```

```
Ser Ile Tyr Arg Gly Val Thr Arg His Arg Trp Thr Gly Arg Tyr Glu
            275                 280                 285

Ala His Leu Trp Asp Asn Ser Cys Arg Arg Glu Gly Gln Thr Arg Lys
        290                 295                 300

Gly Arg Gln Val Tyr Leu Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
                420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
        450                 455                 460

Ala Ser Ala Gln His His His Ala Gly Leu Leu Ser Tyr Asp Leu Gly
465                 470                 475                 480

Arg Val Ala Ser Gln Val Gly Asp Gly Ala Val Ala Ala Ala Tyr
                485                 490                 495

Gly Ala His Tyr His Gly Ala Ala Trp Pro Thr Val Ala Phe Gln Pro
                500                 505                 510

Gly Ala Ala Ser Thr Gly Val Tyr His Pro Tyr Ala Gln Gln Pro Met
            515                 520                 525

Arg Gly Gly Gly Trp Cys Lys Gln Glu Gln Asp His Ala Leu Val Ala
        530                 535                 540

Ala Ala His Ser Val Gln Asp Val His Val Asn Val Gly Ala Ala
545                 550                 555                 560

Gly Ala His Asp Phe Phe Ser Ala Gly Gln Gln Ala Ala Ala Ala
                565                 570                 575

Met His Gly Val Gly Ser Val Asp Ser Ala Ser Val Glu His Ser Thr
            580                 585                 590

Gly Ser Asn Ser Val Val Tyr Asn Gly Leu Gly Asp Ser Asn Gly
            595                 600                 605

Ala Ser Ala Leu Gly Gly Ser Gly Gly Gly Tyr Met Met Pro Met Ser
            610                 615                 620

Ala Ala Gly Ala Thr Thr Thr Ser Ala Met Leu Ser His Glu Gln Leu
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Arg Met Ser
            660                 665                 670

Ala Trp Gly Thr Leu Leu Ser Ala Ala Ala Ala Ala Ala Ser Ser
            675                 680                 685

Asn Asp Asn Met Ala Ala Asp Val Gly His Gly Gly Ala Gln Leu Phe
```

```
          690                 695                 700
Ser Val Trp Asn Asp Thr
705                 710

<210> SEQ ID NO 23
<211> LENGTH: 710
<212> TYPE: PRT
<213> ORGANISM: Artificial Sequence
<220> FEATURE:
<223> OTHER INFORMATION: Synthesized
<220> FEATURE:
<223> OTHER INFORMATION: Variant of Zm-ODP2 having 82.4% amino acid
      sequence identity to SEQ ID NO:2 (Zm-ODP2).

<400> SEQUENCE: 23

Met Ala Thr Ile Asn Asn Trp Leu Ala Phe Ser Leu Ser Pro Gln Glu
 1               5                  10                  15

Ile Pro Pro Ser Gln Thr Thr Asp Ser Thr Ile Leu Ser Gly Gly Thr
            20                  25                  30

Ala Asp His Ile Ser Gly Asp Val Cys Phe Asn Leu Pro Gln Asp Trp
        35                  40                  45

Ser Met Arg Gly Ser Glu Ile Ser Gly Ile Ile Gly Glu Pro Lys Ile
50                  55                  60

Glu Asp Phe Ile Gly Gly Leu Ser Phe Ser Glu Gln His His Lys Gly
65                  70                  75                  80

Asn Cys Asn Met Leu Pro Ser Thr Ser Ser Thr Ile Cys Tyr Gly Ser
                85                  90                  95

Ser Gly Gly Ser Thr Gly Tyr His His Gln Ile Tyr His Gln Pro Thr
            100                 105                 110

Ser Ser Gly Ile His Phe Gly Asp Ser Ile Met Ile Gly Ser Ser Gly
        115                 120                 125

Gly Ile His Asp Gly Gly Met Ile Ser Gly Gly Gly Asn Gly
130                 135                 140

Ile Gly Gly Gly Gly Ser Gly Asn Gly Gly Ile Gly Leu Ser Met
145                 150                 155                 160

Ile Lys Asn Trp Leu Arg Ser Gln Pro Gly Pro Met Gln Pro Arg Ile
                165                 170                 175

Gly Gly Gly Glu Gly Gly Gln Gly Ile Ser Ile Ser Met Asn Met Gly
            180                 185                 190

Gly Thr Thr Gln Gly Gly Gly Met Pro Ile Val Gly Gly Glu Arg
        195                 200                 205

Gly Arg Gly Pro Glu Ser Ile Ser Thr Ser Gly Gln Gly Gly Gly Ile
    210                 215                 220

Ile Ile Thr Gly Pro Lys Glu Asp Ser Gly Ser Gly Leu Gly Gly
225                 230                 235                 240

Gly Val Leu Gly Leu Ser Thr Asp Thr Gly Gly Ser Gly Gly Ser
                245                 250                 255

Gly Asp Asn Thr Gly Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
```

```
            325                 330                 335
Thr Asn Phe Pro Val Ser Asn Tyr Glu Lys Glu Leu Glu Asp Met Lys
        340                 345                 350
His Met Thr Arg Gln Glu Phe Val Ala Ser Leu Arg Arg Lys Ser Ser
            355                 360                 365
Gly Phe Ser Arg Gly Ala Ser Ile Tyr Arg Gly Val Thr Arg His His
        370                 375                 380
Gln His Gly Arg Trp Gln Ala Arg Ile Gly Arg Val Ala Gly Asn Lys
385                 390                 395                 400
Asp Leu Tyr Leu Gly Thr Phe Ser Thr Gln Glu Glu Ala Ala Glu Ala
            405                 410                 415
Tyr Asp Ile Ala Ala Ile Lys Phe Arg Gly Leu Asn Ala Val Thr Asn
        420                 425                 430
Phe Asp Met Ser Arg Tyr Asp Val Lys Ser Ile Leu Asp Ser Ser Ala
            435                 440                 445
Leu Pro Ile Gly Ser Ala Ala Lys Arg Leu Lys Glu Ala Glu Ala Gly
        450                 455                 460
Gly Ser Gly Gln His His Gly Gly Leu Leu Ser Tyr Asp Leu Gly
465                 470                 475                 480
Arg Val Gly Ser Gln Val Gly Asp Gly Gly Val Gly Gly Tyr
            485                 490                 495
Gly Gly His Tyr His Gly Gly Trp Pro Thr Val Gly Phe Gln Pro
        500                 505                 510
Gly Gly Gly Ser Thr Gly Val Tyr His Pro Tyr Gly Gln Gln Pro Met
            515                 520                 525
Arg Gly Gly Gly Trp Cys Lys Gln Glu Gln Asp His Gly Leu Val Gly
        530                 535                 540
Gly Gly His Ser Val Gln Asp Val His Val Asn Val Gly Gly Gly
545                 550                 555                 560
Gly Gly His Asp Phe Phe Ser Gly Gly Gln Gln Gly Gly Gly Ala
            565                 570                 575
Met His Gly Val Gly Ser Val Asp Ser Ala Ser Val Glu His Ser Thr
        580                 585                 590
Gly Ser Asn Ser Val Val Tyr Asn Gly Gly Leu Gly Asp Ser Asn Gly
            595                 600                 605
Ala Ser Ala Leu Gly Gly Ser Gly Gly Gly Tyr Met Met Pro Met Ser
        610                 615                 620
Ala Ala Gly Ala Thr Thr Thr Ser Ala Met Leu Ser His Glu Gln Leu
625                 630                 635                 640
His Ala Arg Ala Tyr Asp Glu Ala Lys Gln Ala Ala Gln Met Gly Tyr
            645                 650                 655
Glu Ser Tyr Leu Val Asn Ala Glu Asn Asn Gly Gly Arg Met Ser
        660                 665                 670
Ala Trp Gly Thr Leu Leu Ser Ala Ala Ala Ala Ala Ser Ser
            675                 680                 685
Asn Asp Asn Met Ala Ala Asp Val Gly His Gly Gly Ala Gln Leu Phe
        690                 695                 700
Ser Val Trp Asn Asp Thr
705                 710

<210> SEQ ID NO 24
<211> LENGTH: 710
<212> TYPE: PRT
<213> ORGANISM: Artificial Sequence
```

```
<220> FEATURE:
<223> OTHER INFORMATION: Synthesized
<220> FEATURE:
<223> OTHER INFORMATION: Consensus sequence of Figure 2.

<400> SEQUENCE: 24

Met Ala Thr Ile Asn Asn Trp Leu Ala Phe Ser Leu Ser Pro Gln Glu
  1               5                  10                  15

Ile Pro Pro Ser Gln Thr Thr Asp Ser Thr Ile Leu Ser Ala Ala Thr
             20                  25                  30

Ala Asp His Ile Ser Gly Asp Val Cys Phe Asn Leu Pro Gln Asp Trp
         35                  40                  45

Ser Met Arg Gly Ser Glu Ile Ser Ala Ile Ala Glu Pro Lys Ile
 50                  55                  60

Glu Asp Phe Ile Gly Gly Leu Ser Phe Ser Glu Gln His His Lys Ala
 65                  70                  75                  80

Asn Cys Asn Met Leu Pro Ser Thr Ser Ser Thr Ile Cys Tyr Ala Ser
                 85                  90                  95

Ser Gly Ala Ser Thr Gly Tyr His His Gln Ile Tyr His Gln Pro Thr
                100                 105                 110

Ser Ser Ala Ile His Phe Ala Asp Ser Ile Met Ile Ala Ser Ser Ala
            115                 120                 125

Gly Ile His Asp Gly Gly Ala Met Ile Ser Ala Ala Ala Asn Gly
130                 135                 140

Ile Ala Gly Ala Ala Ser Ala Asn Gly Gly Gly Ile Gly Leu Ser Met
145                 150                 155                 160

Ile Lys Asn Trp Leu Arg Ser Gln Pro Ala Pro Met Gln Pro Arg Ile
                165                 170                 175

Ala Ala Ala Glu Gly Ala Gln Gly Ile Ser Ile Ser Met Asn Met Ala
            180                 185                 190

Gly Thr Thr Gln Gly Ala Ala Gly Met Pro Ile Val Ala Gly Glu Arg
            195                 200                 205

Ala Arg Ala Pro Glu Ser Ile Ser Thr Ser Ala Gln Gly Gly Ala Ile
210                 215                 220

Ile Ile Thr Ala Pro Lys Glu Asp Ser Gly Ser Gly Leu Ala Gly
225                 230                 235                 240

Ala Val Leu Ala Leu Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
            275                 280                 285

Ala His Leu Trp Asp Asn Ser Cys Arg Arg Glu Gly Gln Thr Arg Lys
290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
            355                 360                 365

Gly Phe Ser Arg Gly Ala Ser Ile Tyr Arg Gly Val Thr Arg His His
370                 375                 380
```

```
Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Leu Leu Ser Tyr Asp Leu Gly
465                 470                 475                 480

Arg Val Ala Ser Gln Val Gly Asp Gly Ala Val Ala Ala Tyr
                485                 490                 495

Gly Ala His Tyr His Gly Ala Ala Trp Pro Thr Val Ala Phe Gln Pro
            500                 505                 510

Gly Ala Ala Ser Thr Gly Val Tyr His Pro Tyr Ala Gln Gln Pro Met
        515                 520                 525

Arg Gly Gly Gly Trp Cys Lys Gln Glu Gln Asp His Ala Leu Val Ala
530                 535                 540

Ala Ala His Ser Val Gln Asp Val His Val Asn Val Gly Ala Ala
545                 550                 555                 560

Gly Ala His Asp Phe Phe Ser Ala Gly Gln Gln Ala Ala Ala Ala Ala
                565                 570                 575

Met His Gly Val Gly Ser Val Asp Ser Ala Ser Val Glu His Ser Thr
            580                 585                 590

Gly Ser Asn Ser Val Val Tyr Asn Gly Gly Leu Gly Asp Ser Asn Gly
        595                 600                 605

Ala Ser Ala Leu Gly Gly Ser Gly Gly Gly Tyr Met Met Pro Met Ser
610                 615                 620

Ala Ala Gly Ala Thr Thr Thr Ser Ala Met Leu Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Gly Arg Met Ser
            660                 665                 670

Ala Trp Gly Thr Val Val Ser Ala Ala Ala Ala Ala Ser Ser
        675                 680                 685

Asn Asp Asn Met Ala Ala Asp Val Gly His Gly Gly Ala Gln Leu Phe
690                 695                 700

Ser Val Trp Asn Asp Thr
705             710

<210> SEQ ID NO 25
<211> LENGTH: 2079
<212> TYPE: DNA
<213> ORGANISM: Oryza sativa
<220> FEATURE:
<221> NAME/KEY: misc_feature
<222> LOCATION: (0)...(0)
<223> OTHER INFORMATION: predicted cDNA of OsANT, Genbank Accession No.
      AP003313 (rice ODP2)
<220> FEATURE:
<221> NAME/KEY: CDS
<222> LOCATION: (1)...(2079)

<400> SEQUENCE: 25
```

-continued

| | |
|---|---|
| atg gcc acc atg aac aac tgg ctg gcc ttc tcc ctc tcc ccg cag gat<br>Met Ala Thr Met Asn Asn Trp Leu Ala Phe Ser Leu Ser Pro Gln Asp<br>1               5                  10                 15 | 48 |
| cag ctc ccg ccg tct cag acc aac tcc act ctc atc tcc gcc gcc gcc<br>Gln Leu Pro Pro Ser Gln Thr Asn Ser Thr Leu Ile Ser Ala Ala Ala<br>         20                 25                 30 | 96 |
| acc acc acc acc gcc ggc gac tcc tcc acc ggc gac gtc tgc ttc aac<br>Thr Thr Thr Thr Ala Gly Asp Ser Ser Thr Gly Asp Val Cys Phe Asn<br>     35                 40                 45 | 144 |
| atc ccc caa gat tgg agc atg agg gga tcg gag ctc tcg gcg ctc gtc<br>Ile Pro Gln Asp Trp Ser Met Arg Gly Ser Glu Leu Ser Ala Leu Val<br> 50                 55                 60 | 192 |
| gcc gag ccg aag ctg gag gac ttc ctc ggc ggc atc tcc ttc tcg gag<br>Ala Glu Pro Lys Leu Glu Asp Phe Leu Gly Gly Ile Ser Phe Ser Glu<br>65                 70                 75                 80 | 240 |
| cag cag cat cat cac ggc ggc aag ggc ggc gtg atc ccg agc agc gcc<br>Gln Gln His His His Gly Gly Lys Gly Gly Val Ile Pro Ser Ser Ala<br>             85                 90                 95 | 288 |
| gcc gct tgc tac gcg agc tcc ggc agc agc gtc ggc tac ctg tac cct<br>Ala Ala Cys Tyr Ala Ser Ser Gly Ser Ser Val Gly Tyr Leu Tyr Pro<br>        100                105                110 | 336 |
| cct cca agc tca tcc tcg ctc cag ttc gcc gac tcc gtc atg gtg gcc<br>Pro Pro Ser Ser Ser Ser Leu Gln Phe Ala Asp Ser Val Met Val Ala<br>    115                120                125 | 384 |
| acc tcc tcg ccc gtc gtc gcc cac gac ggc gtc agc ggc ggc ggc atg<br>Thr Ser Ser Pro Val Val Ala His Asp Gly Val Ser Gly Gly Gly Met<br>130                135                140 | 432 |
| gtg agc gcc gcc gcc gcc gcg gcg gcc agt ggc aac ggc ggc att ggc<br>Val Ser Ala Ala Ala Ala Ala Ala Ser Gly Asn Gly Gly Ile Gly<br>145                150                155                160 | 480 |
| ctg tcc atg atc aag aac tgg ctc cgg agc cag ccg gcg ccg cag ccg<br>Leu Ser Met Ile Lys Asn Trp Leu Arg Ser Gln Pro Ala Pro Gln Pro<br>            165                170                175 | 528 |
| gcg cag gcg ctg tct ctg tcc atg aac atg gcg ggg acg acg acg gcg<br>Ala Gln Ala Leu Ser Leu Ser Met Asn Met Ala Gly Thr Thr Thr Ala<br>        180                185                190 | 576 |
| cag ggc ggc ggc gcc atg gcg ctc ctc gcc ggc gca ggg gag cga ggc<br>Gln Gly Gly Gly Ala Met Ala Leu Leu Ala Gly Ala Gly Glu Arg Gly<br>    195                200                205 | 624 |
| cgg acg acg ccc gcg tca gag agc ctg tcc acg tcg gcg cac gga gcg<br>Arg Thr Thr Pro Ala Ser Glu Ser Leu Ser Thr Ser Ala His Gly Ala<br>210                215                220 | 672 |
| acg acg gcg acg atg gct ggt ggt cgc aag gag att aac gag gaa ggc<br>Thr Thr Ala Thr Met Ala Gly Gly Arg Lys Glu Ile Asn Glu Glu Gly<br>225                230                235                240 | 720 |
| agc ggc agc gcc ggc gcc gtg gtt gcc gtc ggc tcg gag tca ggc ggc<br>Ser Gly Ser Ala Gly Ala Val Val Ala Val Gly Ser Glu Ser Gly Gly<br>            245                250                255 | 768 |
| agc ggc gcc gtg gtg gag gcc ggc gcg gcg gcg gcg gcg gcg agg aag<br>Ser Gly Ala Val Val Glu Ala Gly Ala Ala Ala Ala Ala Arg Lys<br>        260                265                270 | 816 |
| tcc gtc gac acg ttc ggc cag aga aca tcg atc tac cgc ggc gtg aca<br>Ser Val Asp Thr Phe Gly Gln Arg Thr Ser Ile Tyr Arg Gly Val Thr<br>    275                280                285 | 864 |
| agg cat aga tgg aca ggg agg tat gag gct cat ctt tgg gac aac agc<br>Arg His Arg Trp Thr Gly Arg Tyr Glu Ala His Leu Trp Asp Asn Ser<br>290                295                300 | 912 |
| tgc aga aga gag ggc caa act cgc aag ggt cgt caa ggt ggt tat gac<br>Cys Arg Arg Glu Gly Gln Thr Arg Lys Gly Arg Gln Gly Gly Tyr Asp<br>305                310                315                320 | 960 |

-continued

```
aaa gag gaa aaa gct gct aga gct tat gat ttg gct gct ctc aaa tac    1008
Lys Glu Glu Lys Ala Ala Arg Ala Tyr Asp Leu Ala Ala Leu Lys Tyr
            325                 330                 335 tgg ggc ccg acg acg acg aca aat ttt ccg gta aat aac tat gaa aag    1056
Trp Gly Pro Thr Thr Thr Thr Asn Phe Pro Val Asn Asn Tyr Glu Lys
            340                 345                 350 gag ctg gag gag atg aag cac atg aca agg cag gag ttc gta gcc tct    1104
Glu Leu Glu Glu Met Lys His Met Thr Arg Gln Glu Phe Val Ala Ser
            355                 360                 365 ttg aga agg aag agc agt ggt ttc tcc aga ggt gca tcc att tac cgt    1152
Leu Arg Arg Lys Ser Ser Gly Phe Ser Arg Gly Ala Ser Ile Tyr Arg
        370                 375                 380 gga gta act agg cat cac cag cat ggg aga tgg caa gca agg ata gga    1200
Gly Val Thr Arg His His Gln His Gly Arg Trp Gln Ala Arg Ile Gly
385                 390                 395                 400 aga gtt gca ggg aac aag gac ctc tac ttg ggc acc ttc agc acg cag    1248
Arg Val Ala Gly Asn Lys Asp Leu Tyr Leu Gly Thr Phe Ser Thr Gln
                405                 410                 415 gag gag gcg gcg gag gcg tac gac atc gcg gcg atc aag ttc cgg ggg    1296
Glu Glu Ala Ala Glu Ala Tyr Asp Ile Ala Ala Ile Lys Phe Arg Gly
            420                 425                 430 ctc aac gcc gtc acc aac ttc gac atg agc cgc tac gac gtc aag agc    1344
Leu Asn Ala Val Thr Asn Phe Asp Met Ser Arg Tyr Asp Val Lys Ser
            435                 440                 445 atc ctc gac agc gct gcc ctc ccc gtc ggc acc gcc gcc aag cgc ctc    1392
Ile Leu Asp Ser Ala Ala Leu Pro Val Gly Thr Ala Ala Lys Arg Leu
        450                 455                 460 aag gac gcc gag gcc gcc gcc gcc tac gac gtc ggc cgc atc gcc tcg    1440
Lys Asp Ala Glu Ala Ala Ala Ala Tyr Asp Val Gly Arg Ile Ala Ser
465                 470                 475                 480 cac ctc ggc ggc gac ggc gcc tac gcc gcg cat tac ggc cac cac cac    1488
His Leu Gly Gly Asp Gly Ala Tyr Ala Ala His Tyr Gly His His His
                485                 490                 495 cac tcg gcc gcc gcc gcc tgg ccg acc atc gcg ttc cag gcg gcg gcg    1536
His Ser Ala Ala Ala Ala Trp Pro Thr Ile Ala Phe Gln Ala Ala Ala
            500                 505                 510 gcg ccg ccg ccg cac gcc gcc ggg ctt tac cac ccg tac gcg cag ccg    1584
Ala Pro Pro Pro His Ala Ala Gly Leu Tyr His Pro Tyr Ala Gln Pro
            515                 520                 525 ctg cgt ggg tgg tgc aag cag gag cag gac cac gcc gtg atc gcg gcg    1632
Leu Arg Gly Trp Cys Lys Gln Glu Gln Asp His Ala Val Ile Ala Ala
        530                 535                 540 gcg cac agc ctg cag gat ctc cac cac ctc aac ctc ggc gcc gcc gcc    1680
Ala His Ser Leu Gln Asp Leu His His Leu Asn Leu Gly Ala Ala Ala
545                 550                 555                 560 gcc gcg cat gac ttc ttc tcg cag gcg atg cag cag cag cac ggc ctc    1728
Ala Ala His Asp Phe Phe Ser Gln Ala Met Gln Gln Gln His Gly Leu
                565                 570                 575 ggc agc atc gac aac gcg tcg ctc gag cac agc acc ggc tcc aac tcc    1776
Gly Ser Ile Asp Asn Ala Ser Leu Glu His Ser Thr Gly Ser Asn Ser
            580                 585                 590 gtc gtc tac aac ggc gac aat ggc ggc gga ggc ggc tac atc atg        1824
Val Val Tyr Asn Gly Asp Asn Gly Gly Gly Gly Gly Tyr Ile Met
            595                 600                 605 gcg ccg atg agc gcc gtg tcg gcc acg gcc acc gcg gtg gcg agc agc    1872
Ala Pro Met Ser Ala Val Ser Ala Thr Ala Thr Ala Val Ala Ser Ser
            610                 615                 620 cac gat cac ggc ggc gac ggc ggg aag cag gtg cag atg ggg tac gac    1920
His Asp His Gly Gly Asp Gly Gly Lys Gln Val Gln Met Gly Tyr Asp
```

|  |  |  |  |  |  |  |  |  |  |  |  |  |  |  |  |
|---|---|---|---|---|---|---|---|---|---|---|---|---|---|---|---|
| | 625 | | | | 630 | | | | | 635 | | | | 640 | |

```
agc tac ctc gtc ggc gca gac gcc tac ggc ggc ggc gcc ggg agg      1968
Ser Tyr Leu Val Gly Ala Asp Ala Tyr Gly Gly Gly Ala Gly Arg
                645                 650                 655 atg cca tcc tgg gcg atg acg ccg gcg tcg gcg ccg gcc gcg agc      2016
Met Pro Ser Trp Ala Met Thr Pro Ala Ser Ala Pro Ala Ala Thr Ser
            660                 665                 670 agc agc gac atg acc gga gtc tgc cat ggc gca cag ctc ttc agc gtc  2064
Ser Ser Asp Met Thr Gly Val Cys His Gly Ala Gln Leu Phe Ser Val
        675                 680                 685 tgg aac gac aca taa                                              2079
Trp Asn Asp Thr
    690

<210> SEQ ID NO 26
<211> LENGTH: 692
<212> TYPE: PRT
<213> ORGANISM: Oryza sativa

<400> SEQUENCE: 26

Met Ala Thr Met Asn Asn Trp Leu Ala Phe Ser Leu Ser Pro Gln Asp
 1               5                  10                  15

Gln Leu Pro Pro Ser Gln Thr Asn Ser Thr Leu Ile Ser Ala Ala Ala
            20                  25                  30

Thr Thr Thr Thr Ala Gly Asp Ser Ser Thr Gly Asp Val Cys Phe Asn
        35                  40                  45

Ile Pro Gln Asp Trp Ser Met Arg Gly Ser Glu Leu Ser Ala Leu Val
    50                  55                  60

Ala Glu Pro Lys Leu Glu Asp Phe Leu Gly Gly Ile Ser Phe Ser Glu
65                  70                  75                  80

Gln Gln His His His Gly Gly Lys Gly Gly Val Ile Pro Ser Ser Ala
                85                  90                  95

Ala Ala Cys Tyr Ala Ser Ser Gly Ser Ser Val Gly Tyr Leu Tyr Pro
            100                 105                 110

Pro Pro Ser Ser Ser Ser Leu Gln Phe Ala Asp Ser Val Met Val Ala
        115                 120                 125

Thr Ser Ser Pro Val Val Ala His Asp Gly Val Ser Gly Gly Gly Met
    130                 135                 140

Val Ser Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                165                 170                 175

Ala Gln Ala Leu Ser Leu Ser Met Asn Met Ala Gly Thr Thr Thr Ala
            180                 185                 190

Gln Gly Gly Gly Ala Met Ala Leu Leu Ala Gly Ala Gly Glu Arg Gly
        195                 200                 205

Arg Thr Thr Pro Ala Ser Glu Ser Leu Ser Thr Ser Ala His Gly Ala
    210                 215                 220

Thr Thr Ala Thr Met Ala Gly Arg Lys Glu Ile Asn Glu Glu Gly
225                 230                 235                 240

Ser Gly Ser Ala Gly Ala Val Val Ala Val Gly Ser Glu Ser Gly Gly
                245                 250                 255

Ser Gly Ala Val Val Glu Ala Gly Ala Ala Ala Ala Ala Arg Lys
            260                 265                 270

Ser Val Asp Thr Phe Gly Gln Arg Thr Ser Ile Tyr Arg Gly Val Thr
        275                 280                 285
```

```
Arg His Arg Trp Thr Gly Arg Tyr Glu Ala His Leu Trp Asp Asn Ser
    290                 295                 300

Cys Arg Arg Glu Gly Gln Thr Arg Lys Gly Arg Gln Gly Gly Tyr Asp
305                 310                 315                 320

Lys Glu Glu Lys Ala Ala Arg Ala Tyr Asp Leu Ala Ala Leu Lys Tyr
                325                 330                 335

Trp Gly Pro Thr Thr Thr Thr Asn Phe Pro Val Asn Asn Tyr Glu Lys
            340                 345                 350

Glu Leu Glu Glu Met Lys His Met Thr Arg Gln Glu Phe Val Ala Ser
        355                 360                 365

Leu Arg Arg Lys Ser Ser Gly Phe Ser Arg Gly Ala Ser Ile Tyr Arg
    370                 375                 380

Gly Val Thr Arg His His Gln His Gly Arg Trp Gln Ala Arg Ile Gly
385                 390                 395                 400

Arg Val Ala Gly Asn Lys Asp Leu Tyr Leu Gly Thr Phe Ser Thr Gln
                405                 410                 415

Glu Glu Ala Ala Glu Ala Tyr Asp Ile Ala Ala Ile Lys Phe Arg Gly
            420                 425                 430

Leu Asn Ala Val Thr Asn Phe Asp Met Ser Arg Tyr Asp Val Lys Ser
        435                 440                 445

Ile Leu Asp Ser Ala Ala Leu Pro Val Gly Thr Ala Ala Lys Arg Leu
    450                 455                 460

Lys Asp Ala Glu Ala Ala Ala Tyr Asp Val Gly Arg Ile Ala Ser
465                 470                 475                 480

His Leu Gly Gly Asp Gly Ala Tyr Ala Ala His Tyr Gly His His His
                485                 490                 495

His Ser Ala Ala Ala Ala Trp Pro Thr Ile Ala Phe Gln Ala Ala Ala
        500                 505                 510

Ala Pro Pro Pro His Ala Ala Gly Leu Tyr His Pro Tyr Ala Gln Pro
    515                 520                 525

Leu Arg Gly Trp Cys Lys Gln Glu Gln Asp His Ala Val Ile Ala Ala
    530                 535                 540

Ala His Ser Leu Gln Asp Leu His His Leu Asn Leu Gly Ala Ala Ala
545                 550                 555                 560

Ala Ala His Asp Phe Phe Ser Gln Ala Met Gln Gln Gln His Gly Leu
                565                 570                 575

Gly Ser Ile Asp Asn Ala Ser Leu Glu His Ser Thr Gly Ser Asn Ser
            580                 585                 590

Val Val Tyr Asn Gly Asp Asn Gly Gly Gly Gly Tyr Ile Met
        595                 600                 605

Ala Pro Met Ser Ala Val Ser Ala Thr Ala Val Ala Ser Ser
    610                 615                 620

His Asp His Gly Gly Asp Gly Lys Gln Val Gln Met Gly Tyr Asp
625                 630                 635                 640

Ser Tyr Leu Val Gly Ala Asp Ala Tyr Gly Gly Gly Ala Gly Arg
                645                 650                 655

Met Pro Ser Trp Ala Met Thr Pro Ala Ser Pro Ala Ala Thr Ser
            660                 665                 670

Ser Ser Asp Met Thr Gly Val Cys His Gly Ala Gln Leu Phe Ser Val
        675                 680                 685

Trp Asn Asp Thr
    690
```

<210> SEQ ID NO 27
<211> LENGTH: 1794
<212> TYPE: DNA
<213> ORGANISM: oryza sativa
<220> FEATURE:
<221> NAME/KEY: misc_feature
<222> LOCATION: (0)...(0)
<223> OTHER INFORMATION: predicted OsBNM, Genbank Accession No. AY062180, (rice ODP2)
<220> FEATURE:
<221> NAME/KEY: CDS
<222> LOCATION: (1)...(1794)

<400> SEQUENCE: 27

```
atg gcc acc atg aac aac tgg ctg gcc ttc tcc ctc tcc ccg cag gat     48
Met Ala Thr Met Asn Asn Trp Leu Ala Phe Ser Leu Ser Pro Gln Asp
 1               5                  10                  15 cag ctc ccg ccg tct cag acc aac tcc act ttc atc tcc gcc gcc gcc     96
Gln Leu Pro Pro Ser Gln Thr Asn Ser Thr Phe Ile Ser Ala Ala Ala
             20                  25                  30 acc acc acc acc gcc ggc gac tcc tcc acc ggc gac gtc tgc ttc aac    144
Thr Thr Thr Thr Ala Gly Asp Ser Ser Thr Gly Asp Val Cys Phe Asn
         35                  40                  45 atc ccc caa gct cac ccc tcc acg ccg gcc att ggc aac ggc ggc att    192
Ile Pro Gln Ala His Pro Ser Thr Pro Ala Ile Gly Asn Gly Gly Ile
     50                  55                  60 ggc ctg tcc atg atc aag aac tgg ctc cgg agc cag ccg gcg ccg cag    240
Gly Leu Ser Met Ile Lys Asn Trp Leu Arg Ser Gln Pro Ala Pro Gln
 65                  70                  75                  80 ccg gcg cag gcg ctg tct ctg tcc atg aac atg gcg ggg acg acg acg    288
Pro Ala Gln Ala Leu Ser Leu Ser Met Asn Met Ala Gly Thr Thr Thr
                 85                  90                  95 gcg cag ggc ggc ggc gcc atg gcg ctc ctc gcc ggc gca ggg gag cga    336
Ala Gln Gly Gly Gly Ala Met Ala Leu Leu Ala Gly Ala Gly Glu Arg
            100                 105                 110 ggc cgg acg acg ccc gcg tca gag agc ctg tcc acg tcg gcg cac gga    384
Gly Arg Thr Thr Pro Ala Ser Glu Ser Leu Ser Thr Ser Ala His Gly
        115                 120                 125 gcg acg acg gcg acg atg gct ggt ggt cgc aag gag att aac gag gaa    432
Ala Thr Thr Ala Thr Met Ala Gly Gly Arg Lys Glu Ile Asn Glu Glu
    130                 135                 140 ggc agc ggc agc gcc ggc gcc gtg gtt gcc gtc ggc tcg gag tca ggc    480
Gly Ser Gly Ser Ala Gly Ala Val Val Ala Val Gly Ser Glu Ser Gly
145                 150                 155                 160 ggc agc ggc gcc gtg gtg gag gcc ggc gcg gcg gcg gcg gcg gcg agg    528
Gly Ser Gly Ala Val Val Glu Ala Gly Ala Ala Ala Ala Ala Ala Arg
                165                 170                 175 aag tcc gtc gac acg ttc ggc cag aga aca tcg atc tac cgc ggc gtg    576
Lys Ser Val Asp Thr Phe Gly Gln Arg Thr Ser Ile Tyr Arg Gly Val
            180                 185                 190 aca agg cat aga tgg aca ggg agg tat gag gct cat ctt tgg gac aac    624
Thr Arg His Arg Trp Thr Gly Arg Tyr Glu Ala His Leu Trp Asp Asn
        195                 200                 205 agc tgc aga aga gag ggc caa act cgc aag ggt cgt caa ggt ggt tat    672
Ser Cys Arg Arg Glu Gly Gln Thr Arg Lys Gly Arg Gln Gly Gly Tyr
    210                 215                 220 gac aaa gag gaa aaa gct gct aga gct tat gat ttg gct gct ctc aaa    720
Asp Lys Glu Glu Lys Ala Ala Arg Ala Tyr Asp Leu Ala Ala Leu Lys
225                 230                 235                 240 tac tgg ggc ccg acg acg acg aca aat ttt ccg gta aat aac tat gaa    768
Tyr Trp Gly Pro Thr Thr Thr Thr Asn Phe Pro Val Asn Asn Tyr Glu
                245                 250                 255
```

```
aag gag ctg gag gag atg aag cac atg aca agg cag gag ttc gta gcc      816
Lys Glu Leu Glu Glu Met Lys His Met Thr Arg Gln Glu Phe Val Ala
            260                 265                 270 tct ttg aga agg aag agc agt ggt ttc tcc aga ggt gca tcc att tac      864
Ser Leu Arg Arg Lys Ser Ser Gly Phe Ser Arg Gly Ala Ser Ile Tyr
        275                 280                 285 cgt gga gta act agg cat cac cag cat ggg aga tgg caa gca agg ata      912
Arg Gly Val Thr Arg His His Gln His Gly Arg Trp Gln Ala Arg Ile
    290                 295                 300 gga aga gtt gca ggg aac aag gac ctc tac ttg ggc acc ttc agc acg      960
Gly Arg Val Ala Gly Asn Lys Asp Leu Tyr Leu Gly Thr Phe Ser Thr
305                 310                 315                 320 cag gag gag gcg gcg gag gcg tac gac atc gcg gcg atc aag ttc cgg     1008
Gln Glu Glu Ala Ala Glu Ala Tyr Asp Ile Ala Ala Ile Lys Phe Arg
                325                 330                 335 ggg ctc aac gcc gtc acc aac ttc gac atg agc cgc tac gac gtc aag     1056
Gly Leu Asn Ala Val Thr Asn Phe Asp Met Ser Arg Tyr Asp Val Lys
            340                 345                 350 agc atc ctc gac agc gct gcc ctc ccc gtc ggc acc gcc gcc aag cgc     1104
Ser Ile Leu Asp Ser Ala Ala Leu Pro Val Gly Thr Ala Ala Lys Arg
        355                 360                 365 ctc aag gac gcc gag gcc gcc gcc tac gac gtc ggc cgc atc gcc         1152
Leu Lys Asp Ala Glu Ala Ala Ala Tyr Asp Val Gly Arg Ile Ala
    370                 375                 380 tcg cac ctc ggc ggc gac ggc gcc tac gcc gcg cat tac ggc cac cac     1200
Ser His Leu Gly Gly Asp Gly Ala Tyr Ala Ala His Tyr Gly His His
385                 390                 395                 400 cac cac tcg gcc gcc gcc gcc tgg ccg acc atc gcg ttc cag gcg gcg     1248
His His Ser Ala Ala Ala Ala Trp Pro Thr Ile Ala Phe Gln Ala Ala
                405                 410                 415 gcg gcg ccg ccg ccg cac gcc gcc ggg ctt tac cac ccg tac gcg cag     1296
Ala Ala Pro Pro Pro His Ala Ala Gly Leu Tyr His Pro Tyr Ala Gln
            420                 425                 430 ccg ctg cgt ggg tgg tgc aag cag gag cag gac cac gcc gtg atc gcg     1344
Pro Leu Arg Gly Trp Cys Lys Gln Glu Gln Asp His Ala Val Ile Ala
        435                 440                 445 gcg gcg cac agc ctg cag gat ctc cac cac ctc aac ctc ggc gcc gcc     1392
Ala Ala His Ser Leu Gln Asp Leu His His Leu Asn Leu Gly Ala Ala
    450                 455                 460 gcc gcc gcg cat gac ttc ttc tcg cag gcg atg cag cag cag cac ggc     1440
Ala Ala Ala His Asp Phe Phe Ser Gln Ala Met Gln Gln Gln His Gly
465                 470                 475                 480 ctc ggc agc atc gac aac gcg tcg ctc gag cac agc acc ggc tcc aac     1488
Leu Gly Ser Ile Asp Asn Ala Ser Leu Glu His Ser Thr Gly Ser Asn
                485                 490                 495 tcc gtc gtc tac aac ggc gac aat ggc ggc gga ggc ggc ggc tac atc     1536
Ser Val Val Tyr Asn Gly Asp Asn Gly Gly Gly Gly Gly Gly Tyr Ile
            500                 505                 510 atg gcg ccg atg agc gcc gtg tcg gcc acg gcc acc gcg gtg gcg agc     1584
Met Ala Pro Met Ser Ala Val Ser Ala Thr Ala Thr Ala Val Ala Ser
        515                 520                 525 agc cac gat cac ggc ggc gac ggc ggg aag cag gtg cag atg ggg tac     1632
Ser His Asp His Gly Gly Asp Gly Gly Lys Gln Val Gln Met Gly Tyr
    530                 535                 540 gac agc tac ctc gtc ggc gca gac gcc tac ggc ggc ggc ggc gcc ggg     1680
Asp Ser Tyr Leu Val Gly Ala Asp Ala Tyr Gly Gly Gly Gly Ala Gly
545                 550                 555                 560 agg atg cca tcc tgg gcg atg acg ccg gcg tcg gcg ccg gcc gcc acg     1728
Arg Met Pro Ser Trp Ala Met Thr Pro Ala Ser Ala Pro Ala Ala Thr
```

-continued

```
              565                 570                 575
agc agc agc gac atg acc gga gtc tgc cat ggc gca cag ctc ttc agc    1776
Ser Ser Ser Asp Met Thr Gly Val Cys His Gly Ala Gln Leu Phe Ser
            580                 585                 590 gtc tgg aac gac aca taa                                            1794
Val Trp Asn Asp Thr
        595
```

<210> SEQ ID NO 28
<211> LENGTH: 597
<212> TYPE: PRT
<213> ORGANISM: oryza sativa

<400> SEQUENCE: 28

```
Met Ala Thr Met Asn Asn Trp Leu Ala Phe Ser Leu Ser Pro Gln Asp
 1               5                  10                  15

Gln Leu Pro Pro Ser Gln Thr Asn Ser Thr Phe Ile Ser Ala Ala Ala
            20                  25                  30

Thr Thr Thr Thr Ala Gly Asp Ser Ser Thr Gly Asp Val Cys Phe Asn
        35                  40                  45

Ile Pro Gln Ala His Pro Ser Thr Pro Ala Ile Gly Asn Gly Gly Ile
    50                  55                  60

Gly Leu Ser Met Ile Lys Asn Trp Leu Arg Ser Gln Pro Ala Pro Gln
65                  70                  75                  80

Pro Ala Gln Ala Leu Ser Leu Ser Met Asn Met Ala Gly Thr Thr Thr
                85                  90                  95

Ala Gln Gly Gly Gly Ala Met Ala Leu Leu Ala Gly Ala Gly Glu Arg
            100                 105                 110

Gly Arg Thr Thr Pro Ala Ser Glu Ser Leu Ser Thr Ser Ala His Gly
        115                 120                 125

Ala Thr Thr Ala Thr Met Ala Gly Gly Arg Lys Glu Ile Asn Glu Glu
    130                 135                 140

Gly Ser Gly Ser Ala Gly Ala Val Val Ala Val Gly Ser Glu Ser Gly
145                 150                 155                 160

Gly Ser Gly Ala Val Val Glu Ala Gly Ala Ala Ala Ala Ala Ala Arg
                165                 170                 175

Lys Ser Val Asp Thr Phe Gly Gln Arg Thr Ser Ile Tyr Arg Gly Val
            180                 185                 190

Thr Arg His Arg Trp Thr Gly Arg Tyr Glu Ala His Leu Trp Asp Asn
        195                 200                 205

Ser Cys Arg Arg Glu Gly Gln Thr Arg Lys Gly Arg Gln Gly Gly Tyr
    210                 215                 220

Asp Lys Glu Glu Lys Ala Ala Arg Ala Tyr Asp Leu Ala Ala Leu Lys
225                 230                 235                 240

Tyr Trp Gly Pro Thr Thr Thr Asn Phe Pro Val Asn Asn Tyr Glu
                245                 250                 255

Lys Glu Leu Glu Glu Met Lys His Met Thr Arg Gln Glu Phe Val Ala
            260                 265                 270

Ser Leu Arg Arg Lys Ser Ser Gly Phe Ser Arg Gly Ala Ser Ile Tyr
        275                 280                 285

Arg Gly Val Thr Arg His His Gln His Gly Arg Trp Gln Ala Arg Ile
    290                 295                 300

Gly Arg Val Ala Gly Asn Lys Asp Leu Tyr Leu Gly Thr Phe Ser Thr
305                 310                 315                 320

Gln Glu Glu Ala Ala Glu Ala Tyr Asp Ile Ala Ala Ile Lys Phe Arg
```

```
                    325                 330                 335
Gly Leu Asn Ala Val Thr Asn Phe Asp Met Ser Arg Tyr Asp Val Lys
                340                 345                 350

Ser Ile Leu Asp Ser Ala Ala Leu Pro Val Gly Thr Ala Ala Lys Arg
            355                 360                 365

Leu Lys Asp Ala Glu Ala Ala Ala Tyr Asp Val Gly Arg Ile Ala
        370                 375                 380

Ser His Leu Gly Gly Asp Gly Ala Tyr Ala Ala His Tyr Gly His His
385                 390                 395                 400

His His Ser Ala Ala Ala Ala Trp Pro Thr Ile Ala Phe Gln Ala Ala
                405                 410                 415

Ala Ala Pro Pro Pro His Ala Ala Gly Leu Tyr His Pro Tyr Ala Gln
            420                 425                 430

Pro Leu Arg Gly Trp Cys Lys Gln Glu Gln Asp His Ala Val Ile Ala
            435                 440                 445

Ala Ala His Ser Leu Gln Asp Leu His His Leu Asn Leu Gly Ala Ala
        450                 455                 460

Ala Ala Ala His Asp Phe Phe Ser Gln Ala Met Gln Gln Gln His Gly
465                 470                 475                 480

Leu Gly Ser Ile Asp Asn Ala Ser Leu Glu His Ser Thr Gly Ser Asn
                485                 490                 495

Ser Val Val Tyr Asn Gly Asp Asn Gly Gly Gly Gly Gly Gly Tyr Ile
            500                 505                 510

Met Ala Pro Met Ser Ala Val Ser Ala Thr Ala Thr Ala Val Ala Ser
            515                 520                 525

Ser His Asp His Gly Gly Asp Gly Gly Lys Gln Val Gln Met Gly Tyr
        530                 535                 540

Asp Ser Tyr Leu Val Gly Ala Asp Ala Tyr Gly Gly Gly Gly Ala Gly
545                 550                 555                 560

Arg Met Pro Ser Trp Ala Met Thr Pro Ala Ser Ala Pro Ala Ala Thr
                565                 570                 575

Ser Ser Ser Asp Met Thr Gly Val Cys His Gly Ala Gln Leu Phe Ser
            580                 585                 590

Val Trp Asn Asp Thr
        595

<210> SEQ ID NO 29
<211> LENGTH: 655
<212> TYPE: PRT
<213> ORGANISM: Oryza sativa

<400> SEQUENCE: 29

Met Ala Ser Ala Asp Asn Trp Leu Gly Phe Ser Leu Ser Gly Gln Gly
1               5                   10                  15

Asn Pro Gln His His Gln Asn Gly Ser Pro Ser Ala Ala Gly Asp Ala
            20                  25                  30

Ala Ile Asp Ile Ser Gly Ser Gly Asp Phe Tyr Gly Leu Pro Thr Pro
        35                  40                  45

Asp Ala His His Ile Gly Met Ala Gly Glu Asp Ala Pro Tyr Gly Val
    50                  55                  60

Met Asp Ala Phe Asn Arg Gly Thr His Glu Thr Gln Asp Trp Ala Met
65                  70                  75                  80

Arg Gly Leu Asp Tyr Gly Gly Gly Ser Ser Asp Leu Ser Met Leu Val
                85                  90                  95
```

-continued

```
Gly Ser Ser Gly Gly Arg Arg Thr Val Ala Gly Asp Gly Val Gly
            100                 105                 110

Glu Ala Pro Lys Leu Glu Asn Phe Leu Asp Gly Asn Ser Phe Ser Asp
            115                 120                 125

Val His Gly Gln Ala Ala Gly Gly Tyr Leu Tyr Ser Gly Ser Ala Val
            130                 135                 140

Gly Gly Ala Gly Gly Tyr Ser Asn Gly Gly Cys Gly Gly Gly Thr Ile
145                 150                 155                 160

Glu Leu Ser Met Ile Lys Thr Trp Leu Arg Ser Asn Gln Ser Gln Gln
                165                 170                 175

Gln Pro Ser Pro Pro Gln His Ala Asp Gln Gly Met Ser Thr Asp Ala
            180                 185                 190

Ser Ala Ser Ser Tyr Ala Cys Ser Asp Val Leu Val Gly Ser Cys Gly
            195                 200                 205

Gly Gly Gly Ala Gly Gly Thr Ala Ser Ser His Gly Gln Gly Leu Ala
            210                 215                 220

Leu Ser Met Ser Thr Gly Ser Val Ala Ala Gly Gly Gly Gly Gly Ala
225                 230                 235                 240

Val Val Ala Ala Glu Ser Ser Ser Glu Asn Lys Arg Val Asp Ser
                245                 250                 255

Pro Gly Gly Ala Val Asp Gly Ala Val Pro Arg Lys Ser Ile Asp Thr
            260                 265                 270

Phe Gly Gln Arg Thr Ser Ile Tyr Arg Gly Val Thr Arg His Arg Trp
            275                 280                 285

Thr Gly Arg Tyr Glu Ala His Leu Trp Asp Asn Ser Cys Arg Arg Glu
290                 295                 300

Gly Gln Ser Arg Lys Gly Arg Gln Gly Gly Tyr Asp Lys Glu Asp Lys
305                 310                 315                 320

Ala Ala Arg Ala Tyr Asp Leu Ala Ala Leu Lys Tyr Trp Gly Thr Thr
                325                 330                 335

Thr Thr Thr Asn Phe Pro Met Ser Asn Tyr Glu Lys Glu Leu Glu Glu
            340                 345                 350

Met Lys His Met Thr Arg Gln Glu Tyr Ile Ala His Leu Arg Arg Asn
            355                 360                 365

Ser Ser Gly Phe Ser Arg Gly Ala Ser Lys Tyr Arg Gly Val Thr Arg
370                 375                 380

His His Gln His Gly Arg Trp Gln Ala Arg Ile Gly Arg Val Ala Gly
385                 390                 395                 400

Asn Lys Asp Ile Tyr Leu Gly Thr Phe Ser Thr Glu Glu Ala Ala
                405                 410                 415

Glu Ala Tyr Asp Ile Ala Ala Ile Lys Phe Arg Gly Leu Asn Ala Val
            420                 425                 430

Thr Asn Phe Asp Met Ser Arg Tyr Asp Val Lys Ser Ile Leu Asp Ser
            435                 440                 445

Ser Thr Leu Pro Val Gly Gly Ala Ala Arg Arg Leu Lys Glu Ala Glu
            450                 455                 460

Val Ala Ala Ala Ala Gly Gly Val Ile Val Ser His Leu Ala
465                 470                 475                 480

Asp Gly Gly Val Gly Tyr Tyr Tyr Gly Cys Gly Pro Thr Ile Ala
                485                 490                 495

Phe Gly Gly Gly Gln Gln Pro Ala Pro Leu Ala Val His Tyr Pro
            500                 505                 510

Ser Tyr Gly Gln Ala Ser Gly Trp Cys Lys Pro Glu Gln Asp Ala Val
```

```
            515                 520                 525
Ile Ala Ala Gly His Cys Ala Thr Asp Leu Gln His Leu His Leu Gly
    530                 535                 540

Ser Gly Gly Ala Ala Ala Thr His Asn Phe Phe Gln Gln Pro Ala Ser
545                 550                 555                 560

Ser Ser Ala Val Tyr Gly Asn Gly Gly Gly Gly Gly Asn Ala Phe
                565                 570                 575

Met Met Pro Met Gly Ala Val Val Ala Ala Asp His Gly Gly Gln
                580                 585                 590

Ser Ser Ala Tyr Gly Gly Gly Asp Glu Ser Gly Arg Leu Val Val Gly
                595                 600                 605

Tyr Asp Gly Val Val Asp Pro Tyr Ala Ala Met Arg Ser Ala Tyr Glu
    610                 615                 620

Leu Ser Gln Gly Ser Ser Ser Ser Val Ser Val Ala Lys Ala Ala
625                 630                 635                 640

Asn Gly Tyr Pro Asp Asn Trp Ser Ser Pro Phe Asn Gly Met Gly
                645                 650                 655

<210> SEQ ID NO 30
<211> LENGTH: 581
<212> TYPE: PRT
<213> ORGANISM: Arabidopsis thaliana

<400> SEQUENCE: 30

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
                20                  25                  30

Val Asp Val Ala Gly Gly Tyr Cys Phe Asp Leu Ala Ala Pro Ser Asp
            35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Glu Gln Asn Gly
                85                  90                  95

Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
        115                 120                 125

Gly Gly Gly Gly Ser Leu Gly Leu Ser Met Ile Lys Thr Trp Leu Ser
130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240
```

```
Gly Arg Gln Gly Gly Tyr Asp Lys Glu Glu Lys Ala Ala Arg Ala Tyr
                245                 250                 255

Asp Leu Ala Ala Leu Lys Tyr Trp Gly Thr Thr Thr Thr Thr Asn Phe
            260                 265                 270

Pro Leu Ser Glu Tyr Glu Lys Glu Val Glu Glu Met Lys His Met Thr
        275                 280                 285

Arg Gln Glu Tyr Val Ala Ser Leu Arg Arg Lys Ser Ser Gly Phe Ser
    290                 295                 300

Arg Gly Ala Ser Ile Tyr Arg Gly Val Thr Arg His His Gln His Gly
305                 310                 315                 320

Arg Trp Gln Ala Arg Ile Gly Arg Val Ala Gly Asn Lys Asp Leu Tyr
                325                 330                 335

Leu Gly Thr Phe Gly Thr Gln Glu Glu Ala Glu Ala Tyr Asp Ile
            340                 345                 350

Ala Ala Ile Lys Phe Arg Gly Leu Ser Ala Val Thr Asn Phe Asp Met
        355                 360                 365

Asn Arg Tyr Asn Val Lys Ala Ile Leu Glu Ser Pro Ser Leu Pro Ile
    370                 375                 380

Gly Ser Ser Ala Lys Arg Leu Lys Asp Val Asn Asn Pro Val Pro Ala
385                 390                 395                 400

Met Met Ile Ser Asn Asn Val Ser Glu Ser Ala Asn Asn Val Ser Gly
                405                 410                 415

Trp Gln Asn Thr Ala Phe Gln His His Gln Gly Met Asp Leu Ser Leu
            420                 425                 430

Leu Gln Gln Gln Gln Glu Arg Tyr Val Gly Tyr Tyr Asn Gly Gly Asn
        435                 440                 445

Leu Ser Thr Glu Ser Thr Arg Val Cys Phe Lys Gln Glu Glu Glu Gln
    450                 455                 460

Gln His Phe Leu Arg Asn Ser Pro Ser His Met Thr Asn Val Asp His
465                 470                 475                 480

His Ser Ser Thr Ser Asp Asp Ser Val Thr Val Cys Gly Asn Val Val
                485                 490                 495

Ser Tyr Gly Gly Tyr Gln Gly Phe Ala Ile Pro Val Gly Thr Ser Val
            500                 505                 510

Asn Tyr Asp Pro Phe Thr Ala Ala Glu Ile Ala Tyr Asn Ala Arg Asn
        515                 520                 525

His Tyr Tyr Tyr Ala Gln His Gln Gln Gln Gln Ile Gln Gln Ser
    530                 535                 540

Pro Gly Gly Asp Phe Pro Val Ala Ile Ser Asn Asn His Ser Ser Asn
545                 550                 555                 560

Met Tyr Phe His Gly Glu Gly Gly Glu Gly Ala Pro Thr Phe Ser
                565                 570                 575

Val Trp Asn Asp Thr
            580

<210> SEQ ID NO 31
<211> LENGTH: 584
<212> TYPE: PRT
<213> ORGANISM: Arabidopsis thaliana

<400> SEQUENCE: 31

Met Asn Ser Met Asn Asn Trp Leu Gly Phe Ser Leu Ser Pro His Asp
 1               5                  10                  15

Gln Asn His His Arg Thr Asp Val Asp Ser Ser Thr Thr Arg Thr Ala
            20                  25                  30
```

```
Val Asp Val Ala Gly Gly Tyr Cys Phe Asp Leu Ala Ala Pro Ser Asp
         35                  40                  45

Glu Ser Ser Ala Val Gln Thr Ser Phe Leu Ser Pro Phe Gly Val Thr
 50                  55                  60

Leu Glu Ala Phe Thr Arg Asp Asn Asn Ser His Ser Arg Asp Trp Asp
 65                  70                  75                  80

Ile Asn Gly Gly Ala Cys Asn Thr Leu Thr Asn Asn Glu Gln Asn Gly
                 85                  90                  95

Pro Lys Leu Glu Asn Phe Leu Gly Arg Thr Thr Ile Tyr Asn Thr
                100                 105                 110

Asn Glu Thr Val Val Asp Gly Asn Gly Asp Cys Gly Gly Gly Asp Gly
            115                 120                 125

Gly Gly Gly Gly Ser Leu Gly Leu Ser Met Ile Lys Thr Trp Leu Ser
        130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
                180                 185                 190

Val Glu Thr Thr Pro Lys Lys Thr Ile Glu Ser Phe Gly Gln Arg Thr
                195                 200                 205

Ser Ile Tyr Arg Gly Val Thr Arg His Arg Trp Thr Gly Arg Tyr Glu
                210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Pro Thr Thr Thr
                260                 265                 270

Thr Asn Phe Pro Leu Ser Glu Tyr Glu Lys Glu Val Glu Glu Met Lys
                275                 280                 285

His Met Thr Arg Gln Glu Tyr Val Ala Ser Leu Arg Arg Lys Ser Ser
            290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
                340                 345                 350

Tyr Asp Ile Ala Ala Ile Lys Phe Arg Gly Leu Ser Ala Val Thr Asn
                355                 360                 365

Phe Asp Met Asn Arg Tyr Asn Val Lys Ala Ile Leu Glu Ser Pro Ser
 370                 375                 380

Leu Pro Ile Gly Ser Ser Ala Lys Arg Leu Lys Asp Val Asn Asn Pro
385                 390                 395                 400

Val Pro Ala Met Met Ile Ser Asn Asn Val Ser Glu Ser Ala Asn Asn
                405                 410                 415

Val Ser Gly Trp Gln Asn Thr Ala Phe Gln His His Gln Gly Met Asp
                420                 425                 430

Leu Ser Leu Leu Gln Gln Gln Glu Arg Tyr Val Gly Tyr Tyr Asn
                435                 440                 445
```

```
Gly Gly Asn Leu Ser Thr Glu Ser Thr Arg Val Cys Phe Lys Gln Glu
    450                 455                 460

Glu Glu Gln Gln His Phe Leu Arg Asn Ser Pro Ser His Met Thr Asn
465                 470                 475                 480

Val Asp His His Ser Ser Thr Ser Asp Asp Ser Val Thr Val Cys Gly
                485                 490                 495

Asn Val Val Ser Tyr Gly Gly Tyr Gln Gly Phe Ala Ile Pro Val Gly
            500                 505                 510

Thr Ser Val Asn Tyr Asp Pro Phe Thr Ala Ala Glu Ile Ala Tyr Asn
        515                 520                 525

Ala Arg Asn His Tyr Tyr Tyr Ala Gln His Gln Gln Gln Gln Gln Ile
530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Glu Gly Ala Pro
                565                 570                 575

Thr Phe Ser Val Trp Asn Asp Thr
            580

<210> SEQ ID NO 32
<211> LENGTH: 579
<212> TYPE: PRT
<213> ORGANISM: Brassica napus

<400> SEQUENCE: 32

Met Asn Asn Asn Trp Leu Gly Phe Ser Leu Ser Pro Tyr Glu Gln Asn
1               5                   10                  15

His His Arg Lys Asp Val Tyr Ser Ser Thr Thr Thr Val Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Val Asp
    50                  55                  60

Ala Phe Thr Arg Asp Asn Asn Ser His Ser Arg Asp Trp Asp Ile Asn
65                  70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Gly Asp Gly
        115                 120                 125

Gly Gly Gly Ser Leu Gly Leu Ser Met Ile Lys Thr Trp Leu Arg Asn
    130                 135                 140

Gln Pro Val Asp Asn Val Asp Asn Gln Glu Asn Gly Asn Ala Ala Lys
145                 150                 155                 160

Gly Leu Ser Leu Ser Met Asn Ser Ser Thr Ser Cys Asp Asn Asn
                165                 170                 175

Asp Ser Asn Asn Asn Val Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240
```

```
Gly Arg Gln Val Tyr Leu Gly Gly Tyr Asp Lys Glu Lys Ala Ala
            245                 250                 255

Arg Ala Tyr Asp Leu Ala Ala Leu Lys Tyr Trp Gly Thr Thr Thr
            260                 265                 270

Thr Asn Phe Pro Met Ser Glu Tyr Glu Lys Glu Val Glu Met Lys
            275                 280                 285

His Met Thr Arg Gln Glu Tyr Val Ala Ser Leu Arg Arg Lys Ser Ser
290                     295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
            325                 330                 335

Asp Leu Tyr Leu Gly Thr Phe Gly Thr Gln Glu Glu Ala Glu Ala
            340                 345                 350

Tyr Asp Ile Ala Ala Ile Lys Phe Arg Gly Leu Thr Ala Val Thr Asn
            355                 360                 365

Phe Asp Met Asn Arg Tyr Asn Val Lys Ala Ile Leu Glu Ser Pro Ser
            370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Ser Ala Ser Gly Trp Gln Asn Ala Ala Val Gln His His Gln Gly Val
                420                 425                 430

Asp Leu Ser Leu Leu His Gln His Gln Glu Arg Tyr Asn Gly Tyr Tyr
            435                 440                 445

Tyr Asn Gly Gly Asn Leu Ser Ser Glu Ser Ala Arg Ala Cys Phe Lys
            450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Asp Ser Val Thr Val
                485                 490                 495

Cys Gly Asn Val Val Gly Tyr Gly Gly Tyr Gln Gly Phe Ala Ala Pro
                500                 505                 510

Val Asn Cys Asp Ala Tyr Ala Ala Ser Glu Phe Asp Tyr Asn Ala Arg
            515                 520                 525

Asn His Tyr Tyr Phe Ala Gln Gln Gln Thr Gln Ser Pro Gly
            530                 535                 540

Gly Asp Phe Pro Ala Ala Met Thr Asn Asn Val Gly Ser Asn Met Tyr
545                 550                 555                 560

Tyr His Gly Glu Gly Gly Glu Val Ala Pro Thr Phe Thr Val Trp
                565                 570                 575

Asn Asp Asn

<210> SEQ ID NO 33
<211> LENGTH: 579
<212> TYPE: PRT
<213> ORGANISM: Brassica napus

<400> SEQUENCE: 33

Met Asn Asn Asn Trp Leu Gly Phe Ser Leu Ser Pro Tyr Glu Gln Asn
1               5                   10                  15

His His Arg Lys Asp Val Cys Ser Ser Thr Thr Thr Thr Ala Val Asp
            20                  25                  30
```

```
Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Leu Asp
        50                  55                  60

Ala Phe Thr Arg Asp Asn Asn Ser His Ser Arg Asp Trp Asp Ile Asn
65                  70                  75                  80

Gly Ser Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
                100                 105                 110

Asn Val Gly Asp Ile Asp Gly Ser Gly Cys Tyr Gly Gly Asp Gly
                115                 120                 125

Gly Gly Gly Ser Leu Gly Leu Ser Met Ile Lys Thr Trp Leu Arg Asn
        130                 135                 140

Gln Pro Val Asp Asn Val Asp Asn Gln Glu Asn Gly Asn Gly Ala Lys
145                 150                 155                 160

Gly Leu Ser Leu Ser Met Asn Ser Ser Thr Ser Cys Asp Asn Asn Asn
                165                 170                 175

Tyr Ser Asn Asn Leu Val Ala Gln Gly Lys Thr Ile Asp Asp Ser
                180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
        210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
                260                 265                 270

Thr Asn Phe Pro Met Ser Glu Tyr Glu Lys Glu Ile Glu Glu Met Lys
        275                 280                 285

His Met Thr Arg Gln Glu Tyr Val Ala Ser Leu Arg Arg Lys Ser Ser
        290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
                340                 345                 350

Tyr Asp Ile Ala Ala Ile Lys Phe Arg Gly Leu Thr Ala Val Thr Asn
                355                 360                 365

Phe Asp Met Asn Arg Tyr Asn Val Lys Ala Ile Leu Glu Ser Pro Ser
        370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Asn Ala Ser Gly Trp Gln Asn Ala Ala Val Gln His Gln Gly Val
                420                 425                 430

Asp Leu Ser Leu Leu Gln Gln His Gln Glu Arg Tyr Asn Gly Tyr Tyr
                435                 440                 445
```

```
Tyr Asn Gly Gly Asn Leu Ser Ser Glu Ser Ala Arg Ala Cys Phe Lys
    450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Asp Ser Val Thr Val
                485                 490                 495

Cys Gly Asn Val Val Gly Tyr Gly Tyr Gln Gly Phe Ala Ala Pro
                500                 505                 510

Val Asn Cys Asp Ala Tyr Ala Ser Glu Phe Asp Tyr Asn Ala Arg
            515                 520                 525

Asn His Tyr Tyr Phe Ala Gln Gln Gln Thr Gln His Ser Pro Gly
530                 535                 540

Gly Asp Phe Pro Ala Ala Met Thr Asn Asn Val Gly Ser Asn Met Tyr
545                 550                 555                 560

Tyr His Gly Glu Gly Gly Glu Val Ala Pro Thr Phe Thr Val Trp
                565                 570                 575

Asn Asp Asn

<210> SEQ ID NO 34
<211> LENGTH: 565
<212> TYPE: PRT
<213> ORGANISM: Arabidopsis thaliana

<400> SEQUENCE: 34

Met Asn Ser Asn Asn Trp Leu Ala Phe Pro Leu Ser Pro Thr His Ser
1               5                   10                  15

Ser Leu Pro Pro His Ile His Ser Ser Gln Asn Ser His Phe Asn Leu
                20                  25                  30

Gly Leu Val Asn Asp Asn Ile Asp Asn Pro Phe Gln Asn Gln Gly Trp
            35                  40                  45

Asn Met Ile Asn Pro His Gly Gly Gly Glu Gly Gly Glu Val Pro
50                  55                  60

Lys Val Ala Asp Phe Leu Gly Val Ser Lys Ser Gly Asp His His Thr
65                  70                  75                  80

Asp His Asn Leu Val Pro Tyr Asn Asp Ile His Gln Thr Asn Ala Ser
                85                  90                  95

Asp Tyr Tyr Phe Gln Thr Asn Ser Leu Leu Pro Thr Val Val Thr Cys
            100                 105                 110

Ala Ser Asn Ala Pro Asn Asn Tyr Glu Leu Gln Glu Ser Ala His Asn
        115                 120                 125

Leu Gln Ser Leu Thr Leu Ser Met Gly Ser Thr Gly Ala Ala Ala Ala
130                 135                 140

Glu Val Ala Thr Val Lys Ala Ser Pro Ala Glu Thr Ser Ala Asp Asn
145                 150                 155                 160

Ser Ser Ser Thr Thr Asn Thr Ser Gly Gly Ala Ile Val Glu Ala Thr
                165                 170                 175

Pro Arg Arg Thr Leu Glu Thr Phe Gly Gln Arg Thr Ser Ile Tyr Arg
            180                 185                 190

Gly Val Thr Arg His Arg Trp Thr Gly Arg Tyr Glu Ala His Leu Trp
        195                 200                 205

Asp Asn Ser Cys Arg Arg Glu Gly Gln Ser Arg Lys Gly Arg Gln Gly
    210                 215                 220

Gly Tyr Asp Lys Glu Glu Lys Ala Ala Arg Ala Tyr Asp Leu Ala Ala
225                 230                 235                 240
```

```
Leu Lys Tyr Trp Gly Pro Ser Thr Thr Thr Asn Phe Pro Ile Thr Asn
                245                 250                 255

Tyr Glu Lys Glu Val Glu Glu Met Lys Asn Met Thr Arg Gln Glu Phe
            260                 265                 270

Val Ala Ser Ile Arg Arg Lys Ser Ser Gly Phe Ser Arg Gly Ala Ser
        275                 280                 285

Met Tyr Arg Gly Val Thr Arg His His Gln His Gly Arg Trp Gln Ala
    290                 295                 300

Arg Ile Gly Arg Val Ala Gly Asn Lys Asp Leu Tyr Leu Gly Thr Phe
305                 310                 315                 320

Ser Thr Glu Glu Glu Ala Ala Glu Ala Tyr Asp Ile Ala Ala Ile Lys
                325                 330                 335

Phe Arg Gly Leu Asn Ala Val Thr Asn Phe Glu Ile Asn Arg Tyr Asp
            340                 345                 350

Val Lys Ala Ile Leu Glu Ser Asn Thr Leu Pro Ile Gly Gly Gly Ala
        355                 360                 365

Ala Lys Arg Leu Lys Glu Ala Gln Ala Leu Glu Ser Ser Arg Lys Arg
    370                 375                 380

Glu Glu Met Ile Ala Leu Gly Ser Asn Phe His Gln Tyr Gly Ala Ala
385                 390                 395                 400

Ser Gly Ser Ser Ser Val Ala Ser Ser Ser Arg Leu Gln Leu Gln Pro
                405                 410                 415

Tyr Pro Leu Ser Ile Gln Gln Pro Phe Glu His Leu His His His Gln
            420                 425                 430

Pro Leu Leu Thr Leu Gln Asn Asn Asn Asp Ile Ser Gln Tyr His Asp
        435                 440                 445

Ser Phe Ser Tyr Ile Gln Thr Gln Leu His Leu His Gln Gln Gln Thr
    450                 455                 460

Asn Asn Tyr Leu Gln Ser Ser His Thr Ser Gln Leu Tyr Asn Ala
465                 470                 475                 480

Tyr Leu Gln Ser Asn Pro Gly Leu Leu His Gly Phe Val Ser Asp Asn
                485                 490                 495

Asn Asn Thr Ser Gly Phe Leu Gly Asn Asn Gly Ile Gly Ile Gly Ser
            500                 505                 510

Ser Ser Thr Val Gly Ser Ser Ala Glu Glu Glu Phe Pro Ala Val Lys
        515                 520                 525

Val Asp Tyr Asp Met Pro Pro Ser Gly Gly Ala Thr Gly Tyr Gly Gly
    530                 535                 540

Trp Asn Ser Gly Glu Ser Ala Gln Gly Ser Asn Pro Gly Gly Val Phe
545                 550                 555                 560

Thr Met Trp Asn Glu
                565

<210> SEQ ID NO 35
<211> LENGTH: 540
<212> TYPE: PRT
<213> ORGANISM: Arabidopsis thaliana

<400> SEQUENCE: 35

Met Asp Asn Pro Phe Gln Thr Gln Glu Trp Asn Met Ile Asn Pro His
  1               5                  10                  15

Gly Gly Gly Gly Asp Glu Gly Gly Glu Val Pro Lys Val Ala Asp Phe
                 20                  25                  30

Leu Gly Val Ser Lys Pro Asp Glu Asn Gln Ser Asn His Leu Val Ala
             35                  40                  45
```

```
Tyr Asn Asp Ser Asp Tyr Tyr Phe His Thr Asn Ser Leu Met Pro Ser
        50                  55                  60

Val Gln Ser Asn Asp Val Val Ala Ala Cys Asp Ser Asn Thr Pro
65                  70                  75                  80

Asn Asn Ser Ser Tyr His Glu Leu Gln Glu Ser Ala His Asn Leu Gln
                85                  90                  95

Ser Leu Thr Leu Ser Met Gly Thr Thr Ala Gly Asn Asn Val Val Asp
            100                 105                 110

Lys Ala Ser Pro Ser Glu Thr Thr Gly Asp Asn Ala Ser Gly Gly Ala
            115                 120                 125

Leu Ala Val Val Glu Thr Ala Thr Pro Arg Arg Ala Leu Asp Thr Phe
            130                 135                 140

Gly Gln Arg Thr Ser Ile Tyr Arg Gly Val Thr Arg His Arg Trp Thr
145                 150                 155                 160

Gly Arg Tyr Glu Ala His Leu Trp Asp Asn Ser Cys Arg Arg Glu Gly
                165                 170                 175

Gln Ser Arg Lys Gly Arg Gln Gly Gly Tyr Asp Lys Glu Asp Lys Ala
            180                 185                 190

Ala Arg Ser Tyr Asp Leu Ala Ala Leu Lys Tyr Trp Gly Pro Ser Thr
            195                 200                 205

Thr Thr Asn Phe Pro Ile Thr Asn Tyr Glu Lys Glu Val Glu Glu Met
    210                 215                 220

Lys His Met Thr Arg Gln Glu Phe Val Ala Ala Ile Arg Arg Lys Ser
225                 230                 235                 240

Ser Gly Phe Ser Arg Gly Ala Ser Met Tyr Arg Gly Val Thr Arg His
                245                 250                 255

His Gln His Gly Arg Trp Gln Ala Arg Ile Gly Arg Val Ala Gly Asn
            260                 265                 270

Lys Asp Leu Tyr Leu Gly Thr Phe Ser Thr Glu Glu Ala Ala Glu
            275                 280                 285

Ala Tyr Asp Ile Ala Ala Ile Lys Phe Arg Gly Leu Asn Ala Val Thr
            290                 295                 300

Asn Phe Glu Ile Asn Arg Tyr Asp Val Lys Ala Ile Leu Glu Ser Ser
305                 310                 315                 320

Thr Leu Pro Ile Gly Gly Gly Ala Ala Lys Arg Leu Lys Glu Ala Gln
            325                 330                 335

Ala Leu Glu Ser Ser Arg Lys Arg Glu Ala Glu Met Ile Ala Leu Gly
            340                 345                 350

Ser Ser Phe Gln Tyr Gly Gly Ser Ser Thr Gly Ser Gly Ser Thr
            355                 360                 365

Ser Ser Arg Leu Gln Leu Gln Pro Tyr Pro Leu Ser Ile Gln Gln Pro
            370                 375                 380

Leu Glu Pro Phe Leu Ser Leu Gln Asn Asn Asp Ile Ser His Tyr Asn
385                 390                 395                 400

Asn Asn Asn Ala His Asp Ser Ser Phe Asn His His Ser Tyr Ile
                405                 410                 415

Gln Thr Gln Leu His Leu His Gln Gln Thr Asn Asn Tyr Leu Gln Gln
            420                 425                 430

Gln Ser Ser Gln Asn Ser Gln Gln Leu Tyr Asn Ala Tyr Leu His Ser
            435                 440                 445

Asn Pro Ala Leu Leu His Gly Leu Val Ser Thr Ser Ile Val Asp Asn
    450                 455                 460
```

```
Asn Asn Asn Gly Gly Ser Ser Gly Ser Tyr Asn Thr Ala Ala Phe
465                 470                 475                 480

Leu Gly Asn His Gly Ile Gly Ile Gly Ser Ser Ser Thr Val Gly Ser
            485                 490                 495

Thr Glu Glu Phe Pro Thr Val Lys Thr Asp Tyr Asp Met Pro Ser Ser
            500                 505                 510

Asp Gly Thr Gly Gly Tyr Ser Gly Trp Thr Ser Glu Ser Val Gln Gly
            515                 520                 525

Ser Asn Pro Gly Gly Val Phe Thr Met Trp Asn Glu
            530                 535                 540

<210> SEQ ID NO 36
<211> LENGTH: 516
<212> TYPE: PRT
<213> ORGANISM: Arabidopsis thaliana

<400> SEQUENCE: 36

Met Ile Asn Pro His Gly Gly Gly Glu Gly Gly Glu Val Pro Lys
1               5                   10                  15

Val Ala Asp Phe Leu Gly Val Ser Lys Ser Gly Asp His His Thr Asp
            20                  25                  30

His Asn Leu Val Pro Tyr Asn Asp Ile His Gln Thr Asn Ala Ser Asp
            35                  40                  45

Tyr Tyr Phe Gln Thr Asn Ser Leu Leu Pro Thr Val Val Thr Cys Ala
    50                  55                  60

Ser Asn Ala Pro Asn Asn Tyr Glu Leu Gln Glu Ser Ala His Asn Leu
65              70                  75                  80

Gln Ser Leu Thr Leu Ser Met Gly Ser Thr Gly Ala Ala Ala Glu
            85                  90                  95

Val Ala Thr Val Lys Ala Ser Pro Ala Glu Thr Ser Ala Asp Asn Ser
            100                 105                 110

Ser Ser Thr Thr Asn Thr Ser Gly Gly Ala Ile Val Glu Ala Thr Pro
            115                 120                 125

Arg Arg Thr Leu Glu Thr Phe Gly Gln Arg Thr Ser Ile Tyr Arg Gly
130                 135                 140

Val Thr Arg His Arg Trp Thr Gly Arg Tyr Glu Ala His Leu Trp Asp
145                 150                 155                 160

Asn Ser Cys Arg Arg Glu Gly Gln Ser Arg Lys Gly Arg Gln Gly Gly
            165                 170                 175

Tyr Asp Lys Glu Glu Lys Ala Ala Arg Ala Tyr Asp Leu Ala Ala Leu
            180                 185                 190

Lys Tyr Trp Gly Pro Ser Thr Thr Thr Asn Phe Pro Ile Thr Asn Tyr
            195                 200                 205

Glu Lys Glu Val Glu Glu Met Lys Asn Met Thr Arg Gln Glu Phe Val
            210                 215                 220

Ala Ser Ile Arg Arg Lys Ser Ser Gly Phe Ser Arg Gly Ala Ser Met
225                 230                 235                 240

Tyr Arg Gly Val Thr Arg His His Gln His Gly Arg Trp Gln Ala Arg
            245                 250                 255

Ile Gly Arg Val Ala Gly Asn Lys Asp Leu Tyr Leu Gly Thr Phe Ser
            260                 265                 270

Thr Glu Glu Glu Ala Ala Glu Ala Tyr Asp Ile Ala Ala Ile Lys Phe
            275                 280                 285

Arg Gly Leu Asn Ala Val Thr Asn Phe Glu Ile Asn Arg Tyr Asp Val
            290                 295                 300
```

```
Lys Ala Ile Leu Glu Ser Asn Thr Leu Pro Ile Gly Gly Ala Ala
305                 310                 315                 320

Lys Arg Leu Lys Glu Ala Gln Ala Leu Glu Ser Ser Arg Lys Arg Glu
            325                 330                 335

Glu Met Ile Ala Leu Gly Ser Asn Phe His Gln Tyr Gly Ala Ala Ser
            340                 345                 350

Gly Ser Ser Ser Val Ala Ser Ser Arg Leu Gln Leu Gln Pro Tyr
        355                 360                 365

Pro Leu Ser Ile Gln Gln Pro Phe Glu His Leu His His Gln Pro
    370                 375                 380

Leu Leu Thr Leu Gln Asn Asn Asn Asp Ile Ser Gln Tyr His Asp Ser
385                 390                 395                 400

Phe Ser Tyr Ile Gln Thr Gln Leu His Leu His Gln Gln Thr Asn
            405                 410                 415

Asn Tyr Leu Gln Ser Ser Ser His Thr Ser Gln Leu Tyr Asn Ala Tyr
            420                 425                 430

Leu Gln Ser Asn Pro Gly Leu Leu His Gly Phe Val Ser Asp Asn Asn
            435                 440                 445

Asn Thr Ser Gly Phe Leu Gly Asn Asn Gly Ile Gly Ile Gly Ser Ser
    450                 455                 460

Ser Thr Val Gly Ser Ser Ala Glu Glu Glu Phe Pro Ala Val Lys Val
465                 470                 475                 480

Asp Tyr Asp Met Pro Pro Ser Gly Gly Ala Thr Gly Tyr Gly Trp
            485                 490                 495

Asn Ser Gly Glu Ser Ala Gln Gly Ser Asn Pro Gly Gly Val Phe Thr
            500                 505                 510

Met Trp Asn Glu
        515

<210> SEQ ID NO 37
<211> LENGTH: 65
<212> TYPE: PRT
<213> ORGANISM: Artificial Sequence
<220> FEATURE:
<223> OTHER INFORMATION: Synthesized
<220> FEATURE:
<223> OTHER INFORMATION: consensus sequence of Figure 1

<400> SEQUENCE: 37

Met Ser Asn Asn Trp Leu Gly Phe Ser Leu Ser Pro Asp Gln Ser Ser
1               5                   10                  15

Ala Val Asp Ala Phe Ile Gly Ser Val Asp Phe Asn Ser His Arg Asp
            20                  25                  30

Asn Ala Asn Ile Asn Ser Gly Pro Glu Asn Phe Ser Ile Gly Gly Gly
        35                  40                  45

Gly Gly Ile Gly Leu Ser Met Ile Lys Thr Trp Leu Arg Asn Gln Pro
    50                  55                  60

Asn
65

<210> SEQ ID NO 38
<211> LENGTH: 62
<212> TYPE: PRT
<213> ORGANISM: Artificial Sequence
<220> FEATURE:
<223> OTHER INFORMATION: Synthesized
<220> FEATURE:
<223> OTHER INFORMATION: APETALA2 PFAM consensus sequence
```

```
<400> SEQUENCE: 38

Ser Lys Tyr Arg Gly Val Arg Gln Arg Pro Trp Gly Lys Trp Val Ala
 1               5                  10                  15

Glu Ile Arg Asp Pro Arg Lys Gly Thr Arg Val Trp Leu Gly Thr Phe
             20                  25                  30

Asp Thr Ala Glu Glu Ala Ala Arg Ala Tyr Asp Val Ala Ala Leu Lys
             35                  40                  45

Leu Arg Gly Pro Ser Ala Val Leu Asn Phe Pro Asn Glu Leu
         50                  55                  60
```